(12) United States Patent
Fang et al.

(10) Patent No.: US 11,466,005 B2
(45) Date of Patent: *Oct. 11, 2022

(54) TRICYCLIC COMPOUNDS

(71) Applicant: JACOBIO PHARMACEUTICALS CO., LTD., Beijing (CN)

(72) Inventors: Haiquan Fang, Beijing (CN); Mingming Chen, Beijing (CN); Guiqun Yang, Beijing (CN); Yuelei Du, Beijing (CN); Yanping Wang, Beijing (CN); Tong Wu, Beijing (CN); Qinglong Li, Beijing (CN); Lei Zhang, Beijing (CN); Shaojing Hu, Beijing (CN)

(73) Assignee: JACOBIO PHARMACEUTICALS CO., LTD., Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/561,381

(22) Filed: Dec. 23, 2021

(65) Prior Publication Data

US 2022/0119390 A1 Apr. 21, 2022

Related U.S. Application Data

(63) Continuation of application No. 17/129,983, filed on Dec. 22, 2020, which is a continuation of application No. PCT/CN2019/084601, filed on Apr. 26, 2019.

(30) Foreign Application Priority Data

Jun. 25, 2018 (WO) ................ PCT/CN2018/092542

(51) Int. Cl.
  C07D 471/14 (2006.01)
  A61K 31/437 (2006.01)
  A61P 35/00 (2006.01)

(52) U.S. Cl.
  CPC ............ *C07D 471/14* (2013.01); *A61P 35/00* (2018.01); *C07B 2200/05* (2013.01)

(58) Field of Classification Search
  CPC ..... C07D 471/14; A61K 31/437; A61P 35/02; A61P 35/00
  USPC ............................................. 546/82; 514/293
  See application file for complete search history.

(56) References Cited

FOREIGN PATENT DOCUMENTS

| WO | 2014082380 | 6/2014 |
| WO | 2014/164596 | 10/2014 |
| WO | 2015100282 | 7/2015 |
| WO | 2016/183118 | 11/2016 |
| WO | 2017/124936 | 7/2017 |
| WO | 2017133681 | 8/2017 |
| WO | 2017197056 | 11/2017 |
| WO | 2019080941 | 5/2019 |
| WO | 2020200284 | 10/2020 |

OTHER PUBLICATIONS

Mujtaba, S et al. "Structure and acetyl-lysine recognition of the bromodomain." Oncogene vol. 26,37 (2007): 5521-7. doi:10.1038/sj.onc.1210618.

Dhalluin, C et al. "Structure and ligand of a histone acetyltransferase bromodomain." Nature vol. 399,6735 (1999): 491-6. doi:10.1038/20974.

LeRoy, Gary et al. "The double bromodomain proteins Brd2 and Brd3 couple histone acetylation to transcription." Molecular cell vol. 30,1 (2008): 51-60. doi:10.1016/j.molcel.2008.01.018.

Hargreaves, Diana C et al. "Control of inducible gene expression by signal-dependent transcriptional elongation." Cell vol. 138,1 (2009): 129-45. doi:10.1016/j.cell.2009.05.047.

Jones, M H et al. "Identification and characterization of BRDT: A testis-specific gene related to the bromodomain genes RING3 and Drosophila fsh." Genomics vol. 45,3 (1997): 529-34. doi:10.1006/geno.1997.5000.

Shang, Enyuan et al. "The first bromodomain of Brdt, a testis-specific member of the BET sub-family of double-bromodomain-containing proteins, is essential for male germ cell differentiation." Development (Cambridge, England) vol. 134,19 (2007): 3507-15. doi:10.1242/dev.004481.

Dey, Anup et al. "The double bromodomain protein Brd4 binds to acetylated chromatin during interphase and mitosis." Proceedings of the National Academy of Sciences of the United States of America vol. 100,15 (2003): 8758-63. doi:10.1073/pnas.1433065100.

Dawson, Mark A et al. "Inhibition of BET recruitment to chromatin as an effective treatment for MLL-fusion leukaemia." Nature vol. 478,7370 529-33. Oct. 2, 2011, doi:101038/nature10509.

Chapuy, Bjoern et al. "Discovery and characterization of super-enhancer-associated dependencies in diffuse large B cell lymphoma." Cancer cell vol. 24,6 (2013): 777-90. doi:10.1016/j.ccr.2013.11.003.

(Continued)

*Primary Examiner* — Charanjit Aulakh
(74) *Attorney, Agent, or Firm* — Robin L. Teskin; Baker, Donelson, Bearman, Caldwell & Berkowitz, PC

(57) ABSTRACT

Disclosed are tricyclic compounds as bromodomain and extra-terminal (BET) inhibitors which are shown as formula I, their synthesis and their use for treating diseases. More particularly, disclosed are fused heterocyclic derivatives useful as inhibitors of BET, methods for producing such compounds and methods for treating diseases and conditions wherein inhibition of one or more BET bromodomains provides a benefit.

(I)

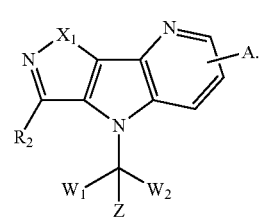

8 Claims, No Drawings

(56) References Cited

OTHER PUBLICATIONS

Lovén, Jakob et al. "Selective inhibition of tumor oncogenes by disruption of super-enhancers." Cell vol. 153,2 (2013): 320-34. doi:10.1016/j.cell.2013.03.036.
Whyte, Warren A et al. "Master transcription factors and mediator establish super-enhancers at key cell identity genes." Cell vol. 153,2 (2013): 307-19. doi:10.1016/j.cell.2013.03.035.
Hnisz, Denes et al. "Super-enhancers in the control of cell identity and disease." Cell vol. 155,4 (2013): 934-47. doi:10.1016/j.cell.2013.09.053.
Sahni, Jennifer M, and Ruth A Keri. "Targeting bromodomain and extraterminal proteins in breast cancer." Pharmacological research vol. 129 (2018): 156-176. doi:10.1016/j.phrs.2017.11.015.
Anand, Priti et al. "BET bromodomains mediate transcriptional pause release in heart failure." Cell vol. 154,3 (2013): 569-82. doi:10.1016/j.cell.2013.07.013.
Wang, Chen-Yi, and Panagis Filippakopoulos. "Beating the odds: BETs in disease." Trends in biochemical sciences vol. 40,8 (2015): 468-79. doi:10.1016/j.tibs.2015.06.002.
Stathis, Anastasios, and Francesco Bertoni. "BET Proteins as Targets for Anticancer Treatment." Cancer discovery vol. 8,1 (2018): 24-36. doi:10.1158/2159-8290.CD-17-0605.
Stathis, Anastasios, and Francesco Bertoni. "BET Proteins as Targets for Anticancer Treatment." Cancer discovery vol. 8,1 (2017): 0F1-0F13. doi:10.1158/2159-8290.CD-17-0605; Published Online First Dec. 20, 2017.

TRICYCLIC COMPOUNDS

CROSS-REFERENCE TO RELATED APPLICATIONS

This application is a continuation of U.S. application Ser. No. 17/129,983, filed Dec. 22, 2020, which is a continuation application of Int'l Appl. No. PCT/CN2019/084601, filed Apr. 26, 2019, which claims priority to Int'l Appl. No. PCT/CN2018/092542, filed Jun. 25, 2018, of which is incorporated herein by reference in its entirety.

TECHNICAL FIELD

This invention relates to certain novel tricyclic compounds (Formula I) as bromodomain and extra-terminal (BET) inhibitors which are shown as Formula I, their synthesis and their use for treating diseases. More particularly, this invention is directed to fused heterocyclic derivatives useful as inhibitors of BET, methods for producing such compounds and methods for treating diseases and conditions wherein inhibition of one or more BET bromodomains provides a benefit.

BACKGROUND ART

Several physiological processes might contribute to epigenetic regulation, including DNA methylation, non-coding RNA-mediated scaffolding and complex formation, and histone modification. Histone modification is a process related to the post-translational covalent modification of histone proteins that markedly influences the ability of associated DNA to be transcribed. Lysine acetylation is a post-translational modification with broad relevance to cellular signaling and disease biology. Enzymes that regulate lysine acetylation in histones are termed as 'writers' or histone acetyltransferases (HATs), and enzymes that regulate lysine deacetylation in histone as 'erasers' or histone deacetylases (HDACs). Bromodomains (BRDs), 'readers' of epigenetic marks, specifically recognize ε-N-acetyl lysine (Kac) residues on histones tails.

BRD is a conserved 110 amino acid structure motif composed of four α-helices (αZ, αA, αB, and αC) that comprise a left-handed bundle (S. Mujtaba, L. Zeng, M. M. Zhou, Oncogene, 2007 (26), 5521-5527). The α-helices are connected together by two loop regions (ZA and BC) and form a surface that interacts with acetylated lysines in nucleosomal histones (C. Dhalluin, J. E. Carlson, L. Zeng et al, Nature, 1999(399), 491-496). There are 46 known bromodomain containing proteins from humans which across eight families based on structure/sequence similarity. Among them, bromodomain and extra-terminal domain (BET) recognize acetylated lysine residues in histones H3 and H4. BET family, containing BRD2, BRD3, BRD4 and BRDT four members, share two N-terminal bromodomains and extra C-terminal domain (ET) exhibiting high levels of sequence conservation. As reported, BRD2 and BRD3 associate with histones along actively transcribed genes and maybe involved in facilitating transcriptional elongation (Leroy et al., Mol. Cell 2008 30(1), 51-60). BRD4 appears to be involved in the recruitment of the positive transcriptional elongation factor complex (pTEF-I3), which plays an essential role in the regulation of transcription by RNA polymerase and increased transcriptional output (Hargreaves et al., Cell, 2009 138(1):1294145). Unlike the other three BET proteins expressed ubiquitously, BRDT expression is normally testis-specific (M. H. Jones et al, Genomics, 1997 (45), 529-534) and BRDT is essential for spermatogenesis (E. Shang et al, Development, 2007 (134), 3507-3515). Binding of BET proteins to acetylated histones leads to recruiting BET proteins to the enhancer and promoter regions of genes for active transcription. By that, they interact with coactivators, repressors, transcription factors and transcriptional machinery to form protein complexes and influence target gene transcription (A. Dey et al, Proc. Natl. Acad. Sci, U.S.A. 2003 (100), 8758-8763). BET proteins, although having a similar structure and usually enhancing transcription, regulate different processes based on their binding partners, which are often tissue-specific.

It is thought that BET proteins primarily mediate their effects in disease pathogenesis and progression mainly by localizing to super-enhancers (SEs) at pathology-associated genes and driving their expression (M. A. Dawson et al, Nature, 2011 (478), 529-533; B. Chapuy et al, Cancer Cell, 2013(24), 777-790). In cancer, SEs are enriched at oncogenes like MYC, RUNX1, FOSL2, CCND1, MCL1, and BCL2L1 (B. Chapuy et al, Cancer Cell, 2013(24), 777-790; J. Loven, Cell, 2013(153), 320-334; W. A. Whyte et al, Cell, 2013 (153), 307-319; D. Hnisz et al Cell, 2013(155), 934-947). Inhibition of BET proteins has become a promising target for human diseases including virology, heart failure, inflammation, central nervous system (CNS) disorders and variety cancers (J. M. Sahni et al, Pharmacol Res, 2017, 1-21; P. Anand et al, Cell, 2013 (154), 569-582; C.-Y. Wang et al, Trends Biochem. Sci, 2015 (40), 468-479; A. Stathis et al, Cancer Discovery, 2017, 8(1), 1-13). Small molecule BET inhibitors that are reported in clinical development include RVX-208, GSK-525762A, GSK2820151, OTX-015, CPI-0610, TEN-010/RO6870810, ABBV-075/ABBV-744, BI 894999, BMS-986158, INCB054329/INCB057643, ZEN-3694 GS-5829, AZD5153 as well as an inhibitor from Celgene. There exists a need for generating further BET inhibitors that have improved properties over existing BET inhibitors, for example, improved potency, safety, tolerability, pharmacokinetics and/or pharmacodynamics.

SUMMARY OF INVENTION

In one aspect, there is provided a compound of formula I, a pharmaceutically acceptable salt thereof or stereoisomer thereof:

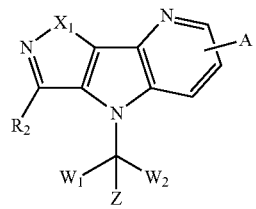

I

Wherein,
$X_1$ is selected from O, S, SO, $SO_2$ or $NR_1$;
$R_1$ is selected from hydrogen; deuterium; —CN; —$SOR_{11}$; —$SO_2R_{11}$; —$SO_2NR_{11}R_{12}$; —$C_{1-6}$alkyl;

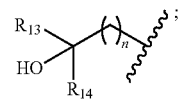

—$C_{2-6}$alkenyl; —$C_{2-6}$alkynyl; carboxyl; —$NO_2$; —$COOR_{11}$; —$COR_{11}$; —$CONR_{11}R_{12}$; —$POR_{11}R_{12}$; —$C_{5-6}$aryl; —$C_{5-6}$heteroaryl containing 1, 2, 3 or 4 heteroatoms selected from N, O, S, SO or $SO_2$; —$C_{3-8}$heterocyclic containing 1, 2, 3 or 4 heteroatoms selected from N, O, S, SO or $SO_2$; or —$C_{3-8}$carbocyclic; and each of which at each occurrence is independently optionally substituted with 1, 2, 3, 4, 5 or 6 substituents, and the said each of substituents at each occurrence is independently selected from deuterium, halogen, —OH, oxo, —CN, —$C_{1-6}$alkyl, —$C_{1-6}$alkoxy, —$NH_2$, —NH($C_{1-6}$alkyl), —N($C_{1-6}$alkyl)$_2$, carboxyl or —$C_{3-8}$carbocyclic;

Each of $R_{11}$ and $R_{12}$ at each occurrence is independently selected from hydrogen; deuterium; —OH; —$NH_2$; —CN; —$C_{1-6}$alkyl; —$C_{1-6}$alkoxy; —$C_{5-6}$aryl; —$C_{5-6}$heteroaryl containing 1, 2, 3 or 4 heteroatoms selected from N, O, S, SO or $SO_2$; —$C_{1-6}$alkylene-$C_{3-8}$carbocyclic; or —$C_{3-8}$carbocyclic; and each of which at each occurrence is independently optionally substituted with 1, 2, 3, 4, 5 or 6 substituents, and the said each of substituents at each occurrence is independently selected from deuterium, halogen, —OH, —CN, —$NH_2$, —NH($C_{1-6}$alkyl), —N($C_{1-6}$alkyl)$_2$, —$C_{1-6}$alkyl, —$C_{1-6}$alkoxy, carboxyl, —$SO_2$($C_{1-6}$alkyl) or —$C_{3-8}$carbocyclic; or $R_{11}$ and $R_{12}$ together with the nitrogen atom to which they are both attached form 4-8 membered heterocyclic ring, and each of the heterocyclic ring at each occurrence can further contains 1, 2, 3 or 4 heteroatoms selected from N, O, S, SO or $SO_2$, and each of the heterocyclic ring at each occurrence is independently optionally substituted with 1, 2, 3, 4, 5 or 6 substituents, and the said each of substituents at each occurrence is independently selected from deuterium; halogen; —OH; oxo; —CN; —$C_{1-6}$alkyl; —$C_{1-6}$alkoxy; —$SO_2$($C_{1-6}$alkyl); —CON($C_{1-6}$alkyl)$_2$; —$SO_2$N($C_{1-6}$alkyl)$_2$; —$NH_2$; —NH($C_{1-6}$alkyl); —N($C_{1-6}$alkyl)$_2$; —$C_{3-6}$heterocyclic containing 1 or 2 heteroatoms selected from N, O or S; or —$C_{1-6}$alkyl substituted with deuterium;

Each of $R_{13}$ and $R_{14}$ at each occurrence is independently selected from hydrogen, deuterium, halogen, —$NH_2$, —$C_{1-6}$alkoxy or —$C_{1-6}$alkyl; or $R_{13}$ and $R_{14}$ together with the carbon atom to which they are both attached form 3-6 membered carbocyclic ring, and each of the carbocyclic ring at each occurrence is independently optionally substituted with 1, 2, 3, 4, 5 or 6 substituents, and the said each of substituents at each occurrence is independently selected from deuterium, halogen, —OH, —$NH_2$, —CN, —$C_{1-6}$alkyl or —$C_{1-6}$alkoxy;

$R_2$ is selected from hydrogen; deuterium; halogen; —$OR_{21}$; —$NR_{21}R_{22}$; —CN; —$SR_{21}$; —$SOR_{21}$; —$SO_2R_{21}$; —$SO_2NR_{21}R_{22}$; —$C_{1-6}$alkyl;

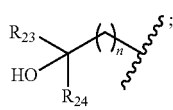

—$C_{2-6}$alkenyl; —$C_{2-6}$alkynyl; carboxyl; —$NO_2$; —$COOR_{21}$; —$COR_{21}$; —$CONR_{21}R_{22}$; —$NR_{21}COR_{22}$; —$NR_{21}CONR_{21}R_{22}$; —$NR_{21}SO_2R_{22}$; —$NR_{21}SO_2NR_{21}R_{22}$; —$OCONR_{21}R_{22}$; —$POR_{21}R_{22}$; —$C_{5-6}$aryl; —$C_{5-6}$heteroaryl containing 1, 2, 3 or 4 heteroatoms selected from N, O, S, SO or $SO_2$; —$C_{3-8}$heterocyclic containing 1, 2, 3 or 4 heteroatoms selected from N, O, S, SO or $SO_2$; or —$C_{3-8}$carbocyclic; and each of which at each occurrence is independently optionally substituted with 1, 2, 3, 4, 5 or 6 substituents, and the said each of substituents at each occurrence is independently selected from deuterium, halogen, —OH, oxo, —CN, —$NH_2$, —$C_{1-6}$alkyl, —$C_{1-6}$alkoxy, carboxyl or —$C_{3-8}$carbocyclic;

Each of $R_{21}$ and $R_{22}$ at each occurrence is independently selected from hydrogen; deuterium; —OH; —$NH_2$; —CN; —$C_{1-6}$alkyl; —$C_{1-6}$alkoxy; —$C_{5-6}$aryl; —$C_{5-6}$heteroaryl containing 1, 2, 3 or 4 heteroatoms selected from N, O, S, SO or $SO_2$; —$C_{1-6}$alkylene-$C_{3-8}$carbocyclic; or —$C_{3-8}$carbocyclic; and each of which at each occurrence is independently optionally substituted with 1, 2, 3, 4, 5 or 6 substituents, and the said each of substituents at each occurrence is independently selected from deuterium, halogen, —OH, —CN, —$NH_2$, —NH($C_{1-6}$alkyl), —N($C_{1-6}$alkyl)$_2$, —$C_{1-6}$alkyl, —$C_{1-6}$alkoxy, carboxyl, —$SO_2$($C_{1-6}$alkyl) or —$C_{3-8}$carbocyclic; or $R_{21}$ and $R_{22}$ together with the nitrogen atom to which they are both attached form 4-8 membered heterocyclic ring, and each of the heterocyclic ring at each occurrence can further contains 1, 2, 3 or 4 heteroatoms selected from N, O, S, SO or $SO_2$, and each of the heterocyclic ring at each occurrence is independently optionally substituted with 1, 2, 3, 4, 5 or 6 substituents, and the said each of substituents at each occurrence is independently selected from deuterium; halogen; —OH; oxo; —CN; —$C_{1-6}$alkyl; —$C_{1-6}$alkoxy; —$SO_2$($C_{1-6}$alkyl); —CON($C_{1-6}$alkyl)$_2$; —$SO_2$N($C_{1-6}$alkyl)$_2$; —$NH_2$; —NH($C_{1-6}$alkyl); —N($C_{1-6}$alkyl)$_2$; —$C_{3-6}$heterocyclic containing 1 or 2 heteroatoms selected from N, O or S; or —$C_{1-6}$alkyl substituted with deuterium;

Each of $R_{23}$ and $R_{24}$ at each occurrence is independently selected from hydrogen, deuterium, halogen, —$NH_2$, —$C_{1-6}$alkoxy or —$C_{1-6}$alkyl; or $R_{23}$ and $R_{24}$ together with the carbon atom to which they are both attached form 3-6 membered carbocyclic ring, and each of the carbocyclic ring at each occurrence is independently optionally substituted with 1, 2, 3, 4, 5 or 6 substituents, and the said each of substituents at each occurrence is independently selected from deuterium, halogen, —OH, —$NH_2$, —CN, —$C_{1-6}$alkyl or —$C_{1-6}$alkoxy;

A is selected from

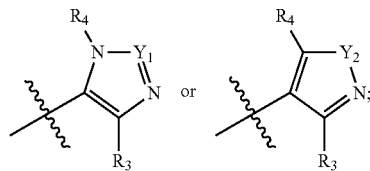

$Y_1$ is selected from N or $CR_{Y1}$;
$Y_2$ is selected from O, S, $CR_{Y1}R_{Y2}$ or $NR_{Y2}$;
Each of $R_{Y1}$ and $R_{Y2}$ at each occurrence is independently selected from hydrogen, deuterium, halogen, —OH, $NH_2$, —CN, —$C_{1-6}$alkyl or —$C_{1-6}$alkoxy;
Each of $R_3$ and $R_4$ at each occurrence is independently selected from hydrogen, deuterium, halogen, —CN, —$SOR_5$, —$SO_2R_5$, —$SO_2NR_5R_6$, —$C_{1-6}$alkyl, —$C_{1-6}$alkoxy, —$COR_5$, —$CONR_5R_6$ or —$POR_5R_6$; and each of which at each occurrence is independently optionally substituted with 1, 2, 3, 4, 5 or 6 substituents, and the said each of substituents at each occurrence is independently selected from deuterium, halogen, —OH, —NH$_2$, —CN, —C$_{1-6}$alkyl or —C$_{1-6}$alkoxy;

Each of R$_5$ and R$_6$ at each occurrence is independently selected from hydrogen; deuterium; —OH; —NH$_2$; —CN; —C$_{1-6}$alkyl; —C$_{1-6}$alkoxy; —C$_{5-6}$aryl; —C$_{5-6}$heteroaryl containing 1, 2, 3 or 4 heteroatoms selected from N, O, S, SO or SO$_2$; —C$_{1-6}$alkylene-C$_{3-8}$carbocyclic; or —C$_{3-8}$carbocyclic; and each of which at each occurrence is independently optionally substituted with 1, 2, 3, 4, 5 or 6 substituents, and the said each of substituents at each occurrence is independently selected from deuterium, halogen, —OH, —CN, —NH$_2$, —NH(C$_{1-6}$alkyl), —N(C$_{1-6}$alkyl)$_2$, —C$_{1-6}$alkyl, —C$_{1-6}$alkoxy, carboxyl, —SO$_2$(C$_{1-6}$alkyl) or —C$_{3-8}$carbocyclic; or R$_5$ and R$_6$ together with the nitrogen atom to which they are both attached form 4-8 membered heterocyclic ring, and each of the heterocyclic ring at each occurrence can further contains 1, 2, 3 or 4 heteroatoms selected from N, O, S, SO or SO$_2$, and each of the heterocyclic ring at each occurrence is independently optionally substituted with 1, 2, 3, 4, 5 or 6 substituents, and the said each of substituents at each occurrence is independently selected from deuterium; halogen; —OH; oxo; —CN; —C$_{1-6}$alkyl; —C$_{1-6}$alkoxy; —SO$_2$(C$_{1-6}$alkyl); —CON(C$_{1-6}$alkyl)$_2$; —SO$_2$N(C$_{1-6}$alkyl)$_2$; —NH$_2$; —NH(C$_{1-6}$alkyl); —N(C$_{1-6}$alkyl)$_2$; —C$_{3-6}$heterocyclic containing 1 or 2 heteroatoms selected from N, O or S; or —C$_{1-6}$alkyl substituted with deuterium;

n is selected from 0, 1, 2, 3, 4, 5 or 6;

W$_1$ is selected from hydrogen; deuterium; halogen; —NH$_2$; —CN; —OH; —NO$_2$; carboxyl; —C$_{1-6}$alkyl; —C$_{1-6}$alkoxy; —C$_{1-6}$alkylene-C$_{1-6}$alkoxy; —C$_{5-10}$aryl; —C$_{5-10}$heteroaryl containing 1, 2, 3 or 4 heteroatoms selected from N, O, S, SO or SO$_2$; —C$_{3-8}$heterocyclic containing 1, 2, 3 or 4 heteroatoms selected from N, O, S, SO or SO$_2$; or —C$_{3-8}$carbocyclic; and each of which at each occurrence is independently optionally substituted;

W$_2$ is selected from hydrogen; deuterium; halogen; —NH$_2$; —CN; —OH; —NO$_2$; carboxyl; —C$_{1-6}$alkyl; —C$_{1-6}$alkoxy; —C$_{5-10}$aryl; —C$_{5-10}$heteroaryl containing 1, 2, 3 or 4 heteroatoms selected from N, O, S, SO or SO$_2$; —C$_{3-8}$heterocyclic containing 1, 2, 3 or 4 heteroatoms selected from N, O, S, SO or SO$_2$; or —C$_{3-8}$carbocyclic; and each of which at each occurrence is independently optionally substituted;

Z is selected from hydrogen, deuterium, halogen, —NH$_2$, —CN, —OH, carboxyl, —C$_{1-6}$alkyl or —C$_{1-6}$alkoxy.

In some embodiments, wherein the compound is of formula I-1:

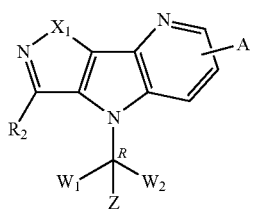

I-1

"R" in the formula I-1 indicates that the absolute configuration of the carbon that contacts with the W$_1$, W$_2$ and Z is R configuration when the carbon is chiral carbon.

In some embodiments, wherein the compound is of formula I-2:

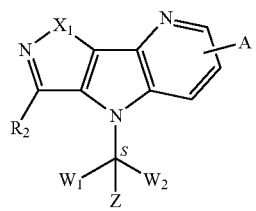

I-2

"S" in the formula I-2 indicates that the absolute configuration of the carbon that contacts with the W$_1$, W$_2$ and Z is S configuration when the carbon is chiral carbon.

In some embodiments, wherein the compound is of formula II:

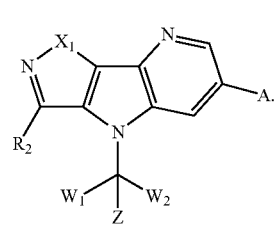

II

In some embodiments, wherein the compound is of formula II-1:

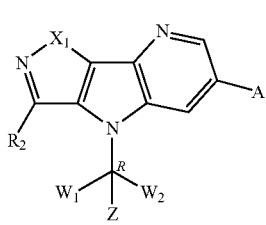

II-1

"R" in the formula II-1 indicates that the absolute configuration of the carbon that contacts with the W$_1$, W$_2$ and Z is R configuration when the carbon is chiral carbon.

In some embodiments, wherein the compound is of formula II-2:

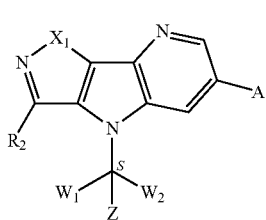

II-2

"S" in the formula II-2 indicates that the absolute configuration of the carbon that contacts with the W$_1$, W$_2$ and Z is S configuration when the carbon is chiral carbon.

In some embodiments, wherein the compound is of formula III:

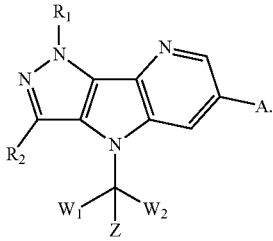

III

In some embodiments, wherein the compound is of formula III-1:

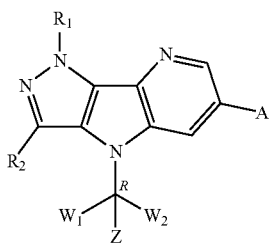

III-1

"R" in the formula III-1 indicates at the absolute configuration of the carbon that contacts with the $W_1$, $W_2$ and Z is R configuration when the carbon is chiral carbon.

In some embodiments, wherein the compound is of formula III-2:

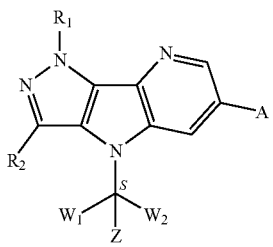

III-2

"S" in the formula III-2 indicates that the absolute configuration of the carbon that contacts with the $W_1$, $W_2$ and Z is S configuration when the carbon is chiral carbon.

In some embodiments, the compound is of formula IV:

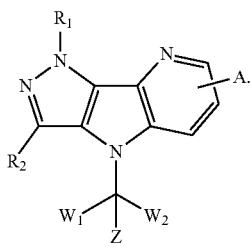

IV

In some embodiments, the compound is of formula IV-1:

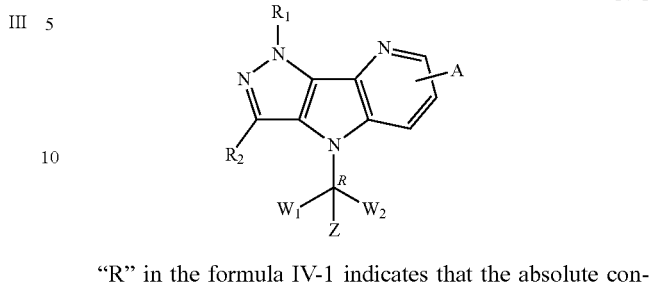

IV-1

"R" in the formula IV-1 indicates that the absolute configuration of the carbon that contacts with the $W_1$, $W_2$ and Z is R configuration when the carbon is chiral carbon.

In some embodiments, the compound is of formula IV-2:

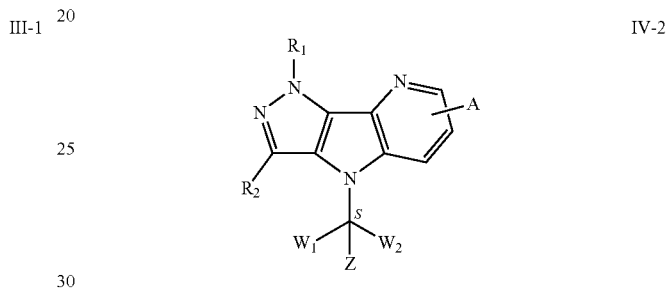

IV-2

"S" in the formula IV-2 indicates that the absolute configuration of the carbon that contacts with the $W_1$, $W_2$ and Z is S configuration when the carbon is chiral carbon.

In some embodiments, wherein $R_1$ is selected from hydrogen; deuterium; —$SOR_{11}$; —$SO_2R_{11}$; —$SO_2NR_{11}R_{12}$; —$C_{1-6}$alkyl;

$$R_{13}\underset{HO}{\overset{R_{14}}{\diagup\!\!\!\diagdown}}\!\!\left(\!\right)_{\!n}\!\!\diagdown\!\!\!\diagup\!\!\!\!\!;$$

—$COOR_{11}$; —$COR_{11}$; —$CONR_{11}R_{12}$; —$POR_{11}R_{12}$; —$C_{5-6}$heteroaryl containing 1, 2, 3 or 4 heteroatoms selected from N, O, S or $SO_2$; —$C_{3-8}$heterocyclic containing 1, 2, 3 or 4 heteroatoms selected from N, O, S or $SO_2$; or —$C_{3-8}$carbocyclic; and each of which at each occurrence is independently optionally substituted with 1, 2, 3, 4, 5 or 6 substituents, and the said each of substituents at each occurrence is independently selected from deuterium, halogen, —OH, —$C_{1-6}$alkyl, —$C_{1-6}$alkoxy, —$NH_2$, —$NH(C_{1-6}$alkyl), —$N(C_{1-6}$alkyl)$_2$ or —$C_{3-8}$carbocyclic;

Each of $R_{11}$ and $R_{12}$ at each occurrence is independently selected from hydrogen, deuterium, —$C_{1-6}$alkyl, —$C_{1-6}$ alkylene-$C_{3-8}$carbocyclic or —$C_{3-8}$carbocyclic; and each of which at each occurrence is independently optionally substituted with 1, 2, 3, 4, 5 or 6 substituents, and the said each of substituents at each occurrence is independently selected from deuterium, halogen, —OH, —CN, —$NH_2$, —$NH(C_{1-6}$alkyl), —$N(C_{1-6}$alkyl)$_2$, —$C_{1-6}$alkyl, —$C_{1-6}$alkoxy, —$SO_2(C_{1-6}$alkyl) or —$C_{3-8}$carbocyclic; or $R_{11}$ and $R_{12}$ together with the nitrogen atom to which they are both attached form 4-6 membered heterocyclic ring, and each of the heterocyclic ring at each occurrence can further contains 1, 2 or 3 heteroatoms selected from N, O, S or SO$_2$, and each of the heterocyclic ring at each occurrence is independently optionally substituted with 1, 2, 3, 4, 5 or 6 substituents, and the said each of substituents at each occurrence is independently selected from deuterium; halogen; —OH; oxo; —CN; —C$_{1-6}$alkyl; —C$_{1-6}$alkoxy; —SO$_2$(C$_{1-6}$alkyl); —CON(C$_{1-6}$alkyl)$_2$; —SO$_2$N(C$_{1-6}$alkyl)$_2$; —NH$_2$; —NH(C$_{1-6}$alkyl); —N(C$_{1-6}$alkyl)$_2$; —C$_{3-6}$heterocyclic containing 1 or 2 heteroatoms selected from N, O or S; or —C$_{1-6}$alkyl substituted with deuterium;

Each of R$_{13}$ and R$_{14}$ at each occurrence is independently selected from hydrogen, deuterium or —C$_{1-6}$alkyl; or R$_{13}$ and R$_{14}$ together with the carbon atom to which they are both attached form 3-6 membered carbocyclic ring, and each of the carbocyclic ring at each occurrence is independently optionally substituted with 1, 2, 3 or 4 substituents, and the said each of substituents at each occurrence is independently selected from deuterium, halogen, —OH, —NH$_2$, —CN, —C$_{1-6}$alkyl or —C$_{1-6}$alkoxy;

n is selected from 0, 1, 2 or 3.

In some embodiments, wherein R$_1$ is selected from hydrogen; deuterium; —SOR$_{11}$; —SO$_2$R$_{11}$; —SO$_2$NR$_{11}$R$_{12}$; —C$_{1-3}$alkyl;

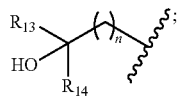

—COOR$_{11}$; —COR$_{11}$; —CONR$_{11}$R$_{12}$; —POR$_{11}$R$_{12}$; —C$_{5-6}$heteroaryl containing 1, 2, 3 or 4 heteroatoms selected from N, O, S or SO$_2$; —C$_{3-6}$heterocyclic containing 1, 2, 3 or 4 heteroatoms selected from N, O, S or SO$_2$; or —C$_{3-6}$carbocyclic; and each of which at each occurrence is independently optionally substituted with 1, 2, 3, 4, 5 or 6 substituents, and the said each of substituents at each occurrence is independently selected from deuterium, —F, —Cl, —Br, —OH, —C$_{1-3}$alkyl, —C$_{1-3}$alkoxy, —NH$_2$, —NH(C$_{1-3}$alkyl), —N(C$_{1-3}$alkyl)$_2$ or —C$_{3-6}$carbocyclic;

Each of R$_{11}$ and R$_{12}$ at each occurrence is independently selected from hydrogen, deuterium, —C$_{1-3}$alkyl, —C$_{1-3}$alkylene-C$_{3-6}$carbocyclic or —C$_{3-6}$carbocyclic, and each of which at each occurrence is independently optionally substituted with 1, 2, 3, 4, 5 or 6 substituents, and the said each of substituents at each occurrence is independently selected from deuterium, —F, —Cl, —Br, —OH, —CN, —NH$_2$, —NH(C$_{1-3}$alkyl), —N(C$_{1-3}$alkyl)$_2$, —C$_{1-3}$alkyl, —C$_{1-3}$alkoxy, —SO$_2$(C$_{1-3}$alkyl) or —C$_{3-6}$carbocyclic; or R$_{11}$ and R$_{12}$ together with the nitrogen atom to which they are both attached form 4-6 membered heterocyclic ring, and each of the heterocyclic ring at each occurrence can further contains 1, 2 or 3 heteroatoms selected from N, O or SO$_2$, and each of the heterocyclic ring at each occurrence is independently optionally substituted with 1, 2, 3, 4, 5 or 6 substituents, and the said each of substituents at each occurrence is independently selected from deuterium; —F; —Cl; —Br; —OH; oxo; —CN; —C$_{1-3}$alkyl; —C$_{1-3}$alkoxy; —SO$_2$(C$_{1-3}$alkyl); —CON(C$_{1-3}$alkyl)$_2$; —SO$_2$N(C$_{1-3}$alkyl)$_2$; —NH$_2$; —NH(C$_{1-3}$alkyl); —N(C$_{1-3}$alkyl)$_2$; —C$_{4-6}$heterocyclic containing 1 heteroatoms selected from N or O; or —C$_{1-3}$alkyl substituted with deuterium;

Each of R$_{13}$ and R$_{14}$ at each occurrence is independently selected from hydrogen, deuterium or —C$_{1-3}$alkyl; or R$_{13}$ and R$_{14}$ together with the carbon atom to which they are both attached form 3-6 membered carbocyclic ring, and each of the carbocyclic ring is independently optionally substituted with 1, 2, 3 or 4 substituents, and the said each of substituents at each occurrence is independently selected from deuterium, —F, —Cl, —Br, —OH, —NH$_2$, —CN, —C$_{1-3}$alkyl or —C$_{1-3}$alkoxy;

n is selected from 0, 1, 2 or 3.

In some embodiments, wherein R$_1$ is selected from hydrogen; deuterium; —SOR$_{11}$; —SO$_2$R$_{11}$; —SO$_2$NR$_{11}$R$_{12}$; methyl; ethyl; propyl; isopropyl;

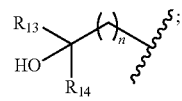

—COOR$_{11}$; —COR$_{11}$; —CONR$_{11}$R$_{12}$; —POR$_{11}$R$_{12}$; 5-membered heteroaryl containing 1, 2 or 3 heteroatoms selected from N, O, S or SO$_2$; 6-membered heteroaryl containing 1, 2 or 3 heteroatoms selected from N, O, S or SO$_2$; 3-membered heterocyclic containing 1, 2 or 3 heteroatoms selected from N, O, S or SO$_2$; 4-membered heterocyclic containing 1, 2 or 3 heteroatoms selected from N, O, S or SO$_2$; 5-membered heterocyclic containing 1, 2 or 3 heteroatoms selected from N, O, S or SO$_2$; 6-membered heterocyclic containing 1, 2 or 3 heteroatoms selected from N, O, S or SO$_2$; 3-membered carbocyclic; 4-membered carbocyclic; 5-membered carbocyclic; or 6-membered carbocyclic; and each of which at each occurrence is independently optionally substituted with 1, 2, 3, 4, 5 or 6 substituents, and the said each of substituents at each occurrence is independently selected from deuterium, —F, —Cl, —Br, —OH, methyl, ethyl, propyl, isopropyl, methoxy, ethoxy, propoxy, isopropoxy, —NH$_2$, —NH(CH$_3$), —NH(CH$_2$CH$_3$), —NH(CH$_2$CH$_2$CH$_3$), —NH(CH(CH$_3$)$_2$), —N(CH$_3$)$_2$, —N(CH$_2$CH$_3$)$_2$, —N(CH$_3$)(CH$_2$CH$_3$), —N(CH$_3$)(CH$_2$CH$_2$CH$_3$), 3-membered carbocyclic, 4-membered carbocyclic, 5-membered carbocyclic or 6-membered carbocyclic;

Each of R$_{11}$ and R$_{12}$ at each occurrence is independently selected from hydrogen, deuterium, methyl, ethyl, propyl, isopropyl, -methylene-3-membered carbocyclic, -methylene-4-membered carbocyclic, -methylene-5-membered carbocyclic, -methylene-6-membered carbocyclic, -ethylene-3-membered carbocyclic, -ethylene-4-membered carbocyclic, -ethylene-5-membered carbocyclic, -ethylene-6-membered carbocyclic, 3-membered carbocyclic, 4-membered carbocyclic, 5-membered carbocyclic or 6-membered carbocyclic; and each of which at each occurrence is independently optionally substituted with 1, 2, 3, 4, 5 or 6 substituents, and the said each of substituents at each occurrence is independently selected from deuterium, —F, —Cl, —Br, —OH, —CN, —NH$_2$, —NH(CH$_3$), —NH(CH$_2$CH$_3$), —NH(CH$_2$CH$_2$CH$_3$), —NH(CH(CH$_3$)$_2$), —N(CH$_3$)$_2$, —N(CH$_2$CH$_3$)$_2$, —N(CH$_3$)(CH$_2$CH$_3$), —N(CH$_3$)(CH$_2$CH$_2$CH$_3$), methyl, ethyl, propyl, isopropyl, methoxy, ethoxy, propoxy, isopropoxy, —SO$_2$CH$_3$, —SO$_2$CH$_2$CH$_3$, —SO$_2$CH$_2$CH$_2$CH$_3$, —SO$_2$CH(CH$_3$)$_2$, 3-membered carbocyclic, 4-membered carbocyclic, 5-membered carbocyclic or 6-membered carbocyclic; or $R_{11}$ and $R_{12}$ together with the nitrogen atom to which they are both attached form 4 membered heterocyclic ring, 5 membered heterocyclic ring or 6 membered heterocyclic ring, and each of the heterocyclic ring at each occurrence can further contains 1 or 2 heteroatoms selected from N, O or $SO_2$, and each of the heterocyclic ring at each occurrence is independently optionally substituted with 1, 2, 3, 4, 5 or 6 substituents, and the said each of substituents at each occurrence is independently selected from deuterium, —F, —Cl, —Br, —OH, oxo, —CN, methyl, ethyl, propyl, isopropyl, methoxy, ethoxy, propoxy, isopropoxy, —$SO_2CH_3$, —$SO_2CH_2CH_3$, —$SO_2CH_2CH_2CH_3$, —$SO_2CH(CH_3)_2$, —$CON(CH_3)_2$, —$CON(CH_2CH_3)_2$, —$CON(CH_2CH_2CH_3)_2$, —$CON(CH(CH_3)_2)_2$, —$SO_2N(CH_3)_2$, —$SO_2N(CH_2CH_3)_2$, —$SO_2N(CH_2CH_2CH_3)_2$, —$SO_2N(CH(CH_3)_2)_2$, —$NH_2$, —$NH(CH_3)$, —$NH(CH_2CH_3)$, —$NH(CH_2CH_2CH_3)$, —$NH(CH(CH_3)_2)$, —$N(CH_3)_2$, —$N(CH_2CH_3)_2$, —$N(CH_3)(CH_2CH_3)$, —$N(CH_3)(CH_2CH_2CH_3)$,

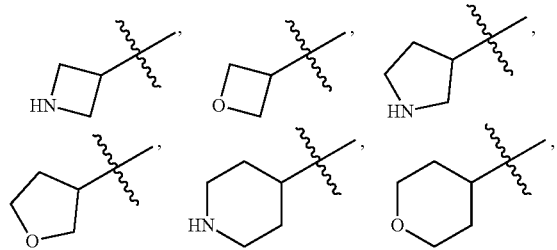

methyl substituted with deuterium, ethyl substituted with deuterium, propyl substituted with deuterium or isopropyl substituted with deuterium;

Each of $R_{13}$ and $R_{14}$ at each occurrence is independently selected from hydrogen, deuterium, methyl, ethyl, propyl or isopropyl; or $R_{13}$ and $R_{14}$ together with the carbon atom to which they are both attached form 3 membered carbocyclic ring, 4 membered carbocyclic ring, 5 membered carbocyclic ring or 6 membered carbocyclic ring, and each of carbocyclic ring at each occurrence is independently optionally substituted with 1, 2, 3 or 4 substituents, and the said each of substituents at each occurrence is independently selected from deuterium, —F, —Cl, —Br, —OH, —$NH_2$, —CN, methyl, ethyl, propyl, isopropyl, methoxy, ethoxy, propoxy or isopropoxy;

n is selected from 0, 1, 2 or 3.

In some embodiments, wherein $R_1$ is selected from hydrogen; deuterium; —$SOR_{11}$; —$SO_2R_{11}$; —$SO_2NR_{11}R_{12}$; methyl; ethyl; propyl; isopropyl;

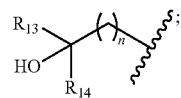

—$COOR_{11}$; —$COR_{11}$; —$CONR_{11}R_{12}$; —$POR_{11}R_{12}$; 5-membered heteroaryl containing 1, 2 or 3 heteroatoms selected from N, O, S or $SO_2$; 6-membered heterocyclic containing 1, 2 or 3 heteroatoms selected from N, O, S or $SO_2$; or 3-membered carbocyclic; and each of which at each occurrence is independently optionally substituted with 1, 2, 3, 4, 5 or 6 substituents, and the said each of substituents at each occurrence is independently selected from deuterium, —F, —Cl, —Br, —OH, methyl, ethyl, propyl, isopropyl, methoxy, ethoxy, propoxy, isopropoxy, —$NH_2$, —$NH(CH_3)$, —$NH(CH_2CH_3)$, —$N(CH_3)_2$, —$N(CH_3)(CH_2CH_3)$ or 3-membered carbocyclic;

Each of $R_{11}$ or $R_{12}$ at each occurrence is independently selected from hydrogen, deuterium, methyl, ethyl, propyl, isopropyl, -methylene-3-membered carbocyclic or 3-membered carbocyclic; and each of which at each occurrence is independently optionally substituted with 1, 2, 3, 4, 5 or 6 substituents, and the said each of substituents at each occurrence is independently selected from deuterium, —F, —Cl, —Br, —OH, —$NH_2$, —$NH(CH_3)$, —$N(CH_3)_2$, methyl, methoxy, —$SO_2CH_3$ or 3-membered carbocyclic; or $R_{11}$ and $R_{12}$ together with the nitrogen atom to which they are both attached form the heterocyclic selected from

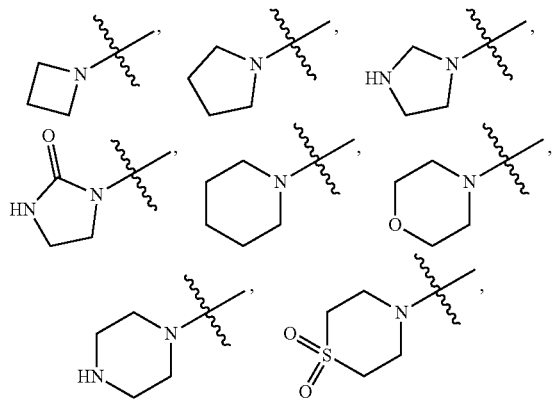

and the heterocyclic ring is independently optionally substituted with 1, 2, 3, 4, 5 or 6 substituents, and the said each of substituents at each occurrence is independently selected from deuterium, —F, —Cl, —Br, —OH, oxo, —CN methyl, methoxy, —$SO_2CH_3$, —$CON(CH_3)_2$, —$SO_2N(CH_3)_2$, —$NH_2$, —$NH(CH_3)$, —$N(CH_3)_2$,

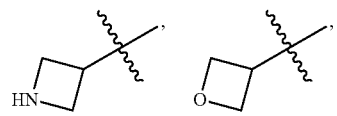 [SMILES: *C1CNC1 ; *C1COC1]

—$CH_2D$, —$CHD_2$ or —$CD_3$;

Each of $R_{13}$ and $R_{14}$ at each occurrence is independently selected from hydrogen, deuterium, methyl, ethyl, propyl or isopropyl; or $R_{13}$ and $R_{14}$ together with the carbon atom to which they are both attached form 3 membered carbocyclic ring, and the carbocyclic ring is independently optionally substituted with 1, 2, 3 or 4 substituents, and the said each of substituents at each occurrence is independently selected from deuterium, —OH, methyl, ethyl, propyl or isopropyl;

n is selected from 0 or 1.

In some embodiments, wherein $R_1$ is selected from hydrogen, deuterium, —$SOCH_3$, —$SOCH_2CH_3$, —$SOCH_2CH_2CH_3$, —$SOCH(CH_3)_2$, —$SO_2CH_3$, —$SO_2CD_3$, —$SO_2CH_2CH_3$, —$SO_2CH_2CH_2CH_3$, —$SO_2CH(CH_3)_2$, —$SO_2CH(CD_3)_2$, —$SO_2NH_2$, —$SO_2NH(CH_3)$, —$SO_2N(CH_3)_2$, —$SO_2NH(CD_3)$, —$SO_2N(CD_3)_2$,

—SO₂NH(CH₂CH₃), —SO₂N(CH₂CH₃)₂, —SO₂NH(CH₂CH₂CH₃), —SO₂N(CH₂CH₂CH₃)₂,

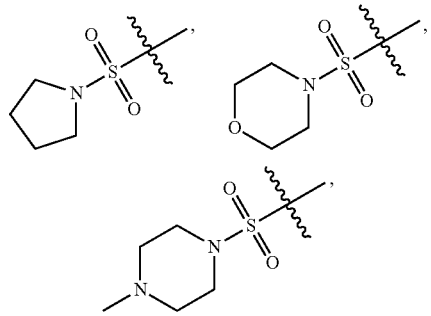

—CH₃, —CH₂D, —CHF₂, —CH₂F, —CD₂H, —CD₃, —CF₃, —CH₂CH₃, —CH₂CH₂F, —CH₂CHF₂, —CH₂CH₂NH₂, —CH₂CH₂NHCH₃, —CH₂CH₂N(CH₃)₂, —CH₂CD₃, —CH₂CF₃, —CH₂CH₂CH₃, —CH₂CH₂CH₂F, —CH₂CH₂CD₃, —CH₂CH₂CF₃, —CH(CH₃)₂, —CH(CH₃)(CD₃), —CH(CF₃)₂, —CH(CD₃)₂,

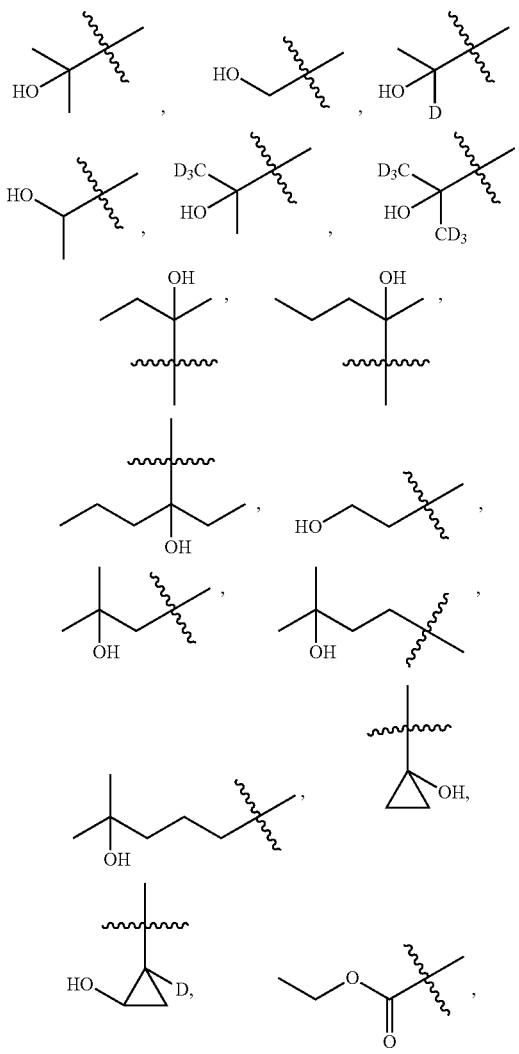

—CONH₂, —CONH(CH₃), —CON(CH₃)₂, —CONH(CD₃), —CON(CD₃)₂, —CONH(CH₂CH₃), —CON(CH₂CH₃)₂, —CONH(CH₂CH₂CH₃), —CON(CH₂CH₂CH₃)₂, —P(O)H₂, —P(O)H(CH₃), —PO(CH₃)₂, —P(O)H(CD₃), —P(O)(CD₃)₂, —P(O)(CH₂CH₃)₂, —P(O)(CH₂CH₂CH₃)₂, —P(O)(CH(CH₃)₂)₂,

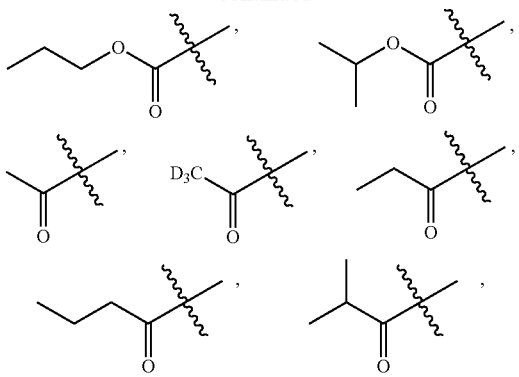

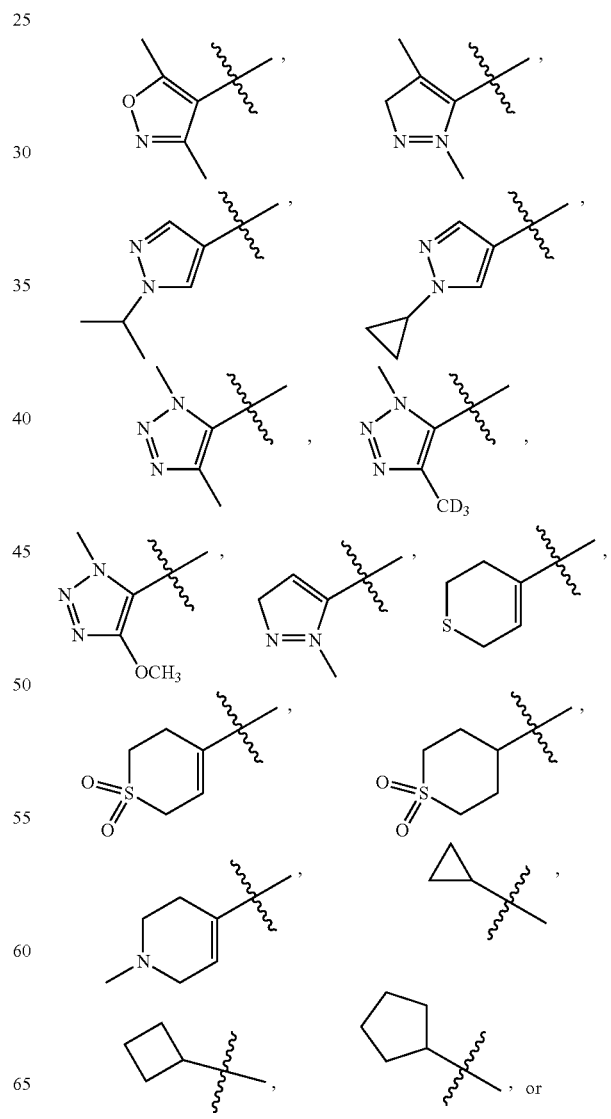

-continued

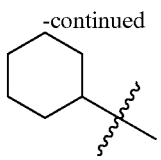

In some embodiments, wherein $R_1$ is selected from $-SO_2R_{11}$, $-C_{1-6}$alkyl,

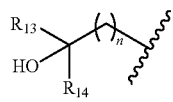

or $-C_{3-8}$carbocyclic; and each of which at each occurrence is independently optionally substituted with 1, 2, 3, 4, 5 or 6 substituents, and the said each of substituents at each occurrence is independently selected from deuterium, halogen, $-OH$, $-C_{1-6}$alkyl, $-C_{1-6}$alkoxy, $-NH_2$, $-NH(C_{1-6}$alkyl), or $-N(C_{1-6}$alkyl)$_2$;

$R_{11}$ is selected from hydrogen, deuterium or $-C_{1-6}$alkyl;

Each of $R_{13}$ and $R_{14}$ at each occurrence is independently selected from hydrogen, deuterium or $-C_{1-6}$alkyl;

n is selected from 0, 1, 2, 3, 4, 5 or 6.

In some embodiments, wherein $R_1$ is selected from $-SO_2R_{11}$, $-C_{1-3}$alkyl,

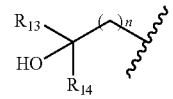

or $-C_{3-6}$carbocyclic; and each of which at each occurrence is independently optionally substituted with 1, 2, 3, 4, 5 or 6 substituents, and the said each of substituents at each occurrence is independently selected from deuterium, halogen, $-OH$, $-C_{1-3}$alkyl, $-C_{1-3}$alkoxy, $-NH_2$, $-NH(C_{1-3}$alkyl) or $-N(C_{1-3}$alkyl)$_2$;

$R_{11}$ is selected from hydrogen, deuterium or $-C_{1-3}$alkyl;

Each of $R_{13}$ and $R_{14}$ at each occurrence is independently selected from hydrogen, deuterium or $-C_{1-3}$alkyl;

n is selected from 0, 1, 2 or 3.

In some embodiments, wherein $R_1$ is selected from $-SO_2R_{11}$, methyl, ethyl, propyl, isopropyl,

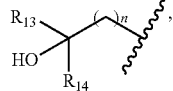

3-membered carbocyclic, 4-membered carbocyclic, 5-membered carbocyclic or 6-membered carbocyclic; and each of which at each occurrence is independently optionally substituted with 1, 2, 3, 4, 5 or 6 substituents, and the said each of substituents at each occurrence is independently selected from deuterium, $-F$, $-Cl$, $-Br$, $-OH$, methyl, ethyl, propyl, isopropyl, methoxy, ethoxy, propoxy, isopropoxy, $-NH_2$, $-NH(CH_3)$, $-NH(CH_2CH_3)$, $-NH(CH_2CH_2CH_3)$, $-NH(CH(CH_3)_2)$, $-N(CH_3)_2$, $-N(CH_2CH_3)_2$, $-N(CH_3)(CH_2CH_3)$ or $-N(CH_3)(CH_2CH_2CH_3)$;

$R_{11}$ is selected from hydrogen, deuterium, methyl, ethyl, propyl or isopropyl;

Each of $R_{13}$ and $R_{14}$ at each occurrence is independently selected from hydrogen, deuterium, methyl, ethyl, propyl or isopropyl;

n is selected from 0, 1, 2 or 3.

In some embodiments, wherein $R_1$ is selected from $-SO_2CH_3$, $-SO_2CD_3$, $-SO_2CH_2CH_3$, $-SO_2CH_2CH_2CH_3$, $-SO_2CH(CH_3)_2$, $-SO_2CH(CD_3)_2$, $-CH_3$, $-CH_2D$, $-CHF_2$, $-CH_2F$, $-CD_2H$, $-CD_3$, $-CF_3$, $-CH_2CH_3$, $-CH_2CH_2F$, $-CH_2CHF_2$, $-CH_2CH_2NH_2$, $-CH_2CH_2NHCH_3$, $-CH_2CH_2N(CH_3)_2$, $-CH_2CD_3$, $-CH_2CF_3$, $-CH_2CH_2CH_3$, $-CH_2CH_2CH_2F$, $-CH_2CH_2CD_3$, $-CH_2CH_2CF_3$, $-CH(CH_3)_2$, $-CH(CH_3)(CD_3)$, $-CH(CF_3)_2$, $-CH(CD_3)_2$,

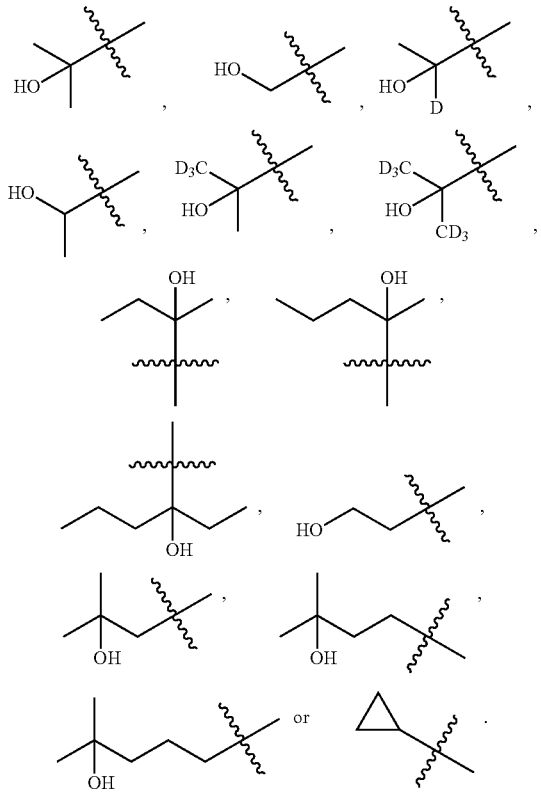

In some embodiments, wherein $R_1$ is selected from hydrogen, deuterium, $-SO_2CH_3$, $-CH_3$, $-CHF_2$, $-CD_3$, $-CH_2CH_3$, $-CH_2CHF_2$, $-CH_2CH_2N(CH_3)_2$, $-CH_2CF_3$, $-CH(CH_3)_2$,

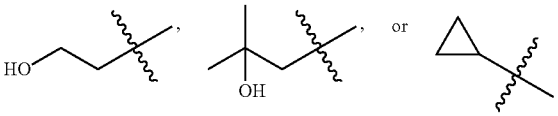

In some embodiments, wherein $R_1$ is selected from $-SO_2CH_3$, $-CH_3$, $-CHF_2$, $-CD_3$, $-CH_2CH_3$, $-CH_2CHF_2$, $-CH_2CH_2N(CH_3)_2$, $-CH_2CF_3$, $-CH(CH_3)_2$,

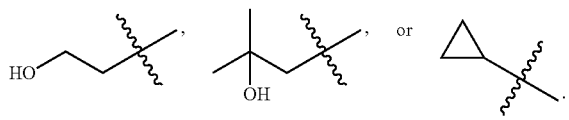

In some embodiments, wherein $R_1$ is —$C_{1-6}$alkyl.

In some embodiments, wherein $R_1$ is —$C_{1-3}$alkyl.

In some embodiments, wherein $R_1$ is selected from methyl, ethyl, propyl or isopropyl.

In some embodiments, wherein $R_1$ is methyl.

In some embodiments, wherein $R_2$ is selected from hydrogen; deuterium; halogen; —$OR_{21}$; —$NR_{21}R_{22}$; —CN; —$SR_{21}$; —$SOR_{21}$; —$SO_2R_{21}$; —$SO_2NR_{21}R_{22}$; —$C_{1-6}$alkyl;

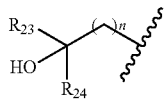

—$C_{2-6}$alkenyl; —$COOR_{21}$; —$COR_{21}$; —$CONR_{21}R_{22}$; —$NR_{21}COR_{22}$; —$NR_{21}SO_2R_{22}$; —$POR_{21}R_{22}$; —$C_{5-6}$heteroaryl containing 1, 2, 3 or 4 heteroatoms selected from N, O, S or $SO_2$; —$C_{3-8}$heterocyclic containing 1, 2, 3 or 4 heteroatoms selected from N, O, S or $SO_2$; or —$C_{3-8}$carbocyclic; and each of which at each occurrence is independently optionally substituted with 1, 2, 3, 4, 5 or 6 substituents, and the said each substituents at each occurrence is independently selected from deuterium, halogen, —OH, —$C_{1-6}$alkyl, —$C_{1-6}$alkoxy or —$C_{3-8}$carbocyclic;

Each of $R_{21}$ and $R_{22}$ at each occurrence is independently selected from hydrogen, deuterium, —$C_{1-6}$alkyl, —$C_{1-6}$alkylene-$C_{3-8}$carbocyclic or —$C_{3-8}$carbocyclic; and each of which at each occurrence is independently optionally substituted with 1, 2, 3, 4, 5 or 6 substituents, and the said each of substituents at each occurrence is independently selected from deuterium, halogen, —OH, —CN, —$NH_2$, —$NH(C_{1-6}$alkyl), —$N(C_{1-6}$alkyl)$_2$, —$C_{1-6}$alkyl, —$C_{1-6}$alkoxy, —$SO_2(C_{1-6}$alkyl) or —$C_{3-8}$carbocyclic; or $R_{21}$ and $R_{22}$ together with the nitrogen atom to which they are both attached form 4-6 membered heterocyclic ring, each of the heterocyclic ring at each occurrence can further contains 1, 2 or 3 heteroatoms selected from N, O, S or $SO_2$, and each of the heterocyclic ring at each occurrence is independently optionally substituted with 1, 2, 3, 4, 5 or 6 substituents, and the said each of substituents at each occurrence is independently selected from deuterium; halogen; —OH; oxo; —CN; —$C_{1-6}$alkyl; —$C_{1-6}$alkoxy; —$SO_2(C_{1-6}$alkyl); —CON($C_{1-6}$alkyl)$_2$; —$SO_2N(C_{1-6}$alkyl)$_2$; —$NH_2$; —$NH(C_{1-6}$akyl); —$N(C_{1-6}$alkyl)$_2$; —$C_{3-6}$heterocyclic containing 1 or 2 heteroatoms selected from N, O or S; or —$C_{1-6}$alkyl substituted with deuterium;

Each of $R_{23}$ and $R_{24}$ at each occurrence is independently selected from hydrogen, deuterium or —$C_{1-6}$alkyl; or $R_{23}$ and $R_{24}$ together with the carbon atom to which they are both attached form 3-6 membered carbocyclic ring, and each of the carbocyclic ring at each occurrence is independently optionally substituted with 1, 2, 3 or 4 substituents, and the said each of substituents at each occurrence is independently selected from deuterium, halogen, —OH, —$NH_2$, —CN, —$C_{1-6}$alkyl or —$C_{1-6}$alkoxy;

n is selected from 0, 1, 2, 3, 4, 5 or 6.

In some embodiments, wherein $R_2$ is selected from hydrogen; deuterium; —F; —Cl; —Br; —$OR_{21}$; —$NR_{21}R_{22}$; —CN; —$SR_{21}$; —$SOR_{21}$; —$SO_2R_{21}$; —$SO_2NR_{21}R_{22}$; —$C_{1-3}$alkyl;

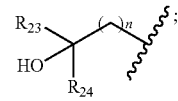

—$C_{2-3}$alkenyl; —$COOR_{21}$; —$COR_{21}$; —$CONR_{21}R_{22}$; —$NR_{21}COR_{22}$; —$NR_{21}SO_2R_{22}$; —$POR_{21}R_{22}$; —$C_{5-6}$heteroaryl containing 1, 2, 3 or 4 heteroatoms selected from N, O, S or $SO_2$; —$C_{3-6}$heterocyclic containing 1, 2, 3 or 4 heteroatoms selected from N, O, S or $SO_2$; or —$C_{3-6}$carbocyclic; and each of which at each occurrence is independently optionally substituted with 1, 2, 3, 4, 5 or 6 substituents, and the said each substituents at each occurrence is independently selected from deuterium, —F, —Cl, —Br, —OH, —$C_{1-3}$alkyl, —$C_{1-3}$alkoxy or —$C_{3-6}$carbocyclic;

Each of $R_{21}$ or $R_{22}$ at each occurrence is independently selected from hydrogen, deuterium, —$C_{1-3}$alkyl, —$C_{1-3}$alkylene-$C_{3-6}$carbocyclic or —$C_{3-6}$carbocyclic; and each of which at each occurrence is independently optionally substituted with 1, 2, 3, 4, 5 or 6 substituents, and the said each of substituents at each occurrence is independently selected from deuterium, —F, —Cl, —Br, —OH, —CN, —$NH_2$, —$NH(C_{1-3}$alkyl), —$N(C_{1-3}$alkyl)$_2$, —$C_{1-3}$alkyl, —$C_{1-3}$alkoxy, —$SO_2(C_{1-3}$alkyl) or —$C_{3-6}$carbocyclic; or $R_{21}$ and $R_{22}$ together with the nitrogen atom to which they are both attached form 4-6 membered heterocyclic ring, each of the heterocyclic ring at each occurrence can further contains 1, 2 or 3 heteroatoms selected from N, O or $SO_2$, and each of the heterocyclic ring at each occurrence is independently optionally substituted with 1, 2, 3, 4, 5 or 6 substituents, and the said each of substituents at each occurrence is independently selected from deuterium; —F; —Cl; —Br; —OH; oxo; —CN; —$C_{1-3}$alkyl; —$C_{1-3}$alkoxy; —$SO_2(C_{1-3}$alkyl); —CON($C_{1-3}$alkyl)$_2$; —$SO_2N(C_{1-3}$alkyl)$_2$; —$NH_2$; —$NH(C_{1-3}$alkyl); —$N(C_{1-3}$alkyl)$_2$; —$C_{4-6}$heterocyclic containing 1 heteroatom selected from N or O; or —$C_{1-3}$alkyl substituted with deuterium;

Each of $R_{23}$ and $R_{24}$ at each occurrence is independently selected from hydrogen, deuterium or —$C_{1-3}$alkyl; or $R_{23}$ and $R_{24}$ together with the carbon atom to which they are both attached form 3-6 membered carbocyclic ring, and each of the carbocyclic ring at each occurrence is independently optionally substituted with 1, 2, 3 or 4 substituents, and the said each of substituents at each occurrence is independently selected from deuterium, halogen, —OH, —$NH_2$, —CN, —$C_{1-3}$alkyl or —$C_{1-6}$alkoxy;

n is selected from 0, 1, 2 or 3.

In some embodiments, wherein $R_2$ is selected from hydrogen; deuterium; —F; —Cl; —Br; —$OR_{21}$; —$NR_{21}R_{22}$; —CN; —$SR_{21}$; —$SOR_{21}$; —$SO_2R_{21}$; —$SO_2NR_{21}R_{22}$; methyl; ethyl; propyl; isopropyl;

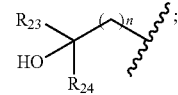

ethenyl; propenyl; —$COOR_{21}$; —$COR_{21}$; —$CONR_{21}R_{22}$; —$NR_{21}COR_{22}$; —$NR_{21}SO_2R_{22}$; —$POR_{21}R_{22}$; 5-membered heteroaryl containing 1, 2 or 3 heteroatoms selected from N, O, S or $SO_2$; 6-membered heteroaryl containing 1, 2 or 3 heteroatoms selected from N, O, S or $SO_2$; 3-membered heterocyclic containing 1, 2 or 3 heteroatoms selected from N, O, S or $SO_2$; 4-membered heterocyclic containing 1, 2 or 3 heteroatoms selected from N, O, S or $SO_2$; 5-membered heterocyclic containing 1, 2 or 3 heteroatoms selected from N, O, S or $SO_2$; 6-membered heterocyclic containing 1, 2 or 3 heteroatoms selected from N, O, S or $SO_2$; 3-membered carbocyclic; 4-membered carbocyclic; 5-membered carbocyclic; or 6-membered carbocyclic; and each of which at each occurrence is independently optionally substituted with 1, 2, 3, 4, 5 or 6 substituents, and the said each of substituents at each occurrence is independently selected from deuterium, —F, —Cl, —Br, —OH, methyl, ethyl, propyl, isopropyl, methoxy, ethoxy, propoxy, isopropoxy, 3-membered carbocyclic, 4-membered carbocyclic, 5-membered carbocyclic or 6-membered carbocyclic;

Each of $R_{21}$ or $R_{22}$ at each occurrence is independently selected from hydrogen, deuterium, methyl, ethyl, propyl, isopropyl, -methylene-3-membered carbocyclic, -methylene-4-membered carbocyclic, -methylene-5-membered carbocyclic, -methylene-6-membered carbocyclic, -ethylene-3-membered carbocyclic, -ethylene-4-membered carbocyclic, -ethylene-5-membered carbocyclic, -ethylene-6-membered carbocyclic, 3-membered carbocyclic, 4-membered carbocyclic, 5-membered carbocyclic or 6-membered carbocyclic; and each of which at each occurrence is independently optionally substituted with 1, 2, 3, 4, 5 or 6 substituents, and the said each of substituents at each occurrence is independently selected from deuterium, —F, —Cl, —Br, —OH, —CN, —$NH_2$, —$NH(CH_3)$, —NH($CH_2CH_3$), —NH($CH_2CH_2CH_3$), —NH($CH(CH_3)_2$), —N($CH_3)_2$, —N($CH_2CH_3)_2$, —N($CH_3)(CH_2CH_3$), —N($CH_3)(CH_2CH_2CH_3$), methyl, ethyl, propyl, isopropyl, methoxy, ethoxy, propoxy, isopropoxy, —$SO_2CH_3$, —$SO_2CH_2CH_3$, —$SO_2CH_2CH_2CH_3$, —$SO_2CH(CH_3)_2$, 3-membered carbocyclic, 4-membered carbocyclic, 5-membered carbocyclic or 6-membered carbocyclic; or $R_{21}$ and $R_{22}$ together with the nitrogen atom to which they are both attached form 4 membered heterocyclic ring, 5 membered heterocyclic ring, 6 membered heterocyclic ring, each of the heterocyclic ring at each occurrence can further contains 1 or 2 heteroatoms selected from N, O or $SO_2$, and each of the heterocyclic ring at each occurrence is independently optionally substituted with 1, 2, 3, 4, 5 or 6 substituents, and the said each of substituents at each occurrence is independently selected from deuterium, —F, —Cl, —Br, —OH, oxo, —CN, methyl, ethyl, propyl, isopropyl, methoxy, ethoxy, propoxy, isopropoxy, —$SO_2CH_3$, —$SO_2CH_2CH_3$, —$SO_2CH_2CH_2CH_3$, —$SO_2CH(CH_3)_2$, —$CON(CH_3)_2$, —$CON(CH_2CH_3)_2$, —$CON(CH_2CH_2CH_3)_2$, —$CON(CH(CH_3)_2)_2$, —$SO_2N(CH_3)_2$, —$SO_2N(CH_2CH_3)_2$, —$SO_2N(CH_2CH_2CH_3)_2$, —$SO_2N(CH(CH_3)_2)_2$, —$NH_2$, —$NH(CH_3)$, —NH($CH_2CH_3$), —NH($CH_2CH_2CH_3$), —NH($CH(CH_3)_2$), —N($CH_3)_2$, —N($CH_2CH_3)_2$, —N($CH_3)(CH_2CH_3$), —N($CH_3)(CH_2CH_2CH_3$),

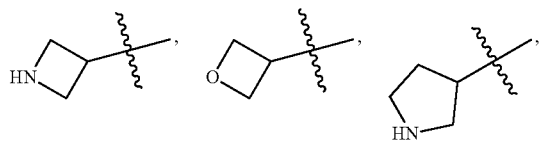

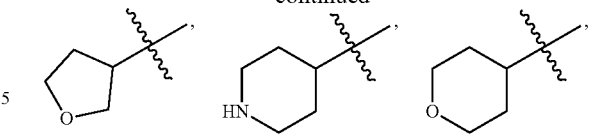

methyl substituted with deuterium, ethyl substituted with deuterium, propyl substituted with deuterium or isopropyl substituted with deuterium;

Each of $R_{23}$ and $R_{24}$ at each occurrence is independently selected from hydrogen, deuterium, methyl, ethyl, propyl or isopropyl; or $R_{23}$ and $R_{24}$ together with the carbon atom to which they are both attached form 3-membered carbocyclic ring, 4-membered carbocyclic ring, 5-membered carbocyclic ring or 6 membered carbocyclic ring, and each of the carbocyclic ring at each occurrence is independently optionally substituted with 1, 2, 3 or 4 substituents, and the said each of substituents at each occurrence is independently selected from deuterium, —F, —Cl, —Br, —OH, —$NH_2$, —CN, methyl, ethyl, propyl, isopropyl methoxy, ethoxy, propoxy or isopropoxy;

n is selected from 0, 1, 2 or 3.

In some embodiments, wherein $R_2$ is independently selected from hydrogen; deuterium; —F; —Cl; —Br; —$OR_{21}$; —$NR_{21}R_{22}$; —CN; —$SR_{21}$; —$SOR_{21}$; —$SO_2R_{21}$; —$SO_2NR_{21}R_{22}$; methyl; ethyl; propyl; isopropyl;

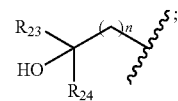

ethenyl; —$COOR_{21}$; —$COR_{21}$; —$CONR_{21}R_{22}$; —$NR_{21}COR_{22}$; —$NR_{21}SO_2R_{22}$; —$POR_{21}R_{22}$; 5-membered heteroaryl containing 1, 2 or 3 heteroatoms selected from N, O, S or $SO_2$; 6-membered heterocyclic containing 1, 2 or 3 heteroatoms selected from N, O, S or $SO_2$; or 3-membered carbocyclic; and each of which at each occurrence is independently optionally substituted with 1, 2, 3, 4, 5 or 6 substituents, and the said each of substituents at each occurrence is independently selected from deuterium, —F, —Cl, —Br, —OH, methyl, ethyl, propyl, isopropyl, methoxy, ethoxy, propoxy, isopropoxy or 3-membered carbocyclic;

Each of $R_{21}$ and $R_{22}$ at each occurrence is independently selected from hydrogen, deuterium, methyl, ethyl, propyl, isopropyl, -methylene-3-membered carbocyclic or 3-membered carbocyclic; and each of which at each occurrence is independently optionally substituted with 1, 2, 3, 4, 5 or 6 substituents, and the said each of substituents at each occurrence is independently selected from deuterium, —F, —Cl, —Br, —OH, —$NH_2$, —$NH(CH_3)$, —N($CH_3)_2$, methyl, methoxy, —$SO_2CH_3$ or 3-membered carbocyclic; or $R_{21}$ and $R_{22}$ together with the nitrogen atom to which they are both attached form the heterocyclic selected from

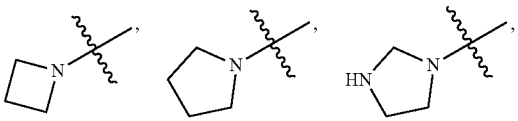

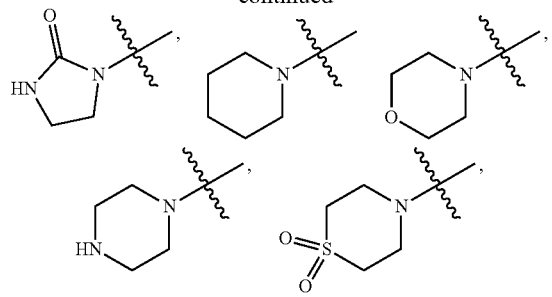

and each of the heterocyclic ring at each occurrence is independently optionally substituted with 1, 2, 3, 4, 5 or 6 substituents, and the said each of substituents at each occurrence is independently selected from deuterium, —F, —Cl, —Br, —OH, oxo, —CN, methyl, ethyl, propyl, isopropyl, methoxy, —SO$_2$CH$_3$, —CON(CH$_3$)$_2$, —SO$_2$N(CH$_3$)$_2$, —NH$_2$, —NH(CH$_3$), —N(CH$_3$)$_2$,

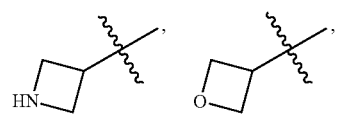

—CH$_2$D, —CHD$_2$ or —CD$_3$;

Each of R$_{23}$ and R$_{24}$ at each occurrence is independently selected from hydrogen, deuterium, methyl, ethyl, propyl or isopropyl; or R$_{23}$ and R$_{24}$ together with the carbon atom to which they are both attached form 3-membered carbocyclic ring, and the carbocyclic ring is independently optionally substituted with 1, 2, 3 or 4 substituents, and the said each of substituents at each occurrence is independently selected from deuterium, —F, —Cl, —Br, —OH, —NH$_2$, —CN, methyl, ethyl, propyl, isopropyl, methoxy, ethoxy, propoxy or isopropoxy;

n is selected from 0 or 1.

In some embodiments, wherein R$_2$ is selected from hydrogen, deuterium, —F, —Cl, —Br, —OH, —OCH$_3$, —OCD$_3$, —OCH$_2$CH$_3$, —OCH$_2$CH$_2$CH$_3$, —OCH(CH$_3$)$_2$, —OCH$_2$CF$_3$, —OCH$_2$CHF$_2$, —OCF$_2$CH$_3$, —OCH$_2$OH, —OCH$_2$CH$_2$OH, —OCH$_2$CH$_2$CH$_2$OH, —OCH$_2$CH$_2$NH$_2$, —OCH$_2$N(CH$_3$)$_2$, —OCH$_2$CH$_2$N(CH$_3$)$_2$, —OCH$_2$CH$_2$CH$_2$N(CH$_3$)$_2$, —OCH$_2$CH$_2$NHCH$_3$,

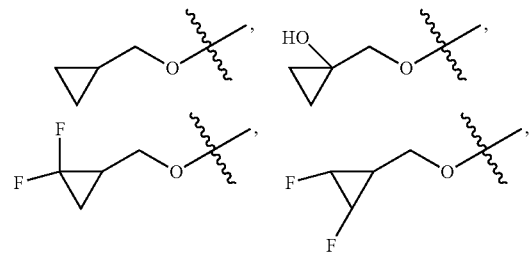

—NH$_2$, —NHCH$_3$, —N(CH$_3$)$_2$, —NHCD$_3$, —N(CD$_3$)$_2$, —NHCH$_2$CH$_3$, —N(CH$_3$CH$_2$)$_2$, —N(CH$_3$)(CH$_3$CH$_2$), —NHCH$_2$CH$_2$CH$_3$, —N(CH$_3$CH$_2$CH$_3$)$_2$, —NHCH(CH$_3$)$_2$, —N(CH$_3$)(CH(CH$_3$)$_2$), —N(CH(CH$_3$)$_2$)$_2$, —NHCH$_2$CF$_3$,

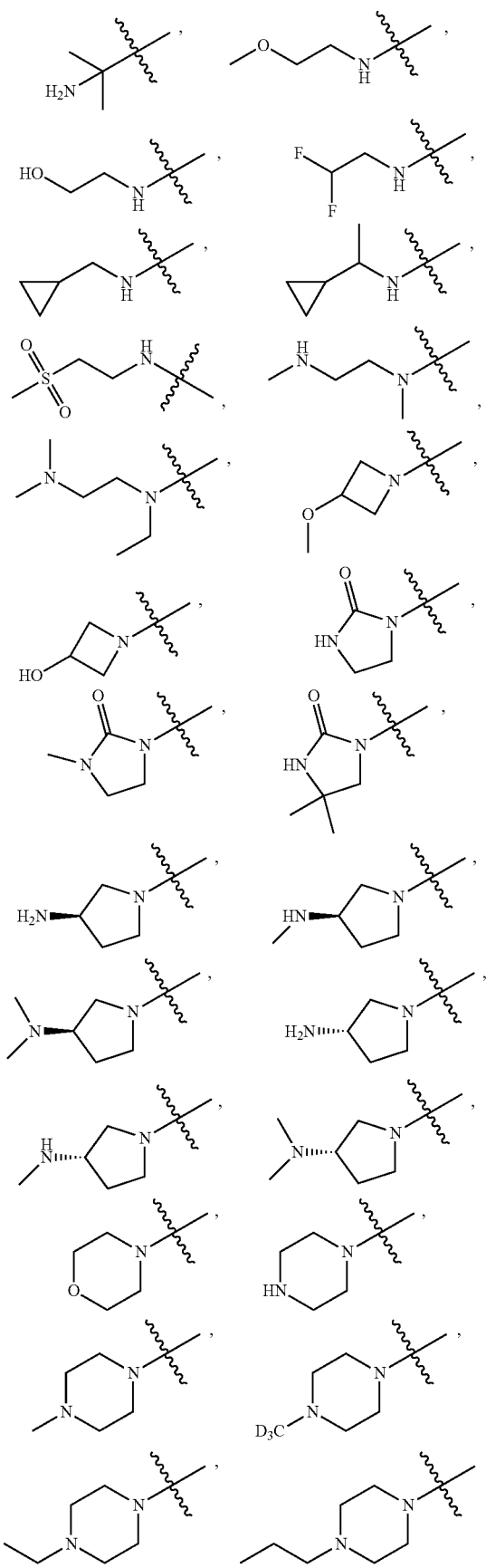

-continued

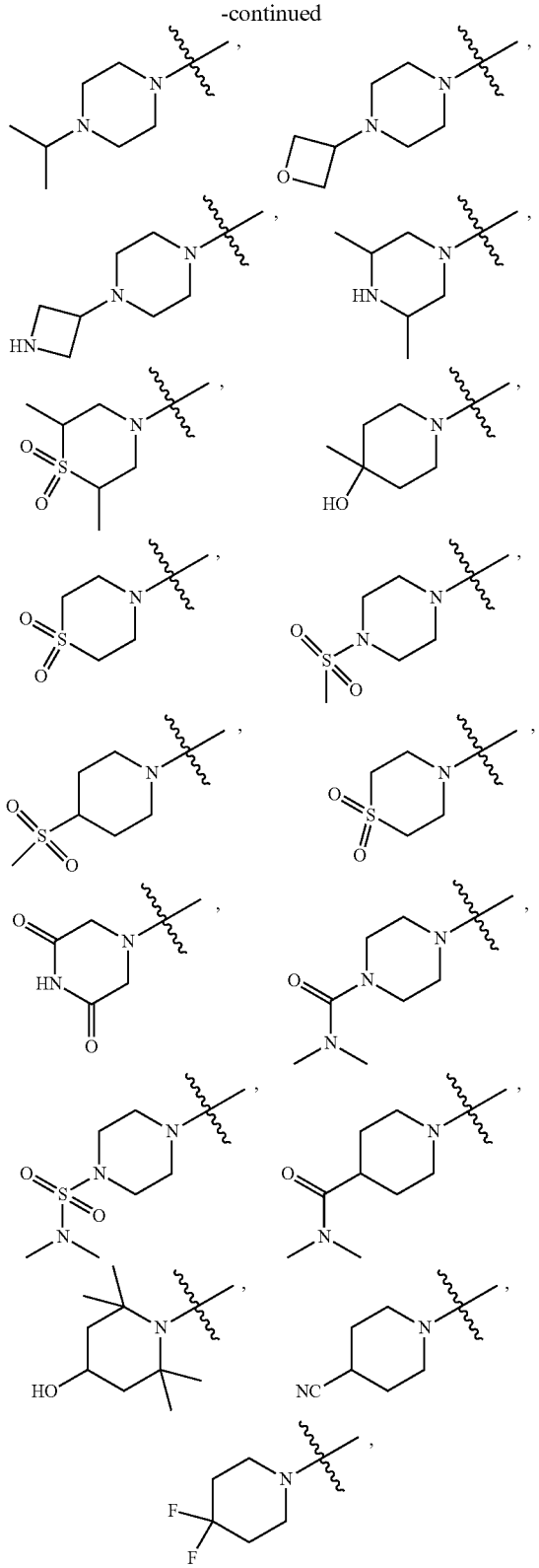

—CN, —SCH$_3$, —SCH$_2$CH$_3$, —SCH$_2$CH$_2$CH$_3$, —SCH(CH$_3$)$_2$, —SOCH$_3$, —SOCH$_2$CH$_3$, —SOCH$_2$CH$_2$CH$_3$, —SOCH(CH$_3$)$_2$, —SO$_2$CH$_3$, —SO$_2$CD$_3$, —SO$_2$CH$_2$CH$_3$, —SO$_2$CH$_2$CH$_2$CH$_3$, —SO$_2$CH(CH$_3$)$_2$, —SO$_2$CH(CD$_3$)$_2$, —SO$_2$NH$_2$, —SO$_2$NH(CH$_3$), —SO$_2$N(CH$_3$)$_2$, —SO$_2$NH(CD$_3$), —SO$_2$N(CD$_3$)$_2$, —SO$_2$NH(CH$_2$CH$_3$), —SO$_2$N(CH$_2$CH$_3$)$_2$, —SO$_2$NH(CH$_2$CH$_3$CH$_2$), —SO$_2$N(CH$_2$CH$_2$CH$_3$)$_2$,

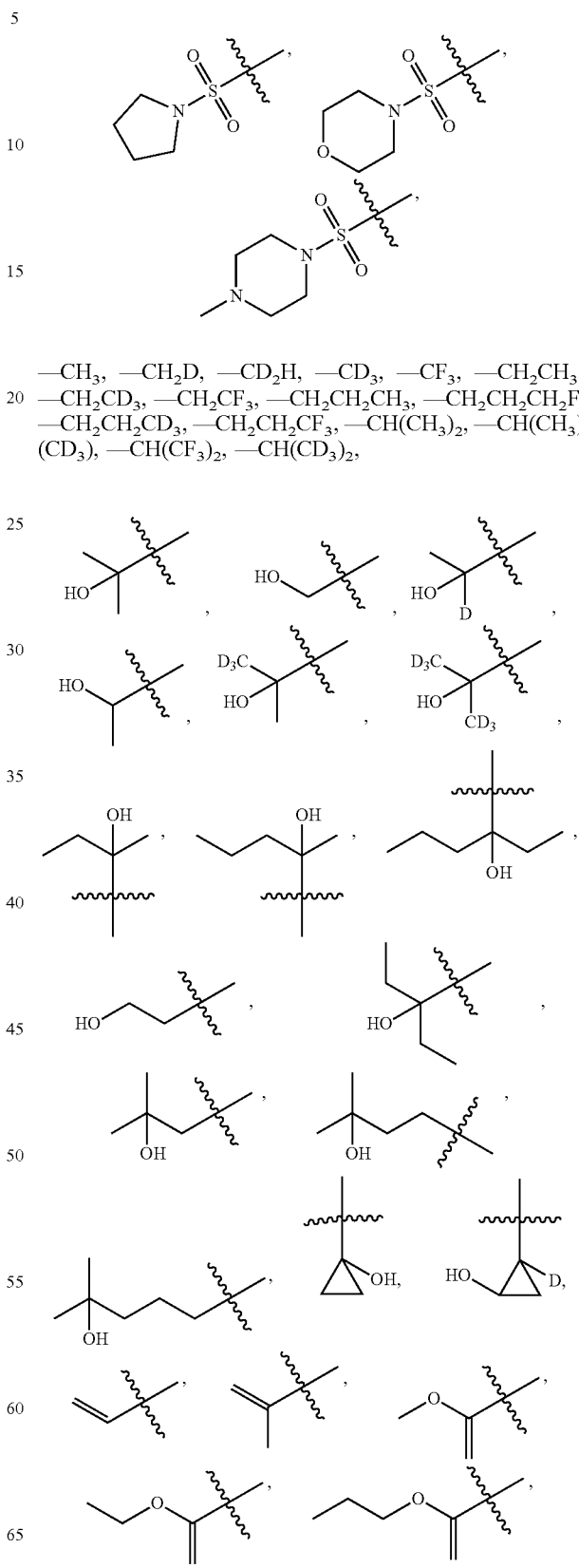

—CH$_3$, —CH$_2$D, —CD$_2$H, —CD$_3$, —CF$_3$, —CH$_2$CH$_3$, —CH$_2$CD$_3$, —CH$_2$CF$_3$, —CH$_2$CH$_2$CH$_3$, —CH$_2$CH$_2$CH$_2$F, —CH$_2$CH$_2$CD$_3$, —CH$_2$CH$_2$CF$_3$, —CH(CH$_3$)$_2$, —CH(CH$_3$)(CD$_3$), —CH(CF$_3$)$_2$, —CH(CD$_3$)$_2$,

—CONH₂, —CONH(CH₃), —CON(CH₃)₂, —CONH(CD₃), —CON(CD₃)₂, —CONH(CH₂CH₃), —CON(CH₂CH₃)₂, —CONH(CH₂CH₂CH₃), —CON(CH₂CH₂CH₃)₂, —NHCOCH₃, —NHCOCH₂CH₃, —NHCOCH₂CH₂CH₃, —NHCOCH(CH₃)₂,

—P(O)H₂, —P(O)H(CH₃), —PO(CH₃)₂, —P(O)H(CD₃), —PO(CD₃)₂, —PO(CH₂CH₃)₂, —PO(CH₂CH₂CH₃)₂, —PO(CH(CH₃)₂)₂,

In some embodiments, wherein R₂ is selected from hydrogen, deuterium, —F, —Cl, —Br, —OH, —OCH₃, —OCD₃, —OCH₂CH₃, —OCH₂CH₂CH₃, —OCH(CH₃)₂, —OCH₂CF₃, —OCH₂CHF₂, —OCF₂CH₃, —OCH₂OH, —OCH₂CH₂OH, —OCH₂CH₂CH₂OH, —OCH₂CH₂NH₂, —OCH₂N(CH₃)₂, —OCH₂CH₂N(CH₃)₂, —OCH₂CH₂CH₂N(CH₃)₂, —OCH₂CH₂NHCH₃, -continued —NH₂, —NHCH₃, —N(CH₃)₂, —NHCD₃, —N(CD₃)₂, —NHCH₂CH₃, —N(CH₃CH₂)₂, —N(CH₃)(CH₃CH₂), —NHCH₂CH₂CH₃, —N(CH₂CH₂CH₃)₂, —NHCH(CH₃)₂, —N(CH₃)(CH(CH₃)₂), —N(CH(CH₃)₂)₂, —NHCH₂CF₃, -continued

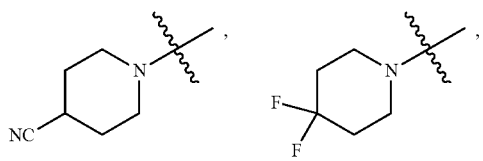

—CN, —SCH₃, —SCH₂CH₃, —SCH₂CH₂CH₃, —SCH(CH₃)₂, —SOCH₃, —SOCH₂CH₃, —SOCH₂CH₂CH₃, —SOCH(CH₃)₂, —SO₂CH₃, —SO₂CD₃, —SO₂CH₂CH₃, —SO₂CH₂CH₂CH₃, —SO₂CH(CH₃)₂, —SO₂CH(CD₃)₂, —SO₂NH₂, —SO₂NH(CH₃), —SO₂N(CH₃)₂, —SO₂NH(CD₃), —SO₂N(CD₃)₂, —SO₂NH(CH₂CH₃), —SO₂N(CH₂CH₃)₂, —SO₂NH(CH₂CH₃CH₂), —SO₂N(CH₂CH₂CH₃)₂,

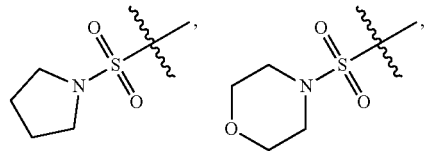

—CH₃, —CH₂D, —CD₂H, —CD₃, —CF₃, —CH₂CH₃, —CH₂CD₃, —CH₂CF₃, —CH₂CH₂CH₃, —CH₂CH₂CH₂F, —CH₂CH₂CD₃, —CH₂CH₂CF₃, —CH(CH₃)₂, —CH(CH₃)(CD₃), —CH(CF₃)₂, —CH(CD₃)₂,

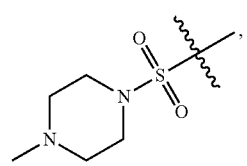

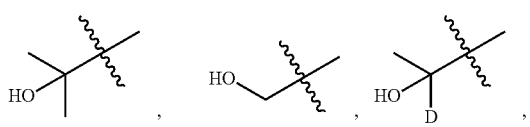

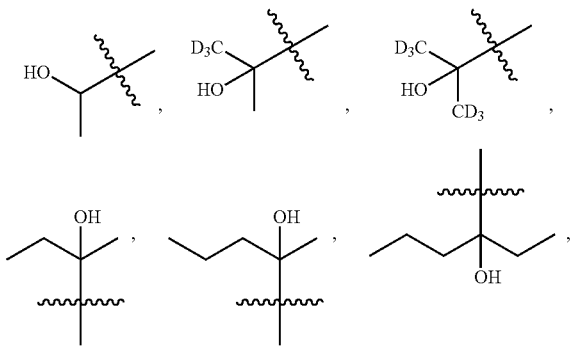

-continued

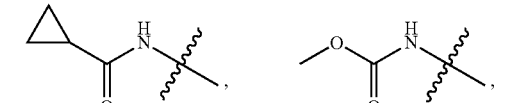

—CONH₂, —CONH(CH₃), —CON(CH₃)₂, —CONH(CD₃), —CON(CD₃)₂, —CONH(CH₂CH₃), —CON(CH₂CH₃)₂, —CONH(CH₂CH₂CH₃), —CON(CH₂CH₂CH₃)₂, —NHCOCH₃, —NHCOCH₂CH₃, —NHCOCH₂CH₂CH₃, —NHCOCH(CH₃)₂,

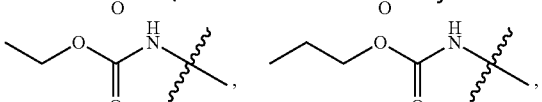

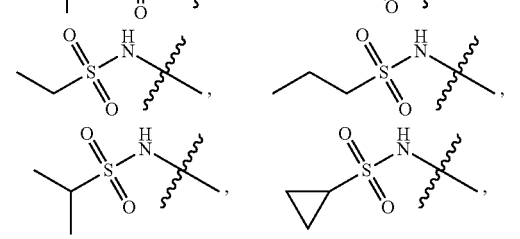

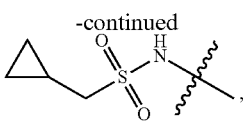

—P(O)H$_2$, —P(O)H(CH$_3$), —PO(CH$_3$)$_2$, —P(O)H(CD$_3$), —PO(CD$_3$)$_2$, —PO(CH$_2$CH$_3$)$_2$, —PO(CH$_2$CH$_2$CH$_3$)$_2$, —PO(CH(CH$_3$)$_2$)$_2$,

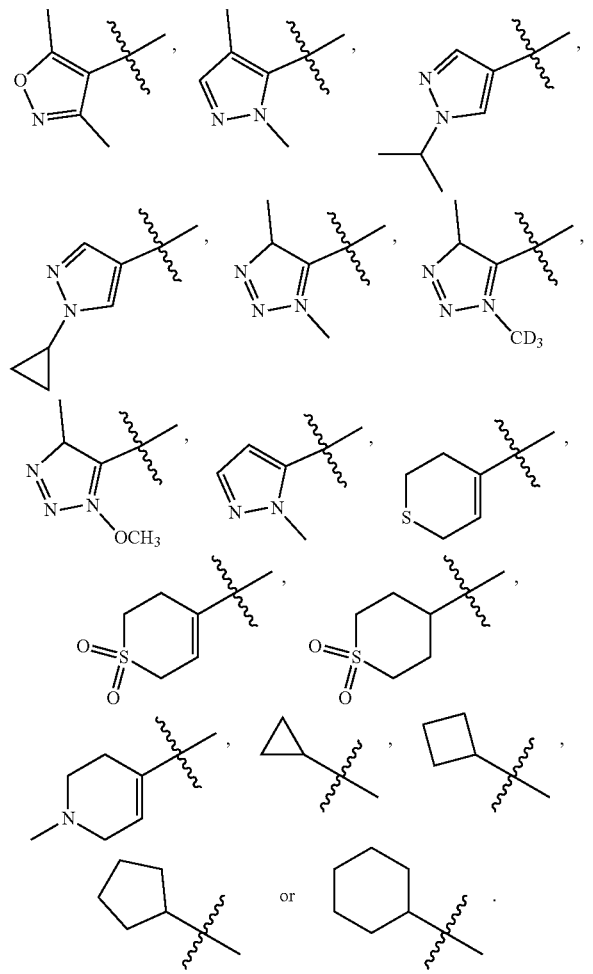

In some embodiments, wherein R$_2$ is selected from hydrogen, deuterium, halogen, —NR$_{21}$R$_{22}$, —SO$_2$R$_{21}$, —SO$_2$NR$_{21}$R$_{22}$, —C$_{1-6}$alkyl,

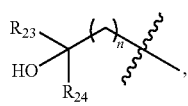

—COOR$_{21}$, —COR$_{21}$, —CONR$_{21}$R$_{22}$, —NR$_{21}$COR$_{22}$, —NR$_{21}$SO$_2$R$_{22}$, —POR$_{21}$R$_{22}$ or —C$_{3-8}$carbocyclic; and each of which at each occurrence is independently optionally substituted with 1, 2, 3, 4, 5 or 6 substituents, and the said each of substituents at each occurrence is independently selected from deuterium, halogen, —OH, —C$_{1-6}$alkyl or —C$_{1-6}$alkoxy;

Each of R$_{21}$ or R$_{22}$ at each occurrence is independently selected from hydrogen, deuterium or —C$_{1-6}$alkyl; or R$_{21}$ and R$_{22}$ together with the nitrogen atom to which they are both attached form 4-6 membered heterocyclic ring, each of the heterocyclic ring at each occurrence can further contains 1, 2 or 3 heteroatoms selected from N, O, S or SO$_2$, and each of the heterocyclic ring at each occurrence is independently optionally substituted with 1, 2, 3, 4, 5 or 6 substituents, and the said each of substituents at each occurrence is independently selected from deuterium; oxo; —C$_{1-6}$alkyl; —NH(C$_{1-6}$ alkyl); or —C$_{3-6}$heterocyclic containing 1 or 2 heteroatoms selected from N or O;

Each of R$_{23}$ and R$_{24}$ at each occurrence is independently selected from hydrogen, deuterium or —C$_{1-6}$alkyl; or R$_{23}$ and R$_{24}$ together with the carbon atom to which they are both attached form 3-6 membered carbocyclic ring, and each of the carbocyclic ring at each occurrence is independently optionally substituted with 1, 2, 3, 4, 5 or 6 substituents, and the said each of substituents at each occurrence is independently selected from deuterium, —OH or —C$_{1-6}$alkyl;

n is selected from 0, 1, 2, 3, 4, 5 or 6.

In some embodiments, wherein R$_2$ is selected from hydrogen, deuterium, halogen, —NR$_{21}$R$_{22}$, —SO$_2$R$_{21}$, —SO$_2$NR$_{21}$R$_{22}$, —C$_{1-3}$alkyl,

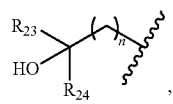

—COOR$_{21}$, —COR$_{21}$, —CONR$_{21}$R$_{22}$, —NR$_{21}$COR$_{22}$, —NR$_{21}$SO$_2$R$_{22}$, —POR$_{21}$R$_{22}$ or —C$_{3-6}$carbocyclic; and each of which at each occurrence is independently optionally substituted with 1, 2, 3, 4, 5 or 6 substituents, and the said each of substituents at each occurrence is independently selected from deuterium, halogen, —OH, —C$_{1-3}$alkyl or —C$_{1-3}$alkoxy;

Each of R$_{21}$ or R$_{22}$ at each occurrence is independently selected from hydrogen, deuterium or —C$_{1-3}$alkyl; or R$_{21}$ and R$_{22}$ together with the nitrogen atom to which they are both attached form 4-membered heterocyclic ring, 5-membered heterocyclic ring, 6-membered heterocyclic ring, each of the heterocyclic ring at each occurrence can further contains 1 or 2 heteroatoms selected from N or O, and each of the heterocyclic ring at each occurrence is independently optionally substituted with 1, 2, 3, 4, 5 or 6 substituents, and the said each of substituents at each occurrence is independently selected from deuterium, oxo, —C$_{1-3}$alkyl, —NH(C$_{1-3}$ alkyl) or —C$_{4-6}$heterocyclic containing 1 heteroatoms selected from N or O;

Each of R$_{23}$ and R$_{24}$ at each occurrence is independently selected from hydrogen, deuterium or —C$_{1-3}$alkyl; or R$_{23}$ and R$_{24}$ together with the carbon atom to which they are both attached form 3-6 membered carbocyclic ring, and each of the carbocyclic ring at each occurrence is independently optionally substituted with 1, 2, 3, 4, 5 or 6 substituents, and the said each of substituents at each occurrence is independently selected from deuterium, —OH or —C$_{1-3}$alkyl;

n is selected from 0, 1, 2 or 3.

In some embodiments, wherein $R_2$ is selected from hydrogen, deuterium, —F, —Cl, —Br, —$NR_{21}R_{22}$, —$SO_2R_{21}$, —$SO_2NR_{21}R_{22}$, methyl, ethyl, propyl, isopropyl,

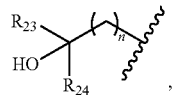

—$COOR_{21}$, —$COR_{21}$, —$CONR_{21}R_{22}$, —$NR_{21}COR_{22}$, —$NR_{21}SO_2R_{22}$, —$POR_{21}R_{22}$, 3-membered carbocyclic, 4-membered carbocyclic, 5-membered carbocyclic or 6-membered carbocyclic; and each of which at each occurrence is independently optionally substituted with 1, 2, 3, 4, 5 or 6 substituents, and the said each of substituents at each occurrence is independently selected from deuterium, —F, —Cl, —Br, —OH, methyl, ethyl, propyl, isopropyl, methoxy, ethoxy, propoxy or isopropoxy;

Each of $R_{21}$ or $R_{22}$ at each occurrence is independently selected from hydrogen, deuterium, methyl, ethyl, propyl or isopropyl; or $R_{21}$ and $R_{22}$ together with the nitrogen atom to which they are both attached form 5-membered heterocyclic ring, 6-membered heterocyclic ring, each of the heterocyclic ring at each occurrence ring can further contains 1 heteroatoms selected from N or O, and each of the heterocyclic ring at each occurrence is independently optionally substituted with 1, 2, 3, 4, 5 or 6 substituents, and the said each of substituents at each occurrence is independently selected from deuterium, oxo, methyl, ethyl, propyl, isopropyl, —$NHCH_3$, —$NHCH_2CH_3$, —$NHCH_2CH_2CH_3$, —$NHCH(CH_3)_2$,

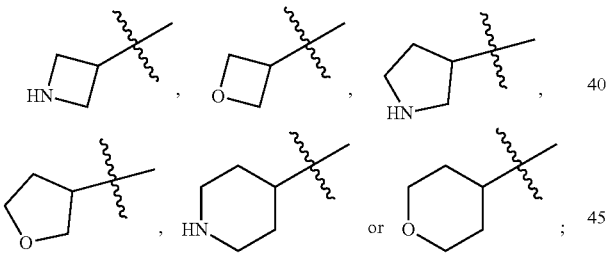

Each of $R_{23}$ and $R_{24}$ at each occurrence is independently selected from hydrogen, deuterium, methyl, ethyl, propyl or isopropyl; or $R_{23}$ and $R_{24}$ together with the carbon atom to which they are both attached form 3-membered carbocyclic ring, 4-membered carbocyclic ring, 5-membered carbocyclic ring, 6-membered carbocyclic ring, and each of the carbocyclic ring at each occurrence is independently optionally substituted with 1, 2, 3, 4, 5 or 6 substituents, and the said each of substituents at each occurrence is independently selected from deuterium, —OH, methyl, ethyl, propyl or isopropyl;

n is selected from 0, 1, 2 or 3.

In some embodiments, wherein $R_2$ is selected from hydrogen, deuterium, —F, —Cl, —Br, —$NH_2$, —$NHCH_3$, —$N(CH_3)_2$, —$NHCD_3$, —$N(CD_3)_2$, —$NHCH_2CH_3$, —$N(CH_3CH_2)_2$, —$N(CH_3)(CH_3CH_2)$, —$NHCH_2CH_2CH_3$, —$N(CH_2CH_2CH_3)_2$, —$NHCH(CH_3)_2$, —$N(CH_3)(CH(CH_3)_2)$, —$N(CH(CH_3)_2)_2$, —$NHCH_2CF_3$,

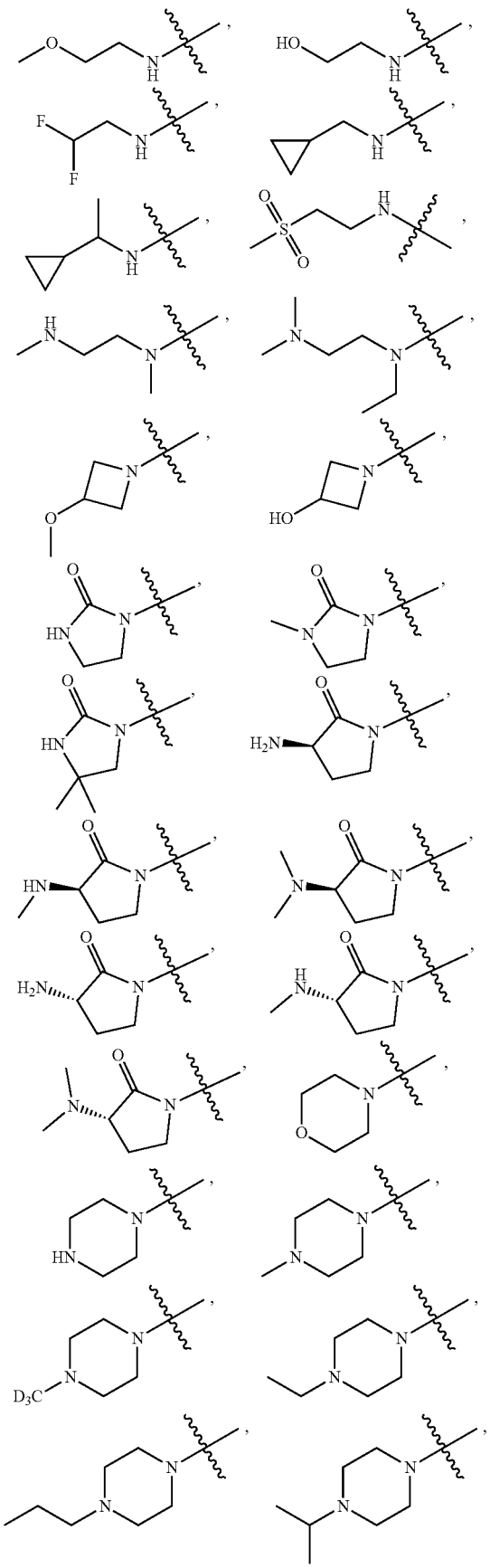

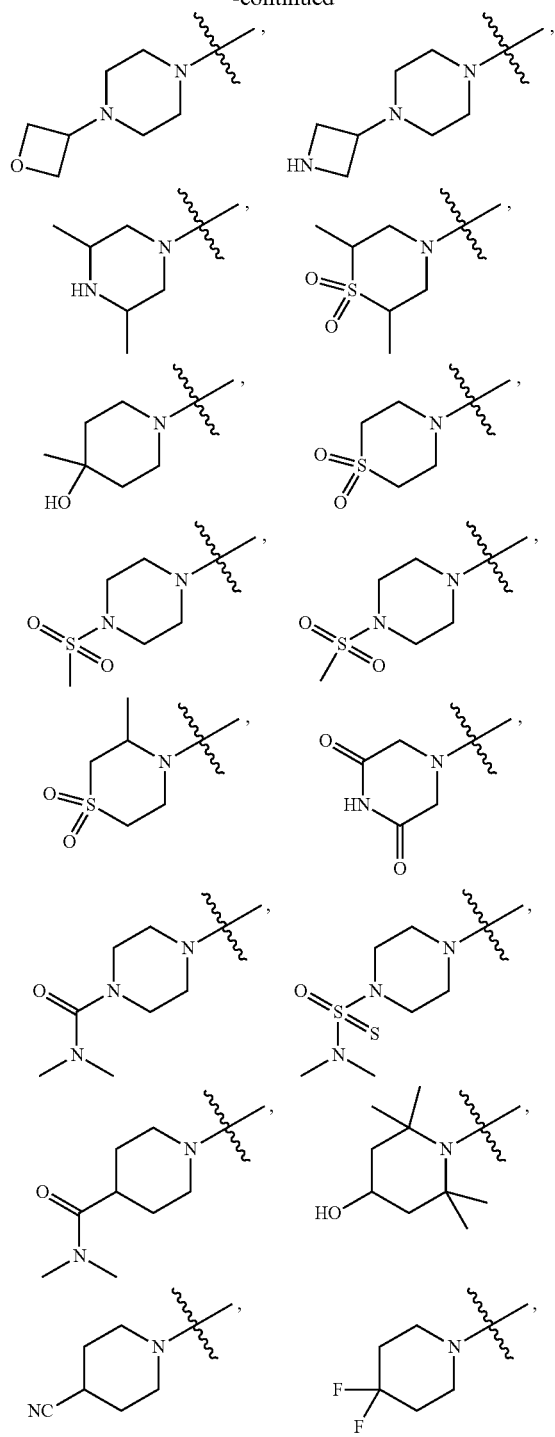

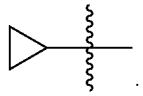 [SMILES: *C1CC1]

—COOCH$_3$, —COOCH$_2$CH$_3$, —COOCH$_2$CH$_2$CH$_3$, —COOCH(CH$_3$)$_2$, —CONH$_2$, —CONH(CH$_3$), —CON(CH$_3$)$_2$, —CONH(CD$_3$), —CON(CD$_3$)$_2$, —CONH(CH$_2$CH$_3$), —CON(CH$_2$CH$_3$)$_2$, —CONH(CH$_2$CH$_2$CH$_3$), —CON(CH$_2$CH$_2$CH$_3$)$_2$, —NHCOCH$_3$, —NHCOCH$_2$CH$_3$, —NHCOCH$_2$CH$_2$CH$_3$, —NHCOCH(CH$_3$)$_2$, —NHSO$_2$CH$_3$, —NHSO$_2$CD$_3$, —NHSO$_2$CH$_2$CH$_3$, —NHSO$_2$CH$_2$CH$_2$CH$_3$, —NHSO$_2$CH(CH$_3$)$_2$, —P(O)H$_2$, —P(O)H(CH$_3$), —P(O)(CH$_3$)$_2$, —P(O)H(CD$_3$), —PO(CD$_3$)$_2$, —PO(CH$_2$CH$_3$)$_2$, —PO(CH$_2$CH$_2$CH$_3$)$_2$, —PO(CH(CH$_3$)$_2$)$_2$ or

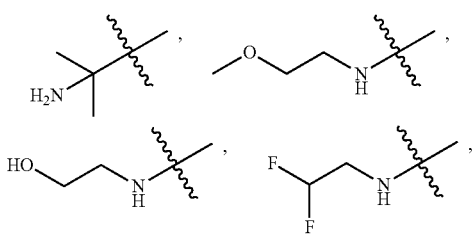

In some embodiments, wherein R$_2$ is selected from hydrogen, deuterium, —F, —Cl, —Br, —NH$_2$, —NHCH$_3$, —N(CH$_3$)$_2$, —NHCD$_3$, —N(CD$_3$)$_2$, —NHCH$_2$CH$_3$, —N(CH$_3$CH$_2$)$_2$, —N(CH$_3$)(CH$_3$CH$_2$), —NHCH$_2$CH$_2$CH$_3$, —N(CH$_2$CH$_2$CH$_3$)$_2$, —NHCH(CH$_3$)$_2$, —N(CH$_3$)(CH(CH$_3$)$_2$), —N(CH(CH$_3$)$_2$)$_2$, —NHCH$_2$CF$_3$, —SO$_2$CH$_3$, —SO$_2$CD$_3$, —SO$_2$CH$_2$CH$_3$, —SO$_2$CH$_2$CH$_2$CH$_3$, —SO$_2$CH(CH$_3$)$_2$, —SO$_2$CH(CD$_3$)$_2$, —SO$_2$NH$_2$, —SO$_2$NH(CH$_3$), —SO$_2$N(CH$_3$)$_2$, —SO$_2$NH(CD$_3$), —SO$_2$N(CD$_3$)$_2$, —SO$_2$NH(CH$_2$CH$_3$), —SO$_2$N(CH$_2$CH$_3$)$_2$, —SO$_2$NH(CH$_2$CH$_2$CH$_3$), —SO$_2$N(CH$_2$CH$_2$CH$_3$)$_2$, —CH$_3$, —CH$_2$D, —CD$_2$H, —CD$_3$, —CF$_3$, —CH$_2$CH$_3$, —CH$_2$CD$_3$, —CH$_2$CF$_3$, —CH$_2$CH$_2$CH$_3$, —CH$_2$CH$_2$CH$_2$F, —CH$_2$CH$_2$CD$_3$, —CH$_2$CH$_2$CF$_3$, —CH(CH$_3$)$_2$, —CH(CH$_3$)(CD$_3$), —CH(CF$_3$)$_2$, —CH(CD$_3$)$_2$, -continued

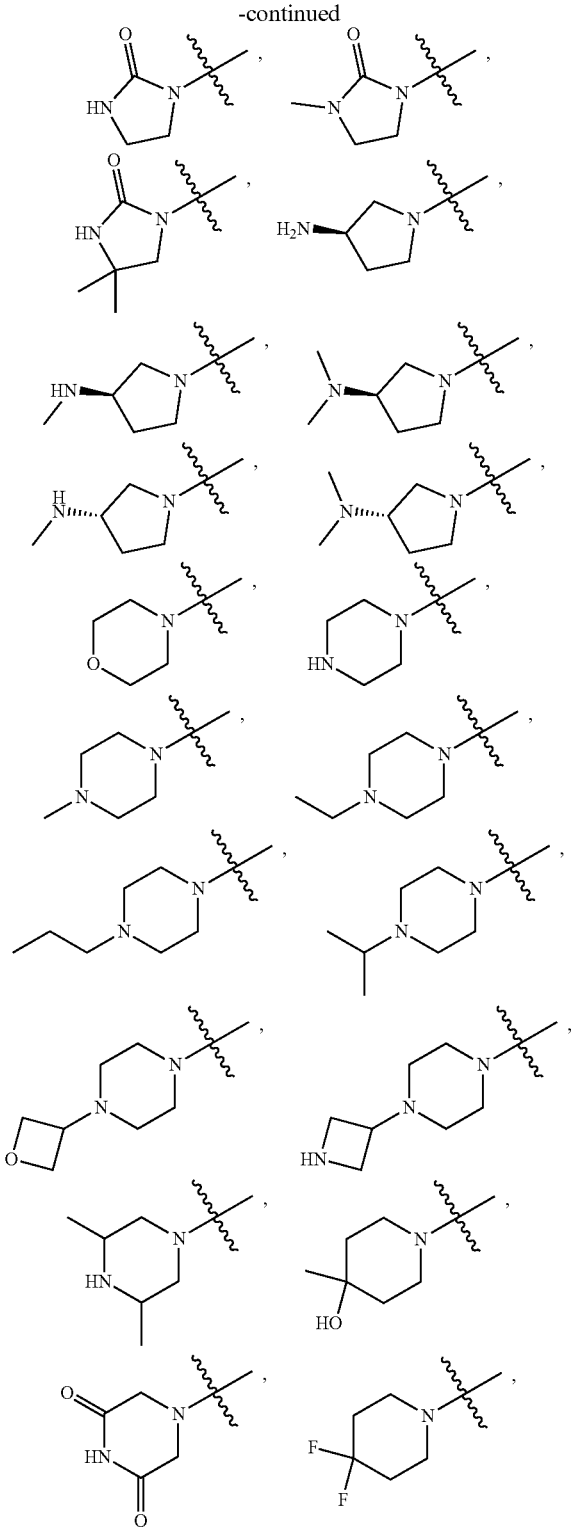

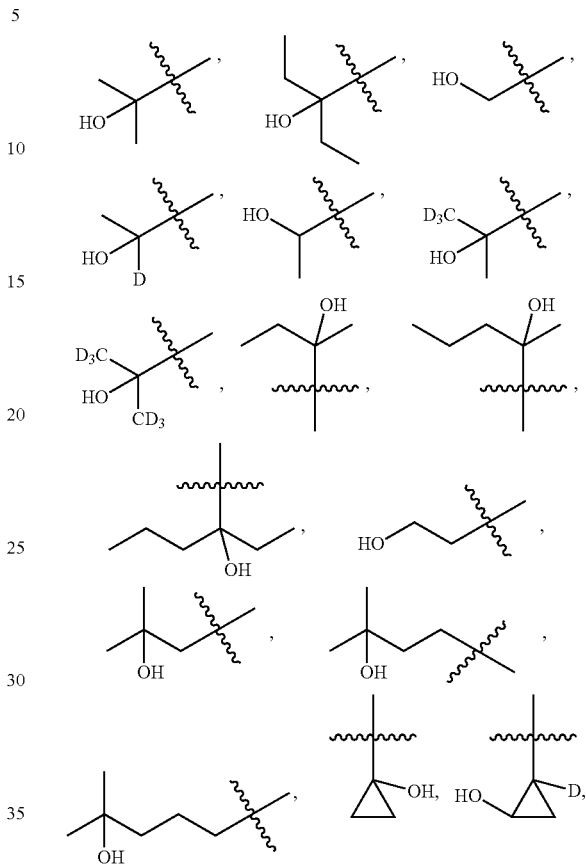

—CH₂CH₂CH₃, —CH₂CH₂CH₂F, —CH₂CD₃, —CH₂CH₂CF₃, —CH(CH₃)₂, —CH(CH₃)(CD₃), —CH(CF₃)₂, —CH(CD₃)₂,

—COOH, —COOCH₃, —COOCH₂CH₃, —COOCH₂CH₂CH₃, —COOCH(CH₃)₂, —CONH₂, —CONH(CH₃), —CON(CH₃)₂, —CONH(CD₃), —CON(CD₃)₂, —CONH(CH₂CH₃), —CON(CH₂CH₃)₂, —CONH(CH₂CH₂CH₃), —CON(CH₂CH₂CH₃)₂, —NHCOCH₃, —NHCOCH₂CH₃, —NHCOCH₂CH₂CH₃, —NHCOCH(CH₃)₂, —NHSO₂CH₃, —NHSO₂CD₃, —NHSO₂CH₂CH₃, —NHSO₂CH₂CH₃, —NHSO₂CH₂CH₂CH₃, —NHSO₂CH(CH₃)₂, —P(O)H₂, —P(O)H(CH₃), —P(O)(CH₃)₂, —P(O)H(CD₃), —PO(CD₃)₂, —PO(CH₂CH₃)₂, —PO(CH₂CH₂CH₃)₂, —PO(CH(CH₃)₂)₂ or

—SO₂CH₃, —SO₂CD₃, —SO₂CH₂CH₃, —SO₂CH₂CH₂CH₃, —SO₂CH(CH₃)₂, —SO₂CH(CD₃)₂, —SO₂NH₂, —SO₂NH(CH₃), —SO₂N(CH₃)₂, —SO₂NH(CD₃), —SO₂N(CD₃)₂, —SO₂NH(CH₂CH₃), —SO₂N(CH₂CH₃)₂, —SO₂NH(CH₂CH₂CH₃), —SO₂N(CH₂CH₂CH₃)₂, —CH₃, —CH₂D, —CD₂H, —CD₃, —CF₃, —CH₂CH₃, —CH₂CD₃, —CH₂CF₃,

In some embodiments, wherein R₂ is selected from hydrogen, —Cl, —Br, —NH₂,

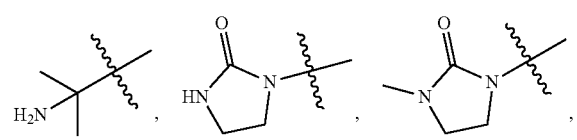

-continued

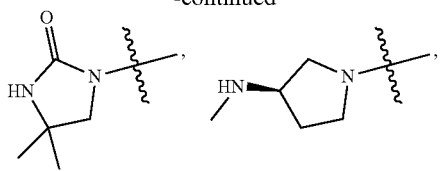

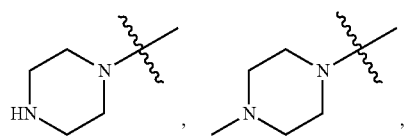

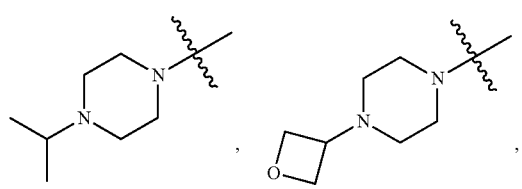

—SO$_2$CH$_3$, —SO$_2$NH$_2$, —SO$_2$NHCH$_3$, —SO$_2$N(CH$_3$)$_2$, —CH$_3$,

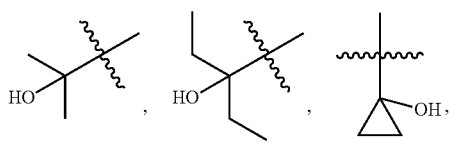

—COOH, —COOCH$_3$, —CONH$_2$, —CONHCH$_3$, —CON(CH$_3$)$_2$, —NHCOCH$_3$, —NHSO$_2$CH$_3$, —PO(CH$_3$)$_2$ or

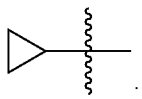.

In some embodiments, wherein R$_2$ is selected from hydrogen, —Cl, —Br, —NH$_2$,

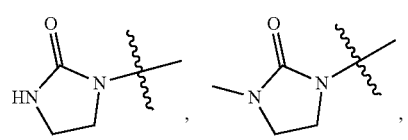

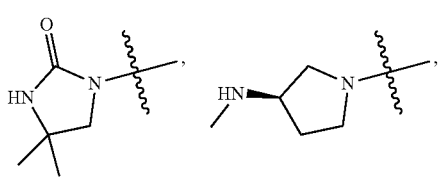

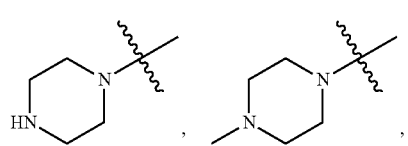

-continued

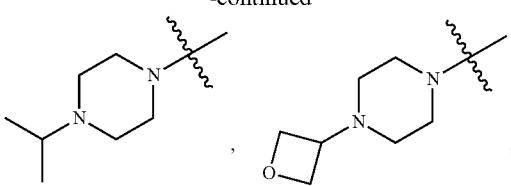

—SO$_2$CH$_3$, —SO$_2$NH$_2$, —SO$_2$NHCH$_3$, —SO$_2$N(CH$_3$)$_2$, —CH$_3$,

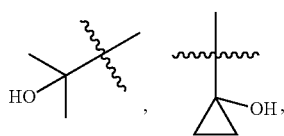

—COOCH$_3$, —CONH$_2$, —CONHCH$_3$, —CON(CH$_3$)$_2$, —NHCOCH$_3$, —NHSO$_2$CH$_3$, —PO(CH$_3$)$_2$ or

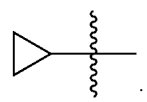 [SMILES: *C1CC1].

In some embodiments, wherein R$_2$ is

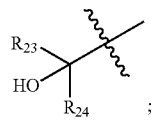;

Each of R$_{23}$ and R$_{24}$ at each occurrence is —C$_{1-6}$alkyl.

In some embodiments, wherein each of R$_{23}$ and R$_{24}$ at each occurrence is —C$_{1-3}$alkyl.

In some embodiments, wherein each of R$_{23}$ and R$_{24}$ at each occurrence is selected from methyl, ethyl, propyl or isopropyl.

In some embodiments, wherein R$_2$ is

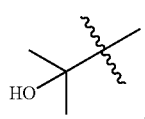.

In some embodiments, wherein the A is

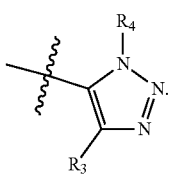

In some embodiments, wherein the A is

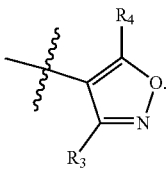

In some embodiments, wherein each of $R_3$ and $R_4$ at each occurrence is independently selected from hydrogen, deuterium, halogen, —CN, —SOR$_5$, —SO$_2$R$_5$, —SO$_2$NH$_2$, —SO$_2$NHR$_5$, —SO$_2$NR$_5$R$_6$, —C$_{1-3}$alkyl, —C$_{1-3}$alkoxy, —COR$_5$, —CONH$_2$, —CONHR$_5$, —CONR$_5$R$_6$, —P(O)H$_2$, —P(O)HR$_5$ or —POR$_5$R$_6$; and each of which at each occurrence is independently optionally substituted with 1, 2, 3, 4, 5 or 6 substituents, and the said each of substituents at each occurrence is independently selected from deuterium, halogen or —OH;

Each of $R_5$ and $R_6$ at each occurrence is independently selected from deuterium; —C$_{1-3}$alkyl; —C$_{5-6}$aryl; —C$_{5-6}$heteroaryl containing 1, 2, 3 or 4 heteroatoms selected from N, O, S, SO or SO$_2$; or —C$_{3-6}$carbocyclic, and each of which at each occurrence is independently optionally substituted with 1, 2, 3, 4, 5 or 6 substituents, and the said each of substituents at each occurrence is independently selected from deuterium, halogen, —C$_{1-3}$alkyl or —C$_{1-3}$alkoxy.

In some embodiments, wherein each of $R_3$ and $R_4$ at each occurrence is independently selected from hydrogen, deuterium, —F, —Cl, —Br, —CN, —SOR$_5$, —SO$_2$R$_5$, —SO$_2$NH$_2$, —SO$_2$NHR$_5$, —SO$_2$NR$_5$R$_6$, methyl, ethyl, propyl, isopropyl, methoxy, ethoxy, propoxy, isopropyl, —CONH$_2$, —CONHR$_5$, —CONR$_5$R$_6$, —P(O)H$_2$, —P(O)HR$_5$ or —POR$_5$R$_6$; and each of which at each occurrence is independently optionally substituted with 1, 2, 3, 4, 5 or 6 substituents, and the said each of substituents at each occurrence is independently selected from deuterium, —F, —Cl, —Br or —OH;

Each of $R_5$ and $R_6$ at each occurrence is independently selected from deuterium; methyl; ethyl; propyl; isopropyl; phenyl; 5-membered heteroaryl containing 1, 2, 3 or 4 heteroatoms selected from N, O, S, SO or SO$_2$; 6-membered heteroaryl containing 1, 2, 3 or 4 heteroatoms selected from N, O, S, SO or SO$_2$; 3-membered carbocyclic; 4-membered carbocyclic; 5-membered carbocyclic; or 6-membered carbocyclic; and each of which at each occurrence is independently optionally substituted with 1, 2, 3, 4, 5 or 6 substituents, and the said each of substituents at each occurrence is independently selected from deuterium, —F, —Cl, —Br, methyl, ethyl, propyl, isopropyl, methoxy, ethoxy, propoxy or isopropyl.

In some embodiments, wherein each of $R_3$ and $R_4$ at each occurrence is independently selected from hydrogen, deuterium, —F, —Cl, —Br, —CN, —SOCH$_3$, —SOCH$_2$CH$_3$, —SOCH$_2$CH$_2$CH$_3$, —SOCH(CH$_3$)$_2$, —SO$_2$CH$_3$, —SO$_2$CH$_2$CH$_3$, —SO$_2$CH$_2$CH$_2$CH$_3$, —SO$_2$CH(CH$_3$)$_2$, —SO$_2$NH$_2$, —SO$_2$NHCH$_3$, —SO$_2$NHCH$_2$CH$_3$, —SO$_2$NHCH$_2$CH$_2$CH$_3$, —SO$_2$NHCH(CH$_3$)$_2$, —SO$_2$N(CH$_3$)$_2$, —SO$_2$N(CH$_2$CH$_3$)$_2$, —SO$_2$N(CH$_3$)(CH$_2$CH$_3$), —SO$_2$N(CH$_2$CH$_2$CH$_3$)$_2$, —CH$_3$, —CH$_2$CH$_3$, —CH$_2$CH$_2$CH$_3$, —CH(CH$_3$)$_2$, —OCH$_3$, —OCH$_2$CH$_3$, —OCH$_2$CH$_2$CH$_3$, —OCH(CH$_3$)$_2$, —CONH$_2$, —CONHCH$_3$, —CONHCH$_2$CH$_3$, —CONHCH$_2$CH$_2$CH$_3$, —CONHCH(CH$_3$)$_2$,

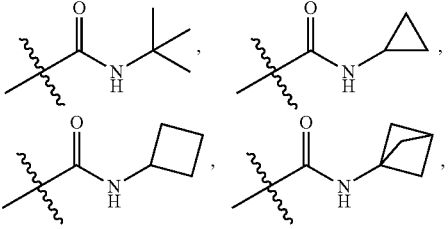

—CON(CH$_3$)$_2$, —CON(CH$_2$CH$_3$)$_2$, —CON(CH$_3$)(CH$_2$CH$_3$), —CON(CH$_2$CH$_2$CH$_3$)$_2$, —P(O)H$_2$, —P(O)HCH$_3$, —P(O)HCH$_2$CH$_3$, —P(O)HCH$_2$CH$_2$CH$_3$, —P(O)HCH(CH$_3$)$_2$, —PO(CH$_3$)$_2$, —PO(CH$_2$CH$_3$)$_2$, —PO(CH$_3$)(CH$_2$CH$_3$) or —PO(CH$_2$CH$_2$CH$_3$)$_2$, and each of which at each occurrence is independently optionally substituted with 1, 2, 3, 4, 5 or 6 substituents, and the said each of substituents at each occurrence is independently selected from deuterium, —F or methyl.

In some embodiments, wherein each of $R_3$ and $R_4$ at each occurrence is independently selected from hydrogen, deuterium, —F, —Cl, —Br, —CN, —SOCH$_3$, —SOCD$_3$, —SOCH$_2$CH$_3$, —SOCH$_2$CH$_2$CH$_3$, —SOCH(CH$_3$)$_2$, —SO$_2$CH$_3$, —SO$_2$CD$_3$, —SO$_2$CH$_2$CH$_3$, —SO$_2$CH$_2$CH$_2$CH$_3$, —SO$_2$CH(CH$_3$)$_2$, —SO$_2$NH$_2$, —SO$_2$NHCH$_3$, —SO$_2$NHCD$_3$, —SO$_2$NHCH$_2$CH$_3$, —SO$_2$NHCH$_2$CH$_2$CH$_3$, —SO$_2$NHCH(CH$_3$)$_2$, —SO$_2$N(CH$_3$)$_2$, —SO$_2$N(CD$_3$)$_2$, —SO$_2$N(CH$_2$CH$_3$)$_2$, —SO$_2$N(CH$_3$)(CH$_2$CH$_3$), —SO$_2$N(CH$_2$CH$_2$CH$_3$)$_2$, —CH$_3$, —CD$_3$, —CH$_2$CH$_3$, —CD$_2$CD$_3$, —CH$_2$CH$_3$, —CH$_2$CH$_2$CD$_3$, —CH(CH$_3$)$_2$, —CH(CD$_3$)$_2$, —OCH$_3$, —OCH$_2$CH$_3$, —OCH$_2$CH$_2$CH$_3$, —OCH(CH$_3$)$_2$, —CONH$_2$, —CONHCH$_3$, —CONHCD$_3$, —CONHCH$_2$CH$_3$, —CONHCD$_2$CD$_3$, —CONHCH$_2$CH$_2$CH$_3$, —CONHCH(CH$_3$)$_2$,

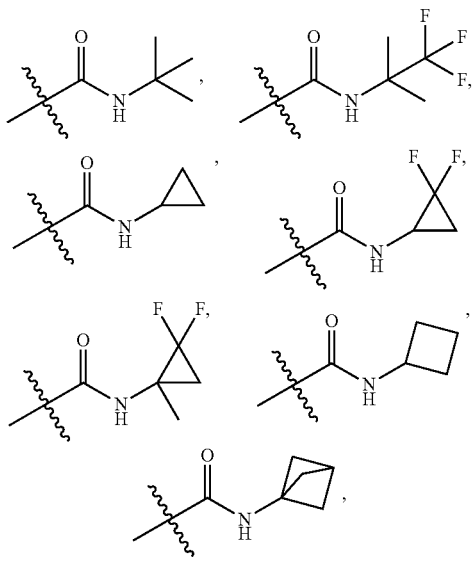

—CON(CH$_3$)$_2$, —CON(CH$_2$CH$_3$)$_2$—CON(CH$_3$)(CH$_2$CH$_3$), —CON(CH$_2$CH$_2$CH$_3$)$_2$, —P(O)H$_2$, —P(O)

HCH₃, —P(O)HCH₂CH₃, —P(O)HCH₂CH₂CH₃, —P(O)HCH(CH₃)₂, —PO(CH₃)₂, —PO(CH₂CH₃)₂, —PO(CH₃)(CH₂CH₃) or —PO(CH₂CH₂CH₃)₂.

In some embodiments, wherein each of R₃ and R₄ at each occurrence is independently selected from —C₁₋₃alkyl, —CONH₂, —CONHR₅ or —CONR₅R₆; and each of which at each occurrence is independently optionally substituted with 1, 2, 3, 4, 5 or 6 substituents, and the said each of substituents at each occurrence is independently selected from deuterium or halogen;

Each of R₅ and R₆ at each occurrence is independently selected from —C₁₋₃alkyl or —C₃₋₆carbocyclic, and each of which at each occurrence is independently optionally substituted with 1, 2, 3, 4, 5 or 6 substituents, and the said each of substituents at each occurrence is independently selected from deuterium, halogen or —C₁₋₃alkyl.

In some embodiments, wherein each of R₃ and R₄ at each occurrence is independently selected from methyl, ethyl, propyl, isopropyl, —CONH₂, —CONHR₅ or —CONR₅R₆; and each of which at each occurrence is independently optionally substituted with 1, 2, 3, 4, 5 or 6 substituents, and the said each of substituents at each occurrence is independently selected from deuterium, —F, —Cl or —Br;

Each of R₅ and R₆ at each occurrence is independently selected from methyl, ethyl, propyl, isopropyl, 3-membered carbocyclic, 4-membered carbocyclic, 5-membered carbocyclic or 6-membered carbocyclic, and each of which at each occurrence is independently optionally substituted with 1, 2, 3, 4, 5 or 6 substituents, and the said each of substituents at each occurrence is independently selected from deuterium, —F, —Cl, —Br, methyl, ethyl, propyl or isopropyl.

In some embodiments, wherein each of R₃ or R₄ at each occurrence is independently selected from —CH₃, —CH₂CH₃, —CH₂CH₂CH₃, —CH(CH₃)₂, —OCH₃, —OCH₂CH₃, —OCH₂CH₂CH₃, —OCH(CH₃)₂, —CONH₂, —CONHCH₃, —CONHCH₂CH₃, —CONHCH₂CH₂CH₃, —CONHCH(CH₃)₂,

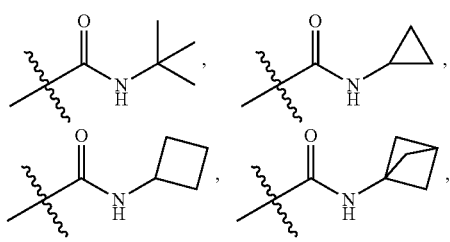

—CON(CH₃)₂, —CON(CH₂CH₃)₂, —CON(CH₃)(CH₂CH₃) or —CON(CH₂CH₂CH₃)₂; and each of which at each occurrence is independently optionally substituted with 1, 2, 3, 4, 5 or 6 substituents, and the said each of substituents at each occurrence is independently selected from deuterium, —F or methyl.

In some embodiments, wherein each of R₃ or R₄ at each occurrence is independently selected from —CH₃, —CD₃, —CH₂CH₃, —CD₂CD₃, —CH₂CH₂CH₃, —CH₂CH₂CD₃, —CH(CH₃)₂, —CH(CD₃)₂, —CONH₂, —CONHCH₃, —CONHCD₃, —CONHCH₂CH₃, —CONHCD₂CD₃, —CONHCH₂CH₂CH₃, —CONHCH(CH₃)₂,

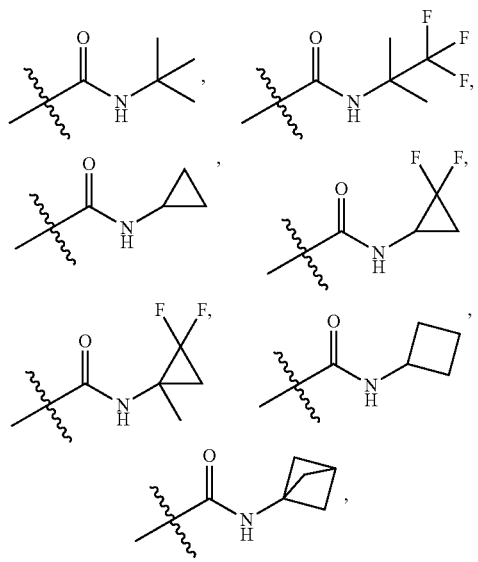

—CON(CH₃)₂, —CON(CH₂CH₃)₂, —CON(CH₃)(CH₂CH₃) or —CON(CH₂CH₂CH₃)₂.

In some embodiments, wherein each of R₃ or R₄ at each occurrence is independently selected from —CH₃, —CD₃, —CONH₂, —CONHCH₃, —CONHCH₂CH₃,

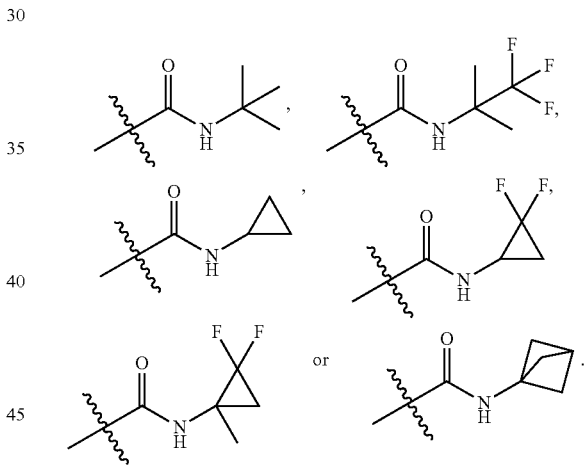

In some embodiments, wherein each of R₃ and R₄ at each occurrence is independently selected from —C₁₋₃alkyl, and the —C₁₋₃alkyl is independently optionally substituted with 1, 2, 3, 4, 5 or 6 substituents, and the said each of substituents at each occurrence is independently selected from deuterium, —F, —Cl or —Br.

In some embodiments, wherein each of R₃ and R₄ at each occurrence is independently selected from methyl, ethyl, propyl or isopropyl; and each of which at each occurrence is independently optionally substituted with 1, 2, 3, 4, 5 or 6 substituents, and the said each of substituents at each occurrence is independently selected from deuterium, —F, —Cl or —Br.

In some embodiments, wherein each of R₃ and R₄ at each occurrence is independently selected from methyl, ethyl, propyl or isopropyl; and each of which at each occurrence is independently optionally substituted with 1, 2, 3, 4, 5 or 6 substituents, and the said each of substituents at each occurrence is independently selected from deuterium or —F.

In some embodiments, wherein each of $R_3$ and $R_4$ at each occurrence is independently selected from —$CH_3$, —$CH_2D$, —$CD_2H$, —$CD_3$, —$CF_3$, —$CH_2CH_3$, —$CH_2CD_3$, —$CH_2CF_3$, —$CH_2CH_2CH_3$, —$CH_2CH_2CH_2F$, —$CH_2CH_2CD_3$, —$CH_2CH_2CF_3$, —$CH(CH_3)_2$, —$CH(CH_3)(CD_3)$, —$CH(CF_3)_2$ or —$CH(CD_3)_2$.

In some embodiments, wherein each of $R_3$ and $R_4$ at each occurrence is selected from —$C_{1-3}$alkyl or the —$C_{1-3}$alkyl substituted with 1, 2, 3, 4, 5 or 6 deuterium.

In some embodiments, wherein each of $R_3$ and $R_4$ at each occurrence is selected from methyl, ethyl, propyl, isopropyl, methyl substituted with deuterium, ethyl substituted with deuterium, propyl substituted with deuterium or isopropyl substituted with deuterium.

In some embodiments wherein the A is selected from:

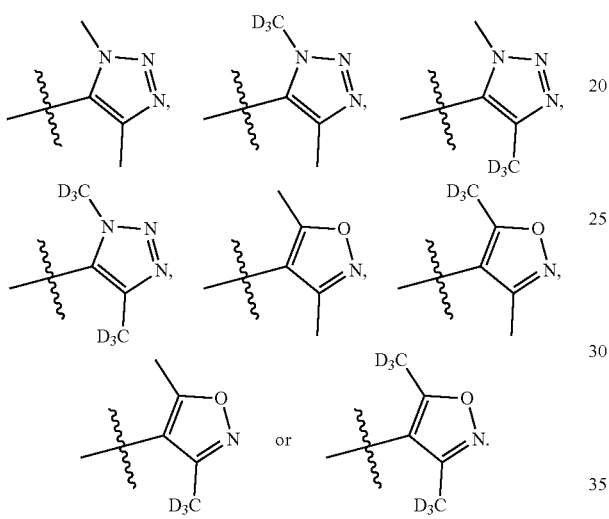

In some embodiments, wherein the A is independently selected from:

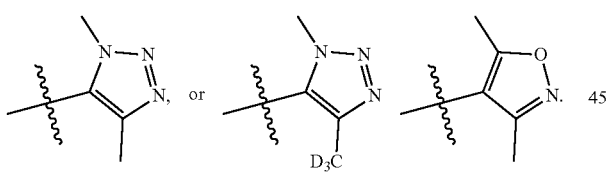

In some embodiments, wherein $W_1$ is selected from hydrogen; deuterium; —F; —Cl; —$NH_2$; —CN; —OH; carboxyl; —$C_{1-6}$alkyl; —$C_{1-6}$alkoxy; —$C_{1-3}$alkylene-$C_{1-3}$alkoxy; phenyl; 5-membered heteroaryl containing 1, 2 or 3 heteroatoms selected from N, O; 6-membered heteroaryl containing 1, 2 or 3 heteroatoms selected from N, O; 3-membered heterocyclic containing 1, 2 or 3 heteroatoms selected from N, O; 4-membered heterocyclic containing 1, 2 or 3 heteroatoms selected from N, O; 5-membered heterocyclic containing 1, 2 or 3 heteroatoms selected from N, O; 6-membered heterocyclic containing 1, 2 or 3 heteroatoms selected from N, O; 3-membered carbocyclic; 4-membered carbocyclic; 5-membered carbocyclic; or 6-membered carbocyclic; and each of which at each occurrence is independently optionally substituted with 1, 2, 3, 4, 5 or 6 substituents, and the said each of substituents at each occurrence is selected from deuterium, halogen, —$NH_2$, —CN, —OH, —$NO_2$, carboxyl, —$C_{1-3}$alkyl, or —$C_{1-3}$alkoxy.

In some embodiments, wherein $W_1$ is selected from hydrogen; deuterium; —F; —Cl; —$NH_2$; —CN; —OH; methyl; ethyl; propyl; isopropyl;

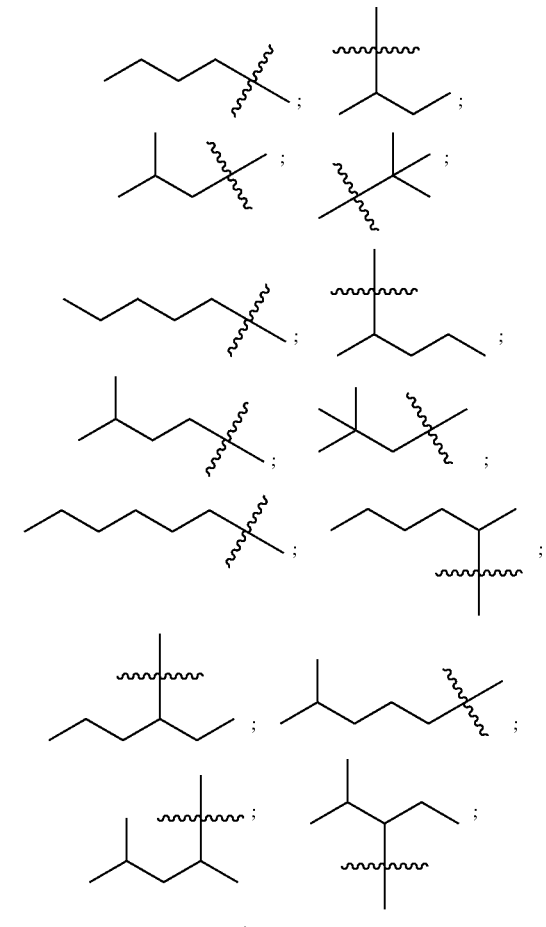

methoxy; ethoxy; propoxy; isopropoxy;

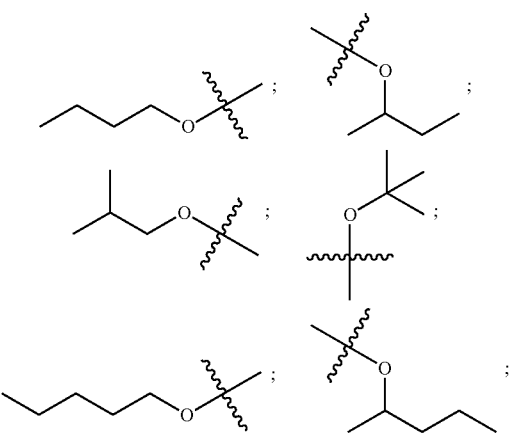

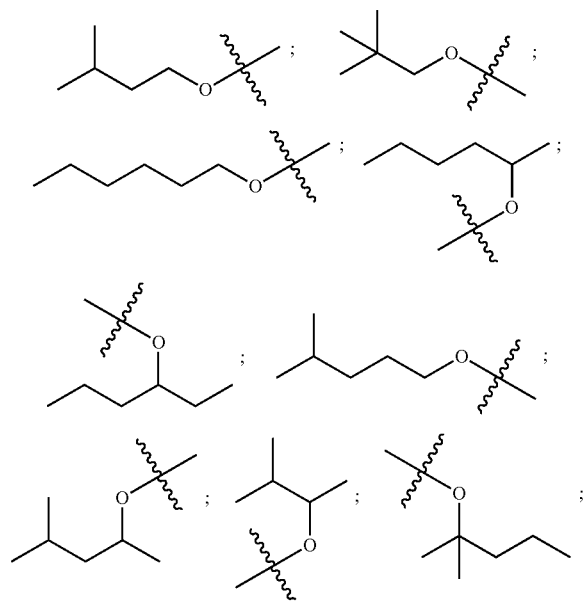

—CH₂OCH₃; —CH₂CH₂OCH₃; —CH₂CH₂OCH₂CH₃; phenyl; 5-membered heteroaryl containing 1 or 2 heteroatoms selected from N or O; 6-membered heteroaryl containing 1 or 2 heteroatoms selected from N or O; 5-membered heterocyclic containing 1 or 2 heteroatoms selected from N or O; 6-membered heterocyclic containing 1 or 2 heteroatoms selected from N or O; 5-membered carbocyclic; or 6-membered carbocyclic; and each of which at each occurrence is independently optionally substituted with 1, 2, 3, 4, 5 or 6 substituents, and the said each of substituents at each occurrence is selected from deuterium, —F, —Cl, —NH₂, —CN, —OH, carboxyl, methyl, ethyl, propyl, isopropyl, methoxy, ethoxy, propoxy, or isopropoxy.

In some embodiments, wherein W₁ is selected from hydrogen; deuterium; —F; methyl; ethyl; propyl; isopropyl;

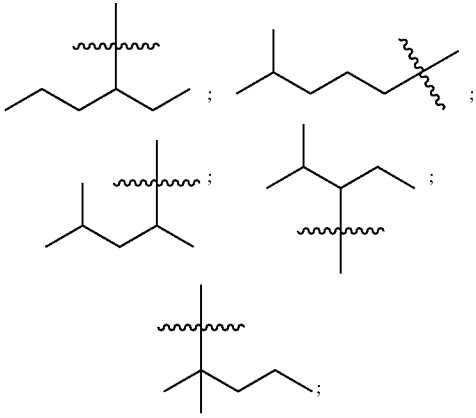

methoxy; —CH₂OCH₃; —CH₂CH₂OCH₃; 6-membered heteroaryl containing 1 or 2 heteroatoms selected from N or O; 5-membered heterocyclic containing 1 or 2 heteroatoms selected from N or O; 6-membered heterocyclic containing 1 or 2 heteroatoms selected from N or O; 5-membered carbocyclic; or 6-membered carbocyclic; and each of which at each occurrence is independently optionally substituted with deuterium or —F.

In some embodiments, wherein W₁ is selected from hydrogen, deuterium, —F, —CH₃, —CD₃, —CH₂F, —CF₂H, —CF₃, —CH₂CH₃, —CH₂CD₃, —CH₂CH₂F, —CH₂CHF₂, —CH₂CF₃, —CH₂CH₂CH₃, —CH₂CH₂CF₃, —CH₂CH₂CD₃, —CH(CH₃)₂, —CH(CF₃)₂, —CH(CD₃)₂,

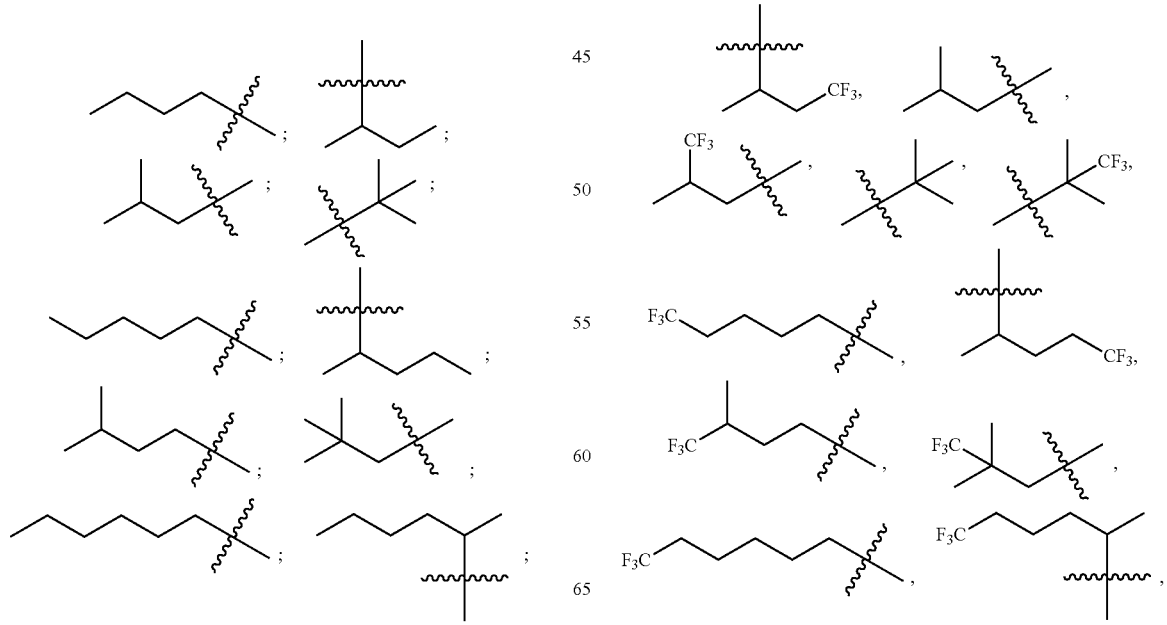

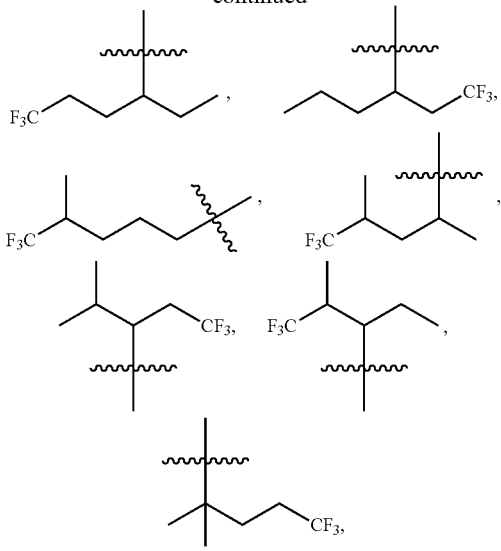

methoxy, —CH₂OCH₃, —CH₂CH₂OCH₃,

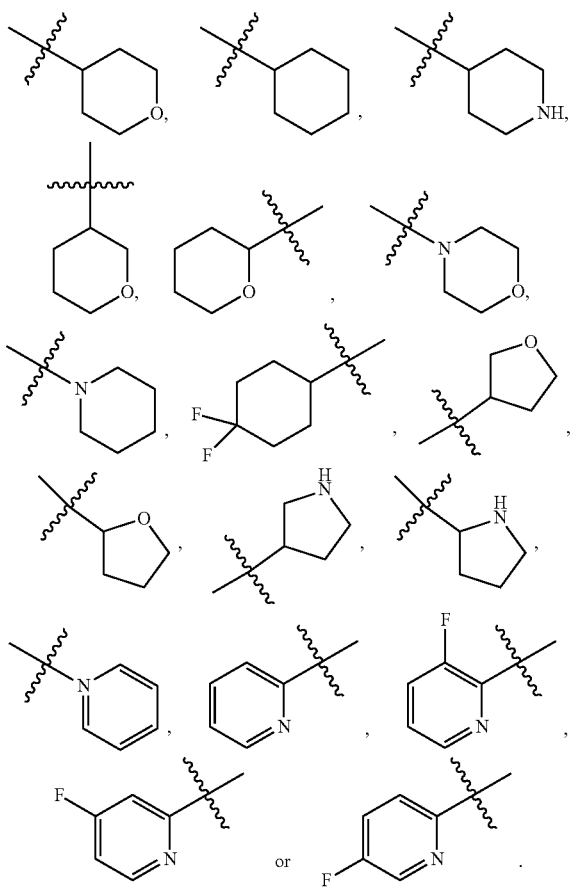

In some embodiments, wherein W₁ is selected from —C₁₋₆alkyl substituted with F or 6-membered heterocyclic containing 1 heteroatoms selected from O.

In some embodiments, wherein W₁ is selected from —C₁₋₆alkyl substituted with F,

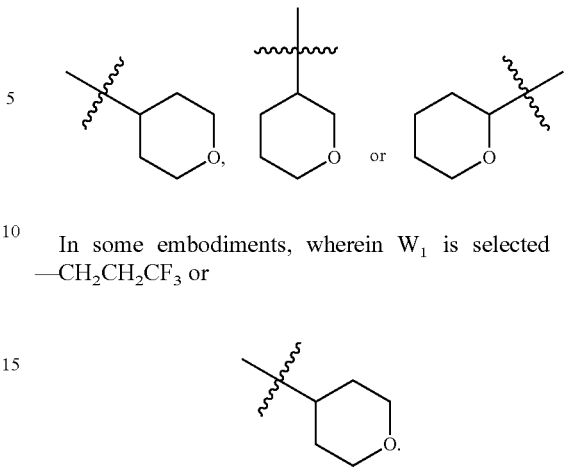

In some embodiments, wherein W₁ is selected from —CH₂CH₂CF₃ or

In some embodiments, wherein W₂ is selected from hydrogen; deuterium; —F; —Cl; —NH₂; —CN; —OH; carboxyl; —C₁₋₃alkyl; —C₁₋₃alkoxy; phenyl; naphthyl; 5-membered heteroaryl containing 1, 2 or 3 heteroatoms selected from N, O or S; 6-membered heteroaryl containing 1, 2 or 3 heteroatoms selected from N, O, or S; 7-membered heteroaryl containing 1, 2 or 3 heteroatoms selected from N, O or S; 8-membered heteroaryl containing 1, 2 or 3 heteroatoms selected from N, O or S; 9-membered heteroaryl containing 1, 2 or 3 heteroatoms selected from N, O or S; 10-membered heteroaryl containing 1, 2 or 3 heteroatoms selected from N, O, or S; 3-membered heterocyclic containing 1, 2 or 3 heteroatoms selected from N, O or S; 4-membered heterocyclic containing 1, 2 or 3 heteroatoms selected from N, O or S; 5-membered heterocyclic containing 1, 2 or 3 heteroatoms selected from N, O or S; 6-membered heterocyclic containing 1, 2 or 3 heteroatoms selected from N, O or S; 3-membered carbocyclic; 4-membered carbocyclic; 5-membered carbocyclic; or 6-membered carbocyclic; and each of which at each occurrence is independently optionally substituted with 1, 2, 3, 4 or 5 substituents, and the said each of substituents at each occurrence is selected from deuterium, halogen, —NH₂, —CN, —OH, —NO₂, carboxyl, methyl, ethyl, propyl, isopropyl, methoxy, ethoxy, propoxy or isopropoxy.

In some embodiments wherein W₂ is selected from hydrogen; deuterium; phenyl; 5-membered heteroaryl containing 1 or 2 heteroatoms selected from N, O or S; or 6-membered heteroaryl containing 1 or 2 heteroatoms selected from N, O or S; and each of which at each occurrence is independently optionally substituted with 1, 2, 3, 4 or 5 substituents, and the said each of substituents at each occurrence is selected from deuterium, —F, —Cl, —Br, —NH₂, —CN, —OH, methyl, ethyl, propyl, isopropyl, methoxy, ethoxy, propoxy or isopropoxy.

In some embodiments, wherein W₂ is selected from phenyl; 5-membered heteroaryl containing 1 or 2 heteroatoms selected from N, O, or S; or 6-membered heteroaryl containing 1 or 2 heteroatoms selected from N, O or S; and each of which at each occurrence is independently optionally substituted with 1, 2 or 3 substituents, and the said each of substituents at each occurrence is selected from —F, —Cl, —Br, methyl, ethyl, propyl, isopropyl, methoxy, ethoxy, propoxy or isopropoxy.

In some embodiments, wherein $W_2$ is selected from
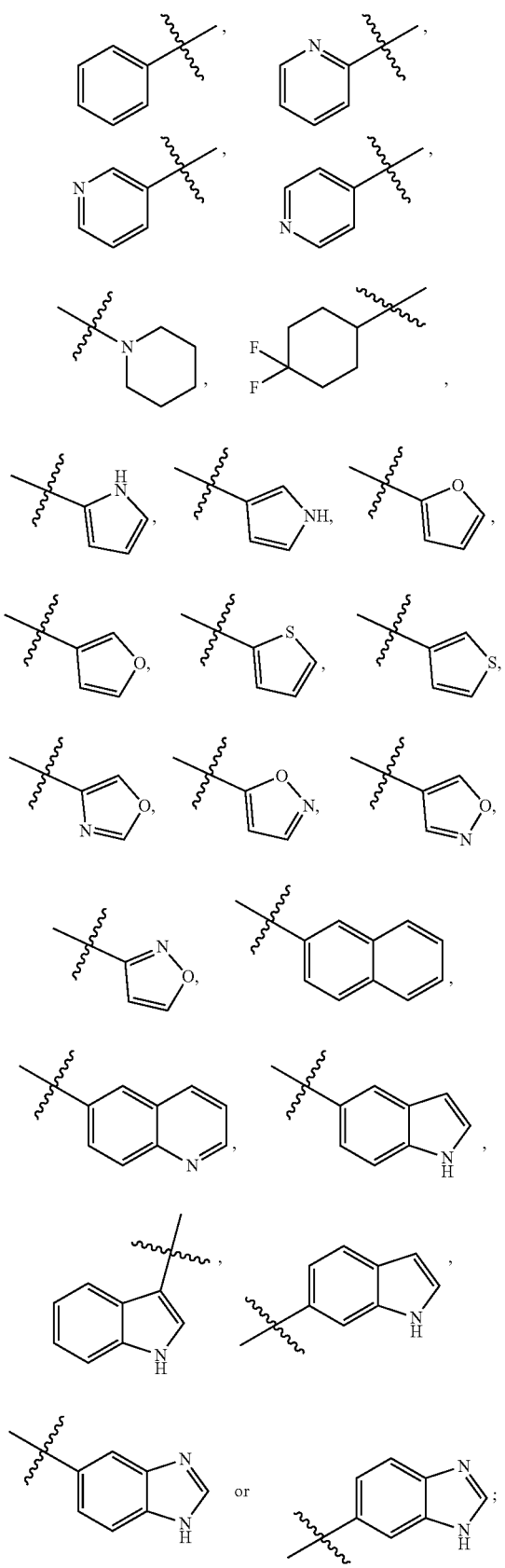
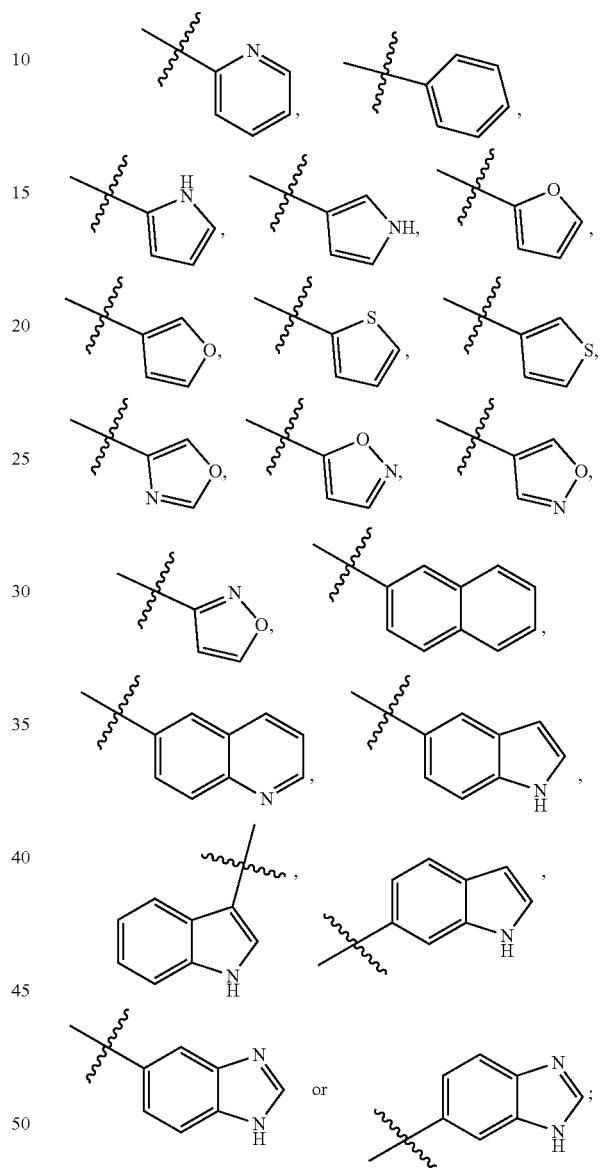
and each of which at each occurrence is independently optionally substituted with 1, 2 or 3 substituents, and the said each of substituents at each occurrence is selected from —F, —Cl, methyl or methoxy.
In some embodiments, wherein $W_2$ is selected from
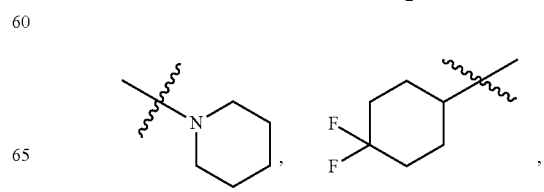

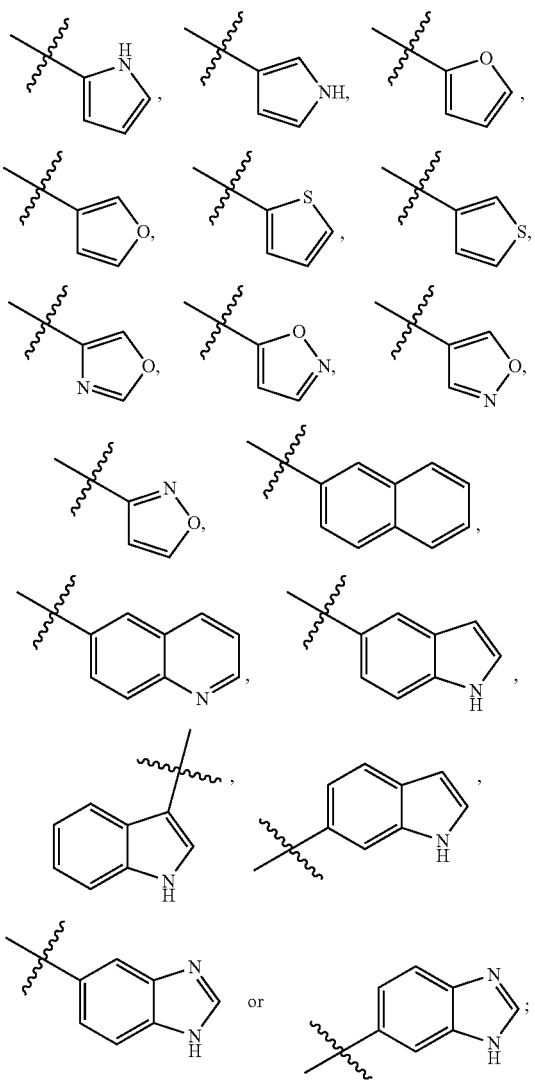

and each of which at each occurrence is independently optionally substituted with 1, 2 or 3 substituents, and the said each of substituents at each occurrence is selected from —F, —Cl, methyl or methoxy.

In some embodiments, wherein $W_2$ is selected from

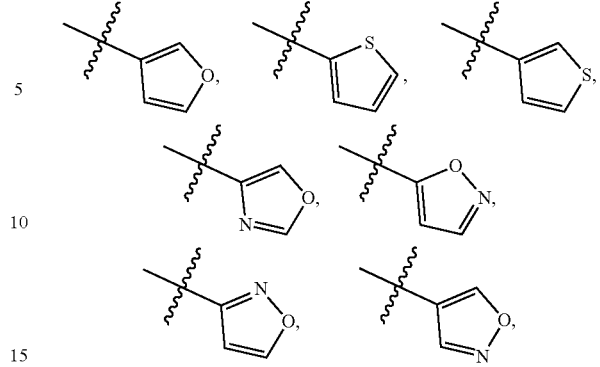

and each of which at each occurrence is independently optionally substituted with 1, 2 or 3 substituents, and the said each of substituents at each occurrence is selected from —F, —Cl, methyl or methoxy.

In some embodiments, wherein $W_2$ is independently selected from:

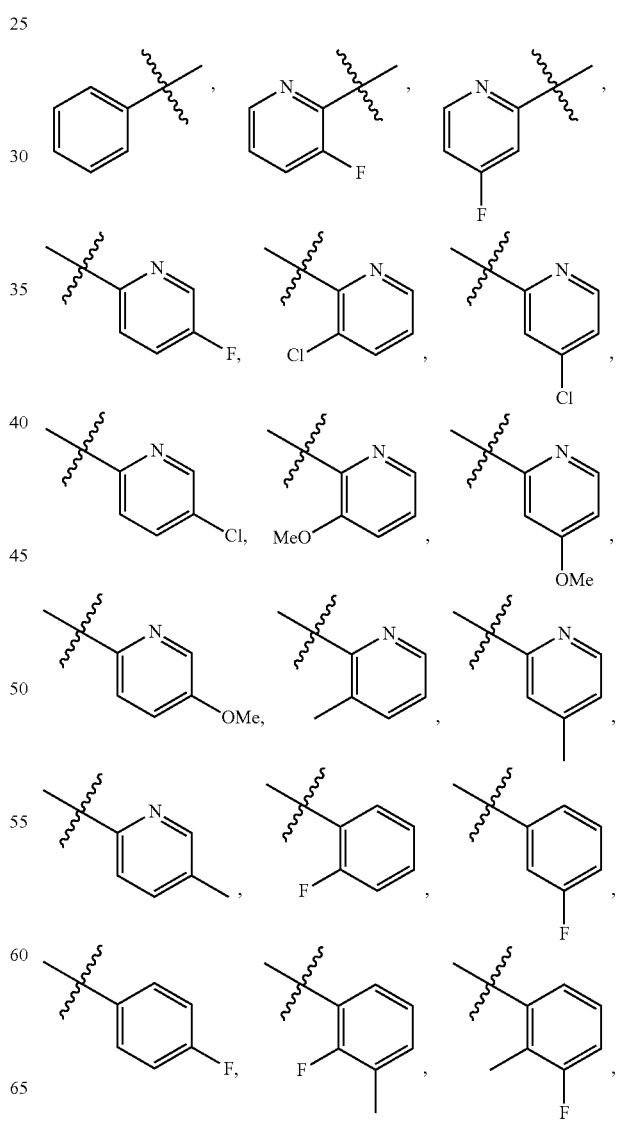

-continued

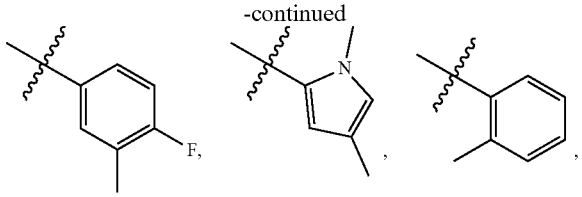
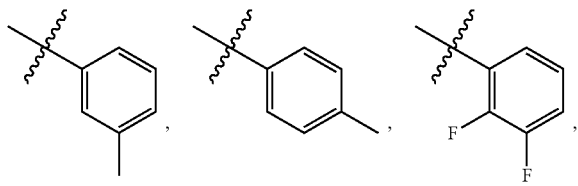
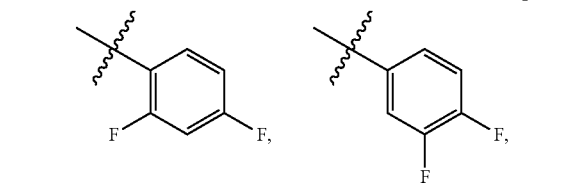
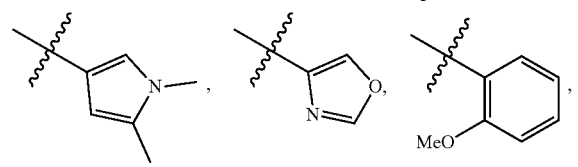
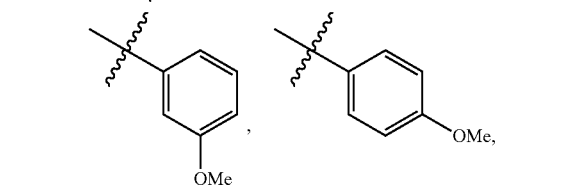
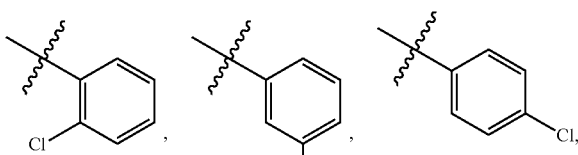
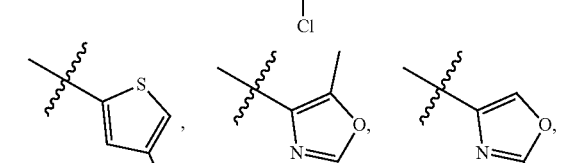
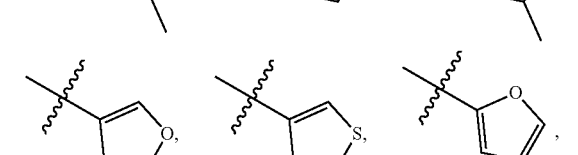
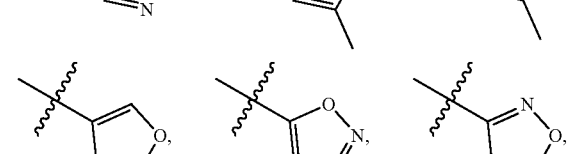
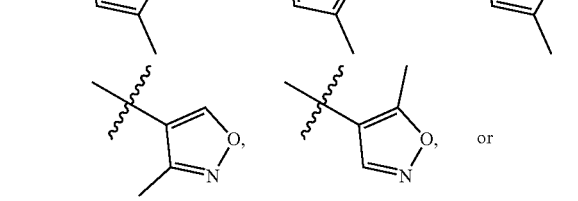 or -continued

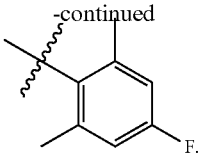

In some embodiments, wherein Z is selected from hydrogen, deuterium, —F, —Cl, —OH, —C$_{1-3}$alkyl or —C$_{1-3}$alkoxy.

In some embodiments, wherein Z is selected from hydrogen, deuterium, —F, —Cl, —OH, methyl, ethyl, propyl, isopropyl, methoxy, ethoxy, propoxy or isopropoxy.

In some embodiments, wherein Z is selected from hydrogen or deuterium.

In some embodiments, wherein Z is hydrogen.

In some embodiments, wherein,

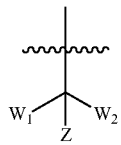

is selected from:

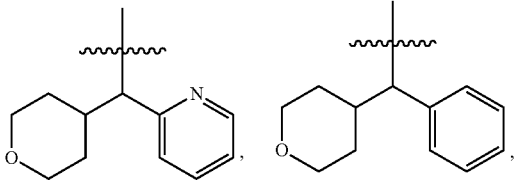
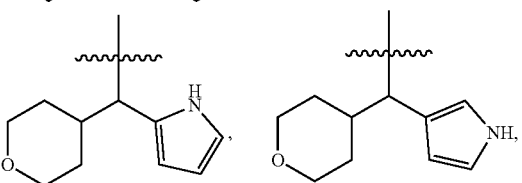
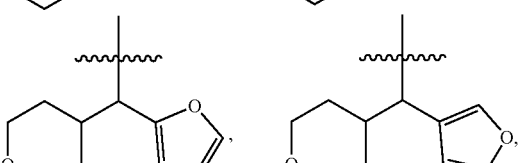
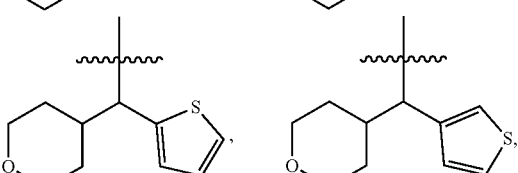
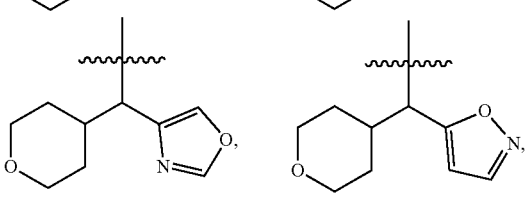

-continued

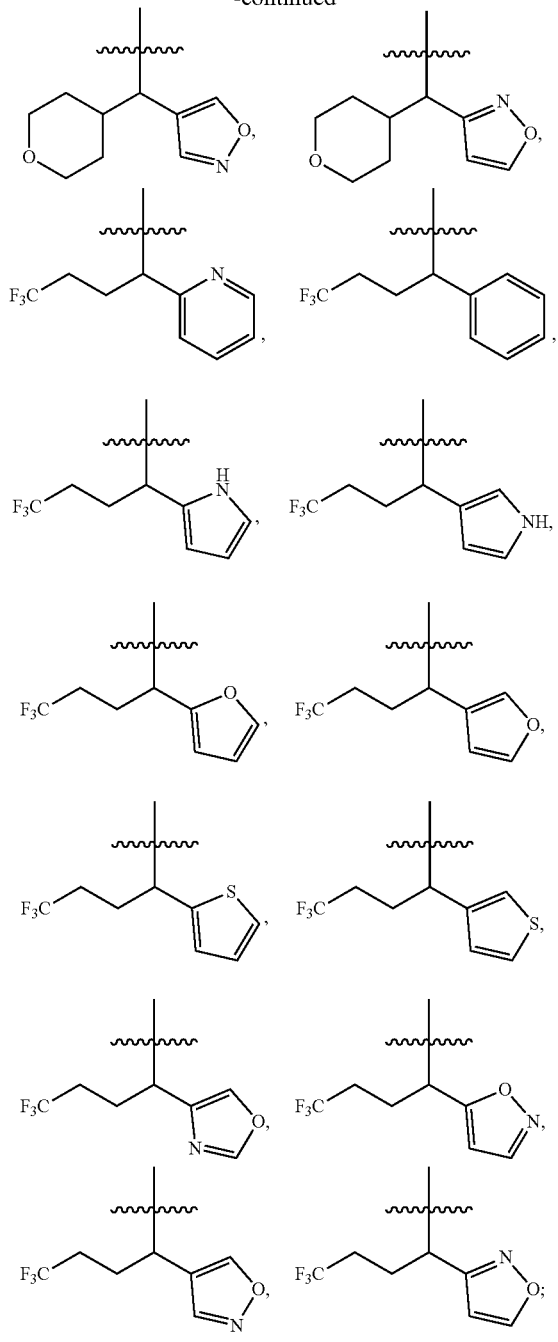

and each of which at each occurrence is independently optionally substituted with 1, 2 or 3 substituents, and the said each of substituents at each occurrence is selected from —F, —Cl, —Br, methyl, ethyl, propyl, isopropyl, methoxy, ethoxy, propoxy or isopropoxy.

In some embodiments, wherein, the

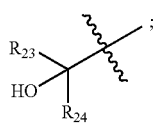

is selected from:

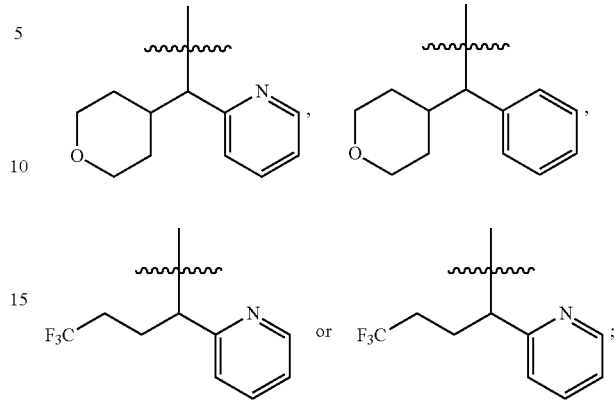

and each of which at each occurrence is independently optionally substituted with 1, 2 or 3 substituents, and the said each of substituents at each occurrence is selected from —F, —Cl, methyl or methoxy.

In some embodiments, wherein the A is independently selected from:

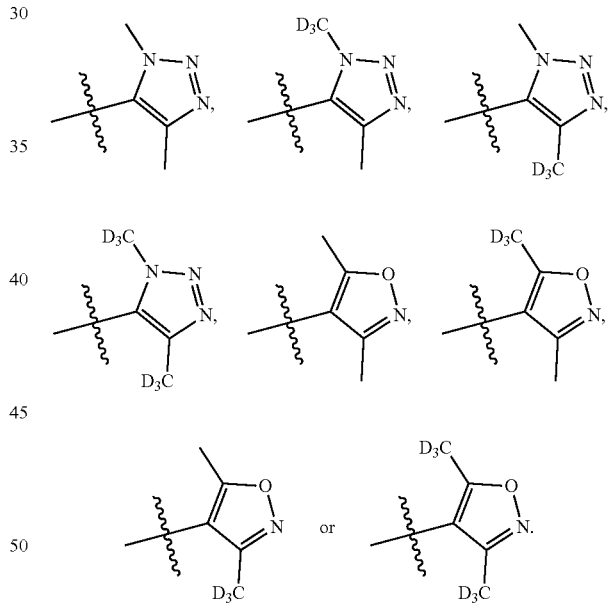

In some embodiments, wherein, $R_1$ is —$C_{1-6}$alkyl;

$R_2$ is

Each of $R_{23}$ and $R_{24}$ at each occurrence is —$C_{1-6}$alkyl;

the A is

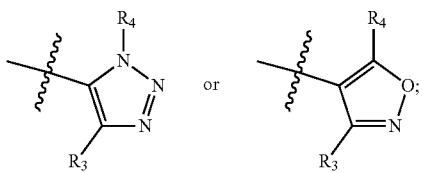 or 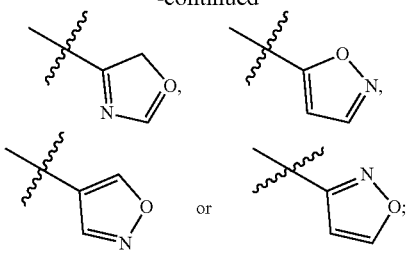

Each of $R_3$ and $R_4$ at each occurrence is selected from —$C_{1-6}$alkyl or —$C_{1-6}$alkyl substituted with 1, 2, 3, 4, 5 or 6 deuterium;

$W_1$ is selected from —$C_{1-6}$alkyl substituted with —F or 6-membered heterocyclic containing 1 heteroatoms selected from O;

$W_2$ is selected from phenyl; 5-membered heteroaryl containing 1 or 2 heteroatoms selected from N, O or S; or 6-membered heteroaryl containing 1 or 2 heteroatoms selected from N, O, or S; and each of which at each occurrence is independently optionally substituted with 1, 2 or 3 substituents, and the said each of substituents at each occurrence is selected from —F, —Cl, —Br, methyl, ethyl, propyl, isopropyl, methoxy, ethoxy, propoxy or isopropoxy;

Z is selected from hydrogen or deuterium.

In some embodiments, wherein, $R_1$ is —$C_{1-3}$alkyl;

Each of $R_{23}$ and $R_{24}$ at each occurrence is —$C_{1-3}$alkyl;

Each of $R_3$ and $R_4$ at each occurrence is selected from —$C_{1-3}$alkyl or —$C_{1-3}$alkyl substituted with 1, 2, 3, 4, 5 or 6 deuterium;

$W_1$ is selected from —$C_{1-6}$alkyl substituted with —F,

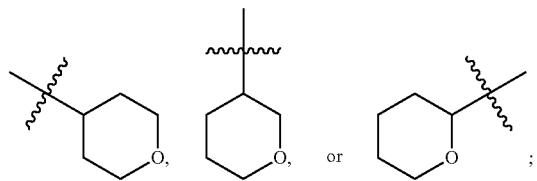

$W_2$ is selected from and each of which at each occurrence is independently optionally substituted with 1, 2 or 3 substituents, and the said each of substituents at each occurrence is selected from —F, —Cl, —Br, methyl, ethyl, propyl, isopropyl, methoxy, ethoxy, propoxy or isopropoxy;

Z is selected from hydrogen.

In some embodiments, wherein, $R_1$ is selected from methyl, ethyl, propyl or isopropyl;

Each of $R_{23}$ or $R_{24}$ at each occurrence is selected from methyl, ethyl, propyl or isopropyl;

Each of $R_3$ and $R_4$ at each occurrence is selected from methyl, ethyl, propyl, isopropyl, methyl substituted with deuterium, ethyl substituted with deuterium, propyl substituted with deuterium or isopropyl substituted with deuterium;

$W_1$ is selected from —$CH_2CH_2CF_3$ or

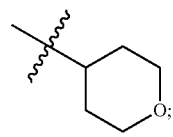 [SMILES: *C1CCOCC1]

$W_2$ is selected from:

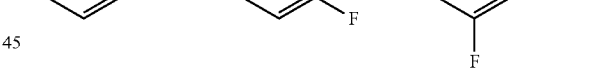

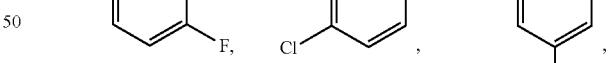

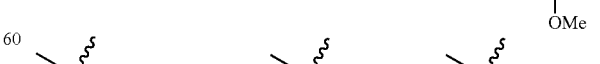

-continued

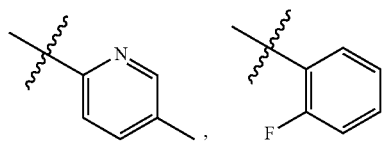 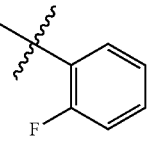 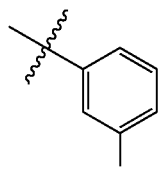

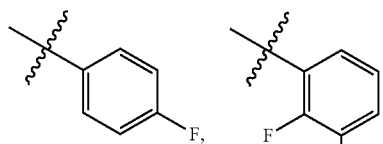 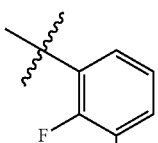 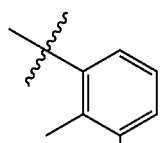

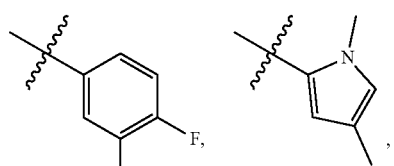 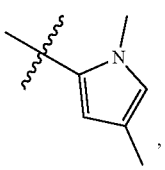 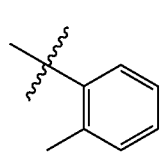

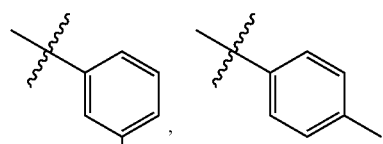 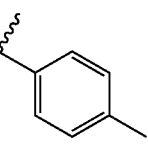 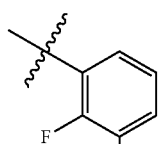

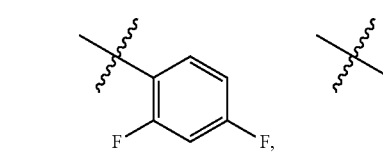 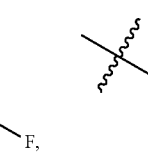 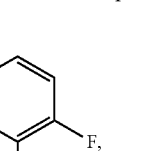

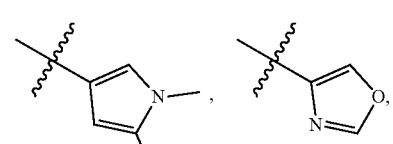 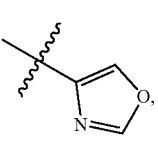

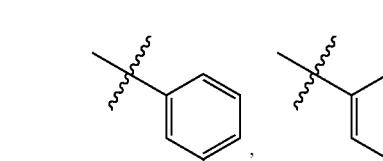 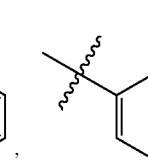

-continued

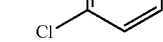  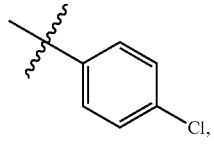

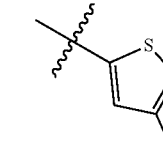 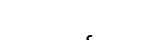 

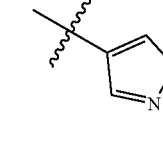 

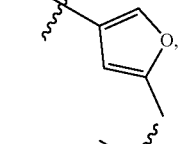 

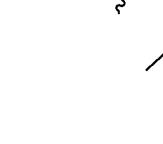  , or

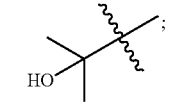

In some embodiments, wherein,
R₁ is methyl;
R₂ is

Each of R₃ and R₄ at each occurrence is independently selected from —CH₃ or —CD₃.

In some embodiments, the compound is:

| | |
|---|---|
| 1 | 2-(6-(1,4-dimethyl-1H-1,2,3-triazol-5-yl)-4-(phenyl(tetrahydro-2H-pyran-4-yl)methyl)-4H-isothiazolo[5',4':4,5]pyrrolo[3,2-b]pyridin-3-yl)propan-2-ol; |
| 2 | 2-(6-(1,4-dimethyl-1H-1,2,3-triazol-5-yl)-4-((3-fluoropyridin-2-yl)(tetrahydro-2H-pyran-4-yl)methyl)-4H-isothiazolo[5',4':4,5]pyrrolo[3,2-b]pyridin-3-yl)propan-2-ol; |
| 3 | 2-(6-(1,4-dimethyl-1H-1,2,3-triazol-5-yl)-4-((3-methylpyridin-2-yl)(tetrahydro-2H-pyran-4-yl)methyl)-4H-isothiazolo[5',4':4,5]pyrrolo[3,2-b]pyridin-3-yl)propan-2-ol; |
| 4 | 2-(6-(1,4-dimethyl-1H-1,2,3-triazol-5-yl)-4-((3-methoxypyridin-2-yl)(tetrahydro-2H-pyran-4-yl)methyl)-4H-isothiazolo[5',4':4,5]pyrrolo[3,2-b]pyridin-3-yl)propan-2-ol; |
| 5 | 2-(6-(1,4-dimethyl-1H-1,2,3-triazol-5-yl)-4-((2-fluorophenyl)(tetrahydro-2H-pyran-4-yl)methyl)-4H-isothiazolo[5',4':4,5]pyrrolo[3,2-b]pyridin-3-yl)propan-2-ol; |
| 6 | 2-(6-(1,4-dimethyl-1H-1,2,3-triazol-5-yl)-4-((2-methoxyphenyl)(tetrahydro-2H-pyran-4-yl)methyl)-4H-isothiazolo[5',4':4,5]pyrrolo[3,2-b]pyridin-3-yl)propan-2-ol; |
| 7 | 2-(4-((3-chloropyridin-2-yl)(tetrahydro-2H-pyran-4-yl)methyl)-6-(1,4-dimethyl-1H-1,2,3-triazol-5-yl)-4H-isothiazolo[5',4':4,5]pyrrolo[3,2-b]pyridin-3-yl)propan-2-ol; |

| | |
|---|---|
| 8 | 2-(4-((2-chlorophenyl)(tetrahydro-2H-pyran-4-yl)methyl)-6-(1,4-dimethyl-1H-1,2,3-triazol-5-yl)-4H-isothiazolo[5',4':4,5]pyrrolo[3,2-b]pyridin-3-yl)propan-2-ol; |
| 9 | 2-(6-(1,4-dimethyl-1H-1,2,3-triazol-5-yl)-4-((4-fluoropyridin-2-yl)(tetrahydro-2H-pyran-4-yl)methyl)-4H-isothiazolo[5',4':4,5]pyrrolo[3,2-b]pyridin-3-yl)propan-2-ol; |
| 10 | 2-(4-((4-chloropyridin-2-yl)(tetrahydro-2H-pyran-4-yl)methyl)-6-(1,4-dimethyl-1H-1,2,3-triazol-5-yl)-4H-isothiazolo[5',4':4,5]pyrrolo[3,2-b]pyridin-3-yl)propan-2-ol; |
| 11 | 2-(6-(1,4-dimethyl-1H-1,2,3-triazol-5-yl)-4-((3-methoxyphenyl)(tetrahydro-2H-pyran-4-yl)methyl)-4H-isothiazolo[5',4':4,5]pyrrolo[3,2-b]pyridin-3-yl)propan-2-ol; |
| 12 | 2-(6-(1,4-dimethyl-1H-1,2,3-triazol-5-yl)-4-((4-methylpyridin-2-yl)(tetrahydro-2H-pyran-4-yl)methyl)-4H-isothiazolo[5',4':4,5]pyrrolo[3,2-b]pyridin-3-yl)propan-2-ol; |
| 13 | 2-(6-(1,4-dimethyl-1H-1,2,3-triazol-5-yl)-4-((5-fluoropyridin-2-yl)(tetrahydro-2H-pyran-4-yl)methyl)-4H-isothiazolo[5',4':4,5]pyrrolo[3,2-b]pyridin-3-yl)propan-2-ol; |
| 14 | 2-(4-((5-chloropyridin-2-yl)(tetrahydro-2H-pyran-4-yl)methyl)-6-(1,4-dimethyl-1H-1,2,3-triazol-5-yl)-4H-isothiazolo[5',4':4,5]pyrrolo[3,2-b]pyridin-3-yl)propan-2-ol; |
| 15 | 2-(6-(1,4-dimethyl-1H-1,2,3-triazol-5-yl)-4-((4-methoxypyridin-2-yl)(tetrahydro-2H-pyran-4-yl)methyl)-4H-isothiazolo[5',4':4,5]pyrrolo[3,2-b]pyridin-3-yl)propan-2-ol; |
| 16 | 2-(6-(1,4-dimethyl-1H-1,2,3-triazol-5-yl)-4-((5-methoxypyridin-2-yl)(tetrahydro-2H-pyran-4-yl)methyl)-4H-isothiazolo[5',4':4,5]pyrrolo[3,2-b]pyridin-3-yl)propan-2-ol; |
| 17 | 2-(6-(3,5-dimethylisoxazol-4-yl)-4-((3-fluoropyridin-2-yl)(tetrahydro-2H-pyran-4-yl)methyl)-4H-isothiazolo[5',4':4,5]pyrrolo[3,2-b]pyridin-3-yl)propan-2-ol; |
| 18 | 2-(6-(3,5-dimethylisoxazol-4-yl)-4-((3-methoxypyridin-2-yl)(tetrahydro-2H-pyran-4-yl)methyl)-4H-isothiazolo[5',4':4,5]pyrrolo[3,2-b]pyridin-3-yl)propan-2-ol; |
| 19 | 2-(4-(((3-chloropyridin-2-yl)(tetrahydro-2H-pyran-4-yl)methyl)-6-(3,5-dimethylisoxazol-4-yl)-4H-isothiazolo[5',4':4,5]pyrrolo[3,2-b]pyridin-3-yl)propan-2-ol; |
| 20 | 2-(6-(3,5-dimethylisoxazol-4-yl)-4-((4-fluoropyridin-2-yl)(tetrahydro-2H-pyran-4-yl)methyl)-4H-isothiazolo[5',4':4,5]pyrrolo[3,2-b]pyridin-3-yl)propan-2-ol; |
| 21 | 2-(4-((4-chloropyridin-2-yl)(tetrahydro-2H-pyran-4-yl)methyl)-6-(3,5-dimethylisoxazol-4-yl)-4H-isothiazolo[5',4':4,5]pyrrolo[3,2-b]pyridin-3-yl)propan-2-ol; |
| 22 | 2-(6-(3,5-dimethylisoxazol-4-yl)-4-((5-fluoropyridin-2-yl)(tetrahydro-2H-pyran-4-yl)methyl)-4H-isothiazolo[5',4':4,5]pyrrolo[3,2-b]pyridin-3-yl)propan-2-ol; |
| 23 | 2-(4-((5-chloropyridin-2-yl)(tetrahydro-2H-pyran-4-yl)methyl)-6-(3,5-dimethylisoxazol-4-yl)-4H-isothiazolo[5',4':4,5]pyrrolo[3,2-b]pyridin-3-yl)propan-2-ol; |
| 24 | 2-(6-(3,5-dimethylisoxazol-4-yl)-4-((4-methoxypyridin-2-yl)(tetrahydro-2H-pyran-4-yl)methyl)-4H-isothiazolo[5',4':4,5]pyrrolo[3,2-b]pyridin-3-yl)propan-2-ol; |
| 25 | 2-(6-(3,5-dimethylisoxazol-4-yl)-4-((5-methoxypyridin-2-yl)(tetrahydro-2H-pyran-4-yl)methyl)-4H-isothiazolo[5',4':4,5]pyrrolo[3,2-b]pyridin-3-yl)propan-2-ol; |
| 26 | 2-(6-(1-methyl-4-(methyl-d3)-1H-1,2,3-triazol-5-yl)-4-(phenyl(tetrahydro-2H-pyran-4-yl)methyl)-4H-isothiazolo[5',4':4,5]pyrrolo[3,2-b]pyridin-3-yl)propan-2-ol; |
| 27 | 2-(6-(1,4-dimethyl-1H-1,2,3-triazol-5-yl)-4-((tetrahydro-2H-pyran-4-yl)(o-tolyl)methyl)-4H-isothiazolo[5',4':4,5]pyrrolo[3,2-b]pyridin-3-yl)propan-2-ol; |
| 28 | 2-(6-(1,4-dimethyl-1H-1,2,3-triazol-5-yl)-4-((3-fluorophenyl)(tetrahydro-2H-pyran-4-yl)methyl)-4H-isothiazolo[5',4':4,5]pyrrolo[3,2-b]pyridin-3-yl)propan-2-ol; |
| 29 | 2-(6-(1,4-dimethyl-1H-1,2,3-triazol-5-yl)-4-((5-methylpyridin-2-yl)(tetrahydro-2H-pyran-4-yl)methyl)-4H-isothiazolo[5',4':4,5]pyrrolo[3,2-b]pyridin-3-yl)propan-2-ol; |
| 30 | 2-(6-(3,5-dimethylisoxazol-4-yl)-4-((3-methylpyridin-2-yl)(tetrahydro-2H-pyran-4-yl)methyl)-4H-isothiazolo[5',4':4,5]pyrrolo[3,2-b]pyridin-3-yl)propan-2-ol; |
| 31 | 2-(6-(3,5-dimethylisoxazol-4-yl)-4-((4-methylpyridin-2-yl)(tetrahydro-2H-pyran-4-yl)methyl)-4H-isothiazolo[5',4':4,5]pyrrolo[3,2-b]pyridin-3-yl)propan-2-ol; |
| 32 | 2-(6-(3,5-dimethylisoxazol-4-yl)-4-((5-methylpyridin-2-yl)(tetrahydro-2H-pyran-4-yl)methyl)-4H-isothiazolo[5',4':4,5]pyrrolo[3,2-b]pyridin-3-yl)propan-2-ol; |
| 33 | 2-(6-(1,4-dimethyl-1H-1,2,3-triazol-5-yl)-4-((4-fluorophenyl)(tetrahydro-2H-pyran-4-yl)methyl)-4H-isothiazolo[5',4':4,5]pyrrolo[3,2-b]pyridin-3-yl)propan-2-ol; |
| 34 | 2-(6-(1,4-dimethyl-1H-1,2,3-triazol-5-yl)-4-((tetrahydro-2H-pyran-4-yl)(m-tolyl)methyl)-4H-isothiazolo[5',4':4,5]pyrrolo[3,2-b]pyridin-3-yl)propan-2-ol; |
| 35 | 2-(6-(1,4-dimethyl-1H-1,2,3-triazol-5-yl)-4-((tetrahydro-2H-pyran-4-yl)(p-tolyl)methyl)-4H-isothiazolo[5',4':4,5]pyrrolo[3,2-b]pyridin-3-yl)propan-2-ol; |
| 36 | 2-(6-(1,4-dimethyl-1H-1,2,3-triazol-5-yl)-4-((4-methoxyphenyl)(tetrahydro-2H-pyran-4-yl)methyl)-4H-isothiazolo[5',4':4,5]pyrrolo[3,2-b]pyridin-3-yl)propan-2-ol; |
| 37 | 2-(6-(1,4-dimethyl-1H-1,2,3-triazol-5-yl)-4-((2-fluoro-3-methylphenyl)(tetrahydro-2H-pyran-4-yl)methyl)-4H-isothiazolo[5',4':4,5]pyrrolo[3,2-b]pyridin-3-yl)propan-2-ol; |
| 38 | 2-(6-(1,4-dimethyl-1H-1,2,3-triazol-5-yl)-4-((3-fluoro-2-methylphenyl)(tetrahydro-2H-pyran-4-yl)methyl)-4H-isothiazolo[5',4':4,5]pyrrolo[3,2-b]pyridin-3-yl)propan-2-ol; |
| 39 | 2-(6-(1,4-dimethyl-1H-1,2,3-triazol-5-yl)-4-((4-fluoro-3-methylphenyl)(tetrahydro-2H-pyran-4-yl)methyl)-4H-isothiazolo[5',4':4,5]pyrrolo[3,2-b]pyridin-3-yl)propan-2-ol; |
| 40 | 2-(4-((2,3-difluorophenyl)(tetrahydro-2H-pyran-4-yl)methyl)-6-(1,4-dimethyl-1H-1,2,3-triazol-5-yl)-4H-isothiazolo[5',4':4,5]pyrrolo[3,2-b]pyridin-3-yl)propan-2-ol; |
| 41 | 2-(4-((2,4-difluorophenyl)(tetrahydro-2H-pyran-4-yl)methyl)-6-(1,4-dimethyl-1H-1,2,3-triazol-5-yl)-4H-isothiazolo[5',4':4,5]pyrrolo[3,2-b]pyridin-3-yl)propan-2-ol; |
| 42 | 2-(4((3,4-difluorophenyl)(tetrahydro-2H-pyran-4-yl)methyl)-6-(1,4-dimethyl-1H-1,2,3-triazol-5-yl)-4H-isothiazolo[5',4':4,5]pyrrolo[3,2-b]pyridin-3-yl)propan-2-ol; |
| 43 | 2-(4-((3-chlrophenyl)(tetrahydro-2H-pyran-4-yl)methyl)-6-(1,4-dimethyl-1H-1,2,3-triazol-5-yl)-4H-isothiazolo[5',4':4,5]pyrrolo[3,2-b]pyridin-3-yl)propan-2-ol; |
| 44 | 2-(4((4-chlorophenyl)(tetrahydro-2H-pyran-4-yl)methyl)-6-(1,4-dimethyl-1H-1,2,3-triazol-5-yl)-4H-isothiazolo[5',4':4,5]pyrrolo[3,2-b]pyridin-3-yl)propan-2-ol; |
| 45 | 2-(6-(1,4-dimethyl-1H-1,2,3-triazol-5-yl)-4-(4,4,4-trifluoro-1-phenylbutyl)-4H-isothiazolo[5',4':4,5]pyrrolo[3,2-b]pyridin-3-yl)propan-2-ol; |
| 46 | 2-(6-(1-methyl-4-(methyl-d3)-1H-1,2,3-triazol-5-yl)-4-(4,4,4-trifluoro-1-phenylbutyl)-4H-isothiazolo[5',4':4,5]pyrrolo[3,2-b]pyridin-3-yl)propan-2-ol; |

-continued

| | |
|---|---|
| 47 | 2-(6-(1,4-dimethyl-1H-1,2,3-triazol-5-yl)-4-(4,4,4-trifluoro-1-(3-fluoropyridin-2-yl)butyl)-4H-isothiazolo[5',4':4,5]pyrrolo[3,2-b]pyridin-3-yl)propan-2-ol; |
| 48 | 2-(6-(1-methyl-4-(methyl-d3)-1H-1,2,3-triazol-5-yl)-4-(4,4,4-trifluoro-1-(3-methylpyridin-2-yl)butyl)-4H-isothiazolo[5',4':4,5]pyrrolo[3,2-b]pyridin-3-yl)propan-2-ol; |
| 49 | 1-(6-(1,4-dimethyl-1H-1,2,3-triazol-5-yl)-4-(phenyl(tetrahydro-2H-pyran-4-yl)methyl)-4H-isothiazolo[5',4':4,5]pyrrolo[3,2-b]pyridin-3-yl)cyclopropan-1-ol; |
| 50 | 1-(6-(1,4-dimethyl-1H-1,2,3-triazol-5-yl)-4-((3-fluoropyridin-2-yl)(tetrahydro-2H-pyran-4-yl)methyl)-4H-isothiazolo[5',4':4,5]pyrrolo[3,2-b]pyridin-3-yl)cyclopropan-1-ol; |
| 51 | 2-(6-(1,4-dimethyl-1H-1,2,3-triazol-5-yl)-4-(4,4,4-trifluoro-1-(oxazol-4-yl)butyl)-4H-isothiazolo[5',4':4,5]pyrrolo[3,2-b]pyridin-3-yl)propan-2-ol; |
| 52 | 2-(6-(1,4-dimethyl-1H-1,2,3-triazol-5-yl)-4-(4,4,4-trifluoro-1-(5-methyloxazol-4-yl)butyl)-4H-isothiazolo[5',4':4,5]pyrrolo[3,2-b]pyridin-3-yl)propan-2-ol; |
| 53 | 2-(6-(1,4-dimethyl-1H-1,2,3-triazol-5-yl)-4-(4,4,4-trifluoro-1-(2-methyloxazol-4-yl)butyl)-4H-isothiazolo[5',4':4,5]pyrrolo[3,2-b]pyridin-3-yl)propan-2-ol; |
| 54 | 2-(6-(1,4-dimethyl-1H-1,2,3-triazol-5-yl)-4-(4,4,4-trifluoro-1-(isoxazol-4-yl)butyl)-4H-isothiazolo[5',4':4,5]pyrrolo[3,2-b]pyridin-3-yl)propan-2-ol; |
| 55 | 2-(6-(1,4-dimethyl-1H-1,2,3-triazol-5-yl)-4-(4,4,4-trifluoro-1-(5-methylisoxazol-4-yl)butyl)-4H-isothiazolo[5',4':4,5]pyrrolo[3,2-b]pyridin-3-yl)propan-2-ol; |
| 56 | 2-(6-(1,4-dimethyl-1H-1,2,3-triazol-5-yl)-4-(4,4,4-trifluoro-1-(3-methylisoxazol-4-yl)butyl)-4H-isothiazolo[5',4':4,5]pyrrolo[3,2-b]pyridin-3-yl)propan-2-ol; |
| 57 | 2-(6-(1,4-dimethyl-1H-1,2,3-triazol-5-yl)-4-((2-methyloxazol-4-yl)(tetrahydro-2H-pyran-4-yl)methyl)-4H-isothiazolo[5',4':4,5]pyrrolo[3,2-b]pyridin-3-yl)propan-2-ol; |
| 58 | 2-(6-(1,4-dimethyl-1H-1,2,3-triazol-5-yl)-4-((5-methylisoxazol-3-yl)(tetrahydro-2H-pyran-4-yl)methyl)-4H-isothiazolo[5',4':4,5]pyrrolo[3,2-b]pyridin-3-yl)propan-2-ol; |
| 59 | 2-(6-(1,4-dimethyl-1H-1,2,3-triazol-5-yl)-4-((3-methylisoxazol-5-yl)(tetrahydro-2H-pyran-4-yl)methyl)-4H-isothiazolo[5',4':4,5]pyrrolo[3,2-b]pyridin-3-yl)propan-2-ol; |
| 60 | 2-(6-(1,4-dimethyl-1H-1,2,3-triazol-5-yl)-4-((5-methylfuran-3-yl)(tetrahydro-2H-pyran-4-yl)methyl)-4H-isothiazolo[5',4':4,5]pyrrolo[3,2-b]pyridin-3-yl)propan-2-ol; |
| 61 | 2-(6-(1,4-dimethyl-1H-1,2,3-triazol-5-yl)-4-((4-methylfuran-2-yl)(tetrahydro-2H-pyran-4-yl)methyl)-4H-isothiazolo[5',4':4,5]pyrrolo[3,2-b]pyridin-3-yl)propan-2-ol; |
| 62 | 2-(6-(1,4-dimethyl-1H-1,2,3-triazol-5-yl)-4-((3-fluoropyridin-2-yl)(tetrahydro-2H-pyran-4-yl)methyl)-1-methyl-1,4-dihydropyrazolo[3',4':4,5]pyrrolo[3,2-b]pyridin-3-yl)propan-2-ol; |
| 63 | 2-(6-(1,4-dimethyl-1H-1,2,3-triazol-5-yl)-1-methyl-4-((3-methylpyridin-2-yl)(tetrahydro-2H-pyran-4-yl)methyl)-1,4-dihydropyrazolo[3',4':4,5]pyrrolo[3,2-b]pyridin-3-yl)propan-2-ol; |
| 64 | 2-(6-(1,4-dimethyl-1H-1,2,3-triazol-5-yl)-4-((3-methoxypyridin-2-yl)(tetrahydro-2H-pyran-4-yl)methyl)-1-methyl-1,4-dihydropyrazolo[3',4':4,5]pyrrolo[3,2-b]pyridin-3-yl)propan-2-ol; |
| 65 | 2-(6-(1,4-dimethyl-1H-1,2,3-triazol-5-yl)-4-((2-fluorophenyl)(tetrahydro-2H-pyran-4-yl)methyl)-1-methyl-1,4-dihydropyrazolo[3',4':4,5]pyrrolo[3,2-b]pyridin-3-yl)propan-2-ol; |
| 66 | 2-(6-(1,4-dimethyl-1H-1,2,3-triazol-5-yl)-4-((2-methoxyphenyl)(tetrahydro-2H-pyran-4-yl)methyl)-1-methyl-1,4-dihydropyrazolo[3',4':4,5]pyrrolo[3,2-b]pyridin-3-yl)propan-2-ol; |
| 67 | 2-(4-((3-chloropyridin-2-yl)(tetrahydro-2H-pyran-4-yl)methyl)-6-(1,4-dimethyl-1H-1,2,3-triazol-5-yl)-1-methyl-1,4-dihydropyrazolo[3',4':4,5]pyrrolo[3,2-b]pyridin-3-yl)propan-2-ol; |
| 68 | 2-(4((2-chlorophenyl)(tetrahydro-2H-pyran-4-yl)methyl)-6-(1,4-dimethyl-1H-1,2,3-triazol-5-yl)-1-methyl-1,4-dihydropyrazolo[3',4':4,5]pyrrolo[3,2-b]pyridin-3-yl)propan-2-ol; |
| 69 | 2-(6-(1,4-dimethyl-1H-1,2,3-triazol-5-yl)-4-((4-fluoropyridin-2-yl)(tetrahydro-2H-pyran-4-yl)methyl)-1-methyl-1,4-dihydropyrazolo[3',4':4,5]pyrrolo[3,2-b]pyridin-3-yl)propan-2-ol; |
| 70 | 2-(4-((4-chloropyridin-2-yl)(tetrahydro-2H-pyran-4-yl)methyl)-6-(1,4-dimethyl-1H-1,2,3-triazol-5-yl)-1-methyl-1,4-dihydropyrazolo[3',4':4,5]pyrrolo[3,2-b]pyridin-3-yl)propan-2-ol; |
| 71 | 2-(6-(1,4-dimethyl-1H-1,2,3-triazol-5-yl)-4-((3-methoxyphenyl)(tetrahydro-2H-pyran-4-yl)methyl)-1-methyl-1,4-dihydropyrazolo[3',4':4,5]pyrrolo[3,2-b]pyridin-3-yl)propan-2-ol; |
| 72 | 2-(6-(1,4-dimethyl-1H-1,2,3-triazol-5-yl)-1-methyl-4-((4-methylpyridin-2-yl)(tetrahydro-2H-pyran-4-yl)methyl)-1,4-dihydropyrazolo[3',4':4,5]pyrrolo[3,2-b]pyridin-3-yl)propan-2-ol; |
| 73 | 2-(6-(1,4-dimethyl-1H-1,2,3-triazol-5-yl)-4-((5-fluoropyridin-2-yl)(tetrahydro-2H-pyran-4-yl)methyl)-1-methyl-1,4-dihydropyrazolo[3',4':4,5]pyrrolo[3,2-b]pyridin-3-yl)propan-2-ol; |
| 74 | 2-(4-((5-chloropyridin-2-yl)(tetrahydro-2H-pyran-4-yl)methyl)-6-(1,4-dimethyl-1H-1,2,3-triazol-5-yl)-1-methyl-1,4-dihydropyrazolo[3',4':4,5]pyrrolo[3,2-b]pyridin-3-yl)propan-2-ol; |
| 75 | 2-(6-(1,4-dimethyl-1H-1,2,3-triazol-5-yl)-4-(4-methoxypyridin-2-yl)(tetrahydro-2H-pyran-4-yl)methyl)-1-methyl-1,4-dihydropyrazolo[3',4':4,5]pyrrolo[3,2-b]pyridin-3-yl)propan-2-ol; |
| 76 | 2-(6-(1,4-dimethyl-1H-1,2,3-triazol-5-yl)-4-((5-methoxypyridin-2-yl)(tetrahydro-2H-pyran-4-yl)methyl)-1-methyl-1,4-dihydropyrazolo[3',4':4,5]pyrrolo[3,2-b]pyridin-3-yl)propan-2-ol; |
| 77 | 2-(6-(3,5-dimethylisoxazol-4-yl)-4-((3-methoxypyridin-2-yl)(tetrahydro-2H-pyran-4-yl)methyl)-1-methyl-1,4-dihydropyrazolo[3',4':4,5]pyrrolo[3,2-b]pyridin-3-yl)propan-2-ol; |
| 78 | 2-(4-((3-chloropyridin-2-yl)(tetrahydro-2H-pyran-4-yl)methyl)-6-(3,5-dimethylisoxazol-4-yl)-1-methyl-1,4-dihydropyrazolo[3',4':4,5]pyrrolo[3,2-b]pyridin-3-yl)propan-2-ol; |
| 79 | 2-(6-(3,5-dimethylisoxazol-4-yl)-4-((4-fluoropyridin-2-yl)(tetrahydro-2H-pyran-4-yl)methyl)-1-methyl-1,4-dihydropyrazolo[3',4':4,5]pyrrolo[3,2-b]pyridin-3-yl)propan-2-ol; |
| 80 | 2-(4-((4-chloropyridin-2-yl)(tetrahydro-2H-pyran-4-yl)methyl)-6-(3,5-dimethylisoxazol-4-yl)-1-methyl-1,4-dihydropyrazolo[3',4':4,5]pyrrolo[3,2-b]pyridin-3-yl)propan-2-ol; |
| 81 | 2-(6-(3,5-dimethylisoxazol-4-yl)-4-((5-fluoropyridin-2-yl)(tetrahydro-2H-pyran-4-yl)methyl)-1-methyl-1,4-dihydropyrazolo[3',4':4,5]pyrrolo[3,2-b]pyridin-3-yl)propan-2-ol; |
| 82 | 2-(4-((5-chloropyridin-2-yl)(tetrahydro-2H-pyran-4-yl)methyl)-6-(3,5-dimethylisoxazol-4-yl)-1-methyl-1,4-dihydropyrazolo[3',4':4,5]pyrrolo[3,2-b]pyridin-3-yl)propan-2-ol; |
| 83 | 2-(6-(3,5-dimethylisoxazol-4-yl)-4-((4-methoxypyridin-2-yl)(tetrahydro-2H-pyran-4-yl)methyl)-1-methyl-1,4-dihydropyrazolo[3',4':4,5]pyrrolo[3,2-b]pyridin-3-yl)propan-2-ol; |
| 84 | 2-(6-(3,5-dimethylisoxazol-4-yl)-4-((5-methoxypyridin-2-yl)(tetrahydro-2H-pyran-4-yl)methyl)-1-methyl-1,4-dihydropyrazolo[3',4':4,5]pyrrolo[3,2-b]pyridin-3-yl)propan-2-ol; |
| 85 | 2-(1-methyl-6-(1-methyl-4-(methyl-d3)-1H-1,2,3-triazol-5-yl)-4-(phenyl(tetrahydro-2H-pyran-4-yl)methyl)-1,4-dihydropyrazolo[3',4':4,5]pyrrolo[3,2-b]pyridin-3-yl)propan-2-ol; |

| | -continued |
|---|---|
| 86 | 2-(6-(1,4-dimethyl-1H-1,2,3-triazol-5-yl)-1-methyl-4-((tetrahydro-2H-pyran-4-yl)(o-tolyl)methyl)-1,4-dihydropyrazolo[3',4':4,5]pyrrolo[3,2-b]pyridin-3-yl)propan-2-ol |
| 87 | 2-(6-(1,4-dimethyl-1H-1,2,3-triazol-5-yl)-4-((3-fluorophenyl)(tetrahydro-2H-pyran-4-yl)methyl)-1-methyl-1,4-dihydropyrazolo[3',4':4,5]pyrrolo[3,2-b]pyridin-3-yl)propan-2-ol; |
| 88 | 2-(6-(1,4-dimethyl-1H-1,2,3-triazol-5-yl)-1-methyl-4-((5-methylpyridin-2-yl)(tetrahydro-2H-pyran-4-yl)methyl)-1,4-dihydropyrazolo[3',4':4,5]pyrrolo[3,2-b]pyridin-3-yl)propan-2-ol; |
| 89 | 2-(6-(3,5-dimethylisoxazol-4-yl)-1-methyl-4-((3-methylpyridin-2-yl)(tetrahydro-2H-pyran-4-yl)methyl)-1,4-dihydropyrazolo[3',4':4,5]pyrrolo[3,2-b]pyridin-3-yl)propan-2-ol; |
| 90 | 2-(6-(3,5-dimethylisoxazol-4-yl)-1-methyl-4-((4-methylpyridin-2-yl)(tetrahydro-2H-pyran-4-yl)methyl)-1,4-dihydropyrazolo[3',4':4,5]pyrrolo[3,2-b]pyridin-3-yl)propan-2-ol; |
| 91 | 2-(6-(3,5-dimethylisoxazol-4-yl)-1-methyl-4-((5-methylpyridin-2-yl)(tetrahydro-2H-pyran-4-yl)methyl)-1,4-dihydropyrazolo[3',4':4,5]pyrrolo[3,2-b]pyridin-3-yl)propan-2-ol; |
| 92 | 2-(6-(1,4-dimethyl-1H-1,2,3-triazol-5-yl)-4-((4-fluorophenyl)(tetrahydro-2H-pyran-4-yl)methyl)-1-methyl-1,4-dihydropyrazolo[3',4':4,5]pyrrolo[3,2-b]pyridin-3-yl)propan-2-ol; |
| 93 | 2-(6-(1,4-dimethyl-1H-1,2,3-triazol-5-yl)-1-methyl-4-((tetrahydro-2H-pyran-4-yl)(m-tolyl)methyl)-1,4-dihydropyrazolo[3',4':4,5]pyrrolo[3,2-b]pyridin-3-yl)propan-2-ol; |
| 94 | 2-(6-(1,4-dimethyl-1H-1,2,3-triazol-5-yl)-1-methyl-4-((tetrahydro-2H-pyran-4-yl)(p-tolyl)methyl)-1,4-dihydropyrazolo[3',4':4,5]pyrrolo[3,2-b]pyridin-3-yl)propan-2-ol; |
| 95 | 2-(6-(1,4-dimethyl-1H-1,2,3-triazol-5-yl)-4-((4-methoxyphenyl)(tetrahydro-2H-pyran-4-yl)methyl)-1-methyl-1,4-dihydropyrazolo[3',4':4,5]pyrrolo[3,2-b]pyridin-3-yl)propan-2-ol; |
| 96 | 2-(6-(1,4-dimethyl-1H-1,2,3-triazol-5-yl)-4-((2-fluoro-3-methylphenyl)(tetrahydro-2H-pyran-4-yl)methyl)-1-methyl-1,4-dihydropyrazolo[3',4':4,5]pyrrolo[3,2-b]pyridin-3-yl)propan-2-ol; |
| 97 | 2-(6-(1,4-dimethyl-1H-1,2,3-triazol-5-yl)-4-((3-fluoro-2-methylphenyl)(tetrahydro-2H-pyran-4-yl)methyl)-1-methyl-1,4-dihydropyrazolo[3',4':4,5]pyrrolo[3,2-b]pyridin-3-yl)propan-2-ol; |
| 98 | 2-(6-(1,4-dimethyl-1H-1,2,3-triazol-5-yl)-4-((4-fluoro-3-methylphenyl)(tetrahydro-2H-pyran-4-yl)methyl)-1-methyl-1,4-dihydropyrazolo[3',4':4,5]pyrrolo[3,2-b]pyridin-3-yl)propan-2-ol; |
| 99 | 2-(4-((2,3-difluorophenyl)(tetrahydro-2H-pyran-4-yl)methyl)-6-(1,4-dimethyl-1H-1,2,3-triazol-5-yl)-1-methyl-1,4-dihydropyrazolo[3',4':4,5]pyrrolo[3,2-b]pyridin-3-yl)propan-2-ol; |
| 100 | 2-(4-((2,4-difluorophenyl)(tetrahydro-2H-pyran-4-yl)methyl)-6-(1,4-dimethyl-1H-1,2,3-triazol-5-yl)-1-methyl-1,4-dihydropyrazolo[3',4':4,5]pyrrolo[3,2-b]pyridin-3-yl)propan-2-ol; |
| 101 | 2-(4-((3,4-difluorophenyl)(tetrahydro-2H-pyran-4-yl)methyl)-6-(1,4-dimethyl-1H-1,2,3-triazol-5-yl)-1-methyl-1,4-dihydropyrazolo[3',4':4,5]pyrrolo[3,2-b]pyridin-3-yl)propan-2-ol; |
| 102 | 2-(4-((3-chlorophenyl)(tetrahydro-2H-pyran-4-yl)methyl)-6-(1,4-dimethyl-1H-1,2,3-triazol-5-yl)-1-methyl-1,4-dihydropyrazolo[3',4':4,5]pyrrolo[3,2-b]pyridin-3-yl)propan-2-ol; |
| 103 | 2-(4-((4-chlorophenyl)(tetrahydro-2H-pyran-4-yl)methyl)-6-(1,4-dimethyl-1H-1,2,3-triazol-5-yl)-1-methyl-1,4-dihydropyrazolo[3',4':4,5]pyrrolo[3,2-b]pyridin-3-yl)propan-2-ol; |
| 104 | 2-(6-(1,4-dimethyl-1H-1,2,3-triazol-5-yl)-1-methyl-4-(4,4,4-trifluoro-1-phenylbutyl)-1,4-dihydropyrazolo[3',4':4,5]pyrrolo[3,2-b]pyridin-3-yl)propan-2-ol; |
| 105 | 2-(1-methyl-6-(1-methyl-4-(methyl-d3)-1H-1,2,3-triazol-5-yl)-4-(4,4,4-trifluoro-1-phenylbutyl)-1,4-dihydropyrazolo[3',4':4,5]pyrrolo[3,2-b]pyridin-3-yl)propan-2-ol; |
| 106 | 2-(6-(1,4-dimethyl-1H-1,2,3-triazol-5-yl)-1-methyl-4-(4,4,4-trifluoro-1-(3-fluoropyridin-2-yl)butyl)-1,4-dihydropyrazolo[3',4':4,5]pyrrolo[3,2-b]pyridin-3-yl)propan-2-ol; |
| 107 | 2-(1-methyl-6-(1-methyl-4-(methyl-d3)-1H-1,2,3-triazol-5-yl)-4-(4,4,4-trifluoro-1-(3-methylpyridin-2-yl)butyl)-1,4-dihydropyrazolo[3',4':4,5]pyrrolo[3,2-b]pyridin-3-yl)propan-2-ol; |
| 108 | 2-(1-methyl-6-(1-methyl-4-(methyl-d3)-1H-1,2,3-triazol-5-yl)-4-(4,4,4-trifluoro-1-(oxazol-4-yl)butyl)-1,4-dihydropyrazolo[3',4':4,5]pyrrolo[3,2-b]pyridin-3-yl)propan-2-ol |
| 109 | 1-(6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-yl)cyclopropan-1-ol; |
| 110 | 1-(6-(1,4-dimethyl-1H-1,2,3-triazol-5-yl)-4-((3-fluoropyridin-2-yl)(tetrahydro-2H-pyran-4-yl)methyl)-1-methyl-1,4-dihydropyrazolo[3',4':4,5]pyrrolo[3,2-b]pyridin-3-yl)cyclopropan-1-ol; |
| 111 | 2-(6-(1,4-dimethyl-1H-1,2,3-triazol-5-yl)-1-methyl-4-(4,4,4-trifluoro-1-(oxazol-4-yl)butyl)-1,4-dihydropyrazolo[3',4':4,5]pyrrolo[3,2-b]pyridin-3-yl)propan-2-ol; |
| 112 | 2-(6-(1,4-dimethyl-1H-1,2,3-triazol-5-yl)-1-methyl-4-(4,4,4-trifluoro-1-(5-methyloxazol-4-yl)butyl)-1,4-dihydropyrazolo[3',4':4,5]pyrrolo[3,2-b]pyridin-3-yl)propan-2-ol; |
| 113 | 2-(6-(1,4-dimethyl-1H-1,2,3-triazol-5-yl)-1-methyl-4-(4,4,4-trifluoro-1-(2-methyloxazol-4-yl)butyl)-1,4-dihydropyrazolo[3',4':4,5]pyrrolo[3,2-b]pyridin-3-yl)propan-2-ol; |
| 114 | 2-(6-(1,4-dimethyl-1H-1,2,3-triazol-5-yl)-1-methyl-4-(4,4,4-trifluoro-1-(isoxazol-4-yl)butyl)-1,4-dihydropyrazolo[3',4':4,5]pyrrolo[3,2-b]pyridin-3-yl)propan-2-ol; |
| 115 | 2-(6-(1,4-dimethyl-1H-1,2,3-triazol-5-yl)-1-methyl-4-(4,4,4-trifluoro-1-(5-methylisoxazol-4-yl)butyl)-1,4-dihydropyrazolo[3,4':4,5]pyrrolo[3,2-b]pyridin-3-yl)propan-2-ol; |
| 116 | 2-(6-(1,4-dimethyl-1H-1,2,3-triazol-5-yl)-1-methyl-4-(4,4,4-trifluoro-1-(3-methylisoxazol-4-yl)butyl)-1,4-dihydropyrazolo[3',4':4,5]pyrrolo[3,2-b]pyridin-3-yl)propan-2-ol; |
| 117 | 2-(6-(1,4-dimethyl-1H-1,2,3-triazol-5-yl)-1-methyl-4-((2-methyloxazol-4-yl)(tetrahydro-2H-pyran-4-yl)methyl)-1,4-dihydropyrazolo[3',4':4,5]pyrrolo[3,2-b]pyridin-3-yl)propan-2-ol; |
| 118 | 2-(6-(1,4-dimethyl-1H-1,2,3-triazol-5-yl)-1-methyl-4-((5-methylisoxazol-3-yl)(tetrahydro-2H-pyran-4-yl)methyl)-1,4-dihydropyrazolo[3',4':4,5]pyrrolo[3,2-b]pyridin-3-yl)propan-2-ol; |
| 119 | 2-(6-(1,4-dimethyl-1H-1,2,3-triazol-5-yl)-1-methyl-4-((3-methylisoxazol-5-yl)(tetrahydro-2H-pyran-4-yl)methyl)-1,4-dihydropyrazolo[3',4':4,5]pyrrolo[3,2-b]pyridin-3-yl)propan-2-ol; |
| 120 | 2-(6-(1,4-dimethyl-1H-1,2,3-triazol-5-yl)-1-methyl-4-((5-methylfuran-3-yl)(tetrahydro-2H-pyran-4-yl)methyl)-1,4-dihydropyrazolo[3',4':4,5]pyrrolo[3,2-b]pyridin-3-yl)propan-2-ol; |
| 121 | 2-(6-(1,4-dimethyl-1H-1,2,3-triazol-5-yl)-1-methyl-4-((4-methylfuran-2-yl)(tetrahydro-2H-pyran-4-yl)methyl)-1,4-dihydropyrazolo[3',4':4,5]pyrrolo[3,2-b]pyridin-3-yl)propan-2-ol; |
| 122 | 2-(6-(1,4-dimethyl-1H-1,2,3-triazol-5-yl)-1-methyl-4-((4-methylthiophen-2-yl)(tetrahydro-2H-pyran-4-yl)methyl)-1,4-dihydropyrazolo[3',4':4,5]pyrrolo[3,2-b]pyridin-3-yl)propan-2-ol; |
| 123 | 2-(6-(1,4-dimethyl-1H-1,2,3-triazol-5-yl)-1-methyl-4-((5-methylthiophen-3-yl)(tetrahydro-2H-pyran-4-yl)methyl)-1,4-dihydropyrazolo[3',4':4,5]pyrrolo[3,2-b]pyridin-3-yl)propan-2-ol; |
| 124 | 2-(6-(1,4-dimethyl-1H-1,2,3-triazol-5-yl)-4-((1,4-dimethyl-1H-pyrrol-2-yl)(tetrahydro-2H-pyran-4-yl)methyl)-1-methyl-1,4-dihydropyrazolo[3',4':4,5]pyrrolo[3,2-b]pyridin-3-yl)propan-2-ol; |

| | |
|---|---|
| 125 | 2-(6-(1,4-dimethyl-1H-1,2,3-triazol-5-yl)-4-((1,5-dimethyl-1H-pyrrol-3-yl)(tetrahydro-2H-pyran-4-yl)methyl)-1-methyl-1,4-dihydropyrazolo[3',4':4,5]pyrrolo[3,2-b]pyridin-3-yl)propan-2-ol; |
| 126 | (S)-2-(6-(3,5-dimethylisoxazol-4-yl)-1-methyl-4-(phenyl(tetrahydro-2H-pyran-4-yl)methyl)-1,4-dihydropyrazolo[3',4':4,5]pyrrolo[3,2-b]pyridin-3-yl)propan-2-ol; |
| 127 | 2-(6-(3,5-dimethylisoxazol-4-yl)-1-methyl-4-((tetrahydro-2H-pyran-4-yl)(o-tolyl)methyl)-1,4-dihydropyrazolo[3',4':4,5]pyrrolo[3,2-b]pyridin-3-yl)propan-2-ol; |
| 128 | 6-(1,4-dimethyl-1H-1,2,3-triazol-5-yl)-1-methyl-3-(methylsulfonyl)-4-(phenyl(tetrahydro-2H-pyran-4-yl)methyl)-1,4-dihydropyrazolo[3',4':4,5]pyrrolo[3,2-b]pyridine; |
| 129 | 6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridine-3-sulfonamide; |
| 130 | 6-(1,4-dimethyl-1H-1,2,3-triazol-5-yl)-N,1-dimethyl-4-(phenyl(tetrahydro-2H-pyran-4-yl)methyl)-1,4-dihydropyrazolo[3',4':4,5]pyrrolo[3,2-b]pyridine-3-sulfonamide; |
| 131 | (6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-yl)dimethylphosphine oxide; |
| 132 | 6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridine-3-carboxamide; |
| 133 | 6-(1,4-dimethyl-1H-1,2,3-triazol-5-yl)-N,1-dimethyl-4-(phenyl(tetrahydro-2H-pyran-4-yl)methyl)-1,4-dihydropyrazolo[3',4':4,5]pyrrolo[3,2-b]pyridine-3-carboxamide; |
| 134 | 6-(1,4-dimethyl-1H-1,2,3-triazol-5-yl)-N,N,1-trimethyl-4-(phenyl(tetrahydro-2H-pyran-4-yl)methyl)-1,4-dihydropyrazolo[3',4':4,5]pyrrolo[3,2-b]pyridine-3-carboxamide; |
| 135 | 6-(1,4-dimethyl-1H-1,2,3-triazol-5-yl)-N,N,1-trimethyl-4-(phenyl(tetrahydro-2H-pyran-4-yl)methyl)-1,4-dihydropyrazolo[3',4':4,5]pyrrolo[3,2-b]pyridine-3-sulfonamide; |
| 136 | 1-(3-chloro-6-(1,4-dimethyl-1H-1,2,3-triazol-5-yl)-4-(phenyl(tetrahydro-2H-pyran-4-yl)methyl)pyrazolo[3',4':4,5]pyrrolo[3,2-b]pyridin-1(4H)-yl)-2-methylpropan-2-ol; |
| 137 | 6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-amine; |
| 138 | N-(6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-yl)acetamide; |
| 139 | N-(6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-yl)methanesulfonamide; |
| 140 | 2-(6-(1,4-dimethyl-1H-1,2,3-triazol-5-yl)-1-ethyl-4-(phenyl(tetrahydro-2H-pyran-4-yl)methyl)-1,4-dihydropyrazolo[3',4':4,5]pyrrolo[3,2-b]pyridin-3-yl)propan-2-ol; |
| 141 | 2-(6-(1,4-dimethyl-1H-1,2,3-triazol-5-yl)-1-isopropyl-4-(phenyl(tetrahydro-2H-pyran-4-yl)methyl)-1,4-dihydropyrazolo[3',4':4,5]pyrrolo[3,2-b]pyridin-3-yl)propan-2-ol; |
| 142 | 2-(6-(1,4-dimethyl-1H-1,2,3-triazol-5-yl)-4-(phenyl(tetrahydro-2H-pyran-4-yl)methyl)-1-(2,2,2-trifluoroethyl)-1,4-dihydropyrazolo[3',4':4,5]pyrrolo[3,2-b]pyridin-3-yl)propan-2-ol; |
| 143 | 3-chloro-6-(1,4-dimethyl-1H-1,2,3-triazol-5-yl)-1-(methylsulfonyl)-4-(phenyl(tetrahydro-2H-pyran-4-yl)methyl)-1,4-dihydropyrazolo[3',4':4,5]pyrrolo[3,2-b]pyridine; |
| 144 | 6-(1,4-dimethyl-1H-1,2,3-triazol-5-yl)-3-methyl-1-(methylsulfonyl)-4-(phenyl(tetrahydro-2H-pyran-4-yl)methyl)-1,4-dihydropyrazolo[3',4':4,5]pyrrolo[3,2-b]pyridine; |
| 145 | 2-(6-(3,5-dimethylisoxazol-4-yl)-1-methyl-4-(4,4,4-trifluoro-1-(3-methylpyridin-2-yl)butyl)-1,4-dihydropyrazolo[3',4':4,5]pyrrolo[3,2-b]pyridin-3-yl)propan-2-ol; |
| 146 | 2-(6-(1,4-dimethyl-1H-1,2,3-triazol-5-yl)-4-(phenyl(tetrahydro-2H-pyran-4-yl)methyl)-4H-isoxazolo[5',4':4,5]pyrrolo[3,2-b]pyridin-3-yl)propan-2-ol; |
| 147 | 2-(6-(1,4-dimethyl-1H-1,2,3-triazol-5-yl)-4-((3-fluoropyridin-2-yl)(tetrahydro-2H-pyran-4-yl)methyl)-4H-isoxazolo[5',4':4,5]pyrrolo[3,2-b]pyridin-3-yl)propan-2-ol; |
| 148 | 2-(6-(1,4-dimethyl-1H-1,2,3-triazol-5-yl)-4-((3-methylpyridin-2-yl)(tetrahydro-2H-pyran-4-yl)methyl)-4H-isoxazolo[5',4':4,5]pyrrolo[3,2-b]pyridin-3-yl)propan-2-ol; |
| 149 | 2-(6-(1,4-dimethyl-1H-1,2,3-triazol-5-yl)-4-((3-methoxypyridin-2-yl)(tetrahydro-2H-pyran-4-yl)methyl)-4H-isoxazolo[5',4':4,5]pyrrolo[3,2-b]pyridin-3-yl)propan-2-ol; |
| 150 | 2-(6-(1,4-dimethyl-1H-1,2,3-triazol-5-yl)-4((2-fluorophenyl)(tetrahydro-2H-pyran-4-yl)methyl)-4H-isoxazolo[5',4':4,5]pyrrolo[3,2-b]pyridin-3-yl)propan-2-ol; |
| 151 | 2-(6-(1,4-dimethyl-1H-1,2,3-triazol-5-yl)-4((2-methoxyphenyl)(tetrahydro-2H-pyran-4-yl)methyl)-4H-isoxazolo[5',4':4,5]pyrrolo[3,2-b]pyridin-3-yl)propan-2-ol; |
| 152 | 2-(4-((3-chloropyridin-2-yl)(tetrahydro-2H-pyran-4-yl)methyl)-6-(1,4-dimethyl-1H-1,2,3-triazol-5-yl)-4H-isoxazolo[5',4':4,5]pyrrolo[3,2-b]pyridin-3-yl)propan-2-ol; |
| 153 | 2-(4((2-chlorophenyl)(tetrahydro-2H-pyran-4-yl)methyl)-6-(1,4-dimethyl-1H-1,2,3-triazol-5-yl)-4H-isoxazolo[5',4':4,5]pyrrolo[3,2-b]pyridin-3-yl)propan-2-ol; |
| 154 | 2-(6-(1,4-dimethyl-1H-1,2,3-triazol-5-yl)-4-((4-fluoropyridin-2-yl)(tetrahydro-2H-pyran-4-yl)methyl)-4H-isoxazolo[5',4':4,5]pyrrolo[3,2-b]pyridin-3-yl)propan-2-ol; |
| 155 | 2-(4-((4-chloropyridin-2-yl)(tetrahydro-2H-pyran-4-yl)methyl)-6-(1,4-dimethyl-1H-1,2,3-triazol-5-yl)-4H-isoxazolo[5',4':4,5]pyrrolo[3,2-b]pyridin-3-yl)propan-2-ol; |
| 156 | 2-(6-(1,4-dimethyl-1H-1,2,3-triazol-5-yl)-4-((3-methoxyphenyl)(tetrahydro-2H-pyran-4-yl)methyl)-4H-isoxazolo[5',4':4,5]pyrrolo[3,2-b]pyridin-3-yl)propan-2-ol; |
| 157 | 2-(6-(1,4-dimethyl-1H-1,2,3-triazol-5-yl)-4-((4-methylpyridin-2-yl)(tetrahydro-2H-pyran-4-yl)methyl)-4H-isoxazolo[5',4':4,5]pyrrolo[3,2-1]pyridin-3-yl)propan-2-ol; |
| 158 | 2-(6-(1,4-dimethyl-1H-1,2,3-triazol-5-yl)-4-((5-fluoropyridin-2-yl)(tetrahydro-2H-pyran-4-yl)methyl)-4H-isoxazolo[5',4':4,5]pyrrolo[3,2-b]pyridin-3-yl)propan-2-ol; |
| 159 | 2-(4-((5-chloropyridin-2-yl)(tetrahydro-2H-pyran-4-yl)methyl)-6-(1,4-dimethyl-1H-1,2,3-triazol-5-yl)-4H-isoxazolo[5',4':4,5]pyrrolo[3,2-b]pyridin-3-yl)propan-2-ol; |
| 160 | 2-(6-(1,4-dimethyl-1H-1,2,3-triazol-5-yl)-4-((4-methoxypyridin-2-yl)(tetrahydro-2H-pyran-4-yl)methyl)-4H-isoxazolo[5',4':4,5]pyrrolo[3,2-b]pyridin-3-yl)propan-2-ol; |
| 161 | 2-(6-(1,4-dimethyl-1H-1,2,3-triazol-5-yl)-4-((5-methoxypyridin-2-yl)(tetrahydro-2H-pyran-4-yl)methyl)-4H-isoxazolo[5',4':4,5]pyrrolo[3,2-b]pyridin-3-yl)propan-2-ol; |
| 162 | 2-(6-(3,5-dimethylisoxazol-4-yl)-4-((3-fluoropyridin-2-yl)(tetrahydro-2H-pyran-4-yl)methyl)-4H-isoxazolo[5',4':4,5]pyrrolo[3,2-b]pyridin-3-yl)propan-2-ol; |
| 163 | 2-(6-(3,5-dimethylisoxazol-4-yl)-4-((3-methoxypyridin-2-yl)(tetrahydro-2H-pyran-4-yl)methyl)-4H-isoxazolo[5',4':4,5]pyrrolo[3,2-b]pyridin-3-yl)propan-2-ol; |

| | |
|---|---|
| 164 | 2-(4-((3-chloropyridin-2-yl)(tetrahydro-2H-pyran-4-yl)methyl)-6-(3,5-dimethylisoxazol-4-yl)-4H-isoxazolo[5',4':4,5]pyrrolo[3,2-b]pyridin-3-yl)propan-2-ol; |
| 165 | 2-(6-(3,5-dimethylisoxazol-4-yl)-4-((4-fluoropyridin-2-yl)(tetrahydro-2H-pyran-4-yl)methyl)-4H-isoxazolo[5',4':4,5]pyrrolo[3,2-b]pyridin-3-yl)propan-2-ol; |
| 166 | 2-(4-((4-chloropyridin-2-yl)(tetrahydro-2H-pyran-4-yl)methyl)-6-(3,5-dimethylisoxazol-4-yl)-4H-isoxazolo[5',4':4,5]pyrrolo[3,2-b]pyridin-3-yl)propan-2-ol; |
| 167 | 2-(6-(3,5-dimethylisoxazol-4-yl)-4-((5-fluoropyridin-2-yl)(tetrahydro-2H-pyran-4-yl)methyl)-4H-isoxazolo[5',4':4,5]pyrrolo[3,2-b]pyridin-3-yl)propan-2-ol; |
| 168 | 2-(4-((5-chloropyridin-2-yl)(tetrahydro-2H-pyran-4-yl)methyl)-6-(3,5-dimethylisoxazol-4-yl)-4H-isoxazolo[5',4':4,5]pyrrolo[3,2-b]pyridin-3-yl)propan-2-ol; |
| 169 | 2-(6-(3,5-dimethylisoxazol-4-yl)-4-((4-methoxypyridin-2-yl)(tetrahydro-2H-pyran-4-yl)methyl)-4H-isoxazolo[5',4':4,5]pyrrolo[3,2-b]pyridin-3-yl)propan-2-ol; |
| 170 | 2-(6-(3,5-dimethylisoxazol-4-yl)-4-((5-methoxypyridin-2-yl)(tetrahydro-2H-pyran-4-yl)methyl)-4H-isoxazolo[5',4':4,5]pyrrolo[3,2-b]pyridin-3-yl)propan-2-ol; |
| 171 | 2-(6-(1-methyl-4-(methyl-d3)-1H-1,2,3-triazol-5-yl)-4-(phenyl(tetrahydro-2H-pyran-4-yl)methyl)-4H-isoxazolo[5',4':4,5]pyrrolo[3,2-b]pyridin-3-yl)propan-2-ol; |
| 172 | 2-(6-(1,4-dimethyl-1H-1,2,3-triazol-5-yl)-4-((tetrahydro-2H-pyran-4-yl)(o-tolyl)methyl)-4H-isoxazolo[5',4':4,5]pyrrolo[3,2-b]pyridin-3-yl)propan-2-ol; |
| 173 | 2-(6-(1,4-dimethyl-1H-1,2,3-triazol-5-yl)-4-((3-fluorophenyl)(tetrahydro-2H-pyran-4-yl)methyl)-4H-isoxazolo[5',4':4,5]pyrrolo[3,2-b]pyridin-3-yl)propan-2-ol; |
| 174 | 2-(6-(1,4-dimethyl-1H-1,2,3-triazol-5-yl)-4-((5-methylpyridin-2-yl)(tetrahydro-2H-pyran-4-yl)methyl)-4H-isoxazolo[5',4':4,5]pyrrolo[3,2-b]pyridin-3-yl)propan-2-ol; |
| 175 | 2-(6-(3,5-dimethylisoxazol-4-yl)-4-((3-methylpyridin-2-yl)(tetrahydro-2H-pyran-4-yl)methyl)-4H-isoxazolo[5',4':4,5]pyrrolo[3,2-b]pyridin-3-yl)propan-2-ol; |
| 176 | 2-(6-(3,5-dimethylisoxazol-4-yl)-4-((4-methylpyridin-2-yl)(tetrahydro-2H-pyran-4-yl)methyl)-4H-isoxazolo[5',4':4,5]pyrrolo[3,2-b]pyridin-3-yl)propan-2-ol; |
| 177 | 2-(6-(3,5-dimethylisoxazol-4-yl)-4-((5-methylpyridin-2-yl)(tetrahydro-2H-pyran-4-yl)methyl)-4H-isoxazolo[5',4':4,5]pyrrolo[3,2-b]pyridin-3-yl)propan-2-ol; |
| 178 | 2-(6-(1,4-dimethyl-1H-1,2,3-triazol-5-yl)-4-((4-fluorophenyl)(tetrahydro-2H-pyran-4-yl)methyl)-4H-isoxazolo[5',4':4,5]pyrrolo[3,2-b]pyridin-3-yl)propan-2-ol; |
| 179 | 2-(6-(1,4-dimethyl-1H-1,2,3-triazol-5-yl)-4-((tetrahydro-2H-pyran-4-yl)(m-tolyl)methyl)-4H-isoxazolo[5',4':4,5]pyrrolo[3,2-b]pyridin-3-yl)propan-2-ol; |
| 180 | 2-(6-(1,4-dimethyl-1H-1,2,3-triazol-5-yl)-4-((tetrahydro-2H-pyran-4-yl)(p-tolyl)methyl)-4H-isoxazolo[5',4':4,5]pyrrolo[3,2-b]pyridin-3-yl)propan-2-ol; |
| 181 | 2-(6-(1,4-dimethyl-1H-1,2,3-triazol-5-yl)-4-((4-methoxyphenyl)(tetrahydro-2H-pyran-4-yl)methyl)-4H-isoxazolo[5',4':4,5]pyrrolo[3,2-b]pyridin-3-yl)propan-2-ol; |
| 182 | 2-(6-(1,4-dimethyl-1H-1,2,3-triazol-5-yl)-4-((2-fluoro-3-methylphenyl)(tetrahydro-2H-pyran-4-yl)methyl)-4H-isoxazolo[5',4':4,5]pyrrolo[3,2-b]pyridin-3-yl)propan-2-ol; |
| 183 | 2-(6-(1,4-dimethyl-1H-1,2,3-triazol-5-yl)-4-((3-fluoro-2-methylphenyl)(tetrahydro-2H-pyran-4-yl)methyl)-4H-isoxazolo[5',4':4,5]pyrrolo[3,2-b]pyridin-3-yl)propan-2-ol; |
| 184 | 2-(6-(1,4-dimethyl-1H-1,2,3-triazol-5-yl)-4-((4-fluoro-3-methylphenyl)(tetrahydro-2H-pyran-4-yl)methyl)-4H-isoxazolo[5',4':4,5]pyrrolo[3,2-b]pyridin-3-yl)propan-2-ol; |
| 185 | 2-(4-((2,3-difluorophenyl)(tetrahydro-2H-pyran-4-yl)methyl)-6-(1,4-dimethyl-1H-1,2,3-triazol-5-yl)-4H-isoxazolo[5',4':4,5]pyrrolo[3,2-b]pyridin-3-yl)propan-2-ol; |
| 186 | 2-(4-((2,4-difluorophenyl)(tetrahydro-2H-pyran-4-yl)methyl)-6-(1,4-dimethyl-1H-1,2,3-triazol-5-yl)-4H-isoxazolo[5',4':4,5]pyrrolo[3,2-b]pyridin-3-yl)propan-2-ol; |
| 187 | 2-(4-((3,4-difluorophenyl)(tetrahydro-2H-pyran-4-yl)methyl)-6-(1,4-dimethyl-1H-1,2,3-triazol-5-yl)-4H-isoxazolo[5',4':4,5]pyrrolo[3,2-b]pyridin-3-yl)propan-2-ol; |
| 188 | 2-(4-((3-chlorophenyl)(tetrahydro-2H-pyran-4-yl)methyl)-6-(1,4-dimethyl-1H-1,2,3-triazol-5-yl)-4H-isoxazolo[5',4':4,5]pyrrolo[3,2-b]pyridin-3-yl)propan-2-ol; |
| 189 | 2-(4-((4-chlorophenyl)(tetrahydro-2H-pyran-4-yl)methyl)-6-(1,4-dimethyl-1H-1,2,3-triazol-5-yl)-4H-isoxazolo[5',4':4,5]pyrrolo[3,2-b]pyridin-3-yl)propan-2-ol; |
| 190 | 2-(6-(1,4-dimethyl-1H-1,2,3-triazol-5-yl)-4-(4,4,4-trifluoro-1-phenylbutyl)-4H-isoxazolo[5',4':4,5]pyrrolo[3,2-b]pyridin-3-yl)propan-2-ol; |
| 191 | 2-(6-(1-methyl-4-(methyl-d3)-1H-1,2,3-triazol-5-yl)-4-(4,4,4-trifluoro-1-phenylbutyl)-4H-isoxazolo[5',4':4,5]pyrrolo[3,2-b]pyridin-3-yl)propan-2-ol; |
| 192 | 2-(6-(1,4-dimethyl-1H-1,2,3-triazol-5-yl)-4-(4,4,4-trifluoro-1-(3-fluoropyridin-2-yl)butyl)-4H-isoxazolo[5',4':4,5]pyrrolo[3,2-b]pyridin-3-yl)propan-2-ol; |
| 193 | 2-(6-(1-methyl-4-(methyl-d3)-1H-1,2,3-triazol-5-yl)-4-(4,4,4-trifluoro-1-(3-methylpyridin-2-yl)butyl)-4H-isoxazolo[5',4':4,5]pyrrolo[3,2-b]pyridin-3-yl)propan-2-ol; |
| 194 | 2-(6-(1,4-dimethyl-1H-1,2,3-triazol-5-yl)-4-(4,4,4-trifluoro-1-(oxazol-4-yl)butyl)-4H-isoxazolo[5',4':4,5]pyrrolo[3,2-b]pyridin-3-yl)propan-2-ol; |
| 195 | 2-(6-(1-methyl-4-(methyl-d3)-1H-1,2,3-triazol-5-yl)-4-(4,4,4-trifluoro-1-(oxazol-4-yl)butyl)-4H-isoxazolo[5',4':4,5]pyrrolo[3,2-b]pyridin-3-yl)propan-2-ol; |
| 196 | 1-(6-(1,4-dimethyl-1H-1,2,3-triazol-5-yl)-4-(phenyl(tetrahydro-2H-pyran-4-yl)methyl)-4H-isoxazolo[5',4':4,5]pyrrolo[3,2-b]pyridin-3-yl)cyclopropan-1-ol; |
| 197 | 1-(6-(1,4-dimethyl-1H-1,2,3-triazol-5-yl)-4-((3-fluoropyridin-2-yl)(tetrahydro-2H-pyran-4-yl)methyl)-4H-isoxazolo[5',4':4,5]pyrrolo[3,2-b]pyridin-3-yl)cyclopropan-1-ol; |
| 198 | 2-(6-(1,4-dimethyl-1H-1,2,3-triazol-5-yl)-4-(4,4,4-trifluoro-1-(5-methyloxazol-4-yl)butyl)-4H-isoxazolo[5',4':4,5]pyrrolo[3,2-b]pyridin-3-yl)propan-2-ol; |
| 199 | 2-(6-(1,4-dimethyl-1H-1,2,3-triazol-5-yl)-4-(4,4,4-trifluoro-1-(2-methyloxazol-4-yl)butyl)-4H-isoxazolo[5',4':4,5]pyrrolo[3,2-b]pyridin-3-yl)propan-2-ol; |
| 200 | 2-(6-(1,4-dimethyl-1H-1,2,3-triazol-5-yl)-4-(4,4,4-trifluoro-1-(isoxazol-4-yl)butyl)-4H-isoxazolo[5',4':4,5]pyrrolo[3,2-b]pyridin-3-yl)propan-2-ol; |
| 201 | 2-(6-(1,4-dimethyl-1H-1,2,3-triazol-5-yl)-4-(4,4,4-trifluoro-1-(5-methylisoxazol-4-yl)butyl)-4H-isoxazolo[5',4':4,5]pyrrolo[3,2-b]pyridin-3-yl)propan-2-ol; |
| 202 | 2-(6-(1,4-dimethyl-1H-1,2,3-triazol-5-yl)-4-(4,4,4-trifluoro-1-(3-methylisoxazol-4-yl)butyl)-4H-isoxazolo[5',4':4,5]pyrrolo[3,2-b]pyridin-3-yl)propan-2-ol; |

| | -continued |
|---|---|
| 203 | 2-(6-(1,4-dimethyl-1H-1,2,3-triazol-5-yl)-4-((2-methyloxazol-4-yl)(tetrahydro-2H-pyran-4-yl)methyl)-4H-isoxazolo[5',4':4,5]pyrrolo[3,2-b]pyridin-3-yl)propan-2-ol; |
| 204 | 2-(6-(1,4-dimethyl-1H-1,2,3-triazol-5-yl)-4-((5-methylisoxazol-3-yl)(tetrahydro-2H-pyran-4-yl)methyl)-4H-isoxazolo[5',4':4,5]pyrrolo[3,2-b]pyridin-3-yl)propan-2-ol; |
| 205 | 2-(6-(1,4-dimethyl-1H-1,2,3-triazol-5-yl)-4-((3-methylisoxazol-5-yl)(tetrahydro-2H-pyran-4-yl)methyl)-4H-isoxazolo[5',4':4,5]pyrrolo[3,2-b]pyridin-3-yl)propan-2-ol; |
| 206 | 2-(6-(1,4-dimethyl-1H-1,2,3-triazol-5-yl)-4-((5-methylfuran-3-yl)(tetrahydro-2H-pyran-4-yl)methyl)-4H-isoxazolo[5',4':4,5]pyrrolo[3,2-b]pyridin-3-yl)propan-2-ol; |
| 207 | 2-(6-(1,4-dimethyl-1H-1,2,3-triazol-5-yl)-4-((4-methylfuran-2-yl)(tetrahydro-2H-pyran-4-yl)methyl)-4H-isoxazolo[5',4':4,5]pyrrolo[3,2-b]pyridin-3-yl)propan-2-ol; |
| 208 | (S)-2-(6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-yl)propan-2-ol; |
| 209 | 2-(6-(1,4-dimethyl-1H-1,2,3-triazol-5-yl)-1-methyl-4-(4,4,4-trifluoro-1-(3-methylpyridin-2-yl)butyl)-1,4-dihydropyrazolo[3',4':4,5]pyrrolo[3,2-b]pyridin-3-yl)propan-2-ol; |
| 210 | 2-(6-(1,4-dimethyl-1H-1,2,3-triazol-5-yl)-4-((3-fluoropyridin-2-yl)(tetrahydro-2H-pyran-4-yl)methyl)-1-methyl-1,4-dihydropyrazolo[3',4':4,5]pyrrolo[3,2-b]pyridine-3-yl)propan-2-ol; |
| 211 | 2-(6-(3,5-dimethylisoxazol-4-yl)-4-((3-fluoropyridin-2-yl)(tetrahydro-2H-pyran-4-yl)methyl)-1-methyl-1,4-dihydropyrazolo[3',4':4,5]pyrrolo[3,2-b]pyridin-3-yl)propan-2-ol; |
| 212 | 6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridine; |
| 213 | 3-bromo-6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridine; |
| 214 | 1-(6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-yl)-4,4-dimethylimidazolidin-2-one; |
| 215 | 6-(1,4-dimethyl-1H-1,2,3-triazol-5-yl)-1-methyl-4-(phenyl(tetrahydro-2H-pyran-4-yl)methyl)-3-(piperazin-1-yl)-1,4-dihydropyrazolo[3',4':4,5]pyrrolo[3,2-b]pyridine |
| 216 | 6-(1,4-dimethyl-1H-1,2,3-triazol-5-yl)-1-methyl-3-(4-methylpiperazin-1-yl)-4-(phenyl(tetrahydro-2H-pyran-4-yl)methyl)-1,4-dihydropyrazolo[3',4':4,5]pyrrolo[3,2-b]pyridine; |
| 217 | 6-(1,4-dimethyl-1H-1,2,3-triazol-5-yl)-1-methyl-3-(4-(oxetan-3-yl)piperazin-1-yl)-4-(phenyl(tetrahydro-2H-pyran-4-yl)methyl)-1,4-dihydropyrazolo[3',4':4,5]pyrrolo[3,2-b]pyridine; |
| 218 | 6-(1,4-dimethyl-1H-1,2,3-triazol-5-yl)-3-(4-isopropylpiperazin-1-yl)-1-methyl-4-(phenyl(tetrahydro-2H-pyran-4-yl)methyl)-1,4-dihydropyrazolo[3',4':4,5]pyrrolo[3,2-b]pyridine; |
| 219 | (3R)-1-(6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-yl)-N-methylpyrrolidin-3-amine; |
| 220 | 1-(6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-yl)imidazolidin-2-one; |
| 221 | 1-(6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-yl)-3-methylimidazolidin-2-one; |
| 222 | methyl 6-(1,4-dimethyl-1H-1,2,3-triazol-5-yl)-4-(phenyl(tetrahydro-2H-pyran-4-yl)methyl)-1,4-dihydropyrazolo[3',4':4,5]pyrrolo[3,2-b]pyridine-3-carboxylate; |
| 223 | 2-(1-cyclopropyl-6-(1,4-dimethyl-1H-1,2,3-triazol-5-yl)-4-(phenyl(tetrahydro-2H-pyran-4-yl)methyl)-1,4-dihydropyrazolo[3',4':4,5]pyrrolo[3,2-b]pyridin-3-yl)propan-2-ol; |
| 224 | 2-(1-(difluoromethyl)-6-(1,4-dimethyl-1H-1,2,3-triazol-5-yl)-4-(phenyl(tetrahydro-2H-pyran-4-yl)methyl)-1,4-dihydropyrazolo[3',4':4,5]pyrrolo[3,2-b]pyridin-3-yl)propan-2-ol; |
| 225 | 2-(1-(2,2-difluoroethyl)-6-(1,4-dimethyl-1H-1,2,3-triazol-5-yl)-4-(phenyl(tetrahydro-2H-pyran-4-yl)methyl)-1,4-dihydropyrazolo[3',4':4,5]pyrrolo[3,2-b]pyridin-3-yl)propan-2-ol; |
| 226 | 2-(6-(1,4-dimethyl-1H-1,2,3-triazol-5-yl)-4-(phenyl(tetrahydro-2H-pyran-4-yl)methyl)-1-(2,2,2-trifluoroethyl)-1,4-dihydropyrazolo[3',4':4,5]pyrrolo[3,2-b]pyridin-3-yl)propan-2-ol; |
| 227 | 2-(6-(1,4-dimethyl-1H-1,2,3-triazol-5-yl)-1-(methyl-d3)-4-(phenyl(tetrahydro-2H-pyran-4-yl)methyl)-1,4-dihydropyrazolo[3,4':4,5]pyrrolo[3,2-b]pyridin-3-yl)propan-2-ol; |
| 228 | 2-(6-(1,4-dimethyl-1H-1,2,3-triazol-5-yl)-1-(2-hydroxyethyl)-4-(phenyl(tetrahydro-2H-pyran-4-yl)methyl)-1,4-dihydropyrazolo[3',4':4,5]pyrrolo[3,2-b]pyridin-3-yl)propan-2-ol; |
| 229 | 2-(6-(1,4-dimethyl-1H-1,2,3-triazol-5-yl)-1-ethyl-4-(phenyl(tetrahydro-2H-pyran-4-yl)methyl)-1,4-dihydropyrazolo[3',4':4,5]pyrrolo[3,2-b]pyridin-3-yl)propan-2-ol; |
| 230 | 2-(6-(1,4-dimethyl-1H-1,2,3-triazol-5-yl)-1-(2-(dimethylamino)ethyl)-4-(phenyl(tetrahydro-2H-pyran-4-yl)methyl)-1,4-dihydropyrazolo[3',4':4,5]pyrrolo[3,2-b]pyridin-3-yl)propan-2-ol; or |
| 231 | 2-(6-(1,4-dimethyl-1H-1,2,3-triazol-5-yl)-1-(methylsulfonyl)-4-(phenyl(tetrahydro-2H-pyran-4-yl)methyl)-1,4-dihydropyrazolo[3',4':4,5]pyrrolo[3,2-b]pyridin-3-yl)propan-2-ol. |

In some embodiments, the compounds further is:

| 232 | 2-(6-(1,4-Dimethyl-1H-1,2,3-triazol-5-yl)-4-((3-fluoropyridin-2-yl)(tetrahydro-2H-pyran-4-yl)methyl)-1,4-dihydropyrazolo[3',4':4,5]pyrrolo[3,2-b]pyridin-3-yl)propan-2-ol; |
|---|---|
| 233 | 2-(4-((3-Fluoropyridin-2-yl)(tetrahydro-2H-pyran-4-yl)methyl)-1-(methyl-d3)-6-(1-methyl-4-(methyl-d3)-1H-1,2,3-triazol-5-yl)-1,4-dihydropyrazolo[3',4':4,5]pyrrolo[3,2-b]pyridin-3-yl)propan-2-ol; |
| 234 | 2-(6-(1,4-Dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-yl)propan-2-amine; |

-continued

| | |
|---|---|
| 235 | 3-(6-(1,4-Dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-yl)pentan-3-ol; |
| 236 | 6-(1,4-Dimethyl-1H-1,2,3-triazol-5-yl)-4((3-fluoropyridin-2-yl)(tetrahydro-2H-pyran-4-yl)methyl)-1-methyl-1,4-dihydropyrazolo[3',4':4,5]pyrrolo[3,2-b]pyridine-3-carboxylicacid; |
| 237 | 6-(1,4-Dimethyl-1H-1,2,3-triazol-5-yl)-4((3-fluoropyridin-2-yl)(tetrahydro-2H-pyran-4-yl)methyl)-1-methyl-1,4-dihydropyrazolo[3',4':4,5]pyrrolo[3,2-b]pyridine-3-carboxamide; |
| 238 | 2-(6-(1,4-Dimethyl-1H-1,2,3-triazol-5-yl)-4-((4-methylpyridin-3-yl)(tetrahydro-2H-pyran-4-yl)methyl)-1-methyl-1,4-dihydropyrazolo[3',4':4,5]pyrrolo[3,2-b]pyridin-3-yl)propan-2-ol; |
| 239 | 2-(4-((3-Fluoropyridin-2-yl)(tetrahydro-2H-pyran-4-yl)methyl)-1-methyl-6-(1-methyl-4-(methyl-d3)-1H-1,2,3-triazol-5-yl)-1,4-dihydropyrazolo[3',4':4,5]pyrrolo[3,2-b]pyridin-3-yl)propan-2-ol; |
| 240 | 2-(6-(1,4-Dimethyl-1H-1,2,3-triazol-5-yl)-4-((3-fluoropyridin-4-yl)(tetrahydro-2H-pyran-4-yl)methyl)-1-methyl-1,4-dihydropyrazolo[3',4':4,5]pyrrolo[3,2-b]pyridin-3-yl)propan-2-ol; |
| 241 | 2-(6-(1,4-dimethyl-1H-1,2,3-triazol-5-yl)-4-((4-methoxypyridin-3-yl)(tetrahydro-2H-pyran-4-yl)methyl)-1-methyl-1,4-dihydropyrazolo[3',4':4,5]pyrrolo[3,2-b]pyridin-3-yl)propan-2-ol; |
| 242 | 2-(6-(1,4-Dimethyl-1H-1,2,3-triazol-5-yl)-4-(1-(4-fluoro-2,6-dimethylphenyl)ethyl)-1-methyl-1,4-dihydropyrazolo[3',4':4,5]pyrrolo[3,2-b]pyridin-3-yl)propan-2-ol; |
| 243 | (S)-N-(6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-yl)methanesulfonamide; |
| 244 | (S)-N-(6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-yl)acetamide; |
| 245 | Methyl 6-(1,4-dimethyl-1H-1,2,3-triazol-5-yl)-4-((3-fluoropyridin-2-yl)(tetrahydro-2H-pyran-4-yl)methyl)-1-methyl-1,4-dihydropyrazolo[3',4':4,5]pyrrolo[3,2-b]pyridine-3-carboxylate; |
| 246 | 2-(6-(3,5-dimethylisoxazol-4-yl)-1-methyl-4-(phenyl(tetrahydro-2H-pyran-4-yl)methyl)-1,4-dihydropyrazolo[3',4':4,5]pyrrolo[3,2-b]pyridin-3-yl)propan-2-ol; |
| 247 | (S)-2-(6-(3,5-dimethylisoxazol-4-yl)-4-((3-fluoropyridin-2-yl)(tetrahydro-2H-pyran-4-yl)methyl)-1-methyl-1,4-dihydropyrazolo[3',4':4,5]pyrrolo[3,2-b]pyridin-3-yl)propan-2-ol; |
| 248 | (S)-2-(6-(1,4-dimethyl-1H-1,2,3-triazol-5-yl)-1-methyl-4-(4,4,4-trifluoro-1-phenylbutyl)-1,4-dihydropyrazolo[3',4':4,5]pyrrolo[3,2-b]pyridin-3-yl)propan-2-ol; |
| 249 | (S)-2-(6-(1,4-dimethyl-1H-1,2,3-triazol-5-yl)-1-methyl-4-(4,4,4-trifluoro-1-(3-fluoropyridin-2-yl)butyl)-1,4-dihydropyrazolo[3',4':4,5]pyrrolo[3,2-b]pyridin-3-yl)propan-2-ol; |
| 250 | (S)-2-(6-(1,4-dimethyl-1H-1,2,3-triazol-5-yl)-1-methyl-4-((3-methylpyridin-2-yl)(tetrahydro-2H-pyran-4-yl)methyl)-1,4-dihydropyrazolo[3',4':4,5]pyrrolo[3,2-b]pyridin-3-yl)propan-2-ol; |
| 251 | 2-(6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-yl)propan-2-ol; |
| 252 | (S)-2-(6-(1,4-dimethyl-1H-1,2,3-triazol-5-yl)-4-((3-fluoropyridin-2-yl)(tetrahydro-2H-pyran-4-yl)methyl)-1-methyl-1,4-dihydropyrazolo[3',4':4,5]pyrrolo[3,2-b]pyridin-3-yl)propan-2-ol; |
| 253 | (S)-2-(6-(3,5-dimethylisoxazol-4-yl)-1-methyl-4-((3-methylpyridin-2-yl)(tetrahydro-2H-pyran-4-yl)methyl)-1,4-dihydropyrazolo[3',4':4,5]pyrrolo[3,2-b]pyridin-3-yl)propan-2-ol; |
| 254 | (S)-2-(6-(3,5-dimethylisoxazol-4-yl)-1-methyl-4-((tetrahydro-2H-pyran-4-yl)(o-tolyl)methyl)-1,4-dihydropyrazolo[3',4':4,5]pyrrolo[3,2-b]pyridin-3-yl)propan-2-ol; |
| 255 | (S)-2-(6-(1,4-dimethyl-1H-1,2,3-triazol-5-yl)-1-methyl-4-(4,4,4-trifluoro-1-(oxazol-4-yl)butyl)-1,4-dihydropyrazolo[3',4':4,5]pyrrolo[3,2-b]pyridin-3-yl)propan-2-ol; |
| 256 | (S)-2-(6-(1,4-dimethyl-1H-1,2,3-triazol-5-yl)-1-methyl-4-(4,4,4-trifluoro-1-(3-methylpyridin-2-yl)butyl)-1,4-dihydropyrazolo[3',4':4,5]pyrrolo[3,2-b]pyridin-3-yl)propan-2-ol; |
| 257 | (S)-2-(6-(1,4-dimethyl-1H-1,2,3-triazol-5-yl)-1-methyl-4-((2-methyloxazol-4-yl)(tetrahydro-2H-pyran-4-yl)methyl)-1,4-dihydropyrazolo[3',4':4,5]pyrrolo[3,2-b]pyridin-3-yl)propan-2-ol; |
| 258 | (S)-2-(6-(1,4-Dimethyl-1H-1,2,3-triazol-5-yl)-4-((3-fluoropyridin-2-yl)(tetrahydro-2H-pyran-4-yl)methyl)-1,4-dihydropyrazolo[3',4':4,5]pyrrolo[3,2-b]pyridin-3-yl)propan-2-ol; |
| 259 | (S)-2-(4-43-Fluoropyridin-2-yl)(tetrahydro-2H-pyran-4-yl)methyl)-1-(methyl-d3)-6-(1-methyl-4-(methyl-d3)-1H-1,2,3-triazol-5-yl)-1,4-dihydropyrazolo[3',4':4,5]pyrrolo[3,2-b]pyridin-3-yl)propan-2-ol; |
| 260 | (S)-6-(1,4-dimethyl-1H-1,2,3-triazol-5-yl)-N,N,1-trimethyl-4-(phenyl(tetrahydro-2H-pyran-4-yl)methyl)-1,4-dihydropyrazolo[3',4':4,5]pyrrolo[3,2-b]pyridine-3-carboxamide; |
| 261 | (S)-6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridine-3-carboxamide; |
| 262 | (S)-6-(1,4-dimethyl-1H-1,2,3-triazol-5-yl)-N,1-dimethyl-4-(phenyl(tetrahydro-2H-pyran-4-yl)methyl)-1,4-dihydropyrazolo[3',4':4,5]pyrrolo[3,2-b]pyridine-3-carboxamide; |
| 263 | (S)-2-(6-(1,4-Dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-yl)propan-2-amine; |
| 264 | (S)-3-(6-(1,4-Dimethyl-1H-1,2,3-triazol-5-yl)-1-methyl-4-(phenyl(tetrahydro-2H-pyran-4-yl)methyl)-1,4-dihydropyrazolo[3,4':4,5]pyrrolo[3,2-b]pyridin-3-yl)pentan-3-ol; |
| 265 | (S)-6-(1,4-Dimethyl-1H-1,2,3-triazol-5-yl)-4-((3-fluoropyridin-2-yl)(tetrahydro-2H-pyran-4-yl)methyl)-1-methyl-1,4-dihydropyrazolo[3',4':4,5]pyrrolo[3,2-b]pyridine-3-carboxylic acid; |
| 266 | (S)-6-(1,4-Dimethyl-1H-1,2,3-triazol-5-yl)-4-((3-fluoropyridin-2-yl)(tetrahydro-2H-pyran-4-yl)methyl)-1-methyl-1,4-dihydropyrazolo[3',4':4,5]pyrrolo[3,2-b]pyridine-3-carboxamide; |
| 267 | (S)-2-(6-(1,4-Dimethyl-1H-1,2,3-triazol-5-yl)-4-((4-methylpyridin-3-yl)(tetrahydro-2H-pyran-4-yl)methyl)-1-methyl-1,4-dihydropyrazolo[3',4':4,5]pyrrolo[3,2-b]pyridin-3-yl)propan-2-ol; |
| 268 | (S)-2-(4-((3-Fluoropyridin-2-yl)(tetrahydro-2H-pyran-4-yl)methyl)-1-methyl-6-(1-methyl-4-(methyl-d3)-1H-1,2,3-triazol-5-yl)-1,4-dihydropyrazolo[3',4':4,5]pyrrolo[3,2-b]pyridin-3-yl)propan-2-ol; |
| 269 | (S)-2-(6-(1,4-Dimethyl-1H-1,2,3-triazol-5-yl)-4-((3-fluoropyridin-4-yl)(tetrahydro-2H-pyran-4-yl)methyl)-1-methyl-1,4-dihydropyrazolo[3',4':4,5]pyrrolo[3,2-b]pyridin-3-yl)propan-2-ol; |
| 270 | (S)-2-(6-(1,4-dimethyl-1H-1,2,3-triazol-5-yl)-4-((4-methoxypyridin-3-yl)(tetrahydro-2H-pyran-4-yl)methyl)-1-methyl-1,4-dihydropyrazolo[3',4':4,5]pyrrolo[3,2-b]pyridin-3-yl)propan-2-ol; |
| 271 | (S)-2-(6-(1,4-dimethyl-1H-1,2,3-triazol-5-yl)-4-((3-methoxypyridin-2-yl)(tetrahydro-2H-pyran-4-yl)methyl)-1-methyl-1,4-dihydropyrazolo[3',4':4,5]pyrrolo[3,2-b]pyridin-3-yl)propan-2-ol; |

| 272 | (S)-2-(6-(1,4-Dimethyl-1H-1,2,3-triazol-5-yl)-4-(1-(4-fluoro-2,6-dimethylphenyl)ethyl)-1-methyl-1,4-dihydropyrazolo[3',4':4,5]pyrrolo[3,2-b]pyridin-3-yl)propan-2-ol; |
| --- | --- |
| 273 | (S)-N-(6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-yl)methanesulfonamide; |
| 274 | N-(6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-yl)acetamide; or |
| 275 | (S)-Methyl 6-(1,4-dimethyl-1H-1,2,3-triazol-5-yl)-4-((3-fluoropyridin-2-yl)(tetrahydro-2H-pyran-4-yl)methyl)-1-methyl-1,4-dihydropyrazolo[3',4':4,5]pyrrolo[3,2-b]pyridine-3-carboxylate. |

In some embodiments, the compounds further is:

| 276 | 6-(1,4-dimethyl-1H-1,2,3-triazol-5-yl)-1-methyl-3-((4-methylpiperazin-1-yl)methyl)-4-(phenyl(tetrahydro-2H-pyran-4-yl)methyl)-1,4-dihydropyrazolo[3',4':4,5]pyrrolo[3,2-b]pyridine; |
| --- | --- |
| 277 | (S)-6-(1,4-dimethyl-1H-1,2,3-triazol-5-yl)-1-methyl-3-((4-methylpiperazin-1-yl)methyl)-4-(phenyl(tetrahydro-2H-pyran-4-yl)methyl)-1,4-dihydropyrazolo[3',4':4,5]pyrrolo[3,2-b]pyridine; |
| 278 | 6-(1,4-dimethyl-1H-1,2,3-triazol-5-yl)-1-methyl-3-((methylsulfonyl)methyl)-4-(phenyl(tetrahydro-2H-pyran-4-yl)methyl)-1,4-dihydropyrazolo[3',4':4,5]pyrrolo[3,2-b]pyridine; |
| 279 | (S)-6-(1,4-dimethyl-1H-1,2,3-triazol-5-yl)-1-methyl-3-((methylsulfonyl)methyl)-4-(phenyl(tetrahydro-2H-pyran-4-yl)methyl)-1,4-dihydropyrazolo[3',4':4,5]pyrrolo[3,2-b]pyridine; |
| 280 | 4-((6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-yl)methyl)morpholine; |
| 281 | (S)-4-((6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-yl)methyl)morpholine; |
| 282 | N-(6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-yl)-N-(methylsulfonyl)acetamide; |
| 283 | (S)-N-(6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-yl)-N-(methylsulfonyl)acetamide; |
| 284 | (R)-2-(6-(1,4-dimethyl-1H-1,2,3-triazol-5-yl)-4-((3-fluoropyridin-2-yl)(tetrahydro-2H-pyran-4-yl)methyl)-1-methyl-1,4-dihydropyrazolo[3',4':4,5]pyrrolo[3,2-b]pyridin-3-yl)propan-2-ol; or |
| 285 | (R)-2-(6-(3,5-dimethylisoxazol-4-yl)-4-((3-fluoropyridin-2-yl)(tetrahydro-2H-pyran-4-yl)methyl)-1-methyl-1,4-dihydropyrazolo[3',4':4,5]pyrrolo[3,2-b]pyridin-3-yl)propan-2-ol. |

In another aspect, there is provided a pharmaceutical composition comprising at least one compound of formula I, a pharmaceutically acceptable salt thereof or stereoisomer thereof of the present invention, and at least one pharmaceutically acceptable excipient. In some embodiments, wherein the said compound in a weight ratio to the said excipient within the range from about 0.0001 to about 10. In some embodiments, wherein the said compound in a weight ratio to the said excipient within the range from about 0.0005 to about 0.25.

In another aspect, there is provided a method of treating a patient having a diseases or conditions related to bromodomain proteins, said method comprising administering to the patient a therapeutically effective amount of at least one compound of formula I, a pharmaceutically acceptable salt thereof or stereoisomer thereof; or the pharmaceutical composition. In some embodiments, wherein the diseases or conditions related to bromodomain proteins is solid tumor and/or blood tumor. In some embodiments, wherein the solid tumor is selected from lung cancer, gastrointestinal cancer, colon cancer, rectal cancer, colorectal cancer and/or ovarian cancer; the blood tumor is selected from myeloma and/or leukemia. In some embodiments, the lung cancer contains non-small cell lung cancer and/or small cell lung cancer; the gastrointestinal cancer contains esophageal cancer; the leukemia contains acute myeloid leukemia (AML)) and/or acute lymphocytic leukemia (ALL); the myeloma contains multiple myeloma.

In another aspect, there is provided the compound of formula I, a pharmaceutically acceptable salt thereof or stereoisomer thereof; or the pharmaceutical composition for use in the treatment of diseases or conditions related to bromodomain protein. In some embodiments, wherein the diseases or conditions related to bromodomain proteins is solid tumor and/or blood tumor. In some embodiments, wherein the solid tumor is selected from lung cancer, gastrointestinal cancer, colon cancer, rectal cancer, colorectal cancer and/or ovarian cancer; the blood tumor is selected from myeloma and/or leukemia. In some embodiments, the lung cancer contains non-small cell lung cancer and/or small cell lung cancer; the gastrointestinal cancer contains esophageal cancer; the leukemia contains acute myeloid leukemia (AML)) and/or acute lymphocytic leukemia (ALL); the myeloma contains multiple myeloma.

In another aspect, there is provided use of the compound of formula I, a pharmaceutically acceptable salt thereof or stereoisomer thereof; or the pharmaceutical composition for the manufacture of a medicament for the treatment of diseases or conditions related to bromodomain protein. In some embodiments, wherein the diseases or conditions related to bromodomain proteins is solid tumor and/or blood tumor. In some embodiments, wherein the solid tumor is selected from lung cancer, gastrointestinal cancer, colon cancer, rectal cancer, colorectal cancer and/or ovarian cancer; the blood tumor is selected from myeloma and/or leukemia. In some embodiments, wherein the lung cancer contains non-small cell lung cancer and/or small cell lung cancer; the gastrointestinal cancer contains esophageal cancer; the leukemia contains acute myeloid leukemia (AML)) and/or acute lymphocytic leukemia (ALL); the myeloma contains multiple myeloma.

Definition

The term "halogen", as used herein, unless otherwise indicated, means fluoro, chloro, bromo or iodo. The preferred halogen groups include F, Cl and Br.

The term "alkyl", as used herein, unless otherwise indicated, alkyl includes saturated monovalent hydrocarbon radicals having straight or branched. For example, alkyl radicals include methyl, ethyl, propyl, isopropyl, cyclcopropyl, n-butyl, isobutyl, sec-butyl, t-butyl, cyclcobutyl, n-pentyl, 3-(2-methyl) butyl, 2-pentyl, 2-methylbutyl, neopentyl, cyclcopentyl, n-hexyl, 2-hexyl, 2-methylpentyl and cyclchexyl. Similarly, $C_{1-6}$, as in $C_{1-6}$alkyl is defined to identify the group as having 1, 2, 3, 4, 5 or 6 carbon atoms in a linear or branched arrangement.

The term "alkylene" means a difunctional group obtained by removal of a hydrogen atom from an alkyl group that is defined above. For example, methylene (i.e., —CH$_2$—), ethylene (i.e., —CH$_2$—CH$_2$— or —CH(CH$_3$)—) and propylene (i.e., —CH$_2$—CH$_2$—CH$_2$—, —CH(—CH$_2$—CH$_3$)— or —CH$_2$—CH(CH$_3$)—).

The term "alkenyl" means a straight or branch-chained hydrocarbon radical containing one or more double bonds and typically from 2 to 20 carbon atoms in length. For example, "$C_{2-6}$alkenyl" contains from 2 to 6 carbon atoms. Alkenyl group include, but are not limited to, for example, ethenyl, propenyl, butenyl, 2-methyl-2-buten-1-yl, hepetenyl, octenyl and the like.

The term "alkynyl" contains a straight- or branch-chained hydrocarbon radical containing one or more triple bonds and typically from 2 to 20 carbon atoms in length. For example, "$C_{2-6}$alkynyl" contains from 2 to 6 carbon atoms. Representative alkynyl groups include, but are not limited to, for example, ethynyl, 1-propynyl, 1-butynyl, heptynyl, octynyl and the like.

The term "alkoxy" radicals are oxygen ethers formed from the previously described alkyl groups.

The term "aryl", as used herein, unless otherwise indicated, refers to an unsubstituted or substituted mono- or polycyclic aromatic ring system containing carbon ring atoms. The preferred aryls are mono cyclic or bicyclic 6-10 membered aromatic ring systems. Phenyl and naphthyl are preferred aryls. The most preferred aryl is phenyl.

The term "heterocyclic", as used herein, unless otherwise indicated, refers to unsubstituted and substituted mono- or polycyclic non-aromatic ring system containing one or more heteroatoms. Preferred heteroatoms include N, O, and S, including N-oxides, sulfur oxides, and dioxides. Preferably the ring is three to eight membered and is either fully saturated or has one or more degrees of unsaturation. Multiple degrees of substitution, preferably one, two or three, are included within the present definition.

Examples of such heterocyclic groups include, but are not limited to azetidinyl, pyrrolidinyl, piperidinyl, piperazinyl, oxopiperazinyl, oxopiperidinyl, oxoazepinyl, azepinyl, tetrahydrofuranyl, dioxolanyl, tetrahydroimidazolyl, tetrahydrothiazolyl, tetrahydrooxazolyl, tetrahydropyranyl, morpholinyl, thiomorpholinyl, thiamorpholinyl sulfoxide, thiamorpholinyl sulfone and oxadiazolyl.

The term "heteroaryl", as used herein, unless otherwise indicated, represents an aromatic ring system containing carbon(s) and at least one heteroatom. Heteroaryl may be monocyclic or polycyclic, substituted or unsubstituted. A monocyclic heteroaryl group may have 1 to 4 heteroatoms in the ring, while a polycyclic heteroaryl may contain 1 to 10 hetero atoms. A polycyclic heteroaryl ring may contain fused, spiro or bridged ring junction, for example, bicyclic heteroaryl is a polycyclic heteroaryl. Bicyclic heteroaryl rings may contain from 8 to 12 member atoms. Monocyclic heteroaryl rings may contain from 5 to 8 member atoms (carbons and heteroatoms). Examples of heteroaryl groups include, but are not limited to thienyl, furanyl, imidazolyl, isoxazolyl, oxazolyl, pyrazolyl, pyrrolyl, thiazolyl, thiadiazolyl, triazolyl, pyridyl, pyridazinyl, indolyl, azaindolyl, indazolyl, benzimidazolyl, benzofuranyl, benzothienyl, benzisoxazolyl, benzoxazolyl, benzopyrazolyl, benzothiazolyl, benzothiadiazolyl, benzotriazolyl adeninyl, quinolinyl or isoquinolinyl.

The term "carbocyclic" refers to a substituted or unsubstituted monocyclic, bicyclic or polycyclic non-aromatic saturated ring, which optionally includes an alkylene linker through which the cycloalkyl may be attached. Exemplary "cycloalkyl" groups includes but not limited to, cyclopropyl, cyclobutyl, cyclopentyl, cyclohexyl and so on.

The term "oxo" refers to oxygen atom together with the attached carbon atom forms the group

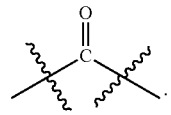 [SMILES: *C(*)=O]

The term "carboxyl" refers to the group C(O)OH.

The term "composition", as used herein, is intended to encompass a product comprising the specified ingredients in the specified amounts, as well as any product which results, directly or indirectly, from combinations of the specified ingredients in the specified amounts. Accordingly, pharmaceutical compositions containing the compounds of the present invention as the active ingredient as well as methods of preparing the instant compounds are also part of the present invention. Furthermore, some of the crystalline forms for the compounds may exist as polymorphs and as such are intended to be included in the present invention. In addition, some of the compounds may form solvates with water (i.e., hydrates) or common organic solvents and such solvates are also intended to be encompassed within the scope of this invention.

The compounds of the present invention may also be present in the form of pharmaceutically acceptable salts. For use in medicine, the salts of the compounds of this invention refer to non-toxic "pharmaceutically acceptable salts". The pharmaceutically acceptable salt forms include pharmaceutically acceptable acidic/anionic or basic/cationic salts. The pharmaceutically acceptable acidic/anionic salt generally takes a form in which the basic nitrogen is protonated with an inorganic or organic acid. Representative organic or inorganic acids include hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic. Pharmaceutically acceptable basic/cationic salts include, and are not limited to aluminum, calcium, chloroprocaine, choline, diethanolamine, ethylenediamine, lithium, magnesium, potassium, sodium and zinc.

The present invention includes within its scope the prodrugs of the compounds of this invention. In general, such prodrugs will be functional derivatives of the compounds that are readily converted in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "Design of Prodrugs", ed. H. Bundgaard, Elsevier, 1985.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques know in the art as well as those methods set forth herein.

The present invention includes compounds described can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof.

The present invention includes all stereoisomers of the compound and pharmaceutically acceptable salts thereof. Further, mixtures of stereoisomers as well as isolated specific stereoisomers are also included. During the course of the synthetic procedures used to prepare such compounds or in using racemization or epimerization procedures known to those skilled in the art, the products of such procedures can be a mixture of stereoisomers.

The term "stereoisomer" as used in the present invention refers to an isomer in which atoms or groups of atoms in the molecule are connected to each other in the same order but differ in spatial arrangement, including conformational isomers and conformational isomers. The configuration isomers include geometric isomers and optical isomers, and optical isomers mainly include enantiomers and diastereomers. The invention includes all possible stereoisomers of the compound, in particular, when the carbon atom directly attached to $W_1$, $W_2$, Z in formula (I) is a chiral carbon, the present invention includes stereoisomers in which the

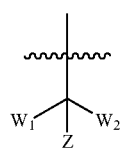

in the formula (I) is "R" configuration, and stereoisomers in which the

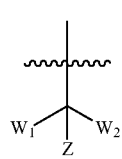

in the formula (I) is "S" configuration. By way of general example and without limitation, the stereoisomers encompassed by the present invention. include:

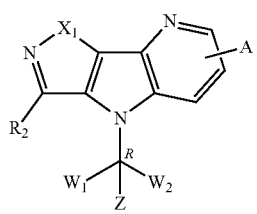
I-1

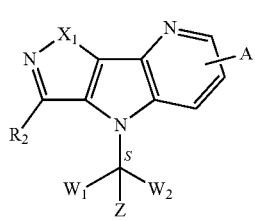
I-2

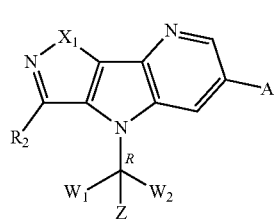
II-1

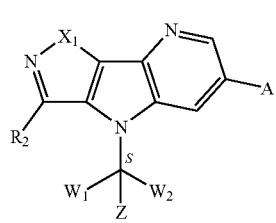
II-2

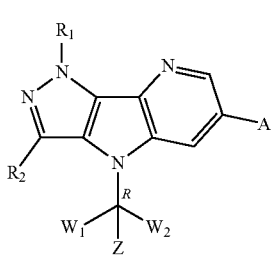
III-1

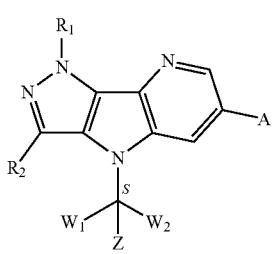
III-2

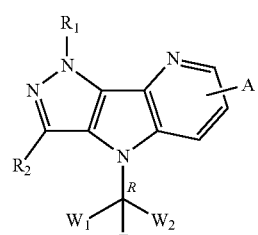
IV-1

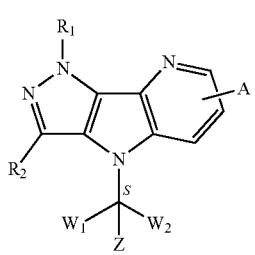

IV-2

"R" in the formulae I-1, II-1, III-1, IV-1 indicates that when the carbon atom bonded to $W_1$, $W_2$ and $Z$ is a chiral carbon, the absolute configuration of the chiral carbon is the R configuration.

"S" in the formulae I-2, II-2, III-2, IV-2 indicates that when the carbon atom bonded to $W_1$, $W_2$ and $Z$ is a chiral carbon, the absolute configuration of the chiral carbon is the S configuration.

The present invention is intended to include all isotopes of atoms occurring in the present compounds. Isotopes include those atoms having the same atomic number but different mass numbers. By way of general example and without limitation, isotopes of hydrogen include deuterium and tritium. The isotopes of hydrogen can be denoted as $^1H$ (hydrogen), $^2H$ (deuterium) and $^3H$ (tritium). They are also commonly denoted as D for deuterium and T for tritium. In the application, $CD_3$ denotes a methyl group wherein all of the hydrogen atom are deuterium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent.

When a tautomer of the compound of Formula (I) exists, the present invention includes any possible tautomers and pharmaceutically acceptable salts thereof, and mixtures thereof, except where specifically stated otherwise.

When the compound of Formula (I) and pharmaceutically acceptable salts thereof exist in the form of solvates or polymorphic forms, the present invention includes any possible solvates and polymorphic forms. A type of solvent that forms the solvate is not particularly limited so long as the solvent is pharmacologically acceptable. For example, water, ethanol, propanol, acetone or the like can be used.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. When the compound of the present invention is basic, its corresponding salt can be conveniently prepared from pharmaceutically acceptable non-toxic acids, including inorganic and organic acids. Since the compounds of Formula (I) are intended for pharmaceutical use they are preferably provided in substantially pure form, for example at least 60% pure, more suitably at least 75% pure, especially at least 98% pure (% are on a weight for weight basis).

The pharmaceutical compositions of the present invention comprise a compound represented by Formula I (or a pharmaceutically acceptable salt thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds represented by Formula I or a prodrug or a metabolite or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration, e.g. oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compound represented by Formula I or a pharmaceutically acceptable salt thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt, of Formula I. The compounds of Formula I or pharmaceutically acceptable salts thereof, can also be included in pharmaceutical compositions in combination with one or more other therapeutically active compounds.

The pharmaceutical carrier employed can be, for example, a solid, liquid or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen. In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient. For example, a formulation intended for the oral administration to humans may contain from about 0.5 mg to about 5 g of active agent, compounded with an appropriate and convenient amount of carrier material which may vary from about 0.05 to about 95 percent of the total composition. Unit dosage forms will generally contain between from about 0.01 mg to about 2 g of the active ingredient, typically 0.01 mg, 0.02 mg, 1 mg, 2 mg, 3 mg, 4 mg, 5 mg, 6 mg, 7 mg, 8 mg, 9 mg, 10 mg, 25 mg, 50 mg, 100 mg, 200 mg, 300 mg, 400 mg, 500 mg, 600 mg, 800 mg or 1000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder or the like. Further, the compositions can be in a form suitable for use in transdermal devices. These formulations may be prepared, utilizing a compound represented by Formula I of this invention or a pharmaceutically acceptable salt thereof, via conventional processing methods. As an example, a cream or ointment is prepared by admixing hydrophilic material and water, together with about 0.05 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including antioxidants) and the like. Furthermore, other adjuvants can be included to render the formulation isotonic with the blood of the intended recipient. Compositions containing a compound described by Formula I or pharmaceutically acceptable salts thereof, may also be prepared in powder or liquid concentrate form.

Generally, dosage levels on the order of from about 0.001 mg/kg to about 150 mg/kg of body weight per day are useful in the treatment of the above-indicated conditions or alternatively about 0.05 mg to about 7 g per patient per day. For example, inflammation, cancer, psoriasis, allergy/asthma, disease and conditions of the immune system, disease and conditions of the central nervous system (CNS), may be effectively treated by the administration of from about 0.001 to 50 mg of the compound per kilogram of body weight per day or alternatively about 0.05 mg to about 3.5 g per patient per day.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

These and other aspects will become apparent from the following written description of the invention.

Methods of Preparation

The compounds in the present invention can be synthesized in a number of ways well to one skilled in the art of organic synthesis described below, together with synthetic methods known in the art of synthetic organic chemistry, or variations thereon as appreciated by those skilled in the art. Preferred methods are not limited as those described below. The references cited here are incorporated by reference in their entirety.

The methods of synthesis described hereinafter are intended as an illustration of the invention, without restricting its subject matter and the scope of the compounds claimed to these examples. Where the preparation of starting compounds is not described, they are commercially obtainable or may be prepared analogously to known compounds or methods described herein. Substances described in the literature are prepared according to the published methods of synthesis. Compounds of formula (I) may be synthesized by reference to methods illustrated in the following schemes. As shown herein, the end compound is a product having the same structural formula depicted as formula (I). It will be understood that any compound of formula (I) may be prepared by the selection of reagents with appropriate substitution. Solvents, temperature, pressures, and other reaction conditions may be readily selected by one of ordinary skill in the art. Protecting groups are manipulated according to standard methods of organic synthesis (T. W. Green and P. G. M. Wuts (1999) Protective Groups in Organic Synthesis, $3^{rd}$ edition, John Wiley & Sons). These groups are removed at certain stage of the compound synthesis using the methods that are apparent to those skilled in the art.

General synthetic routes to compounds illustrated in the invention is described in Schemes 1-3, where the $R_1$, $R_2$, $R_3$, $Y_1$, $Y_2$, $W_1$, $W_2$ and Z substituents are defined previously in the text or a functional group that can be converted to the desired final substituent. The substituent Hal is a halide, and L is a leaving group such as a halide or OH that can easily converted to a leaving group such as triflate or tosylate. M is a suitable coupling partner, such as boronic acid, bonic ester or stannane As depicted in Scheme 1, Suzuki coupling of pyrazole 1 with the aromatic heterocycle 2, such as 2,5-dibromo-3-nitropyridine using a suitable coupling catalyst, such as Pd(dppf)Cl$_2$ at the present of a base, like K$_3$PO$_4$ in THF/H$_2$O (5:1 volume ratio) can give the 3. Cadogan reductive cyclization of 3 at the present of a phosphine reagent, such as 1,2-bis(diphenylphosphino)ethane (DPPE) or triethyl phosphate P(OEt)$_3$ and solvent, such as 1,2-dichlorobenze or 1,2-dimethyl-benzene with heating can give the tricycle 4. Mitsunobu reaction of 4 with an alkylating agent 5 using triphenophosphine and diisopropyl azodicarboxylate (DIAD) to provide 7. Alternatively, the 7 can be generated from a reaction between 4 and an alkylating agent 6, where L is a leaving group such as a halide, mesylate or triflate, in the presence of a base, such as potassium carbonate. A coupling of 7 with 8 (where M is a suitable coupling partner, such as boronic acid, boronic ester or stannane) by a Suzuki or Stille reaction can generate 9. In cases where 9 is a racemate, chiral separation can provide enantiomerically pure products. Further derivatization of R$_1$ and R$_2$ can provide additional compounds of the invention. For example, when R$_1$ is a protecting group, it can be further functionalized after de-protecting; when R$_2$ is an ester, addition of a Grignard reagent or alky lithium can generate tertiary alcohols. The ester could instead be hydrolyzed using, for example, potassium hydroxide to give a carboxylic acid, which could be further functionalized using alky amines; when R$_2$ is a —H, it can be replaced by a halogen, for example —Br, through a halogenation reaction using a reagent like NBS and can be further functionalized through a reaction, such as Buchwall, Mitszunobu or Stille reaction.

As illustrated in Scheme 2, a heterocyclic aromatic 10, can be directly coupled to 7 (prepared as in Scheme 1) via palladium-mediated C—H activation to afford compound 9.

Alternatively, heterocyclic aromatic 10 can be deprotonated with a strong base such as n-BuLi and transmetallated to zinc or tin reagent to afford compound 8 which can be coupled by a Negishi or Stille reaction to 7 (prepared as in Scheme 1) at the present of a suitable palladium catalyst to afford compounds 9. This is illustrated in Scheme 3.

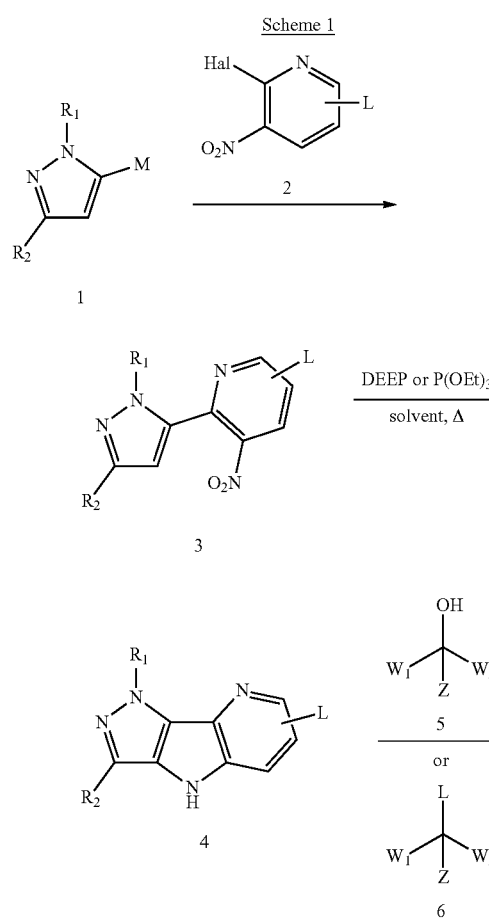

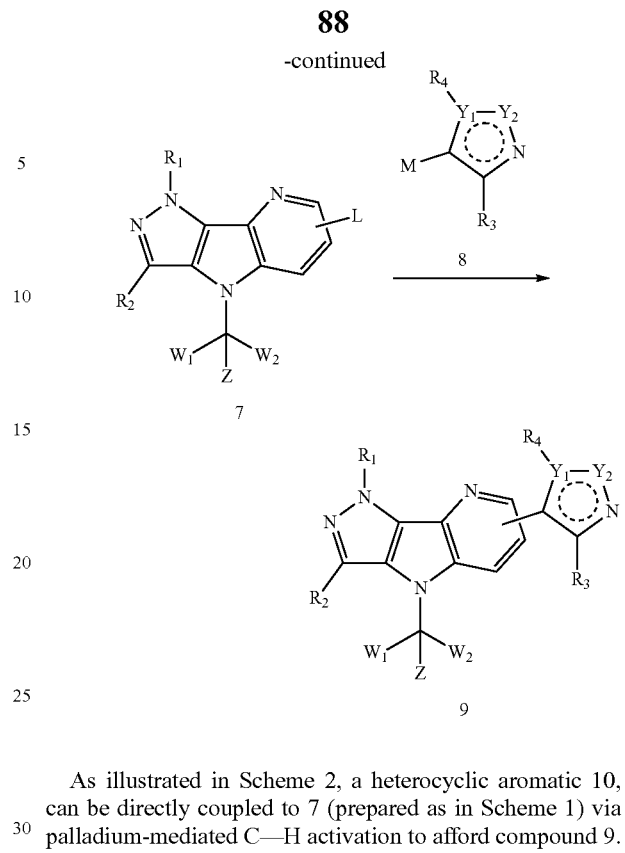

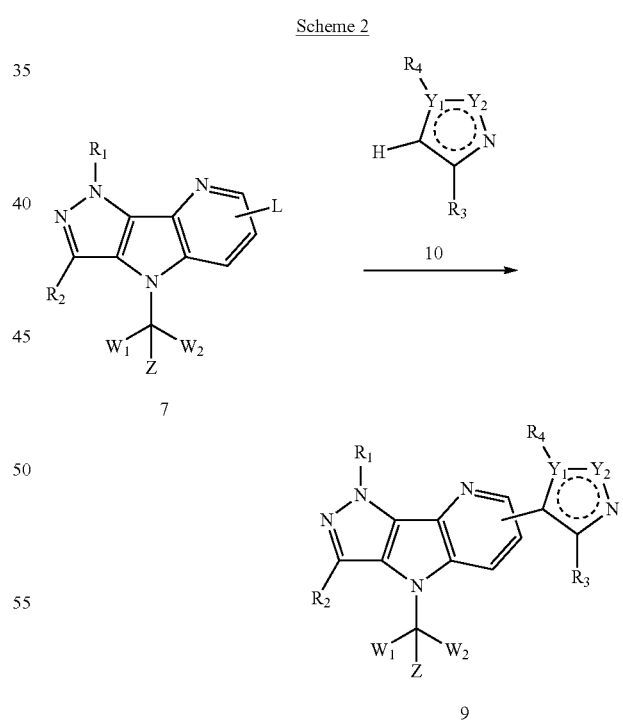

Scheme 3

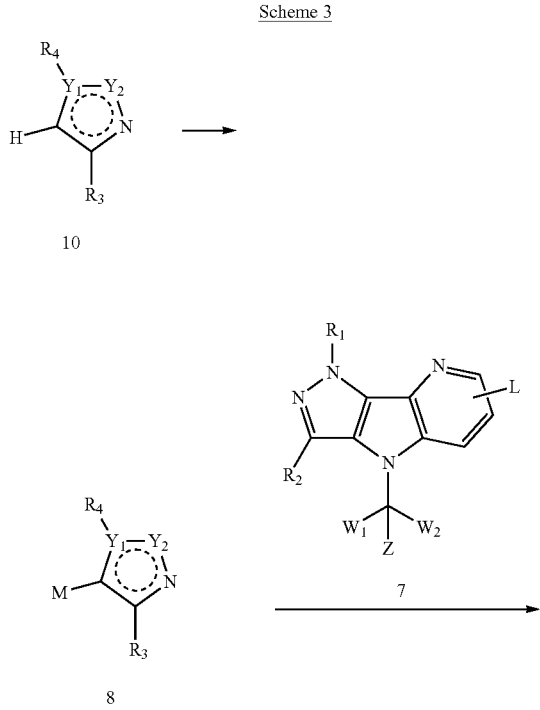

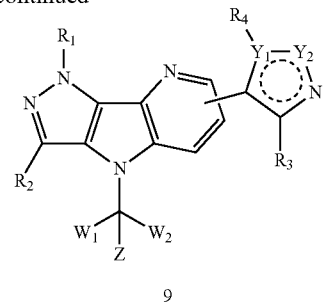

EXAMPLES

The invention is further defined using the following Examples and it should be understood that these examples are used by way of illustration only. One skilled in the art can determine with certainty the essential feature of the invention, and without departure from the spirit and scope thereof, can make versatile modifications to accommodate the invention to various uses and conditions. Hence, the invention is not restricted by the exemplifying examples set forth herein below, but rather is specified by the claims appended hereto.

Table 1 shows the part abbreviations of the present invention:

TABLE 1

| | | | |
|---|---|---|---|
| aq | aqueous | KOtBu | potassium tert-butoxide |
| Bn | benzyl | LC-MS | Liquid Chromatography-Mass Spectroscopy |
| Boc | tert-butoxycarbonyl | LDA | lithium diisopropylamide |
| Boc₂O | di-tert-butyl dicarbonate | LiHMDS | lithium bis(trimethylsily)amide |
| CuI | copper iodide | Me | methane |
| DCM | dichloromethane | MeI | methyl iodide |
| DIAD | diisopropyl azodicarboxylate | MeCN | Acetonitrile |
| DIEA | diisopropylethylamine | MeOH | methanol |
| DMAP | 4-dimethylaminopyridine | min | minute(s) |
| DMF | dimethylformamide | mL | milliliter(s) |
| DMSO | dimethyl sulfoxide | mmol | millimolar |
| DPPE | 1,2-bis(diphenylphosphino)ethane | MTBE | methyl t-butyl ether |
| dtbpy | iodo(4,4-di-tert-butyl-2,2-bipyridine)methylpalladium(II) | NaHCO₃ | sodium hydrogen carbonate |
| equiv. | equivalent(s) | NaHMDS | sodium bis(trimethylsityl)amide |
| Et₃N | triethylamine | n-BuLi | n-butyl lithium |
| Et₂O | diethyl ether | NH₄OAc | amonium acetate |
| EtOAc | ethyl acetate | Pd(OAc)₂ | polladium acetate |
| EtOH | ethanol | Pd(dppf)Cl₂ | [1,1'-bis(diphenylphosphino)ferrocene]dichloropalladium(II) |
| g | gram(s) | Prep-TLC | prep thin layer chromatography |
| h or hr | hour(s) | r.t. | room temperature |
| HBPin | Pinacolborane | TEA | triethylamine |
| HPLC | high pressure liquid chromatography | THF | Tetrahydrofuran |
| iPrOH | isopropyl alcohol | sat. | saturated |
| RT | retention time | SEMCl | 2-(trimethylsilyl)ethoxymethyl chloride |
| DTAD | Ditert-butyl azodicarboxylate | TMSN₃ | Trimethylsilyl azide |
| HATU | 1-[Bis(dimethylamino)methylene]-1H-1,2,3-triazolo[4,5-b]pyridinium 3-oxid hexafluorophosphate | DEA | diethylamine |

Intermediate Preparation

Unless otherwise stated, starting materials for the preparation of intermediates and Examples are commercially available.

Enantiomer a1 and Enantiomer b1

((R)-(3-fluoropyridin-2-yl)(tetrahydro-2H-pyran-4-yl)methanol) ("Enantiomer a1")

And ((S)-(3-fluoropyridin-2-yl)(tetrahydro-2H-pyran-4-yl)methanol) ("Enantiomer b1")

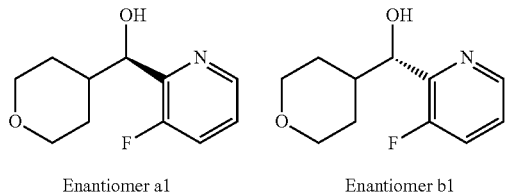

Enantiomer a1          Enantiomer b1

To a suspension of magnesium (24.3 g, 1.00 mol) in THF (500 mL) was added three crystals of iodine followed by dropwise addition of neat 4-bromotetrahydro-2H-pyran (100 g, 607 mmoL) through an additional funnel under $N_2$, during which the inner temperature was controlled under 45° C. The reaction mixture was continued stirring for 2 h at ambient temperature. The reaction mixture was cooled to −30° C. followed by dropwise addition of 3-fluoropicolinaldehyde (50.3 g, 402 mmoL) in THF (300 mL) through an additional funnel, during which the inner temperature was kept between −20° C. to −30° C. After 1 h, the reaction mixture was filtered through a thin pad of celite. To the filtrate was added sat. aq. $NH_4Cl$ (100 mL) and the two layers were separated. The organic phase was dried over anhydrous $Na_2SO_4$ and collected by filtration and washing with EtOAc (200 ml). The filtrate was concentrated on a rotary evaporator. The crude compound was purified using a reverse phase chromatography eluting with 40~50% MeCN in $H_2O$ to afford the racemic compound (52 g, 61% yield), which was separated by chiral prep SFC to give Enantiomer a1, (R)-(3-fluoropyridin-2-yl)(tetrahydro-2H-pyran-4-yl)methanol (25.1 g, 29.6% yield) and Enantiomer b1, (S)-(3-fluoropyridin-2-yl)(tetrahydro-2H-pyran-4-yl)methanol (25.3 g, 29.7%).

Enantiomer a1: LC-MS [M+H]$^+$=212. Chiral Chromatography Report: RT=12.25 min (Column: Chiralpak AY-H (ADH0CE-VC001) 0.46×25 cm; Mobile Phase: 90/10/0.1 Hexane/EtOH/DEA; Flow: 1.0 mL/min). Chiral Chromatography Report: RT=14.023 min (Column: YMC, Chiral ART-amylose-C Neo (5 μm, 250×4.6 mm; Mobile Phase: 90/10/0.1 Hexane/EtOH/TFA; Flow: 1.0 mL/min). $^1$H NMR (400 MHz, DMSO-d$_6$) δ 8.42 (dd, J=3.20, 1.32 Hz, 1H), 7.66 (ddd, J=9.8, 8.36, 1.12 Hz, 1H), 7.35-7.42 (m, 1H), 5.23 (d, J=6.52 Hz, 1H), 4.52 (dd, J=7.32, 7.28 Hz, 1H), 3.88 (dd, J=11.4, 2.92 Hz, 1H), 3.75 (dd, J=11.2, 3.02 Hz, 1H), 3.26 (dt, J=12.0, 2.04 Hz, 1H), 3.17 (dt, J=11.8, 2.24 Hz, 1H), 2.01-2.12 (m, 1H), 1.82 (dd, J=13.3, 1.52 Hz, 1H), 1.24-1.38 (m, 1H), 1.12-1.24 (m, 1H), 1.00 (dd, J=12.9, 1.34, 1H).

Enantiomer b1: LC-MS [M+H]$^+$=212. Chiral Chromatography Report: RT=13.57 min (Column: Chiralpak AY-H (ADH0CE-VC001) 0.46×25 cm; Mobile Phase: 90/10/0.1 Hexane/EtOH/DEA; Flow: 1.0 mL/min). Chiral Chromatography Report: RT=12.760 min (Column: YMC, Chiral ART-amylose-C Neo (5 μm, 250×4.6 mm; Mobile Phase: 90/10/0.1 Hexane/EtOH/TFA; Flow: 1.0 mL/min). $^1$H NMR (400 MHz, DMSO-d$_6$) δ 8.42 (dd, J=3.2, 1.35 Hz, 1H), 7.66 (ddd, J=1.12, 8.4, 9.8 Hz, 1H), 7.35-7.42 (m, 1H), 5.23 (d, J=6.48 Hz, 1H), 4.52 (dd, J=7.32, 7.24 Hz, 1H), 3.88 (dd, J=11.3, 2.96, 1H), 3.75 (dd, J=2.96, 11.2 Hz, 11H), 3.26 (dt, J=12.0, 2.0 Hz, 1H), 3.17 (dt, J=11.8, 2.24 Hz, 1H), 2.01-2.12 (m, 1H), 1.82 (dd, J=13.3, 1.52 Hz, 11H), 1.24-1.38 (m, 1H), 1.12-1.24 (m, 11H), 1.00 (dd, J=12.9, 1.34, 11H).

Intermediate 3-17

The intermediates in Table 2 were prepared Using the same method described for the racemate of Enantiomer a1 and Enantiomer b1:

TABLE 2

| Intermediate | Structure | LCMS (M + H) |
|---|---|---|
| 3 | OH, tetrahydropyran-CH(OH)-(2-fluorophenyl) | 211 |
| 4 | OH, tetrahydropyran-CH(OH)-(3-fluorophenyl) | 211 |
| 5 | OH, tetrahydropyran-CH(OH)-(3-methylpyridin-2-yl) | 208 |
| 6 | OH, tetrahydropyran-CH(OH)-(5-fluoropyridin-2-yl) | 212 |
| 7 | OH, $F_3C$-CH$_2$CH$_2$-CH(OH)-(3-fluoropyridin-2-yl) | 224 |
| 8 | OH, $F_3C$-CH$_2$CH$_2$-CH(OH)-phenyl | 205 |
| 9 | OH, tetrahydropyran-CH(OH)-(2-methylphenyl) | 207 |

TABLE 2-continued

| Intermediate | Structure | LCMS (M + H) |
|---|---|---|
| 10 | F₃C—CH(OH)—oxazole | 196 |
| 11 | F₃C—CH(OH)—(3-methylpyridin-2-yl) | 220 |
| 12 | (tetrahydropyran-4-yl)(2-methyloxazol-4-yl)methanol | 198 |
| 13 | (tetrahydropyran-4-yl)(4-methylpyridin-3-yl)methanol | 208 |
| 14 | (tetrahydropyran-4-yl)(3-fluoropyridin-4-yl)methanol | 212 |
| 15 | 1-(4-fluoro-2,6-dimethylphenyl)ethan-1-ol | 169 |
| 16 | (tetrahydropyran-4-yl)(4-methoxypyridin-3-yl)methanol | 224 |
| 17 | (tetrahydropyran-4-yl)(4-methoxypyridin-2-yl)methanol | 224 |

Example 1

(S)-2-(6-(3,5-dimethylisoxazol-4-yl)-1-methyl-4-(phenyl(tetrahydro-2H-pyran-4-yl)methyl)-1,4-dihydropyrazolo[3',4':4,5]pyrrolo[3,2-b]pyridin-3-yl)propan-2-ol ("Compound 1")

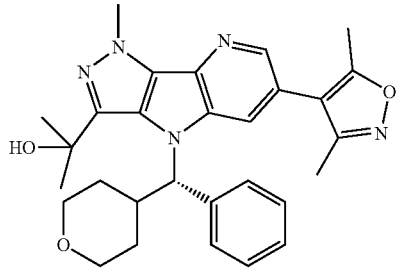 [SMILES: Cc1noc(C)c1-c1cnc2c3c(c(C(C)(C)O)nn3C)n([C@H](c3ccccc3)C3CCOCC3)c2c1]

Step 1: Methyl 5-(5-bromo-3-nitropyridin-2-yl)-1-methyl-1H-pyrazole-3-carboxylate To a solution of HBPin (26.4 g, 0.21 mmol), dtbpy (1.06 g, 3.95 mmol) and (1,5-cyclooctadiene)-(methoxy)iridium (I)dimer (1.02 g, 1.54 mmol) in THF (125 mL) was added methyl 1-methyl-1H-pyrazole-3-carboxylate (20.2 g, 0.14 mol) at room temperature under $N_2$. The resulting solution was vacuumed, backfilled with $N_2$, and this sequence was repeated three times, then the reaction mixture was refluxed for 12 h under $N_2$. Then the reaction mixture was concentrated under reduced pressure to afford a red substance. To the resulting crude substance in a 1 L round bottom flask was added THF (500 mL), water (100 mL), $K_3PO_4$ (65.13 g, 0.31 mol) and 2,5-dibromo-3-nitropyridine (47.1 g, 0.17 mol). The flask was vacuumed, filled with $N_2$, and this process was repeated three times, followed by addition of Pd(dppf)Cl₂ (11.3 g, 0.014 mmol) under $N_2$. The mixture was refluxed for 3 h under $N_2$. After cooling to room temperature, the reaction mixture was extracted with EtOAc (500 mL). The extract was washed with brine, dried over anhydrous sodium sulfate, and concentrated under reduced pressure. The residue was purified by silica gel chromatography using 0-30% EtOAC in hexane to afford methyl 5-(5-bromo-3-nitropyridin-2-yl)-1-methyl-1H-pyrazole-3-carboxylate (27.6 g, 0.081 mol, 57% yield), LC-MS [M+H]⁺=341.

Step 2: Methyl 6-bromo-1-methyl-1,4-dihydropyrazolo[3',4':4,5]pyrrolo[3,2-b]pyridine-3-carboxylate A mixture of methyl 5-(5-bromo-3-nitropyridin-2-yl)-1-methyl-1H-pyrazole-3-carboxylate (22.1 g, 0.065 mol), DPPE (38.8 g, 0.088 mol) in 1,2-dichlorobenzene (250 mL) was heated to 150° C. and stirred for 4 h under $N_2$. The reaction was then cooled slowly to room temperature. The solvent was concentrated under reduced pressure. The crude product was purified by silica gel chromatography using 30-50% EtOAC in hexane to afford Methyl 6-bromo-1-methyl-1,4-dihydropyrazolo[3',4':4,5]pyrrolo[3,2-b]pyridine-3-carboxylate (3.98 g, 0.013 mol, 20% yield), LC-MS [M+H]⁺=309.

Step 3: Methyl (S)-6-bromo-1-methyl-4-(phenyl(tetrahydro-2H-pyran-4-yl)methyl)-1,4-dihydropyrazolo[3',4':4,5]pyrrolo[3,2-b]pyridine-3-carboxylate A solution of methyl 6-bromo-1-methyl-1,4-dihydropyrazolo[3',4':4,5]pyrrolo[3,2-b]pyridine-3-carboxylate (207 mg, 0.67 mmol), (R)-phenyl(tetrahydro-2H-pyran-4-yl) methanol (169 mg, 0.88 mmol) and triphenylphosphane (446 mg, 1.70 mmol) in dry THF (10 mL) was vacuumed, backfilled with nitrogen gas, and this sequence was repeated three times. Diisopropyl azodicarboxylate (321 mg, 1.59 mmol) was added dropwise at room temperature and the resulting solution was stirred for 2 h. Then the reaction was extracted with EtOAc (50 mL), washed with brine, dried over anhydrous sodium sulfate, filtered and the filtrate was concentrated under reduced pressure. The residue was purified by silica gel chromatography with 0-30% EtOAc in hexane to afford Methyl (S)-6-bromo-1-methyl-4-(phenyl (tetrahydro-2H-pyran-4-yl)methyl)-1,4-dihydropyrazolo[3′,4′:4,5]pyrrolo[3,2-b]pyridine-3-carboxylate (315 mg, 97% yield), LC-MS [M+H]+=483,485.

Step 4: Methyl (S)-6-(3,5-dimethylisoxazol-4-yl)-1-methyl-4-(phenyl(tetrahydro-2H-pyran-4-yl) methyl)-1,4-dihydropyrazolo[3′,4′:4,5]pyrrolo[3,2-b] pyridine-3-carboxylate To a solution of methyl (S)-6-bromo-1-methyl-4-(phenyl (tetrahydro-2H-pyran-4-yl)methyl)-1,4-dihydropyrazolo[3′,4′:4,5]pyrrolo[3,2-b]pyridine-3-carboxylate (315 mg, 0.65 mmol) in 1,4-dioxane (20 mL) and water (5 mL) was added 3,5-dimethyl-4-(4,4,5,5-tetramethyl-1,3,2-dioxaborolan-2-yl) isoxazole (208 mg, 0.93 mmol), Pd(dppf)Cl$_2$ (74 mg, 0.091 mmol) and K$_3$PO$_4$ (402 mg, 1.89 mmol). The mixture was vacuumed, backfilled with nitrogen gas, and this sequence was repeated. The resulting mixture was stirred at 80° C. for 2 h. The reaction mixture was cooled to r.t., diluted with water (50 mL) and extracted with EtOAc (3×50 mL). After separation, the organic layer was washed with brine, dried over anhydrous sodium sulfate, and concentrated. The residue was purified by silica gel chromatography using 0-50% EtOAc in hexane to afford Methyl (S)-6-(3,5-dimethylisoxazol-4-yl)-1-methyl-4-(phenyl (tetrahydro-2H-pyran-4-yl)methyl)-1,4-dihydropyrazolo[3′,4′:4,5]pyrrolo[3,2-b]pyridine-3-carboxylate (272 mg, 84% yield), LC-MS [M+H]+=500.

Step 5: (S)-2-(6-(3,5-dimethylisoxazol-4-yl)-1-methyl-4-(phenyl(tetrahydro-2H-pyran-4-yl) methyl)-1,4-dihydropyrazolo[3′,4′:4,5]pyrrolo[3,2-b] pyridin-3-yl)propan-2-ol MeMgBr (1M in THF, 5.0 mL, 5.03 mmol) was slowly added to a solution of methyl (S)-6-(3,5-dimethylisoxazol-4-yl)-1-methyl-4-(phenyl(tetrahydro-2H-pyran-4-yl) methyl)-1,4-dihydropyrazolo[3′,4′:4,5]pyrrolo[3,2-b]pyridine-3-carboxylate (272 mg, 0.54 mmol) in dry THF (10 ml) at −30° C. under N$_2$ over 1 min. After addition, the reaction was warmed to r.t. and stirred for 2 hr. The reaction was quenched with sat. NH$_4$Cl, and extracted with EtOAc (30 mL). The collected organic layer was washed with brine, dried over anhydrous sodium sulfate, and concentrated. The residue was purified by silica gel chromatography using 0-4% MeOH in DCM to afford (S)-2-(6-(3,5-dimethylisoxazol-4-yl)-1-methyl-4-(phenyl(tetrahydro-2H-pyran-4-yl) methyl)-1,4-dihydropyrazolo[3′,4′:4,5]pyrrolo[3,2-b]pyridin-3-yl)propan-2-ol (Compound 1, 121 mg, 44% yield), LC-MS [M+H]+=500.

$^1$H NMR (400 MHz, DMSO-d$_6$) δ 8.27 (d, J=1.5 Hz, 1H), 7.75 (d, J=1.3 Hz, 1H), 7.70 (d, J=7.6 Hz, 2H), 7.31 (t, J=7.5 Hz, 2H), 7.22 (t, J=7.3 Hz, 1H), 6.44 (d, J=11.2 Hz, 1H), 5.77 (s, 1H), 4.13 (s, 3H), 3.85 (d, J=8.8 Hz, 1H), 3.74 (d, J=8.7 Hz, 1H), 3.47 (t, J=11.2 Hz, 1H), 3.25 (dd, J=22.1, 11.0 Hz, 2H), 2.34 (s, 3H), 2.15 (s, 3H), 1.79 (d, J=12.8 Hz, 1H), 1.70 (s, 3H), 1.71 (s, 3H), 1.54 (qd, J=12.5, 4.2 Hz, 1H), 1.37 (ddd, J=15.6, 12.6, 4.1 Hz, 1H), 0.78 (d, J=12.6 Hz, 1H).

Example 2

(S)-2-(6-(3,5-dimethylisoxazol-4-yl)-4-((3-fluoropyridin-2-yl)(tetrahydro-2H-pyran-4-yl)methyl)-1-methyl-1,4-dihydropyrazolo[3′,4′:4,5]pyrrolo[3,2-b] pyridin-3-yl)propan-2-ol ("Compound 2")

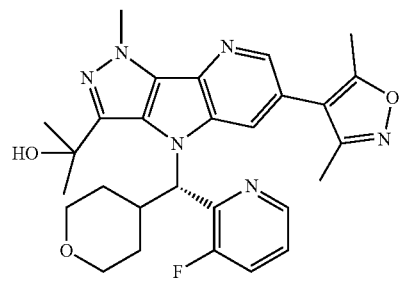 [SMILES: Cc1noc(C)c1-c1cnc2c3c(c(C(C)(C)O)nn3C)n([C@H](c3ncccc3F)C3CCOCC3)c2c1]

Step 1: (R)-(3-fluoropyridin-2-yl)(tetrahydro-2H-pyran-4-yl)methanol ("Enantiomer a1") and (S)-(3-fluoropyridin-2-yl)(tetrahydro-2H-pyran-4-yl)methanol ("Enantiomer b1")

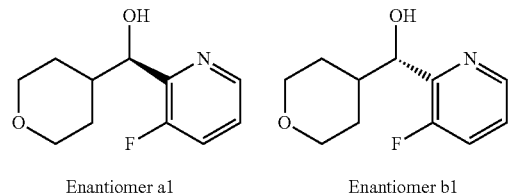

Enantiomer a1        Enantiomer b1

To a suspension of magnesium (24.3 g, 1.00 mol) in THF (500 mL) was added three crystals of iodine followed by dropwise addition of neat 4-bromotetrahydro-2H-pyran (100 g, 607 mmoL) under N$_2$, during which the inner temperature was controlled under 45° C. The reaction mixture was continued stirring for 2 h at ambient temperature. The reaction mixture was cooled to −30° C. followed by addition of 3-fluoropicolinaldehyde (50.3 g, 402 mmoL) in THF (300 mL), during which the inner temperature was kept between −20° C. to −30° C. After 1 h, the reaction mixture was filtered through a thin pad of celite. To the filtrate was added sat. aq. NH$_4$Cl (100 mL) and the two layers were separated. The organic phase was dried over anhydrous Na$_2$SO$_4$ and collected by filtration. The filtrate was concentrated on a rotary evaporator. The crude compound was purified using a reverse phase chromatography eluting with 40~50% MeCN in H$_2$O to afford the racemic compound (52 g, 61% yield), which was separated by chiral prep SFC to give Enantiomer a1 of (R)-(3-fluoropyridin-2-yl)(tetrahydro-2H-pyran-4-yl) methanol (25.1 g, 29.6% yield) and Enantiomer b1 of (S)-(3-fluoropyridin-2-yl)(tetrahydro-2H-pyran-4-yl)methanol (25.3 g, 29.7%).

Enantiomer a1: LC-MS [M+H]+=212. Chiral Chromatography Report: RT=12.25 min (Column: Chiralpak AY-H (ADH0CE-VC001) 0.46×25 cm; Mobile Phase: 90/10/0.1 Hexane/EtOH/DEA; Flow: 1.0 mL/min). Chiral Chromatography Report: RT=14.023 min (Column: YMC, Chiral ART-amylose-C Neo (5 μm, 250×4.6 mm; Mobile Phase: 90/10/0.1 Hexane/EtOH/TFA; Flow: 1.0 mL/min). $^1$H NMR (400 MHz, DMSO-$d_6$) δ 8.42 (dd, J=3.20, 1.32 Hz, 1H), 7.66 (ddd, J=9.8, 8.36, 1.12 Hz, 1H), 7.35-7.42 (m, 1H), 5.23 (d, J=6.52 Hz, 1H), 4.52 (dd, J=7.32, 7.28 Hz, 1H), 3.88 (dd, J=11.4, 2.92 Hz, 1H), 3.75 (dd, J=11.2, 3.02 Hz, 1H), 3.26 (dt, J=12.0, 2.04 Hz, 1H), 3.17 (dt, J=11.8, 2.24 Hz, 1H), 2.01-2.12 (m, 1H), 1.82 (dd, J=13.3, 1.52 Hz, 1H), 1.24-1.38 (m, 1H), 1.12-1.24 (m, 1H), 1.00 (dd, J=12.9, 1.34 Hz, 1H).

Enantiomer b1: LC-MS [M+H]$^+$=212. Chiral Chromatography Report: RT=13.57 min (Column: Chiralpak AY-H (ADH0CE-VC001) 0.46×25 cm; Mobile Phase: 90/10/0.1 Hexane/EtOH/DEA; Flow: 1.0 mL/min). Chiral Chromatography Report: RT=12.760 min (Column: YMC, Chiral ART-amylose-C Neo (5 μm, 250×4.6 mm; Mobile Phase: 90/10/0.1 Hexane/EtOH/TFA; Flow: 1.0 mL/min). $^1$H NMR (400 MHz, DMSO-$d_6$) δ 8.42 (dd, J=3.2, 1.35 Hz, 1H), 7.66 (ddd, J=1.12, 8.4, 9.8 Hz, 1H), 7.35-7.42 (m, 1H), 5.23 (d, J=6.48 Hz, 1H), 4.52 (dd, J=7.32, 7.24 Hz, 1H), 3.88 (dd, J=11.3, 2.96, 1H), 3.75 (dd, J=2.96, 11.2 Hz, 1H), 3.26 (dt, J=12.0, 2.0 Hz, 1H), 3.17 (dt, J=11.8, 2.24 Hz, 1H), 2.01-2.12 (m, 1H), 1.82 (dd, J=13.3, 1.52 Hz, 1H), 1.24-1.38 (m, 1H), 1.12-1.24 (m, 1H), 1.00 (dd, J=12.9, 1.34 Hz, 1H).

Step 2: (S)-Methyl 6-bromo-4-((3-fluoropyridin-2-yl)(tetrahydro-2H-pyran-4-yl) methyl)-1-methyl-1,4-dihydropyrazolo[3',4':4,5]pyrrolo[3,2-b]pyridine-3-carboxylate A solution of methyl 6-bromo-1-methyl-1,4-dihydropyrazolo[3',4':4,5]pyrrolo[3,2-b]pyridine-3-carboxylate (obtained from Example 1, step 2, 202 mg, 0.65 mmol), (R)-(3-fluoropyridin-2-yl)(tetrahydro-2H-pyran-4-yl)methanol (Enantiomer a1, from Step 1, 185 mg, 0.88 mmol) and triphenylphosphane (438 mg, 1.67 mmol) in dry THF (10 mL) was vacuumed, backfilled with nitrogen gas, and this sequence was repeated three times. Diisopropyl azodicarboxylate (336 mg, 1.66 mmol) in THF (2 mL) was added dropwise at room temperature and the resulting solution was stirred for 2 h. Then the reaction was extracted with EtOAc (50 mL) and the extract was washed with brine, dried over anhydrous sodium sulfate and filtered. The filtrate was concentrated under reduced pressure. The resulting residue was purified by silica gel chromatography with 0-35% EtOAc in hexane to afford (S)-methyl 6-bromo-4-((3-fluoropyridin-2-yl)(tetrahydro-2H-pyran-4-yl)methyl)-1-methyl-1,4-dihydropyrazolo[3',4':4,5]pyrrolo[3,2-b]pyridine-3-carboxylate (317 mg, 92% yield), LC-MS [M+H]$^+$=502.

Step 3: (S)-Methyl 6-(3,5-dimethylisoxazol-4-yl)-4-((3-fluoropyridin-2-yl)(tetrahydro-2H-pyran-4-yl)methyl)-1-methyl-1,4-dihydropyrazolo[3',4':4,5]pyrrolo[3,2-b]pyridine-3-carboxylate To a solution of (S)-methyl 6-bromo-4-((3-fluoropyridin-2-yl)(tetrahydro-2H-pyran-4-yl)methyl)-1-methyl-1,4-dihydropyrazolo[3',4':4,5]pyrrolo[3,2-b]pyridine-3-carboxylate (from Step 2, 317 mg, 0.63 mmol) in 1,4-dioxane (20 mL) and water (5 mL) was added 3,5-dimethyl-4-(4,4,5,5-tetramethyl-1,3,2-dioxaborolan-2-yl)isoxazole (207 mg, 0.93 mmol), and $K_3PO_4$ (386 mg, 1.82 mmol). The mixture was vacuumed, backfilled with nitrogen gas, and this sequence was repeated three times, followed by addition of Pd(dppf)Cl$_2$ (82 mg, 0.10 mmol) in one portion and the resulting mixture was stirred at 80° C. for 2 h under N$_2$. The reaction mixture was cooled to r.t., diluted with water (50 mL) and extracted with EtOAc (3×50 mL). After separation, the organic layer was washed with brine, dried over anhydrous sodium sulfate, and concentrated. The residue was purified by silica gel chromatography using 0-5% EtOAc in MeOH to afford (S)-methyl 6-(3,5-dimethylisoxazol-4-yl)-4-((3-fluoropyridin-2-yl)(tetrahydro-2H-pyran-4-yl)methyl)-1-methyl-1,4-dihydropyrazolo[3',4':4,5]pyrrolo[3,2-b]pyridine-3-carboxylate (254 mg, 78% yield), LC-MS [M+H]$^+$=519.

Step 4: (S)-2-(6-(3,5-dimethylisoxazol-4-yl)-4-((3-fluoropyridin-2-yl)(tetrahydro-2H-pyran-4-yl)methyl)-1-methyl-1,4-dihydropyrazolo[3',4':4,5]pyrrolo[3,2-b]pyridin-3-yl)propan-2-ol MeMgBr (1M in THF, 4.8 mL, 4.77 mmol) was slowly added to a solution of (S)-methyl 6-(3,5-dimethylisoxazol-4-yl)-4-((3-fluoropyridin-2-yl)(tetrahydro-2H-pyran-4-yl)methyl)-1-methyl-1,4-dihydropyrazolo[3',4':4,5]pyrrolo[3,2-b]pyridine-3-carboxylate (from Step 3, 254 mg, 0.49 mmol) in dry THF (10 ml) at −30° C. under N$_2$ over 1 min. After addition, the reaction was warmed to r.t. and stirred for 2 hr. The reaction was quenched with sat. NH$_4$Cl, and extracted with EtOAc (30 mL). The organic layer was washed with sat. aqueous NaCl, dried over anhydrous sodium sulfate, and concentrated. The residue was purified by silica gel chromatography using 0-4% MeOH in DCM to afford (S)-2-(6-(3,5-dimethyl isoxazol-4-yl)-4-((3-fluoropyridin-2-yl)(tetrahydro-2H-pyran-4-yl)methyl)-1-methyl-1,4-dihydropyrazolo[3',4':4,5]pyrrolo[3,2-b]pyridin-3-yl)propan-2-ol (Compound 2, 93 mg, 37% yield), LC-MS [M+H]$^+$=519.

$^1$H NMR (400 MHz, DMSO-$d_6$) δ 8.54 (d, J=4.6 Hz, 1H), 8.32 (d, J=1.6 Hz, 1H), 8.10 (d, J=1.6 Hz, 1H), 7.72 (t, J=8.9 Hz, 1H), 7.47 (dt, J=8.5, 4.3 Hz, 1H), 6.98 (d, J=10.7 Hz, 1H), 5.68 (s, 1H), 4.13 (s, 3H), 3.80 (d, J=8.9 Hz, 1H), 3.68 (d, J=8.6 Hz, 1H), 3.28 (d, J=11.6 Hz, 1H), 3.23-3.06 (m, 2H), 2.41 (s, 3H), 2.23 (s, 3H), 1.73 (s, 3H), 1.66-1.60 (m, 1H), 1.57 (s, 3H), 1.51 (d, J=12.4 Hz, 1H), 1.40 (ddd, J=24.2, 12.2, 4.2 Hz, 1H), 0.50 (d, J=12.2 Hz, 1H).

Example 3

2-(6-(1,4-Dimethyl-1H-1,2,3-triazol-5-yl)-1-methyl-4-(4,4,4-trifluoro-1-phenylbutyl)-1,4-dihydropyrazolo[3',4':4,5]pyrrolo[3,2-b]pyridin-3-yl)propan-2-ol ("Compound 3")

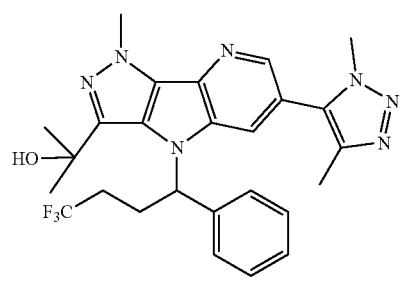 [SMILES: Cc1nnn(C)c1-c1cnc2c3c(c(C(C)(C)O)nn3C)n(C(CCC(F)(F)F)c3ccccc3)c2c1]

Step 1: Methyl 6-bromo-1-methyl-4-(4,4,4-trifluoro-1-phenylbutyl)-1,4-dihydropyrazolo [3',4':4,5]pyrrolo[3,2-b]pyridine-3-carboxylate To a solution of methyl 6-bromo-1,4-dihydropyrazolo[3',4':4,5]pyrrolo[3,2-b]pyridine-3-carboxylate (from Example 1 step 2, 213 mg, 0.69 mmol), 4,4,4-trifluoro-1-phenylbutan-1-ol (Intermediate 8, 179 mg, 0.88 mmol) and triphenylphosphine (449 mg, 1.71 mmol) in dry THF (10 mL) was dropwise added diisopropyl azodicarboxylate (350 mg, 1.73 mmol) in THF (2 mL) at room temperature and the resulting solution was stirred for 2 h. Then the reaction was extracted with EtOAc (50 mL). The extract was washed with brine, dried over anhydrous sodium sulfate, filtered and the filtrate was concentrated under reduced pressure. The resulting residue was purified by silica gel chromatography with 0-35% EtOAc in hexane to afford methyl 6-bromo-1-methyl-4-(4,4,4-trifluoro-1-phenylbutyl)-1,4-dihydropyrazolo[3',4':4,5]pyrrolo[3,2-b]pyridine-3-carboxylate (314 mg, 92% yield), LC-MS [M+H]$^+$=495, 497.

Step 2: Methyl 6-(1,4-dimethyl-1H-1,2,3-triazol-5-yl)-1-methyl-4-(4,4,4-trifluoro-1-phenylbutyl)-1,4-dihydropyrazolo[3',4':4,5]pyrrolo[3,2-b]pyridine-3-carboxylate To a solution of methyl 6-bromo-1-methyl-4-(4,4,4-trifluoro-1-phenylbutyl)-1,4-dihydropyrazolo [3',4':4,5]pyrrolo [3,2-b]pyridine-3-carboxylate (314 mg, 0.63 mmol) in DMF (10 mL) was added 1,4-dimethyl-5-(tributylstannyl)-1H-1,2,3-triazole (521 mg, 1.35 mmol), tetrakis(triphenylphosphine) palladium (102 mg, 0.088 mmol), CuI (30 mg, 0.16 mmol) and TEA (221 mg, 2.00 mmol). The mixture was degassed under vacuum, backfilled with nitrogen gas, and this sequence was repeated three times. The resulting mixture was stirred at 110° C. for 2 h. The reaction mixture was cooled to r.t., diluted with water (50 mL) and extracted with EtOAc (3×50 mL). After separation, the organic layer was washed with brine, dried over anhydrous sodium sulfate, and concentrated. The residue was purified by silica gel chromatography using 0-5% MeOH in DCM to afford methyl 6-(1,4-dimethyl-1H-1,2,3-triazol-5-yl)-1-methyl-4-(4,4,4-trifluoro-1-phenylbutyl)-1,4-dihydropyrazolo[3',4':4,5]pyrrolo[3,2-b]pyridine-3-carboxylate (176 mg, 55% yield), LC-MS [M+H]$^+$=512.

Step 3: 2-(6-(1,4-Dimethyl-1H-1,2,3-triazol-5-yl)-1-methyl-4-(4,4,4-trifluoro-1-phenylbutyl)-1,4-dihydropyrazolo[3',4':4,5]pyrrolo[3,2-b]pyridin-3-yl)propan-2-ol MeMgBr (1M in THF, 3.2 mL, 3.20 mmol) was slowly added to a solution of methyl 6-(1,4-dimethyl-1H-1,2,3-triazol-5-yl)-1-methyl-4-(4,4,4-trifluoro-1-phenylbutyl)-1,4-dihydropyrazolo[3',4':4,5]pyrrolo[3,2-b]pyridine-3-carboxylate (176 mg, 0.34 mmol) in dry THF (10 ml) at −30° C. under N$_2$ over 1 min. After addition, the reaction was warmed to r.t. and stirred for 2 hr. The reaction was quenched with sat. NH$_4$Cl, and extracted with EtOAc (30 mL). The organic layer was washed with sat. aqueous NaCl, dried over anhydrous sodium sulfate, and concentrated. The residue was purified by silica gel chromatography using 0-6% MeOH in DCM to afford 2-(6-(1,4-dimethyl-1H-1,2,3-triazol-5-yl)-1-methyl-4-(4,4,4-trifluoro-1-phenylbutyl)-1,4-dihydropyrazolo[3',4':4,5]pyrrolo[3,2-b]pyridin-3-yl)propan-2-ol (Compound 3, 94 mg, 53% yield), LC-MS [M+H]$^+$=512.

$^1$H NMR (400 MHz, DMSO-d$_6$) δ 8.40 (d, J=1.2 Hz, 1H), 7.61 (s, 1H), 7.32 (d, J=4.2 Hz, 4H), 7.25 (dd, J=8.3, 4.0 Hz, 1H), 6.77 (t, J=8.0 Hz, 1H), 5.77 (s, 1H), 4.19 (s, 3H), 3.73 (s, 3H), 2.80 (dd, J=16.2, 8.0 Hz, 2H), 2.70-2.55 (m, 1H), 2.07 (s, 3H), 1.88-1.74 (m, 1H), 1.69 (s, 3H), 1.52 (s, 3H).

Example 4

2-(6-(1,4-Dimethyl-1H-1,2,3-triazol-5-yl)-1-methyl-4-(4,4,4-trifluoro-1-(3-fluoropyridin-2-yl)butyl)-1,4-dihydropyrazolo[3',4':4,5]pyrrolo[3,2-b]pyridin-3-yl)propan-2-ol, ("Compound 4")

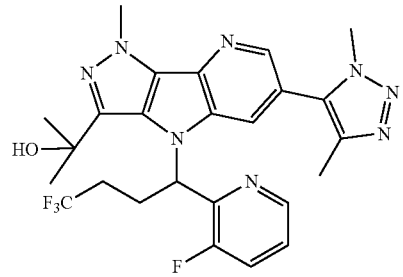 [SMILES: Cc1nnn(C)c1-c1cnc2c3c(c(C(C)(C)O)nn3C)n(C(CCC(F)(F)F)c3ncccc3F)c2c1]

Step 1: Methyl 6-bromo-1-methyl-4-(4,4,4-trifluoro-1-(3-fluoropyridin-2-yl)butyl)-1,4-dihydro pyrazolo[3',4':4,5]pyrrolo[3,2-b]pyridine-3-carboxylate To a solution of methyl 6-bromo-1,4-dihydropyrazolo[3',4':4,5]pyrrolo[3,2-b]pyridine-3-carboxylate (from Example 1 step 2, 221 mg, 0.71 mmol), 4,4,4-trifluoro-1-(3-fluoropyridin-2-yl)butan-1-ol (Intermediate 7, 215 mg, 0.97 mmol) and triphenylphosphine (471 mg, 1.80 mmol) in dry THF (10 mL) was vacuumed and backfilled with nitrogen, and this sequence was repeated three times. Diisopropyl azodicarboxylate (353 mg, 1.75 mmol) in THF (3 mL) was added dropwise at room temperature and the resulting solution was stirred for 2 h. Then the reaction was extracted EtOAc (50 mL). The extract was washed with brine, dried over anhydrous sodium sulfate and filtered. The filtrate was concentrated under reduced pressure. The residue was purified by silica gel chromatography with 0-40% EtOAc in hexane to afford methyl 6-bromo-1-methyl-4-(4,4,4-trifluoro-1-(3-fluoropyridin-2-yl)butyl)-1,4-dihydropyrazolo [3',4':4,5]pyrrolo[3,2-b]pyridine-3-carboxylate (339 mg, 93% yield), LC-MS [M+H]$^+$=514, 516.

Step 2: Methyl 6-(1,4-dimethyl-1H-1,2,3-triazol-5-yl)-1-methyl-4-(4,4,4-trifluoro-1-(3-fluoropyridin-2-yl)butyl)-1,4-dihydropyrazolo[3',4':4,5]pyrrolo[3,2-b]pyridine-3-carboxylate To a solution of methyl 6-bromo-1-methyl-4-(4,4,4-trifluoro-1-(3-fluoropyridin-2-yl)butyl)-1,4-dihydropyrazolo [3',4':4,5]pyrrolo[3,2-b]pyridine-3-carboxylate (339 mg, 0.66 mmol) in DMF (10 mL) was added 1,4-dimethyl-5-(tributylstannyl)-1H-1,2,3-triazole (568 mg, 1.47 mmol), tetrakis(triphenylphosphine)palladium (130 mg, 0.11 mmol), CuI (26 mg, 0.14 mmol) and TEA (243 mg, 2.20 mmol). The mixture was vacuumed and backfilled with nitrogen, and this sequence was repeated three times. The resulting mixture was stirred at 110° C. for 2 h. The reaction mixture was cooled to r.t., diluted with water (50 mL) and extracted with EtOAc (3×50 mL). After separation, the organic layer was washed with brine, dried over anhydrous sodium sulfate, and concentrated. The residue was purified by silica gel chromatography using 0-6% MeOH in DCM to afford methyl 6-(1,4-dimethyl-1H-1,2,3-triazol-5-yl)-1-methyl-4-(4,4,4-trifluoro-1-(3-fluoropyridin-2-yl)butyl)-1,4-dihydropyrazolo[3',4':4,5]pyrrolo[3,2-b]pyridine-3-carboxylate (194 mg, 55% yield), LC-MS [M+H]$^+$=531.

Step 3:2-(6-(1,4-Dimethyl-1H-1,2,3-triazol-5-yl)-1-methyl-4-(4,4,4-trifluoro-1-(3-fluoropyridin-2-yl)butyl)-1,4-dihydropyrazolo[3',4':4,5]pyrrolo[3,2-b]pyridin-3-yl)propan-2-ol MeMgBr (1M in THF, 3.7 mL, 3.72 mmol) was slowly added to a solution of methyl 6-(1,4-dimethyl-1H-1,2,3-triazol-5-yl)-1-methyl-4-(4,4,4-trifluoro-1-(3-fluoropyridin-2-yl)butyl)-1,4-dihydropyrazolo[3',4':4,5]pyrrolo[3,2-b]pyridine-3-carboxylate (194 mg, 0.37 mmol) in dry THF (10 ml) at −30° C. under $N_2$ over 1 min. After addition, the reaction was warmed to r.t. and stirred for 2 hr. The reaction was quenched with sat. $NH_4Cl$, and extracted with EtOAc (30 mL). The organic layer was washed with sat. aqueous NaCl, dried over anhydrous sodium sulfate, and concentrated. The residue was purified by silica gel chromatography using 0-6% MeOH in DCM to afford 2-(6-(1,4-dimethyl-1H-1,2,3-triazol-5-yl)-1-methyl-4-(4,4,4-trifluoro-1-(3-fluoropyridin-2-yl)butyl)-1,4-dihydropyrazolo[3',4':4,5]pyrrolo[3,2-b]pyridin-3-yl)propan-2-ol (Compound 4, 101 mg, 53% yield), LC-MS [M+H]$^+$=531. $^1$H NMR (400 MHz, DMSO-$d_6$) δ 8.55 (d, J=4.6 Hz, 1H), 8.40 (d, J=1.6 Hz, 1H), 7.76-7.66 (m, 1H), 7.58-7.47 (m, 2H), 7.09 (t, J=7.0 Hz, 1H), 5.78 (s, 1H), 4.17 (s, 3H), 3.82 (s, 3H), 2.88-2.76 (m, 1H), 2.69-2.53 (m, 2H), 2.07 (s, 3H), 2.02-1.89 (m, 1H), 1.72 (s, 3H), 1.62-1.51 (m, 3H).

Example 5

2-(6-(1,4-Dimethyl-1H-1,2,3-triazol-5-yl)-1-methyl-4-((3-methylpyridin-2-yl)(tetrahydro-2H-pyran-4-yl)methyl)-1,4-dihydropyrazolo[3',4':4,5]pyrrolo[3,2-b]pyridin-3-yl)propan-2-ol ("Compound 5")

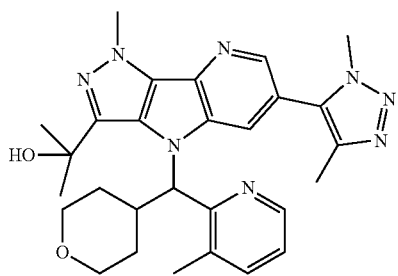 [SMILES: Cc1cccnc1C(C1CCOCC1)n1c2cc(-c3c(C)nnn3C)cnc2c2c1c(C(C)(C)O)nn2C]

Step 1: Methyl 6-bromo-1-methyl-4-((3-methylpyridin-2-yl)(tetrahydro-2H-pyran-4-yl)methyl)-1,4-dihydropyrazolo[3',4':4,5]pyrrolo[3,2-b]pyridine-3-carboxylate Following the procedure analogous to that described for the synthesis of methyl 6-bromo-4-((3-fluoropyridin-2-yl) (tetrahydro-2H-pyran-4-yl)methyl)-1-methyl-1,4-dihydropyrazolo[3',4':4,5]pyrrolo[3,2-b]pyridine-3-carboxylate, methyl 6-bromo-1-methyl-1,4-dihydropyrazolo[3',4':4,5] pyrrolo[3,2-b]pyridine-3-carboxylate (from Example 1 step 2, 237 mg, 0.77 mmol), (3-methylpyridin-2-yl)(tetrahydro-2H-pyran-4-yl)methanol (Intermediate 5, 249 mg, 1.20 mmol) were converted to methyl 6-bromo-1-methyl-4-((3-methylpyridin-2-yl)(tetrahydro-2H-pyran-4-yl)methyl)-1,4-dihydropyrazolo[3',4':4,5]pyrrolo[3,2-b]pyridine-3-carboxylate (331 mg, 86% yield), LC-MS [M+H]$^+$=498, 500.

Step 2: Methyl 6-(1,4-dimethyl-1H-1,2,3-triazol-5-yl)-1-methyl-4-((3-methylpyridin-2-yl) (tetrahydro-2H-pyran-4-yl)methyl)-1,4-dihydropyrazolo[3',4':4,5]pyrrolo[3,2-b]pyridine-3-carboxylate Following the procedure analogous to that described for the synthesis of methyl 6-(1,4-dimethyl-1H-1,2,3-triazol-5-yl)-1-methyl-4-(4,4,4-trifluoro-1-phenylbutyl)-1,4-dihydropyrazolo[3',4':4,5]pyrrolo[3,2-b]pyridine-3-carboxylate, methyl 6-bromo-1-methyl-4-((3-methylpyridin-2-yl)(tetrahydro-2H-pyran-4-yl) methyl)-1,4-dihydropyrazolo[3',4':4,5]pyrrolo[3,2-b]pyridine-3-carboxylate (331 mg, 0.66 mmol) and 1,4-dimethyl-5-(tributylstannyl)-1H-1,2,3-triazole (528 mg, 1.37 mmol) were converted to methyl 6-(1,4-dimethyl-1H-1,2,3-triazol-5-yl)-1-methyl-4-((3-methylpyridin-2-yl)(tetrahydro-2H-pyran-4-yl) methyl)-1,4-dihydropyrazolo[3',4':4,5]pyrrolo[3,2-b]pyridine-3-carboxylate (217 mg, 64% yield), LC-MS [M+H]$^+$=515.

Step 3:2-(6-(1,4-Dimethyl-1H-1,2,3-triazol-5-yl)-1-methyl-4-((3-methylpyridin-2-yl) (tetrahydro-2H-pyran-4-yl)methyl)-1,4-dihydropyrazolo[3',4':4,5] pyrrolo[3,2-b]pyridin-3-yl)propan-2-ol Following the procedure analogous to that described for the synthesis of 2-(6-(3,5-dimethylisoxazol-4-yl)-4-((3-fluoropyridin-2-yl) (tetrahydro-2H-pyran-4-yl)methyl)-1-methyl-1,4-dihydropyrazolo [3',4':4,5]pyrrolo[3,2-b]pyridin-3-yl)propan-2-ol, methyl 6-(1,4-dimethyl-1H-1,2,3-triazol-5-yl)-1-methyl-4-((3-methylpyridin-2-yl) (tetrahydro-2H-pyran-4-yl)methyl)-1,4-dihydropyrazolo[3', 4':4,5]pyrrolo[3,2-b]pyridine-3-carboxylate (217 mg, 0.42 mmol) was converted to 2-(6-(1,4-dimethyl-1H-1,2,3-triazol-5-yl)-1-methyl-4-((3-methylpyridin-2-yl)(tetrahydro-2H-pyran-4-yl)methyl)-1,4-dihydropyrazolo[3',4':4,5]pyrrolo[3,2-b]pyridin-3-yl)propan-2-ol (Compound 5, 115 mg, 53% yield), LC-MS [M+H]$^+$=515.

$^1$H NMR (400 MHz, DMSO-$d_6$) δ 8.54 (d, J=3.9 Hz, 1H), 8.36 (d, J=1.2 Hz, 1H), 7.89 (s, 1H), 7.57 (d, J=7.3 Hz, 1H), 7.26 (dd, J=7.5, 4.8 Hz, 1H), 6.92 (d, J=10.4 Hz, 1H), 5.97 (s, 1H), 4.16 (s, 3H), 3.85 (s, 3H), 3.80 (d, J=8.5 Hz, 1H), 3.69 (d, J=9.2 Hz, 1H), 3.33 (s, 1H), 3.28 (s, 1H), 3.12 (t, J=11.5 Hz, 1H), 2.25 (d, J=18.8 Hz, 3H), 2.11 (s, 3H), 1.72 (s, 3H), 1.67 (s, 1H), 1.66-1.60 (m, 1H), 1.57 (s, 3H), 1.44-1.31 (m, 1H), 0.46 (d, J=12.3 Hz, 1H).

Example 6

(S)-2-(6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-yl)propan-2-ol ("Compound 6")

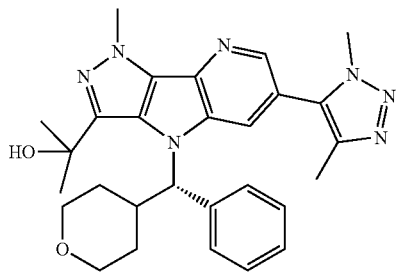 [SMILES: Cc1nnn(C)c1-c1cnc2c3c(c(C(C)(C)O)nn3C)n([C@H](c3ccccc3)C3CCOCC3)c2c1]

Step 1: 5-bromo-2-(1-methyl-1H-pyrazol-5-yl)-3-nitropyridine

To a solution of 2,5-dibromo-3-nitropyridine (34.4 g, 122 mmol) in THF (500 mL) and water (150 mL) was added (1-methyl-1H-pyrazol-5-yl)boronic acid (12.6 g, 99.7 mmol), Pd(dppf)Cl$_2$ (8.38 g, 10.3 mmol), and K$_3$PO$_4$ (42.3 g, 199.1 mmol) under N$_2$. The mixture was vacuumed, backfilled with N$_2$ and this process was repeated three times. The resulting mixture was heated to reflux and stirred for 5 h under N$_2$. After cooling to r.t., the reaction mixture was poured into water and extracted with EtOAc (2×100 mL). The combined organic layers were washed with brine, dried over anhydrous sodium sulfate, and concentrated under reduced pressure. The residue was purified by silica gel chromatography using 10-30% EtOAc in hexane to afford 5-bromo-2-(1-methyl-1H-pyrazol-5-yl)-3-nitropyridine (9.47 g, 33.5 mmol, 34% yield), LC-MS [M+H]$^+$=283.

Step 2: 6-bromo-1-methyl-1,4-dihydropyrazolo[3',4':4,5]pyrrolo[3,2-b]pyridine A mixture of 5-bromo-2-(1-methyl-1H-pyrazol-5-yl)-3-nitropyridine (9.47 g, 33.5 mmol) and DPPE (22.8 g, 57.3 mmol) in 1,2-dichlorobenzene (100 mL) was heated to 180° C. and stirred for 4 h under N$_2$. The reaction was then cooled slowly to room temperature. The reaction mixture was concentrated under a reduced pressure. The crude product was purified by silica gel chromatography using 30-50% EtOAc in hexane to afford 6-bromo-1-methyl-1,4-dihydropyrazolo[3',4':4,5]pyrrolo[3,2-b]pyridine (4.12 g, 16.4 mmol, 49% yield), LC-MS [M+H]$^+$=251.

Step 3: (S)-6-bromo-1-methyl-4-(phenyl(tetrahydro-2H-pyran-4-yl)methyl)-1,4-dihydro pyrazolo[3',4':4,5]pyrrolo[3,2-b]pyridine To a solution of 6-bromo-1-methyl-1,4-dihydropyrazolo[3',4':4,5]pyrrolo[3,2-b]pyridine (1.24 g, 4.96 mmol), (R)-phenyl(tetrahydro-2H-pyran-4-yl)methanol (2.52 g, 13.1 mmol) and triphenylphosphane (4.71 g, 18.0 mmol) in dry THF (30 mL) was added diisopropyl azodicarboxylate (4.02 g, 19.9 mmol) at r.t. under N$_2$. The resulting solution was refluxed for 2 h under N$_2$. After cooling to r.t., the reaction mixture was extracted with EtOAc (50 mL). The resulting organic layer was washed with brine, dried over anhydrous sodium sulfate, and concentrated under reduced pressure. The residue was purified by silica gel chromatography using 30-50% EtOAc in hexane to afford (S)-6-bromo-1-methyl-4-(phenyl (tetrahydro-2H-pyran-4-yl)methyl)-1,4-dihydropyrazolo[3',4':4,5]pyrrolo[3,2-b]pyridine (0.95 g, 2.23 mmol, 45%), LC-MS [M+H]$^+$=425.

Step 4: (S)-6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridine To a solution of (S)-6-bromo-1-methyl-4-(phenyl(tetrahydro-2H-pyran-4-yl)methyl)-1,4-dihydro pyrazolo[3',4':4,5]pyrrolo[3,2-b]pyridine (0.95 g, 2.23 mmol) in DMF (40 mL) was added 1,4-dimethyl-5-(tributylstannyl)-1H-1,2,3-triazole (2.51 g, 6.50 mmol), tetrakis(triphenylphosphine)palladium (0.54 g, 0.47 mmol), CuI (0.18 g, 0.95 mmol) and TEA (1.02 g, 9.26 mmol) under N$_2$. The mixture was vacuumed, backfilled with N$_2$ and this process was repeated three times. The resulting mixture was stirred at 85° C. for 3 h and then cooled to room temperature. The reaction mixture was poured into water and extracted with EtOAc (100 mL). The organic phase was washed with brine, dried over anhydrous sodium sulfate, and concentrated. The residue was purified by silica gel chromatography using 0-5% MeOH in DCM to afford (S)-6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridine (0.63 g, 1.43 mmol, 64% yield), LC-MS [M+H]$^+$=442.

Step 5: (S)-3-bromo-6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridine N-bromosuccinimide (0.62 g, 3.48 mmol) was added in small batches to a solution of (S)-6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridine (0.63 g, 1.43 mmol) in THF (20 mL) and water (10 mL) at room temperature over 10 min. After addition, the reaction was stirred at room temperature for 2 h. The reaction was quenched with sat. NaHCO$_3$ and extracted with EtOAc (100 mL). The organic layer was washed with brine, dried over anhydrous sodium sulfate, and concentrated. The residue was purified by silica gel chromatography using 0-3% MeOH in DCM to afford the expected (S)-3-bromo-6-(1,4-dimethyl-1H-1,2,3-triazol-5-yl)-1-methyl-4-(phenyl (tetrahydro-2H-pyran-4-yl)methyl)-1,4-dihydropyrazolo[3',4':4,5]pyrrolo[3,2-b]pyridine (0.71 g, 1.36 mmol, 95%), LC-MS [M+H]$^+$=520.

Step 6: (S)-1-(6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-yl)ethan-1-one To a solution of (S)-3-bromo-6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridine (0.71 g, 1.36 mmol) in 1,4-dioxane (20 mL) was added tributyl(1-ethoxyvinyl)-stannane (1.08 g, 2.99 mmol), tetrakis(triphenylphosphine)palladium (0.27 g, 0.23 mmol), cesium fluoride (0.71 g, 4.67 mmol) under N$_2$. The mixture was vacuumed, backfilled with N$_2$ and this process was repeated three times. The resulting mixture was refluxed for 20 h. Then the solvent was taken off under a reduced pressure to afford a light yellow substance.

To this substance was added THF (10 mL) and followed by 2N HCl (2 mL) at room temperature, and stirred for 2 h. Then the reaction was quenched with sat. NaHCO$_3$ and extracted with EtOAc (100 mL). The organic phase was washed with brine, dried over anhydrous sodium sulfate, and concentrated. The residue was purified by silica gel chromatography using 0-5% MeOH in DCM to afford the expected (S)-1-(6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-yl)ethan-1-one (390 mg, 0.81 mmol, 60% yield), LC-MS [M+H]$^+$=484.

Step 7: (S)-2-(6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-yl)propan-2-ol MeMgBr (1M in THF, 10.0 mL, 10.0 mmol) was dropwise added to a solution of (S)-1-(6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-yl)ethan-1-one (390 mg, 0.81 mmol) in THF (30 ml) at −30° C. over 10 min under N$_2$. After addition, the reaction was stirred at room temperature for 2 h. The reaction was quenched with sat. NH$_4$Cl, and extracted with EtOAc (100 mL). The organic layer was washed with brine, dried over sodium sulfate, and concentrated. The residue was purified by silica gel chromatography using 0-6% MeOH in DCM to afford the expected (S)-2-(6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-yl)propan-2-ol (Compound 6, 84 mg, 0.17 mmol, 44% yield), LC-MS [M+H]$^+$=500.

$^1$H NMR (400 MHz, DMSO-d$_6$) δ 8.35 (d, J=1.2 Hz, 1H), 7.94 (s, 1H), 7.71 (d, J=7.6 Hz, 2H), 7.26 (m, 3H), 6.46 (d, J=11.2 Hz, 1H), 5.81 (s, 1H), 4.15 (s, 3H), 3.85 (s, 3H), 3.52-3.39 (m, 2H), 3.29-3.19 (m, 2H), 2.17 (s, 3H), 2.00 (m, 1H), 1.71 (d, J=13.2 Hz, 4H), 1.23 (s, 6H).

Example 7

(S)-2-(6-(1,4-dimethyl-1H-1,2,3-triazol-5-yl)-4-((3-fluoropyridin-2-yl)(tetrahydro-2H-pyran-4-yl)methyl)-1-methyl-1,4-dihydropyrazolo[3',4':4,5]pyrrolo[3,2-b]pyridin-3-yl)propan-2-ol ("Compound 7")

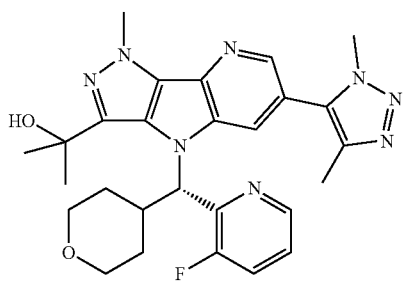 [SMILES: Cc1nnn(C)c1-c1cnc2c3c(c(C(C)(C)O)nn3C)n([C@H](c3ncccc3F)C3CCOCC3)c2c1]

Step 1: (S)-methyl 6-bromo-4-((3-fluoropyridin-2-yl)(tetrahydro-2H-pyran-4-yl)methyl)-1-methyl-1,4-dihydropyrazolo[3',4':4,5]pyrrolo[3,2-b]pyridine-3-carboxylate To a solution of methyl 6-bromo-1-methyl-1,4-dihydropyrazolo[3',4':4,5]pyrrolo[3,2-b]pyridine-3-carboxylate (from Example 1 step 2, 409 mg, 1.32 mmol), (R)-(3-fluoropyridin-2-yl)(tetrahydro-2H-pyran-4-yl)methanol (Enantiomer a1 from Example 2, 352 mg, 1.67 mmol) and triphenylphosphane (0.52 g, 1.98 mol) in dry THF (30 mL) was added diisopropyl azodicarboxylate (0.49 g, 2.42 mmol) at r.t. under N$_2$. The resulting solution was refluxed for 2 hr under N$_2$. After cooling to r.t., the reaction mixture was extracted with EtOAc (50 mL). The resulting organic layer was washed with brine, dried over anhydrous sodium sulfate, and concentrated under reduced pressure. The residue was purified by silica gel chromatography using 30-50% EtOAc in hexane to afford (S)-methyl 6-bromo-4-((3-fluoropyridin-2-yl)(tetrahydro-2H-pyran-4-yl)methyl)-1-methyl-1,4-dihydropyrazolo[3',4':4,5]pyrrolo[3,2-b]pyridine-3-carboxylate (442 mg, 0.88 mmol, 67% yield), LC-MS [M+H]$^+$=502.

Step 2: (S)-Methyl 6-(1,4-dimethyl-1H-1,2,3-triazol-5-yl)-4-((3-fluoropyridin-2-yl)(tetrahydro-2H-pyran-4-yl)methyl)-1-methyl-1,4-dihydropyrazolo[3',4':4,5]pyrrolo[3,2-b]pyridine-3-carboxylate ("Compound 7-2")

To a solution of (S)-methyl 6-bromo-4-((3-fluoropyridin-2-yl)(tetrahydro-2H-pyran-4-yl)methyl)-1-methyl-1,4-dihydropyrazolo[3',4':4,5]pyrrolo[3,2-b]pyridine-3-carboxylate (442 mg, 0.88 mmol) in DMF (30 mL) was added 1,4-dimethyl-5-(tributylstannyl)-1H-1,2,3-triazole (680 mg, 1.76 mmol), tetrakis(triphenylphosphine)palladium (168 mg, 0.15 mmol), CuI (65 mg, 0.34 mmol) and TEA (0.92 g, 8.35 mmol) under N$_2$. The mixture was vacuumed, backfilled with N$_2$ and this process was repeated three times. The resulting mixture was stirred at 85° C. for 3 h and then cooled to room temperature. The reaction mixture was poured into water and extracted with EtOAc (50 mL). The organic phase was washed with brine, dried over anhydrous sodium sulfate, and concentrated. The residue was purified by silica gel chromatography using 0-5% MeOH in DCM to afford (S)-methyl 6-(1,4-dimethyl-1H-1,2,3-triazol-5-yl)-4-((3-fluoropyridin-2-yl)(tetrahydro-2H-pyran-4-yl)methyl)-1-methyl-1,4-dihydropyrazolo[3',4':4,5]pyrrolo[3,2-b]pyridine-3-carboxylate (Compound 7-2, 201 mg, 0.38 mmol, 43% yield), LC-MS [M+H]$^+$=519.

Step 3: (S)-2-(6-(1,4-dimethyl-1H-1,2,3-triazol-5-yl)-4-((3-fluoropyridin-2-yl)(tetrahydro-2H-pyran-4-yl)methyl)-1-methyl-1,4-dihydropyrazolo[3',4':4,5]pyrrolo[3,2-b]pyridin-3-yl)propan-2-ol Following the procedure analogous to that described for the synthesis of 2-(6-(3,5-dimethylisoxazol-4-yl)-4-((3-fluoropyridin-2-yl)(tetrahydro-2H-pyran-4-yl)methyl)-1-methyl-1,4-dihydropyrazolo[3',4':4,5]pyrrolo[3,2-b]pyridin-3-yl)propan-2-ol, (S)-methyl 6-(1,4-dimethyl-1H-1,2,3-triazol-5-yl)-4-((3-fluoropyridin-2-yl)(tetrahydro-2H-pyran-4-yl)methyl)-1-methyl-1,4-dihydropyrazolo[3',4':4,5]pyrrolo[3,2-b]pyridine-3-carboxylate (0.20 g, 0.38 mmol) was converted to (S)-2-(6-(1,4-dimethyl-1H-1,2,3-triazol-5-yl)-4-((3-fluoropyridin-2-yl)(tetrahydro-2H-pyran-4-yl)methyl)-1-methyl-1,4-dihydropyrazolo[3', 2-b]pyridin-3-yl)propan-2-ol (Compound 7, 38 mg, 0.073 mmol, 19% yield), LC-MS[M+H]$^+$=519.

$^1$H NMR (600 MHz, DMSO-d$_6$) δ 8.50 (d, J=4.6 Hz, 1H), 8.40 (d, J=1.6 Hz, 1H), 8.27 (d, J=1.6 Hz, 1H), 7.71 (t, J=9.3 Hz, 1H), 7.45 (dt, J=8.5, 4.3 Hz, 1H), 6.99 (d, J=10.9 Hz, 1H), 5.70 (s, 1H), 4.12 (s, 3H), 3.94 (s, 3H), 3.81-3.74 (m, 1H), 3.65 (dd, J=11.3, 2.9 Hz, 1H), 3.26 (dd, J=11.7, 9.9 Hz, 1H), 3.22-3.15 (m, 1H), 3.09 (t, J=11.2 Hz, 1H), 2.21 (s, 3H), 1.70 (s, 3H), 1.59 (ddd, J=25.2, 12.7, 4.6 Hz, 1H), 1.53 (s, 3H), 1.44 (d, J=12.0 Hz, 1H), 1.41-1.32 (m, 1H), 0.52 (d, J=12.5 Hz, 1H).

Example 8

2-(6-(3,5-dimethylisoxazol-4-yl)-1-methyl-4-((3-methylpyridin-2-yl)(tetrahydro-2H-pyran-4-yl) methyl)-1,4-dihydropyrazolo[3',4':4,5]pyrrolo[3,2-b] pyridin-3-yl)propan-2-ol ("Compound 8")

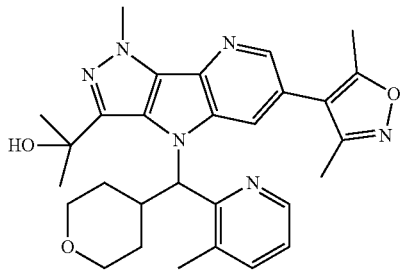 [SMILES: Cc1cccnc1C(C1CCOCC1)n1c2cc(-c3c(C)noc3C)cnc2c2c1c(C(C)(C)O)nn2C]

Step 1: Methyl 6-bromo-1-methyl-4-((3-methylpyridin-2-yl)(tetrahydro-2H-pyran-4-yl) methyl)-1,4-dihydropyrazolo[3',4':4,5]pyrrolo[3,2-b]pyridine-3-carboxylate Following the procedure analogous to that described for the synthesis of methyl 6-bromo-4-((3-fluoropyridin-2-yl)(tetrahydro-2H-pyran-4-yl)methyl)-1-methyl-1,4-dihydropyrazolo[3',4':4,5]pyrrolo[3,2-b]pyridine-3-carboxylate, methyl 6-bromo-1-methyl-1,4-dihydropyrazolo[3',4':4,5] pyrrolo[3,2-b]pyridine-3-carboxylate (from Example 1 step 2, 200 mg, 0.65 mmol) and (3-methylpyridin-2-yl) (tetrahydro-2H-pyran-4-yl)methanol (Intermediate 5, 184 mg, 0.89 mmol) were converted to methyl 6-bromo-1-methyl-4-((3-methylpyridin-2-yl)(tetrahydro-2H-pyran-4-yl)methyl)-1,4-dihydropyrazolo[3',4':4,5]pyrrolo[3,2-b]pyridine-3-carboxylate (210 mg, 0.42 mmol, 65%), LC-MS [M+H]$^+$=497.

Step 2: Methyl 6-(3,5-dimethylisoxazol-4-yl)-1-methyl-4-((3-methylpyridin-2-yl)(tetrahydro-2H-pyran-4-yl)methyl)-1,4-dihydropyrazolo[3',4':4,5] pyrrolo[3,2-b]pyridine-3-carboxylate To a solution of methyl 6-bromo-1-methyl-4-((3-methylpyridin-2-yl)(tetrahydro-2H-pyran-4-yl) methyl)-1,4-dihydropyrazolo[3',4':4,5]pyrrolo[3,2-b]pyridine-3-carboxylate (210 mg, 0.42 mmol) in THF (20 mL) and water (5 mL), was added 3,5-dimethyl-4-(4,4,5,5-tetramethyl-1,3,2-dioxaborolan-2-yl) isoxazole (210 mg, 0.90 mmol), Pd(dppf)Cl$_2$ (112 mg, 0.14 mmol), and K$_3$PO$_4$ (428 mg, 2.02 mmol) under N$_2$. The mixture was vacuumed, backfilled with N$_2$ and this process was repeated three times. The resulting mixture was heated to reflux and stirred for 5 h under N$_2$. After cooling to r.t., the reaction mixture was poured into water and extracted with EtOAc (50 mL). The organic layer was washed with brine, dried over anhydrous sodium sulfate, and concentrated under reduced pressure. The residue was purified by silica gel chromatography using 30-50% EtOAc in hexane to afford 6-(3,5-dimethylisoxazol-4-yl)-1-methyl-4-((3-methylpyridin-2-yl)(tetrahydro-2H-pyran-4-yl)methyl)-1,4-dihydropyrazolo[3',4':4,5]pyrrolo[3,2-b] pyridine-3-carboxylate (160 mg, 0.31 mmol, 73% yield), LC-MS [M+H]$^+$=515.

Step 3: 2-(6-(3,5-Dimethylisoxazol-4-yl)-1-methyl-4-((3-methylpyridin-2-yl)(tetrahydro-2H-pyran-4-yl) methyl)-1,4-dihydropyrazolo[3',4':4,5]pyrrolo[3,2-b] pyridin-3-yl)propan-2-ol Following the procedure analogous to that described for the synthesis of 2-(6-(3,5-dimethylisoxazol-4-yl)-4-((3-fluoropyridin-2-yl)(tetrahydro-2H-pyran-4-yl)methyl)-1-methyl-1,4-dihydropyrazolo[3',4':4,5]pyrrolo[3,2-b]pyridin-3-yl)propan-2-ol, methyl 6-(3,5-dimethylisoxazol-4-yl)-1-methyl-4-((3-methyl pyridin-2-yl)(tetrahydro-2H-pyran-4-yl)methyl)-1,4-dihydropyrazolo[3',4':4,5]pyrrolo[3,2-b] pyridine-3-carboxylate (160 mg, 0.31 mmol) was converted to 2-(6-(3,5-dimethylisoxazol-4-yl)-1-methyl-4-((3-methylpyridin-2-yl)(tetrahydro-2H-pyran-4-yl)methyl)-1,4-dihydropyrazolo[3',4':4,5]pyrrolo[3,2-b]pyridin-3-yl)propan-2-ol (Compound 8, 33 mg, 0.064 mmol, 21% yield), LC-MS [M+H]$^+$=515.

$^1$H NMR (400 MHz, DMSO-d$_6$) δ 8.56 (d, J=4.4 Hz, 1H), 8.27 (s, 1H), 7.71 (s, 1H), 7.56 (d, J=7.2 Hz, 1H), 7.25 (m, 1H), 6.90 (d, J=10.0 Hz, 1H), 5.96 (s, 1H), 4.15 (s, 1H), 4.11 (d, J=6.0 Hz, 3H), 3.80 (d, J=10.8 Hz, 1H), 3.69 (d, J=12.8 Hz, 1H), 3.36 (s, 2H), 3.27-3.20 (m, 1H), 3.13 (m, 3H), 2.64 (t, J=1.6, 1.6 Hz, 3H), 2.31 (t, J=1.6, 1.6 Hz, 3H), 2.19 (s, 2H), 2.12 (s, 1H), 1.74-1.62 (m, 6H).

Example 9

2-(6-(3,5-dimethylisoxazol-4-yl)-1-methyl-4-((tetrahydro-2H-pyran-4-yl)(o-tolyl)methyl)-1,4-dihydropyrazolo[3',4':4,5]pyrrolo[3,2-b]pyridin-3-yl)propan-2-ol ("Compound 9")

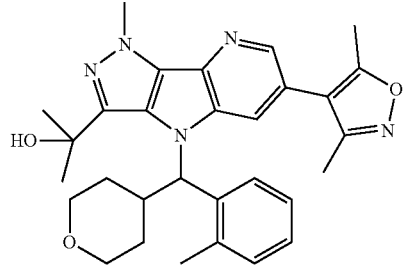 [SMILES: Cc1ccccc1C(C1CCOCC1)n1c2cc(-c3c(C)noc3C)cnc2c2c1c(C(C)(C)O)nn2C]

Step 1: Methyl 6-bromo-1-methyl-4-((tetrahydro-2H-pyran-4-yl)(o-tolyl)methyl)-1,4-dihydropyrazolo [3',4':4,5]pyrrolo[3,2-b]pyridine-3-carboxylate Following the procedure analogous to that described for the synthesis of methyl 6-bromo-4-((3-fluoropyridin-2-yl) (tetrahydro-2H-pyran-4-yl)methyl)-1-methyl-1,4-dihydropyrazolo[3',4':4,5]pyrrolo[3,2-b]pyridine-3-carboxylate, methyl 6-bromo-1-methyl-1,4-dihydropyrazolo[3',4':4,5]pyrrolo[3,2-b]pyridine-3-carboxylate (from Example 1 step 2, 200 mg, 0.65 mmol) and (tetrahydro-2H-pyran-4-yl)(o-tolyl) methanol (Intermediate 9, 191 mg, 0.93 mmol) were converted to methyl 6-bromo-1-methyl-4-((tetrahydro-2H-pyran-4-yl)(o-tolyl)methyl)-1,4-dihydropyrazolo[3',4':4,5]pyrrolo[3,2-b]pyridine-3-carboxylate (280 mg, 0.56 mmol, 86%), LC-MS [M+H]+=497.

Step 2: Methyl 6-(3,5-dimethylisoxazol-4-yl)-1-methyl-4-((tetrahydro-2H-pyran-4-yl)(o-tolyl)methyl)-1,4-dihydropyrazolo[3',4':4,5]pyrrolo[3,2-b]pyridine-3-carboxylate To a solution of methyl 6-bromo-1-methyl-4-((tetrahydro-2H-pyran-4-yl)(o-tolyl)methyl)-1,4-dihydropyrazolo[3',4':4,5]pyrrolo[3,2-b]pyridine-3-carboxylate (280 mg, 0.56 mmol) in THF (20 mL) and water (5 mL) was added 3,5-dimethyl-4-(4,4,5,5-tetramethyl-1,3,2-dioxaborolan-2-yl)isoxazole (210 mg, 0.90 mmol), Pd(dppf)Cl$_2$ (102 mg, 0.12 mmol), and K$_3$PO$_4$ (389 mg, 1.83 mmol) under N$_2$. The mixture was vacuumed, backfilled with N$_2$ and this process was repeated three times. The resulting mixture was heated to reflux and stirred for 5 h under N$_2$. After cooling to r.t., the reaction mixture was poured into water and extracted with EtOAc (100 mL). The organic layer was washed with brine, dried over anhydrous sodium sulfate, and concentrated under reduced pressure. The residue was purified by silica gel chromatography using 0-5% MeOH in DCM to afford methyl 6-(3,5-dimethylisoxazol-4-yl)-1-methyl-4-((tetrahydro-2H-pyran-4-yl)(o-tolyl)methyl)-1,4-dihydropyrazolo[3',4':4,5]pyrrolo[3,2-b]pyridine-3-carboxylate (218 mg, 0.42 mmol, 75% yield), LC-MS [M+H]+=514.

Step 3: 2-(6-(3,5-dimethylisoxazol-4-yl)-1-methyl-4-((tetrahydro-2H-pyran-4-yl)(o-tolyl) methyl)-1,4-dihydropyrazolo[3',4':4,5]pyrrolo[3,2-b]pyridin-3-yl)propan-2-ol Following the procedure analogous to that described for the synthesis of 2-(6-(3,5-dimethylisoxazol-4-yl)-4-((3-fluoropyridin-2-yl)(tetrahydro-2H-pyran-4-yl)methyl)-1-methyl-1,4-dihydropyrazolo[3',4':4,5]pyrrolo[3,2-b]pyridin-3-yl)propan-2-ol, methyl 6-(3,5-dimethylisoxazol-4-yl)-1-methyl-4-((tetrahydro-2H-pyran-4-yl)(o-tolyl)methyl)-1,4-dihydropyrazolo[3',4':4,5]pyrrolo[3,2-b]pyridine-3-carboxylate (218 mg, 0.42 mmol) was converted to 2-(6-(3,5-dimethylisoxazol-4-yl)-1-methyl-4-((tetrahydro-2H-pyran-4-yl)(o-tolyl)methyl)-1,4-dihydropyrazolo[3',4':4,5]pyrrolo[3,2-b]pyridin-3-yl)propan-2-ol (Compound 9, 59 mg, 0.11 mmol, 26% yield), LC-MS [M+H]+=514.

$^1$H NMR (400 MHz, DMSO-d$_6$) δ 8.24 (d, J=1.6 Hz, 1H), 7.98 (d, J=7.6 Hz, 1H), 7.48 (s, 1H), 7.32 (t, J=7.2, 7.6 Hz, 1H), 7.18 (t, J=7.6, 7.2 Hz, 1H), 7.10 (d, J=15.2 Hz, 1H), 6.79 (d, J=10.8 Hz, 1H), 5.92 (s, 1H), 4.15 (s, 3H), 3.83 (d, J=11.6 Hz, 1H), 3.72 (d, J=10.8 Hz 1H), 3.45 (t, J=11.6 Hz, 10.8 Hz, 1H), 3.17 (t, J=11.2, 11.6 Hz, 2H), 2.23 (s, 3H), 2.04 (d, J=2.8 Hz, 6H), 1.89-1.72 (m, 2H), 1.69 (d, J=9.2 Hz, 6H), 1.51-1.31 (m, 2H).

Example 10

2-(6-(1,4-dimethyl-1H-1,2,3-triazol-5-yl)-1-methyl-4-(4,4,4-trifluoro-1-(oxazol-4-yl)butyl)-1,4-dihydropyrazolo[3',4':4,5]pyrrolo[3,2-b]pyridin-3-yl)propan-2-ol ("Compound 10")

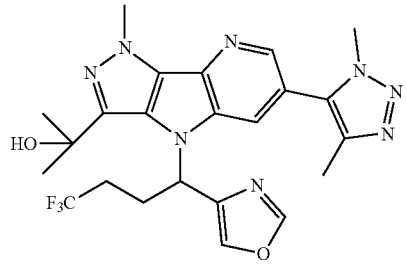 [SMILES: Cc1nnn(C)c1-c1cnc2c3c(c(C(C)(C)O)nn3C)n(C(CCC(F)(F)F)c3cocn3)c2c1]

Step 1: Methyl 6-bromo-1-methyl-4-(4,4,4-trifluoro-1-(oxazol-4-yl)butyl)-1,4-dihydro pyrazolo[3',4':4,5]pyrrolo[3,2-b]pyridine-3-carboxylate Following the procedure analogous to that described for the synthesis of methyl 6-bromo-4-((3-fluoropyridin-2-yl)(tetrahydro-2H-pyran-4-yl)methyl)-1-methyl-1,4-dihydropyrazolo[3',4':4,5]pyrrolo[3,2-b]pyridine-3-carboxylate, methyl 6-bromo-1-methyl-1,4-dihydropyrazolo[3',4':4,5]pyrrolo[3,2-b]pyridine-3-carboxylate (from Example 1 step 2, 200 mg, 0.65 mmol) and 4,4,4-trifluoro-1-(oxazol-4-yl)butan-1-ol (Intermediate 10, 280 mg, 1.43 mmol) were converted to methyl 6-bromo-1-methyl-4-(4,4,4-trifluoro-1-(oxazol-4-yl)butyl)-1,4-dihydropyrazolo[3',4':4,5]pyrrolo[3,2-b]pyridine-3-carboxylate (277 mg, 0.57 mmol, 87%), LC-MS [M+H]+=486.

Step 2: Methyl 6-(1,4-dimethyl-1H-1,2,3-triazol-5-yl)-1-methyl-4-(4,4,4-trifluoro-1-(oxazol-4-yl)butyl)-1,4-dihydropyrazolo[3',4':4,5]pyrrolo[3,2-b]pyridine-3-carboxylate Following the procedure analogous to that described for the synthesis of methyl 6-(1,4-dimethyl-1H-1,2,3-triazol-5-yl)-1-methyl-4-(4,4,4-trifluoro-1-phenylbutyl)-1,4-dihydropyrazolo[3',4':4,5]pyrrolo[3,2-b]pyridine-3-carboxylate, methyl 6-bromo-1-methyl-4-(4,4,4-trifluoro-1-(oxazol-4-yl)butyl)-1,4-dihydropyrazolo[3',4':4,5]pyridine-3-carboxylate (277 mg, 0.57 mmol) and 1,4-dimethyl-5-(tributylstannyl)-1H-1,2,3-triazole (485 mg, 1.26 mmol) were converted to methyl 6-(1,4-dimethyl-1H-1,2,3-triazol-5-yl)-1-methyl-4-(4,4,4-trifluoro-1-(oxazol-4-yl)butyl)-1,4-dihydropyrazolo[3',4':4,5]pyrrolo[3,2-b]pyridine-3-carboxylate (211 mg, 0.42 mmol, 73% yield), LC-MS [M+H]+=442.

Step 3: 2-(6-(1,4-dimethyl-1H-1,2,3-triazol-5-yl)-1-methyl-4-(4,4,4-trifluoro-1-(oxazol-4-yl) butyl)-1,4-dihydropyrazolo[3',4':4,5]pyrrolo[3,2-b]pyridin-3-yl)propan-2-ol Following the procedure analogous to that described for the synthesis of 2-(6-(3,5-dimethylisoxazol-4-yl)-4-((3-fluoropyridin-2-yl)(tetrahydro-2H-pyran-4-yl)methyl)-1-methyl-1,4-dihydropyrazolo[3',4':4,5]pyrrolo[3,2-b]pyridin-3-yl)propan-2-ol, methyl 6-(1,4-dimethyl-1H-1,2,3- triazol-5-yl)-1-methyl-4-(4,4,4-trifluoro-1-(oxazol-4-yl) butyl)-1,4-dihydropyrazolo[3',4':4,5]pyrrolo[3,2-b] pyridine-3-carboxylate (211 mg, 0.42 mmol) was converted to 2-(6-(1,4-dimethyl-1H-1,2,3-triazol-5-yl)-1-methyl-4-(4, 4,4-trifluoro-1-(oxazol-4-yl)butyl)-1,4-dihydropyrazolo[3', 4':4,5]pyrrolo[3,2-b]pyridin-3-yl)propan-2-ol (Compound 10, 94 mg, 0.19 mmol, 45% yield), LC-MS [M+H]$^+$=503.

$^1$H NMR (400 MHz, DMSO-d$_6$) δ 8.38 (d, =42.4 Hz, 2H), 7.98 (s, 1H), 6.72 (s, 1H), 5.74 (s, 1H), 4.16 (s, 2H), 3.89 (s, 2H), 3.31 (s, 6H), 2.74 (s, 1H), 2.26 (s, 3H), 1.65 (s, 6H).

Example 11

2-(6-(1,4-dimethyl-1H-1,2,3-triazol-5-yl)-1-methyl-4-(4,4,4-trifluoro-1-(3-methylpyridin-2-yl)butyl)-1, 4-dihydropyrazolo[3',4':4,5]pyrrolo[3,2-b]pyridin-3-yl)propan-2-ol ("Compound 11")

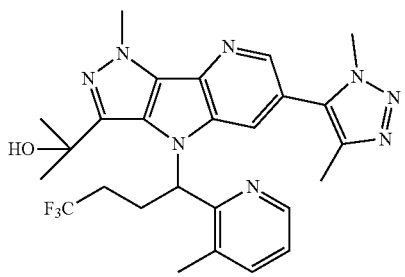 [SMILES: Cc1cccnc1C(CCC(F)(F)F)n1c2cc(-c3c(C)nnn3C)cnc2c2c1c(C(C)(C)O)nn2C]

Step 1: Methyl 6-bromo-1-methyl-4-(4,4,4-trifluoro-1-(3-methylpyridin-2-yl)butyl)-1,4-dihydro pyrazolo [3',4':4,5]pyrrolo[3,2-b]pyridine-3-carboxylate Following the procedure analogous to that described for the synthesis of methyl 6-bromo-4-((3-fluoropyridin-2-yl)(tetrahydro-2H-pyran-4-yl)methyl)-1-methyl-1,4-dihydro-pyrazolo[3',4':4,5]pyrrolo[3,2-b]pyridine-3-carboxylate, methyl 6-bromo-1-methyl-1,4-dihydropyrazolo[3',4':4,5] pyrrolo[3,2-b]pyridine-3-carboxylate (from Example 6 step 2, 200 mg, 0.65 mmol) and 4,4,4-trifluoro-1-(3-methylpyridin-2-yl)butan-1-ol (Intermediate 11, 202 mg, 1.48 mmol) and triphenylphosphane (387 mg, 1.48 mmol) were converted to methyl 6-bromo-1-methyl-4-(4,4,4-trifluoro-1-(3-methylpyridin-2-yl)butyl)-1,4-dihydropyrazolo[3',4':4,5] pyrrolo[3,2-b]pyridine-3-carboxylate (257 mg, 0.50 mmol, 77%), LC-MS [M+H]$^+$=510.

Step 2: Methyl 6-(1,4-dimethyl-1H-1,2,3-triazol-5-yl)-1-methyl-4-(4,4,4-trifluoro-1-(3-methylpyridin-2-yl)butyl)-1,4-dihydropyrazolo[3',4':4,5]pyrrolo[3, 2-b]pyridine-3-carboxylate Following the procedure analogous to that described for the synthesis of methyl 6-(1,4-dimethyl-1H-1,2,3-triazol-5-yl)-1-methyl-4-(4,4,4-trifluoro-1-phenylbutyl)-1,4-dihydropyrazolo[3',4':4,5]pyrrolo[3,2-b]pyridine-3-carboxylate, methyl 6-bromo-1-methyl-4-(4,4,4-trifluoro-1-(3-methylpyridin-2-yl)butyl)-1,4-dihydropyrazolo[3',4':4,5]pyrrolo [3,2-b]pyridine-3-carboxylate (257 mg, 0.50 mmol) and 1,4-dimethyl-5-(tributylstannyl)-1H-1,2,3-triazole (788 mg, 2.04 mmol) were converted to methyl 6-(1,4-dimethyl-1H-1,2,3-triazol-5-yl)-1-methyl-4-(4,4,4-trifluoro-1-(3-methylpyridin-2-yl)butyl)-1,4-dihydropyrazolo[3',4':4,5]pyrrolo [3,2-b]pyridine-3-carboxylate (200 mg, 0.38 mmol, 76% yield), LC-MS [M+H]$^+$=527.

Step 3: 2-(6-(1,4-dimethyl-1H-1,2,3-triazol-5-yl)-1-methyl-4-(4,4,4-trifluoro-1-(3-methylpyridin-2-yl) butyl)-1,4-dihydropyrazolo[3',4':4,5]pyrrolo[3,2-b] pyridin-3-yl)propan-2-ol Following the procedure analogous to that described for the synthesis of 2-(6-(3,5-dimethylisoxazol-4-yl)-4-((3-fluoropyridin-2-yl)(tetrahydro-2H-pyran-4-yl)methyl)-1-methyl-1,4-dihydropyrazolo[3',4':4,5]pyrrolo[3,2-b]pyridin-3-yl)propan-2-ol, methyl 6-(1,4-dimethyl-1H-1,2,3-triazol-5-yl)-1-methyl-4-(4,4,4-trifluoro-1-(3-methylpyridin-2-yl)butyl)-1,4-dihydropyrazolo[3',4':4,5] pyrrolo[3,2-b]pyridine-3-carboxylate (200 mg, 0.38 mmol) was converted to 2-(6-(1,4-dimethyl-1H-1,2,3-triazol-5-yl)-1-methyl-4-(4,4,4-trifluoro-1-(3-methylpyridin-2-yl)butyl)-1,4-dihydropyrazolo[3',4':4,5]pyrrolo[3,2-b]pyridin-3-yl) propan-2-ol (Compound 11, 89 mg, 0.17 mmol, 45% yield), LC-MS [M+H]$^+$=527.

$^1$H NMR (400 MHz, DMSO-d$_6$) δ8.53 (d, J=4.2 Hz, 1H), 8.27 (s, 1H), 7.69 (s, 1H), 7.56 (d, J=7.6 Hz, 1H), 7.25 (m, 1H), 6.95 (d, J=9.8 Hz, 1H), 5.93 (s, 1H), 4.13 (s, 3H), 3.21 (s, 6H), 2.86 (s, 2H) 2.72 (s, 2H), 2.23 (s, 3H), 1.62 (d, J=9.4 Hz, 6H).

Example 12

2-(6-(1,4-Dimethyl-1H-1,2,3-triazol-5-yl)-1-methyl-4-((2-methyloxazol-4-yl)(tetrahydro-2H-pyran-4-yl) methyl)-1,4-dihydropyrazolo[3',4':4,5]pyrrolo[3,2-b] pyridin-3-yl)propan-2-ol ("Compound 12")

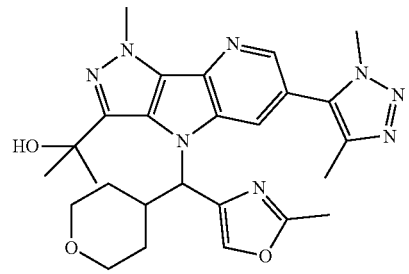 [SMILES: Cc1nc(C(C2CCOCC2)n2c3cc(-c4c(C)nnn4C)cnc3c3c2c(C(C)(C)O)nn3C)co1]

Step 1: (2-methyloxazol-4-yl)(tetrahydro-2H-pyran-4-yl)methanol 4-bromooxane (2.24 g, 13.6 mmol) was added dropwise to a stirred suspension of magnesium (683 mg, 29.1 mmol) and one crystal of iodine in THF (25 mL) at ambient temperature. The reaction mixture was stirred for 1 h before it was cooled in an ice-water bath. 2-methyloxazole-4-carbaldehyde (1.00 g, 9.00 mmol) was added dropwise. The reaction mixture was then stirred overnight. The reaction mixture was quenched with saturated aqueous ammonium chloride (40 mL) and diluted with ethyl acetate (100 mL). The product was extracted into the organic phase before the layers were separated. The aqueous layer was extracted with a second portion of ethyl acetate (50 mL), and the combined organics were dried over sodium sulfate. The volatiles were removed under reduced pressure. The crude reaction material was purified on silica gel column to afford (2-methyl-oxazol-4-yl)(tetrahydro-2H-pyran-4-yl)methanol (330 mg, 1.67 mmol, 19% yield), LC-MS [M+H]⁺=198.

Step 2: Methyl 6-bromo-1-methyl-4-((2-methyloxa-zol-4-yl)(tetrahydro-2H-pyran-4-yl) methyl)-1,4-dihydropyrazolo[3',4':4,5]pyrrolo[3,2-b]pyridine-3-carboxylate To a solution of methyl 6-bromo-1-methyl-1,4-dihydro-pyrazolo[3',4':4,5]pyrrolo[3,2-b]pyridine-3-carboxylate (200 mg, 0.65 mmol), (2-methyloxazol-4-yl)(tetrahydro-2H-pyran-4-yl) methanol (Intermediate 12, 195 mg, 0.99 mmol) and triphenylphosphane (384 mg, 1.33 mmol) in dry THF (20 mL) was added DIAD (289 mg, 1.43 mmol) at 0° C. under N₂. After addition, the reaction was heated to 28° C. for 16 h. The reaction mixture was poured into water, and extracted with EtOAc (100 mL). The organic phase was washed with brine, dried over anhydrous sodium sulfate, and concentrated under reduced pressure. The residue was purified by silica gel chromatography using 0~50% EtOAc in hexane to afford methyl 6-bromo-1-methyl-4-((2-methyl-oxazol-4-yl)(tetrahydro-2H-pyran-4-yl)methyl)-1,4-dihydro pyrazolo[3',4':4,5]pyrrolo[3,2-b]pyridine-3-carboxylate (404 mg, crude), LC-MS[M+H]⁺=489.

Step 3: Methyl 6-(1,4-dimethyl-1H-1,2,3-triazol-5-yl)-1-methyl-4-((2-methyloxazol-4-yl) (tetrahydro-2H-pyran-4-yl)methyl)-1,4-dihydropyrazolo[3',4':4, 5]pyrrolo[3,2-b]pyridine-3-carboxylate To a solution of methyl 6-bromo-1-methyl-4-((2-methyl-oxazol-4-yl)(tetrahydro-2H-pyran-4-yl) methyl)-1,4-dihy-dropyrazolo[3',4':4,5]pyrrolo[3,2-b]pyridine-3-carboxylate (300 mg, 0.614 mmol) in DMF (10 mL) was added 1-methyl-4-(methyl)-5-(tributylstannyl)-1H-1,2,3-triazole (498 mg, 1.29 mmol), tetrakis(triphenylphosphine)palla-dium (92 mg, 0.08 mmol), CuI (29 mg, 0.15 mmol) and TEA (203 mg, 1.842 mmol). The mixture was degassed and flushed with nitrogen for three times and stirred at 110° C. for 16 h. The mixture was cooled to room temperature, diluted with water (50 mL) and extracted with EtOAc (3×50 mL). The combined organic layer was washed with brine, dried over anhydrous sodium sulfate, filtered and the fil-trated was concentrated under reduced pressure. The residue was purified by Prep-TLC with 5% MeOH in DCM to afford methyl 6-(1,4-dimethyl-1H-1,2,3-triazol-5-yl)-1-methyl-4-((2-methyloxazol-4-yl)(tetrahydro-2H-pyran-4-yl)methyl)-1,4-dihydropyrazolo[3',4':4,5]pyrrolo[3,2-b]pyridine-3-car-boxylate (85 mg, 27% yield), LC-MS [M+H]J=505.

Step 4: 2-(6-(1,4-Dimethyl-1H-1,2,3-triazol-5-yl)-1-methyl-4-((2-methyloxazol-4-yl)(tetrahydro-2H-pyran-4-yl)methyl)-1,4-dihydropyrazolo[3',4':4,5] pyrrolo[3,2-b]pyridin-3-yl)propan-2-ol Following the procedure analogous to that described for the synthesis of 2-(6-(3,5-dimethyl isoxazol-4-yl)-4-((3-fluoropyridin-2-yl)(tetrahydro-2H-pyran-4-yl)methyl)-1-methyl-1,4-dihydro pyrazolo[3',4':4,5]pyrrolo[3,2-b]pyri-din-3-yl)propan-2-ol, the methyl 6-(1,4-dimethyl-1H-1,2,3-triazol-5-yl)-1-methyl-4-((2-methyloxazol-4-yl)(tetrahydro-2H-pyran-4-yl)methyl)-1,4-dihydropyrazolo[3',4':4,5] pyrrolo[3,2-b]pyridine-3-carboxylate (85 mg, 0.17 mmol) was converted to 2-(6-(1,4-dimethyl-1H-1,2,3-triazol-5-yl)-1-methyl-4-((2-methyloxazol-4-yl)(tetrahydro-2H-pyran-4-yl)methyl)-1,4-dihydropyrazolo[3',4':4,5]pyrrolo[3,2-b] pyridin-3-yl)propan-2-ol (Compound 12, 15 mg, 18% yield), LC-MS [M+H⁺]=505.

¹H NMR (400 MHz, DMSO-d₆) δ 8.42 (d, J=3.2 Hz, 2H), 8.09 (s, 1H), 6.36 (d, J=11.2 Hz, 1H), 5.67 (s, 1H), 4.14 (s, 3H), 4.02 (s, 3H), 3.82 (d, J=8.1 Hz, 1H), 3.66 (d, J=8.5 Hz, 1H), 3.17-3.04 (m, 1H), 2.97 (d, J=11.2 Hz, 1H), 2.33 (s, 3H), 2.31 (s, 3H), 1.70 (s, 3H), 1.66 (s, 3H), 1.61 (s, 1H), 1.40 (dd, J=12.3, 3.8 Hz, 1H), 1.26 (dd, J=15.1, 6.4 Hz, 1H), 1.10 (s, 1H), 0.66 (d, J=12.5 Hz, 1H).

Example 13

(S)-2-(6-(1,4-Dimethyl-1H-1,2,3-triazol-5-yl)-4-((3-fluoropyridin-2-yl)(tetrahydro-2H-pyran-4-yl) methyl)-1,4-dihydropyrazolo[3',4':4,5]pyrrolo[3,2-b] pyridin-3-yl)propan-2-ol ("Compound 13")

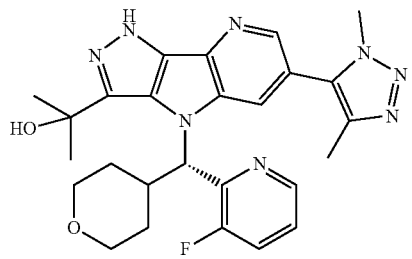 [SMILES: Cc1nnn(C)c1-c1cnc2c3[nH]nc(C(C)(C)O)c3n([C@H](c3ncccc3F)C3CCOCC3)c2c1]

Step 1: Methyl 1-(2-trimethylsilylethoxymethyl) pyrazole-3-carboxylate

To a solution of methyl 1H-pyrazole-3-carboxylate (20.1 g, 159 mmol) in THF (400 mL) in a three-neck round bottom flask was added NaH (8.20 g, 342 mmol) at r.t. The resulting mixture was stirred for 10 min under a N₂ atmosphere. The reaction mixture was cooled to 0° C. in an ice-water bath and followed by dropwise addition of SEMCl (29.1 g, 175 mmol) under N₂ atmosphere. Then the reaction mixture was slowly warmed to room temperature and continued stirring for 2 h. The reaction was quenched with sat. aq. NH₄Cl and extracted with EtOAc (100 mL). After separation, the organic phase was washed with brine, dried over anhydrous sodium sulfate, and concentrated. The residue was purified by silica gel chromatography using 0-10% EtOAc in Hexane to afford methyl 1-(2-trimethylsilylethoxymethyl)pyrazole-3-carboxylate (29.3 g, 114 mmol, 71.7% yield). LC/MS [M+H]⁺=257.

Step 2: [5-Methoxycarbonyl-2-(2-trimethylsily-lethoxymethyl)pyrazol-3-yl]boronic acid To a solution of methyl 1-(2-trimethylsilylethoxymethyl) pyrazole-3-carboxylate, (29.10 g, 113.51 mmol) in THF (10 mL) in a three-neck round bottom flask were added Dtbpy (113.51 mmol) and (1,5-cyclooctadiene)-(methoxy)iridium (I)dimer (2.71 g, 4.07 mmol) at r.t. The mixture was vacu-umed and backfilled with N₂, and this sequence was repeated three times. The resulting mixture was added HBin (38.10 g, 289.32 mmol). Then the reaction mixture was slowly warmed to 55° C. and continued stirring for 1 h, then quenched with water (80 mL). The resulting mixture was concentrated under reduced pressure to give [5-methoxycar-bonyl-2-(2-trimethylsilylethoxymethyl)pyrazol-3-yl]boronic acid (33.6 g, 98.6% yield) as a black substance, which was directly used in the next step without further purification. LC/MS [M+H]$^+$=301.

Step 3: Methyl 5-(5-bromo-3-nitro-2-pyridyl)-1-(2-trimethylsilylethoxymethyl)pyrazole-3-carboxylate To a three-neck bottom flask were added [5-methoxycarbonyl-2-(2-trimethylsilylethoxy methyl)pyrazol-3-yl]boronic acid (37.51 g, 124.92 mmol), 2,5-dibromo-3-nitropyridine (38.7 g, 137 mm ol), Pd(dppf)Cl$_2$, (4.63 g, 6.24 mmol), K$_3$PO$_4$ (57.5 g, 216 mmol) and THF (400 mL) under N$_2$. The mixture was purged with a N$_2$ stream for 3 min, attached with a condenser, then warmed to 38° C. and stirred for 3 h under a N$_2$ atmosphere. The reaction mixture was cooled to room temperature, poured into water (300 mL) and extracted with EtOAc (3×200 mL). The collected organic phases were washed with brine, dried over anhydrous sodium sulfate, and concentrated on a rotary evaporator. The resulting residue was purified by a silica gel chromatography eluting with 0-40% EtOAC in hexane to afford methyl 5-(5-bromo-3-nitro-2-pyridyl)-1-(2-trimethylsilylethoxymethyl)pyrazole-3-carboxylate (17.5 g, 30.6% yield). LC/MS [M+H]$^+$=458.

Step 4: Methyl 6-bromo-1-((2-(trimethylsilyl)ethoxy)methyl)-1,4-dihydropyrazolo[3',4':4,5]pyrrolo[3,2-b]pyridine-3-carboxylate To a three-neck round bottom flask was added methyl 5-(5-bromo-3-nitro-2-pyridyl)-1-(2-trimethyl silylethoxymethyl)pyrazole-3-carboxylate (15.0 g, 32.8 mmol), Triethyl phosphite (10.5 g, 63.4 mmol) and 1,2-Dichlorobenzene (160 mL) under N$_2$. The mixture was purged with a N$_2$ stream for 3 min, attached with a condenser, then warmed to 140° C. and stirred for 2 h under a N$_2$ atmosphere. The reaction mixture was cooled to room temperature, then poured into water (200 mL) and extracted with EtOAc (3×150 mL). The collected organic phases were washed with brine, dried over anhydrous sodium sulfate, and concentrated under reduced pressure. The resulting residue was purified by silica gel chromatography eluting with 0-10% EtOAc in hexane to afford methyl 6-bromo-1-((2-(trimethylsilyl)ethoxy)methyl)-1,4-dihydropyrazolo[3',4':4,5]pyrrolo[3,2-b]pyridine-3-carboxylate (3.40 g, 24.3% yield). LC/MS [M+H]$^+$=426.

Step 5: (S)-Methyl 6-bromo-4-((3-fluoropyridin-2-yl)(tetrahydro-2H-pyran-4-yl)methyl)-1-((2-(trimethylsilyl)ethoxy)methyl)-1,4-dihydropyrazolo[3',4':4,5]pyrrolo[3,2-b]pyridine-3-carboxylate To a three-neck round bottom flask were added methyl 6-bromo-1-((2-(trimethylsilyl)ethoxy)methyl)-1,4-dihydropyrazolo[3',4':4,5]pyrrolo[3,2-b]pyridine-3-carboxylate (2.01 g, 4.73 mmol), (R)-(3-fluoro-2-pyridyl)-tetrahydropyran-4-yl-methanol (Enantiomer a1, 1.40 g, 6.63 mmol), 2-(diphenylphosphanyl)pyridine (3.47 g, 13.19 mmol) and THF (30 mL) under N$_2$. The mixture was purged with a N$_2$ stream for 3 min, followed by dropwise addition of DTAD (3.04 g, 13.19 mmol) under N$_2$ atmosphere. Then the reaction mixture was slowly warmed to 32° C. and continued stirring for 2 h. The reaction mixture was cooled to room temperature, poured into 4N HCl (30 mL) and extracted with EtOAC (2×60 mL). The collected organic phases were washed with brine, dried over anhydrous sodium sulfate, and concentrated under reduced pressure. The resulting residue was purified by silica gel chromatography eluting with 0-20% EtOAc in hexane to afford (S)-methyl 6-bromo-4-((3-fluoropyridin-2-yl)(tetrahydro-2H-pyran-4-yl)methyl)-1-((2-(trimethylsilyl)ethoxy)methy 1)-1,4-dihydropyrazolo[3',4':4,5]pyrrolo[3,2-b]pyridine-3-carboxylate (3.02 g, 74% yield). LC/MS [M+H]$^+$=619.

Step 6: (S)-Methyl 6-(1,4-dimethyl-1H-1,2,3-triazol-5-yl)-4-((3-fluoropyridin-2-yl)(tetrahydro-2H-pyran-4-yl)methyl)-1-((2-(trimethylsilyl)ethoxy)methyl)-1,4-dihydropyrazolo[3',4':4,5]pyrrolo [3,2-b]pyridine-3-carboxylate To a three-neck bottle was added 1,4-dimethyltriazole (312 mg, 3.21 mmol), (S)-Methyl 6-bromo-4-((3-fluoropyridin-2-yl)(tetrahydro-2H-pyran-4-yl)methyl)-1-((2-(trimethylsilyl)ethoxy)methyl)-1, 4-dihydropyrazolo[3',4':4,5]pyrrolo[3,2-b]pyridine-3-carboxylate (1.51 g, 2.38 mmol), Bis(triphenylphosphine) palladium(II) chloride (167 mg, 238 μmol), tetramethylammonium acetate (634 mg, 4.76 mmol) and DMF (15 mL) under N$_2$. The mixture was purged with a N$_2$ stream for 3 min, attached with a condenser, then warmed to 110° C. and stirred for 16 h under a N$_2$ atmosphere. The reaction mixture was cooled to room temperature, poured into water (30 mL) and extracted with EtOAC (3×20 mL). The collected organic phases were washed with brine, dried over anhydrous sodium sulfate, and concentrated under reduced pressure. The resulting residue was purified by silica gel chromatography eluting with 0-75% EtOAc in hexane to afford (S)-methyl 6-(1,4-dimethyl-1H-1,2,3-triazol-5-yl)-4-((3-fluoropyridin-2-yl)(tetrahydro-2H-pyran-4-yl)methyl)-1-((2-(trimethylsilyl)ethoxy)methyl)-1,4-dihydropyrazolo[3',4':4,5]pyrrolo[3,2-b]pyridine-3-carboxylate (700 mg, 48% yield) as a brown substance. LC/MS [M+H]$^+$=635.

Step 7: (S)-Methyl 6-(1,4-dimethyl-1H-1,2,3-triazol-5-yl)-4-((3-fluoropyridin-2-yl)(tetrahydro-2H-pyran-4-yl)methyl)-1,4-dihydropyrazolo[3',4':4,5]pyrrolo[3,2-b]pyridine-3-carboxylate To a vial were added (S)-methyl 6-(1,4-dimethyl-1H-1,2,3-triazol-5-yl)-4-((3-fluoropyridin-2-yl) (tetrahydro-2H-pyran-4-yl)methyl)-1-((2-(trimethylsilyl)ethoxy)methyl)-1, 4-dihydropyrazolo[3',4':4,5]pyrrolo[3,2-b]pyridine-3-carboxylate (98 mg, 154 μmol), 0.8 mL HCl (12N) and 0.8 mL EtOH. The mixture was warmed to 75° C. and stirred for 5 h. The reaction mixture was cooled to room temperature and concentrated under reduced pressure. The resulting residue was purified by a thin layer chromatography with 5% MeOH in DCM as a developing solvent to afford (S)-methyl 6-(1,4-dimethyl-1H-1,2,3-triazol-5-yl)-4-((3-fluoropyridin-2-yl)(tetrahydro-2H-pyran-4-yl)methyl)-1,4-dihydropyrazolo[3',4':4,5]pyrrolo[3,2-b]pyridine-3-carboxylate (62 mg, 80% yield). LC/MS [M+H]$^+$=505.

Step 8: (S)-2-(6-(1,4-Dimethyl-1H-1,2,3-triazol-5-yl)-4-((3-fluoropyridin-2-yl)(tetrahydro-2H-pyran-4-yl)methyl)-1,4-dihydropyrazolo[3',4':4,5]pyrrolo[3,2-b]pyridin-3-yl)propan-2-ol To a vial was added (S)-methyl 6-(1,4-dimethyl-1H-1,2,3-triazol-5-yl)-4-((3-fluoropyridin-2-yl)(tetrahydro-2H-pyran-4-yl)methyl)-1,4-dihydropyrazolo[3',4':4,5]pyrrolo[3,2-b]pyridine-3-carboxylate (62 mg, 0.123 mmol), The reaction mixture was cooled to 0° C. in an ice-water bath, followed by dropwise addition of 1 mL MeMgBr in Et$_2$O (3M) under N₂ atmosphere. Then the reaction mixture was slowly warmed to room temperature and continued stirring for 1 h. The reaction was quenched with sat. NH₄Cl. The reaction mixture was concentrated under reduced pressure. The resulting residue was purified by a thin layer chromatography with 5% MeOH in DCM as a developing solvent to afford (S)-2-(6-(1,4-dimethyl-1H-1,2,3-triazol-5-yl)-4-((3-fluoropyridin-2-yl)(tetrahydro-2H-pyran-4-yl)methyl)-1,4-dihydropyrazolo[3',4':4,5]pyrrolo[3,2-b]pyridin-3-yl)propan-2-ol (Compound 13, 34 mg, 54.8% yield). LC/MS [M+H]⁺=505.

¹H NMR (400 MHz, MeOD) δ 8.50 (s, 1H), 8.49 (s, 1H), 8.35 (s, 1H), 7.56 (t, J=9.1 Hz, 1H), 7.40 (dt, J=8.4, 4.3 Hz, 1H), 7.15 (d, J=10.1 Hz, 1H), 4.02 (s, 3H), 3.91 (d, J=11.2 Hz, 1H), 3.79 (d, J=8.1 Hz, 1H), 3.45 (d, J=22.8 Hz, 1H), 3.25 (d, J=12.5 Hz, 2H), 3.13 (s, 1H), 2.32 (s, 3H), 1.82 (d, J=17.7 Hz, 3H), 1.76 (dd, J=12.9, 4.1 Hz, 1H), 1.70 (s, 3H), 1.60 (s, 2H), 0.71 (d, J=11.0 Hz, 1H).

Example 14

(S)-2-(4-((3-Fluoropyridin-2-yl)(tetrahydro-2H-pyran-4-yl)methyl)-1-(methyl-d3)-6-(1-methyl-4-(methyl-d3)-1H-1,2,3-triazol-5-yl)-1,4-dihydropyrazolo[3',4':4,5]pyrrolo[3,2-b]pyridin-3-yl)propan-2-ol ("Compound 14")

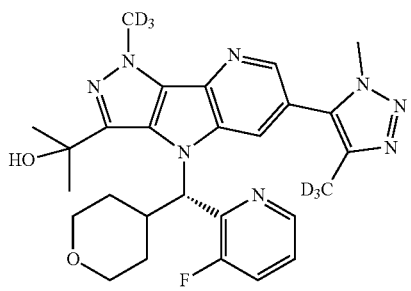 [SMILES: [2H]C([2H])([2H])c1nnn(C)c1-c1cnc2c3c(c(C(C)(C)O)nn3C([2H])([2H])[2H])n([C@H](c3ncccc3F)C3CCOCC3)c2c1]

Step 1: (S)-Methyl 4-((3-fluoropyridin-2-yl)(tetrahydro-2H-pyran-4-yl)methyl)-6-(1-methyl-4-(methyl-d3)-1H-1,2,3-triazol-5-yl)-1-((2-(trimethylsilyl)ethoxy)methyl)-1,4-dihydropyrazolo[3',4':4,5]pyrrolo[3,2-b]pyridine-3-carboxylate To a three-neck round bottom flask were added 1-methyl-4-(methyl-d3)-1H-1,2,3-triazole (622 mg, 6.22 mmol), (S)-methyl 6-bromo-4-((3-fluoropyridin-2-yl)(tetrahydro-2H-pyran-4-yl)methyl)-1-((2-(trimethylsilyl)ethoxy)methyl)-1,4-dihydropyrazolo[3',4':4,5]pyrrolo[3,2-b]pyridine-3-carboxylate (from Example 13 step 5, 1.42 g, 2.24 mmol), Bis(triphenylphosphine) palladium(II) chloride (345 mg, 492 μmol), tetramethylammonium acetate (820 mg, 6.16 mmol) and DMF (15 mL) under N₂. The mixture was purged with a N₂ stream for 3 min, attached with a condenser, then warmed to 110° C. and stirred for 16 h under a N₂ atmosphere. The reaction mixture was cooled to room temperature, poured into water (30 mL) and extracted with EtOAc (3×20 mL). The collected organic phases were washed with brine, dried over anhydrous sodium sulfate, and concentrated under reduced pressure. The resulting residue was purified by silica gel chromatography eluting with 0-75% EtOAc in hexane to afford (S)-methyl 4-((3-fluoropyridin-2-yl)(tetrahydro-2H-pyran-4-yl)methyl)-6-(1-methyl-4-(methyl-d3)-1H-1,2,3-triazol-5-yl)-1-((2-(trimethylsilyl)ethoxy)methyl)-1,4-dihydropyrazolo[3',4':4,5]pyrrolo[3,2-b]pyridine-3-carboxylate (750 mg, 54% yield), LC-MS [M+H]⁺=638.

Step 2: (S)-Methyl 4-((3-fluoropyridin-2-yl)(tetrahydro-2H-pyran-4-yl)methyl)-6-(1-methyl-4-(methyl-d3)-1H-1,2,3-triazol-5-yl)-1,4-dihydropyrazolo[3',4':4,5]pyrrolo[3,2-b]pyridine-3-carboxylate To a vial was added (S)-methyl 4-((3-fluoropyridin-2-yl)(tetrahydro-2H-pyran-4-yl)methyl)-6-(1-methyl-4-(methyl-d3)-1H-1,2,3-triazol-5-yl)-1-((2-(trimethylsilyl)ethoxy)methyl)-1,4-dihydropyrazolo[3',4':4,5]pyrrolo[3,2-b]pyridine-3-carboxylate (750 mg, 1.18 mol), 7 mL HCl (12 N) and 7 mL EtOH. The mixture warmed to 75° C. and stirred for 5 h. The reaction mixture was cooled to room temperature and concentrated under reduced pressure. The resulting residue was purified by Prep-TLC with 5% MeOH in DCM as a developing solvent to afford (S)-methyl 4-((3-fluoropyridin-2-yl)(tetrahydro-2H-pyran-4-yl)methyl)-6-(1-methyl-4-(methyl-d3)-1H-1,2,3-triazol-5-yl)-1,4-dihydropyrazolo[3',4':4,5]pyrrolo[3,2-b]pyridine-3-carboxylate (450 mg, 75% yield), LC-MS [M+H]⁺=508.

Step 3: (S)-Methyl 4-((3-fluoropyridin-2-yl)(tetrahydro-2H-pyran-4-yl)methyl)-1-(methyl-d3)-6-(1-methyl-4-(methyl-d3)-1H-1,2,3-triazol-5-yl)-1,4-dihydropyrazolo[3',4':4,5]pyrrolo[3,2-b]pyridine-3-carboxylate To a solution of (S)-methyl 4-((3-fluoropyridin-2-yl)(tetrahydro-2H-pyran-4-yl)methyl)-6-(1-methyl-4-(methyl-d3)-1H-1,2,3-triazol-5-yl)-1,4-dihydropyrazolo[3',4':4,5]pyrrolo[3,2-b]pyridine-3-carboxylate (601 mg, 1.18 mmol) in DMF (6 mL) were added Cs₂CO₃ (1.16 g, 3.56 mmol) in a vial at r.t., followed by dropwise addition of CD₃I (215 mg, 1.48 mmol) under N₂ atmosphere. Then the reaction mixture was slowly warmed to 60° C. and continued to stir for 2 h. The reaction was quenched with 10 mL HCl (1N) and extracted with EtOAc (10 mL). After separation, the organic phase was washed with brine, dried over anhydrous sodium sulfate, and concentrated. The residue was purified by Prep-TLC using 10% MeOH in DCM as a developing solvent to afford (S)-methyl 4-((3-fluoropyridin-2-yl)(tetrahydro-2H-pyran-4-yl) methyl)-1-(methyl-d3)-6-(1-methyl-4-(methyl-d3)-1H-1,2,3-triazol-5-yl)-1,4-dihydropyrazolo[3',4':4,5]pyrrolo[3,2-b]pyridine-3-carboxylate (150 mg, 24% yield). LC/MS [M+H]⁺=525.

Step 4: (S)-2-(4-((3-Fluoropyridin-2-yl)(tetrahydro-2H-pyran-4-yl)methyl)-1-(methyl-d3)-6-(1-methyl-4-(methyl-d3)-1H-1,2,3-triazol-5-yl)-1,4-dihydropyrazolo[3',4':4,5]pyrrolo[3,2-b]pyridin-3-yl)propan-2-ol To a vial was added (S)-methyl 4-((3-fluoropyridin-2-yl)(tetrahydro-2H-pyran-4-yl)methyl)-1-(methyl-d3)-6-(1-methyl-4-(methyl-d3)-1H-1,2,3-triazol-5-yl)-1,4-dihydropyrazolo[3',4':4,5]pyrrolo[3,2-b]pyridine-3-carboxylate (148 mg, 0.282 mmol) and THF (10 ml). The reaction mixture was cooled to 0° C. in an ice-water bath, followed by dropwise addition of 1.5 mL MeMgBr (3M in THF, 4.5 mmol) under N₂ atmosphere. Then the reaction mixture was slowly warmed to room temperature and continued stirring for 1 h. The reaction was quenched with sat. NH₄Cl. The reaction mixture was concentrated under reduced pressure.

The resulting residue was purified by a reverse phase flash chromatography to afford (S)-2-(4-((3-Fluoropyridin-2-yl)(tetrahydro-2H-pyran-4-yl)methyl)-1-(methyl-d3)-6-(1-methyl-4-(methyl-d3)-1H-1,2,3-triazol-5-yl)-1,4-dihydropyrazolo[3',4':4,5]pyrrolo[3,2-b]pyridin-3-yl)propan-2-ol (Compound 14, 93 mg, 63% yield). LC/MS [M+H]$^+$=525.

$^1$H NMR (400 MHz, DMSO-d$_6$) δ 8.52 (d, J=4.6 Hz, 1H), 8.41 (d, J=1.7 Hz, 1H), 8.29 (d, J=1.6 Hz, 1H), 7.78-7.66 (m, 1H), 7.47 (dt, J=8.5, 4.3 Hz, 1H), 7.01 (d, J=10.8 Hz, 11H), 5.69 (s, 1H), 3.96 (s, 3H), 3.80 (d, J=9.6 Hz, 1H), 3.67 (dd, J=11.0, 2.5 Hz, 1H), 3.33-3.24 (m, 1H), 3.20 (d, J=11.1 Hz, 1H), 3.12 (t, J=11.3 Hz, 1H), 1.73 (s, 3H), 1.68-1.59 (m, 1H), 1.56 (s, 3H), 1.47 (d, J=12.5 Hz, 1H), 1.43-1.34 (m, 1H), 0.55 (d, J=12.5 Hz, 1H).

Example 15

6-(1,4-Dimethyl-1H-1,2,3-triazol-5-yl)-N,N,1-trimethyl-4-(phenyl(tetrahydro-2H-pyran-4-yl)methyl)-1,4-dihydropyrazolo[3',4':4,5]pyrrolo[3,2-b]pyridine-3-carboxamide ("Compound 15")

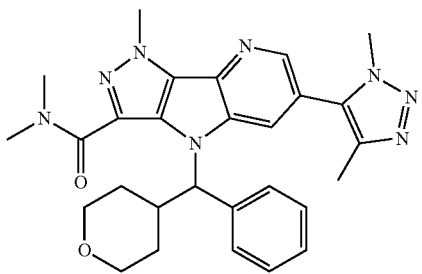 [SMILES: Cc1nnn(C)c1-c1cnc2c3c(c(C(=O)N(C)C)nn3C)n(C(c3ccccc3)C3CCOCC3)c2c1]

Step 1: Methyl 6-bromo-1-methyl-4-(phenyl(tetrahydro-2H-pyran-4-yl)methyl)-1,4-dihydro pyrazolo[3',4':4,5]pyrrolo[3,2-b]pyridine-3-carboxylate To a solution of methyl 6-bromo-1-methyl-1,4-dihydropyrazolo[3',4':4,5]pyrrolo[3,2-b]pyridine-3-carboxylate (from Example 1 step 2, 1.00 g, 3.23 mmol), phenyl(tetrahydro-2H-pyran-4-yl)methanol (933 mg, 4.85 mmol) and Triphenyl phosphine (1.29 g, 6.82 mmol) in dry THF (6 mL) was added DIAD (600 mg, 2.97 mmol) at r.t. under N$_2$. The reaction system was stirred for 3 hours. The reaction mixture was poured into water and extracted with EtOAc (400 mL). The organic phase was washed with brine, dried over anhydrous sodium sulfate, and concentrated under reduced pressure. The residue was purified by silica gel chromatography using 5-30% EtOAc in hexane to afford of methyl 6-bromo-1-methyl-4-(phenyl(tetrahydro-2H-pyran-4-yl)methyl)-1,4-dihydropyrazolo[3',4':4,5]pyrrolo[3,2-b]pyridine-3-carboxylate (1.31 g, 83% yield). LC/MS [M+H]$^+$=483, 485.

Step 2: Methyl 6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridine-3-carboxylate Following the procedure analogous to that described in Step 4 for the synthesis of Example 6, methyl 6-bromo-1-methyl-4-(phenyl(tetrahydro-2H-pyran-4-yl)methyl)-1,4-dihydropyrazolo[3',4':4,5]pyrrolo[3,2-b]pyridine-3-carboxylate (1.95 g, 4.04 mmol) and 1,4-dimethyl-5-(tributylstannyl)-1H-1,2,3-triazole (2.81 g, 7.27 mmol) were converted to methyl 6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridine-3-carboxylate (1.29 g, 2.59 mmol, 64% yield), LC-MS [M+H]$^+$=500.

Step 3: 6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridine-3-carboxylic acid To a solution of methyl 6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridine-3-carboxylate (148 mg, 0.30 mmol) in methanol (5 mL) and H$_2$O (2 mL), was added LiOH (74 mg, 3.09 mmol). The reaction mixture was stirred at ambient temperature for 16 h. The mixture was poured into water (10 mL), adjusted pH=7 with 4N HCl aqueous and extracted with EtOAc (2×50 mL). The combined organic layers were washed with brine, dried over anhydrous sodium sulfate, filtered and the filtrate was concentrated under reduced pressure to afford the crude 6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridine-3-carboxylic acid (143 mg, crude), LC-MS [M+H]$^+$=486.

Step 4: 6-(1,4-Dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridine-3-carbonyl chloride To a solution of crude 6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridine-3-carboxylic acid (143 mg, 0.30 mmol) in DCM (5 mL) was added SOCl$_2$ (2 mL). The reaction mixture was stirred at ambient temperature for 4 h. The mixture was concentrated under reduced pressure to afford the crude 6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridine-3-carbonyl chloride (163 mg, crude).

Step 5: 6-(1,4-Dimethyl-1H-1,2,3-triazol-5-yl)-N,N,1-trimethyl-4-(phenyl(tetrahydro-2H-pyran-4-yl)methyl)-1,4-dihydropyrazolo[3',4':4,5]pyrrolo[3,2-b]pyridine-3-carboxamide To a solution of crude 6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridine-3-carbonyl chloride (54 mg, 0.10 mmol) in THF (3 mL), dimethylamine (126 mg, 2.53 mmol) was added and then stirred at ambient temperature for 1 hour. The mixture was concentrated under vacuum and the residue was purified by Prep-HPLC to afford 6-(1,4-dimethyl-1H-1,2,3-triazol-5-yl)-5-yl)-N,N,1-trimethyl-4-(phenyl(tetrahydro-2H-pyran-4-yl)methyl)-1,4-dihydropyrazolo[3',4':4,5]pyrrolo[3,2-b]pyridine-3-carboxamide (Compound 15, 15 mg, 29% yield for three steps), LC-MS [M+H]$^+$=513.

$^1$H NMR (400 MHz, DMSO-d$_6$) δ8.46 (s, 1H), 8.33 (s, 1H), 7.66 (s, 1H), 7.65 (s, 1H), 7.31-7.28 (m, 2H), 7.24-7.20 (m, 1H), 5.92 (d, J=10.8 Hz, 1H), 4.25 (s, 3H), 3.96 (s, 3H), 3.86-3.78 (m, 2H), 3.37-3.20 (m, 3H), 3.14 (s, 6H), 2.25 (s, 3H), 1.51-1.48 (m, 1H), 1.41-1.18 (m, 3H).

Example 16

6-(1,4-Dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridine-3-carboxamide ("Compound 16")

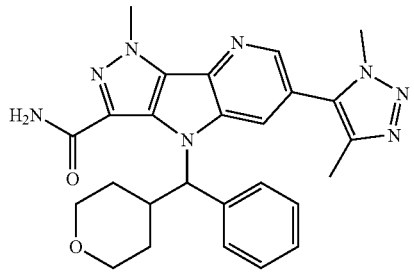 [SMILES: Cc1nnn(C)c1-c1cnc2c3c(c(C(N)=O)nn3C)n(C(c3ccccc3)C3CCOCC3)c2c1]

Step 1: 6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridine-3-carboxamide To a solution of ammonia (25% in 1,4-dioxane, 5 mL) was added a solution of crude 6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridine-3-carbonyl chloride (from Example 15 step 4, 52 mg, 0.10 mmol) in THF (3 mL). The mixture was stirred at ambient temperature for 1 hour. The mixture was concentrated under vacuum and the residue was purified by Prep-HPLC to afford 6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridine-3-carboxamide (16 mg, 33% yield), LC-MS [M+H]$^+$=485.

$^1$HNMR (400 MHz, DMSO-d$_6$) δ8.44 (s, 1H), 8.19 (s, 1H), 7.80 (s, 1H), 7.67 (d, J=7.6 Hz, 2H), 7.53 (s, 1H), 7.31 (t, J=7.6 Hz, 2H), 7.22-7.20 (m, 1H), 6.92 (d, J=11.2 Hz, 1H), 4.28 (s, 3H), 3.91 (s, 3H), 3.86 (d, J=11.2 Hz, 1H), 3.75 (d, J=10.8 Hz, 1H), 3.46-3.38 (m, 2H), 3.29-3.22 (m, 1H), 2.22 (s, 3H), 1.69 (d, J=12.4 Hz, 1H), 1.40-1.23 (m, 2H), 1.03 (d, J=12.4 Hz, 1H).

Example 17

6-(1,4-dimethyl-1H-1,2,3-triazol-5-yl)-N,1-dimethyl-4-(phenyl(tetrahydro-2H-pyran-4-yl)methyl)-1,4-dihydropyrazolo[3',4':4,5]pyrrolo[3,2-b]pyridine-3-carboxamide ("Compound 17")

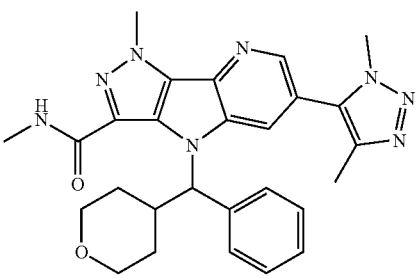 [SMILES: CNC(=O)c1nn(C)c2c3ncc(-c4c(C)nnn4C)cc3n(C(c3ccccc3)C3CCOCC3)c12]

Step 1: 6-(1,4-Dimethyl-1H-1,2,3-triazol-5-yl)-N,1-dimethyl-4-(phenyl(tetrahydro-2H-pyran-4-yl)methyl)-1,4-dihydropyrazolo[3',4':4,5]pyrrolo[3,2-b]pyridine-3-carboxamide To a solution of crude 6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridine-3-carbonyl chloride (from Example 15 step 4, 55 mg, 0.10 mmol) in THF (3 mL), was added a solution of methylamine in THF (3M, 3 mL). The mixture was stirred at ambient temperature for 1 hour. The mixture was concentrated under vacuum and the residue was purified by Prep-HPLC to afford 12 mg of 6-(1,4-dimethyl-1H-1,2,3-triazol-5-yl)-N,1-dimethyl-4-(phenyl(tetrahydro-2H-pyran-4-yl)methyl)-1,4-dihydropyrazolo[3',4':4,5]pyrrolo[3,2-b]pyridine-3-carboxamide (Compound 17, 11 mg, 24% yield of three steps), LC-MS [M+H]$^+$=499.

$^1$HNMR (400 MHz, DMSO-d$_6$) δ8.44-8.41 (m, 2H), 8.21 (d, J=1.2 Hz, 1H), 7.67 (d, J=7.2 Hz, 2H), 7.31 (t, J=7.6 Hz, 2H), 7.22 (d, J=7.6 Hz, 1H), 6.92 (d, J=11.2 Hz, 1H), 4.28 (s, 3H), 3.91 (s, 3H), 3.86 (d, J=11.2 Hz, 1H), 3.75 (d, J=10.8 Hz, 1H), 3.46-3.38 (m, J=8.2 Hz, 2H), 3.29-3.22 (m, 1H), 2.89 (d, J=4.8 Hz, 3H), 2.22 (s, 3H), 1.69 (d, J=12.4 Hz, 1H), 1.40-1.23 (m, 2H), 1.03 (d, J=12.8 Hz, 1H).

Example 18

2-(6-(1,4-Dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-yl)propan-2-amine ("Compound 18")

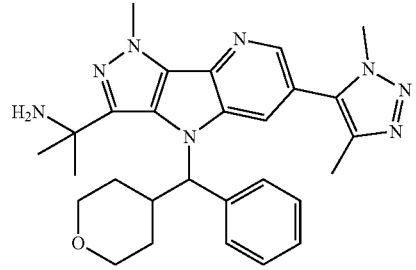 [SMILES: Cc1nnn(C)c1-c1cnc2c3c(c(C(C)(C)N)nn3C)n(C(c3ccccc3)C3CCOCC3)c2c1]

Step 1: 2-(6-(1,4-Dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-yl)propan-2-ol Following the procedure analogous to that described in Step 5 for the synthesis of Example 1, methyl 6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridine-3-carboxylate (from Example 15 step 2, 125 mg, 0.250 mmol) was converted to 2-(6-(1,4-Dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-yl)propan-2-ol (94 mg, 750% yield), LC-MS [M+H]$^+$=499.

Step 2: 3-(2-Azidopropan-2-yl)-6-(1,4-dimethyl-1H-1,2,3-triazol-5-yl)-1-methyl-4-(phenyl (tetrahydro-2H-pyran-4-yl)methyl)-1,4-dihydropyrazolo[3',4':4,5]pyrrolo[3,2-b]pyridine To a solution of 2-(6-(1,4-dimethyl-1H-1,2,3-triazol-5-yl)-1-methyl-4-(phenyl(tetrahydro-2H-pyran-4-yl)methyl)-

1,4-dihydropyrazolo[3',4':4,5]pyrrolo[3,2-b]pyridin-3-yl) propan-2-ol (94 mg, 0.19 mmol) in DCM (3 mL) was added TMSN₃ (62 mg, 0.54 mmol) at 0° C. under N₂. The mixture was stirred at 0° C. for 10 min and BF₃.OEt₂ (118 mg, 0.83 mmol) was added. The mixture was stirred at ambient temperature for 2 days. The mixture was added to sat. aqueous NaHCO₃ (5 mL) and extracted with EtOAc (3×20 mL). The combined organic layers were dried over Na₂SO₄ and concentrated under a rotary vacuum to afford 3-(2-Azidopropan-2-yl)-6-(1,4-dimethyl-1H-1,2,3-triazol-5-yl)-1-methyl-4-(phenyl (tetrahydro-2H-pyran-4-yl)methyl)-1,4-dihydropyrazolo[3',4':4,5]pyrrolo[3,2-b]pyridine (110 mg, crude).

Step 3: 2-(6-(1,4-Dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-yl)propan-2-amine To a solution of the crude 3-(2-azidopropan-2-yl)-6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridine (110 mg, 0.19 mmol) in methanol (3 mL) was added wet Pd/C (20 mg, 18% w/w). The mixture was vacuumed, back filled with H₂, and this sequence was repeated three times. The resulting mixture was stirred at ambient temperature for 3 h. The mixture was filtered and the filtrate was concentrated under vacuum. The residue was purified by Prep-HPLC to afford 2-(6-(1,4-Dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-yl)propan-2-amine (Compound 18, 20 mg, 21% yield for two steps), LC-MS [M+H]⁺=499.

¹HNMR (400 MHz, DMSO-d₆) δ9.08-8.48 (br, J=10.2 Hz, 2H), 8.39 (s, 1H), 7.86 (s, 1H), 7.62-7.60 (m, 2H), 7.34-7.30 (m, J=6.5 Hz, 2H), 7.26-7.22 (m, J=9.3 Hz, 1H), 6.92 (d, J=11.2 Hz, 1H), 4.19 (s, 3H), 3.88-3.85 (m, J=8.45 Hz, 1H), 3.82 (s, 3H), 3.74-3.71 (m, 1H), 3.50-3.44 (m, 1H), 3.34-3.20 (m, J=7.5 Hz, 2H), 2.14 (s, 3H), 1.90-1.80 (m, J=7.3 Hz, 1H), 1.71 (s, 6H), 1.60-1.43 (m, 2H), 0.80-0.78 (m, 1H).

Example 19

3-(6-(1,4-Dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-yl)pentan-3-ol ("Compound 19")

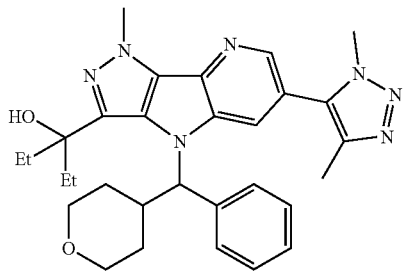 [SMILES: CCC(O)(CC)c1nn(C)c2c3ncc(-c4c(C)nnn4C)cc3n(C(c3ccccc3)C3CCOCC3)c12]

To a solution of methyl 6-(1,4-dimethyl-1H-1,2,3-triazol-5-yl)-1-methyl-4-(phenyl(tetrahydro-2H-pyran-4-yl) methyl)-1,4-dihydropyrazolo[3',4':4,5]pyrrolo[3,2-b]pyridine-3-carboxylate (from Example 15 step 2, 103 mg, 0.21 mmol) in THF (3 mL) was added EtMgBr (1 M in THF, 0.2 mL), The mixture was stirred at ambient temperature for 1 h. The mixture was poured into water (20 mL) and extracted with EtOAc (3×20 mL). The combined organic layers were dried over Na₂SO₄, and concentrated on a rotary vacuum evaporator. The residue was purified by Prep-HPLC to afford 3-(6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-yl)pentan-3-ol (Compound 19, 38 mg, 34% yield), LC-MS [M+H]⁺=528.

¹HNMR (400 MHz, DMSO-d₆) δ 8.47 (s, 1H), 8.23 (s, 1H), 7.66 (d, J=7.2 Hz, 2H), 7.33 (t, J=7.2 Hz, 2H), 7.26-7.22 (m, 1H), 6.53 (d, J=11.6 Hz, 1H), 5.40-5.31 (m, 1H), 4.31 (s, 3H), 3.91 (s, 3H), 3.90-3.85 (m, 1H), 3.77-3.74 (m, 1H), 3.48-3.37 (m, 2H), 3.29-3.23 (m, 1H), 2.51 (m, 4H), 2.21 (s, 3H), 1.76-1.73 (m, 1H), 1.41 (t, J=6.8 Hz, 6H), 1.37-1.25 (m, 2H), 1.07-1.04 (m, 1H).

Example 20

(S)-6-(1,4-Dimethyl-1H-1,2,3-triazol-5-yl)-4-((3-fluoropyridin-2-yl)(tetrahydro-2H-pyran-4-yl) methyl)-1-methyl-1,4-dihydropyrazolo[3',4':4,5] pyrrolo[3,2-b]pyridine-3-carboxylic acid ("Compound 20")

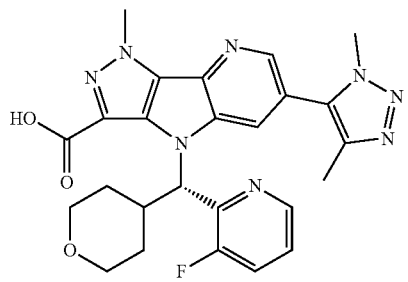 [SMILES: Cc1nnn(C)c1-c1cnc2c3c(c(C(=O)O)nn3C)n([C@H](c3ncccc3F)C3CCOCC3)c2c1]

To a solution of (S)-methyl 6-(1,4-dimethyl-1H-1,2,3-triazol-5-yl)-4-((3-fluoropyridin-2-yl) (tetrahydro-2H-pyran-4-yl)methyl)-1-methyl-1,4-dihydropyrazolo[3',4':4,5]pyrrolo[3,2-b]pyridine-3-carboxylate (from Example 7 step 2, 36 mg, 0.069 mmol) in MeOH (5 ml) and H₂O (10 ml) was added LiOH (28 mg, 1.17 mmol). The resulting mixture was stirred at 25° C. for 1 hr. The reaction mixture was adjusted pH to 1 with CH₃COOH and extracted with EtOAc (10 mL). The organic phase was washed with brine, dried over anhydrous sodium sulfate, and concentrated. The residue was purified by silica gel chromatography using 0-5% MeOH in DCM to afford (S)-6-(1,4-dimethyl-1H-1,2,3-triazol-5-yl)-4-((3-fluoropyridin-2-yl)(tetrahydro-2H-pyran-4-yl)methyl)-1-methyl-1,4-dihydropyrazolo[3',4':4,5] pyrrolo[3,2-b]pyridine-3-carboxylic acid (Compound 20, 8 mg, 0.016 mmol, 23% yield), LC-MS [M+H]⁺=505.

¹H NMR (400 MHz, DMSO-d₆) δ 8.57 (d, J=4.5 Hz, 1H), 8.48 (d, J=1.0 Hz, 1H), 8.15 (s, 1H), 7.67 (t, J=9.0 Hz, 1H), 7.47 (dt, J=8.3, 4.3 Hz, 1H), 7.20 (d, J=8.8 Hz, 1H), 4.31 (d, J=14.4 Hz, 3H), 3.92 (s, 3H), 3.82 (d, J=9.6 Hz, 1H), 3.72 (d, J=9.9 Hz, 1H), 3.37 (d, J=10.5 Hz, 2H), 3.22 (t, J=11.3 Hz, 1H), 2.18 (s, 3H), 1.63 (d, J=11.9 Hz, 1H), 1.53-1.40 (m, 2H), 1.37-1.24 (m, 1H), 0.83 (d, J=12.1 Hz, 1H).

Example 21

6-(1,4-Dimethyl-1H-1,2,3-triazol-5-yl)-4-((3-fluoropyridin-2-yl)(tetrahydro-2H-pyran-4-yl)methyl)-1-methyl-1,4-dihydropyrazolo[3',4':4,5]pyrrolo[3,2-b]pyridine-3-carboxamide ("Compound 21")

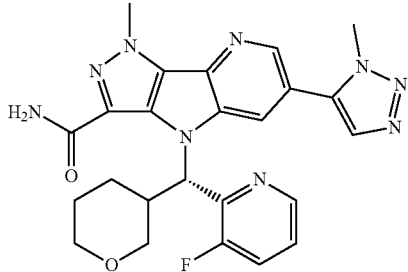 [SMILES: Cn1nncc1-c1cnc2c3c(c(C(N)=O)nn3C)n([C@H](c3ncccc3F)C3CCCOC3)c2c1]

To a solution of (S)-6-(1,4-dimethyl-1H-1,2,3-triazol-5-yl)-4-((3-fluoropyridin-2-yl)(tetrahydro-2H-pyran-4-yl)methyl)-1-methyl-1,4-dihydropyrazolo[3',4':4,5]pyrrolo[3,2-b]pyridine-3-carboxylic acid (from Example 20, 100 mg, 0.20 mmol) in DMF (15 mL) was added HATU (68 mg, 0.18 mmol), NH$_4$Cl (48 mg, 0.90 mmol) and DIEA (72 mg, 0.56 mmol) under N$_2$. The mixture was vacuumed, backfilled with N$_2$, and this sequence was repeated three times. The resulting mixture was stirred at 25° C. for 1.5 hr. The reaction mixture was poured into water and extracted with EtOAc (100 mL). The organic phase was washed with brine, dried over anhydrous sodium sulfate, and concentrated. The residue was purified by silica gel chromatography using 0-5% MeOH in DCM to afford (S)-6-(1,4-dimethyl-1H-1,2,3-triazol-5-yl)-4-((3-fluoropyridin-2-yl)(tetrahydro-2H-pyran-4-yl)methyl)-1-methyl-1,4-dihydropyrazolo[3',4':4,5]pyrrolo[3,2-b]pyridine-3-carboxamide (Compound 21, 10 mg, 0.020 mmol, 10% yield), LC-MS [M+H]$^+$=504.
$^1$H NMR (400 MHz, DMSO-d$_6$) δ 8.57 (d, J=4.6 Hz, 1H), 8.47 (d, J=1.6 Hz, 1H), 8.09 (d, J=1.6 Hz, 1H), 7.75 (s, 1H), 7.66 (t, J=8.8 Hz, 1H), 7.49 (s, 1H), 7.46 (dd, J=8.5, 4.3 Hz, 1H), 7.37 (d, J=10.8 Hz, 1H), 4.28 (s, 3H), 3.91 (s, 3H), 3.83 (d, J=9.6 Hz, 1H), 3.72 (d, J=11.6 Hz, 1H), 3.38 (s, 2H), 3.21 (t, J=11.1 Hz, 1H), 2.17 (s, 3H), 1.64 (d, J=12.3 Hz, 1H), 1.49 (qd, J=12.4, 4.3 Hz, 1H), 1.33 (ddd, J=15.9, 12.3, 4.2 Hz, 1H), 0.78 (d, J=12.2 Hz, 1H).

Example 22

2-(6-(1,4-Dimethyl-1H-1,2,3-triazol-5-yl)-4-((4-methylpyridin-3-yl)(tetrahydro-2H-pyran-4-yl)methyl)-1-methyl-1,4-dihydropyrazolo[3',4':4,5]pyrrolo[3,2-b]pyridin-3-yl)propan-2-ol ("Compound 22")

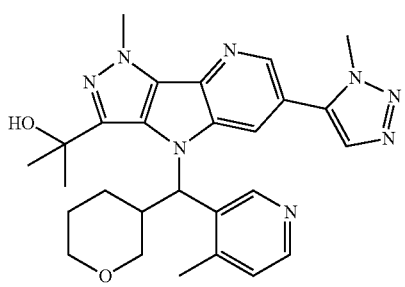 [SMILES: Cc1ccncc1C(C1CCCOC1)n1c2cc(-c3cnnn3C)cnc2c2c1c(C(C)(C)O)nn2C]

Step 1: Methyl 6-bromo-1-methyl-4-((4-methylpyridin-3-yl)(tetrahydro-2H-pyran-4-yl) methyl)-1,4-dihydropyrazolo[3',4':4,5]pyrrolo[3,2-b]pyridine-3-carboxylate To a solution of methyl 6-bromo-1-methyl-1,4-dihydropyrazolo[3',4':4,5]pyrrolo[3,2-b]pyridine-3-carboxylate (from Example 1 Step 2, 400 mg, 1.29 mmol), (4-methylpyridin-3-yl)(tetrahydro-2H-pyran-4-yl)methanol (Intermediate 13, 600 mg, 2.89 mmol) and Triphenyl phosphine (850 mg, 3.24 mmol) in dry THF (30 mL) was added DIAD (600 mg, 2.97 mmol) at r.t. under N$_2$. The mixture was stirred for 18 hours. The reaction mixture was poured into water and extracted with EtOAc (200 mL). The resulting organic phase was washed with brine, dried over anhydrous sodium sulfate, and concentrated under reduced pressure. The residue was purified by silica gel chromatography using 5-50% EtOAc in hexane to afford methyl 6-bromo-1-methyl-4-((4-methylpyridin-3-yl)(tetrahydro-2H-pyran-4-yl)methyl)-1,4-dihydropyrazolo[3',4':4,5]pyrrolo[3,2-b]pyridine-3-carboxylate (170 mg, 26.35% yield), LC-MS [M+H]$^+$=498, 500.

Step 2: Methyl 6-(1,4-dimethyl-1H-1,2,3-triazol-5-yl)-1-methyl-4-((4-methylpyridin-3-yl) (tetrahydro-2H-pyran-4-yl)methyl)-1,4-dihydropyrazolo[3',4':4,5]pyrrolo[3,2-b]pyridine-3-carboxylate Following the procedure analogous to that described in Step 2 for the synthesis of Example 3, methyl 6-bromo-1-methyl-4-((4-methylpyridin-3-yl)(tetrahydro-2H-pyran-4-yl)methyl)-1,4-dihydro pyrazolo[3',4':4,5]pyrrolo[3,2-b]pyridine-3-carboxylate (170 mg, 0.34 mmol) in DMF (5 mL) and 1,4-dimethyl-5-(tributylstannyl)-1H-1,2,3-triazole (274 mg, 0.71 mmol) were converted to methyl 6-(1,4-dimethyl-1H-1,2,3-triazol-5-yl)-1-methyl-4-((4-methylpyridin-3-yl)(tetrahydro-2H-pyran-4-yl)methyl)-1,4-dihydropyrazolo[3',4':4,5]pyrrolo[3,2-b]pyridine-3-carboxylate (80 mg, 47.00% yield). LC/MS [M+H]$^+$=514.

Step 3: 2-(6-(1,4-Dimethyl-1H-1,2,3-triazol-5-yl)-4-((4-methylpyridin-3-yl)(tetrahydro-2H-pyran-4-yl)methyl)-1-methyl-1,4-dihydropyrazolo[3',4':4,5]pyrrolo[3,2-b]pyridin-3-yl)propan-2-ol Following the procedure analogous to that described in Step 3 for the synthesis of Example 3, methyl 6-(1,4-dimethyl-1H-1,2,3-triazol-5-yl)-1-methyl-4-((4-methylpyridin-3-yl)(tetrahydro-2H-pyran-4-yl)methyl)-1,4-dihydropyrazolo[3',4':4,5]pyrrolo[3,2-b]pyridine-3-carboxylate (130 mg, 0.26 mmol) was converted to 2-(6-(1,4-Dimethyl-1H-1,2,3-triazol-5-yl)-4-((4-methylpyridin-3-yl)(tetrahydro-2H-pyran-4-yl)methyl)-1-methyl-1,4-dihydropyrazolo[3',4':4,5]pyrrolo[3,2-b]pyridin-3-yl)propan-2-ol (Compound 22, 20 mg). LC/MS [M+H]$^+$=514.

Example 23

2-(4-((3-Fluoropyridin-2-yl)(tetrahydro-2H-pyran-4-yl)methyl)-1-methyl-6-(1-methyl-4-(methyl-d3)-1H-1,2,3-triazol-5-yl)-1,4-dihydropyrazolo[3',4':4,5]pyrrolo[3,2-b]pyridin-3-yl)propan-2-ol ("Compound 23")

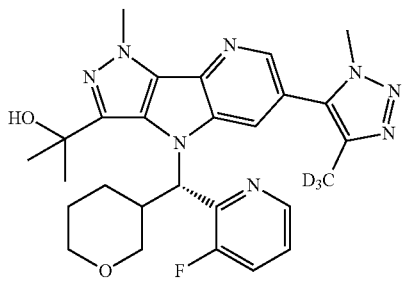 [SMILES: [2H]C([2H])([2H])c1nnn(C)c1-c1cnc2c3c(c(C(C)(C)O)nn3C)n([C@H](c3ncccc3F)C3CCCOC3)c2c1]

Step 1: (S)-Methyl 4-((3-fluoropyridin-2-yl)(tetrahydro-2H-pyran-4-yl)methyl)-1-methyl-6-(1-methyl-4-(methyl-d3)-1H-1,2,3-triazol-5-yl)-1,4-dihydropyrazolo[3',4':4,5]pyrrolo[3,2-b]pyridine-3-carboxylate To a solution of (S)-methyl 6-bromo-4-((3-fluoropyridin-2-yl)(tetrahydro-2H-pyran-4-yl)methyl)-1-methyl-1,4-dihydropyrazolo[3',4':4,5]pyrrolo[3,2-b]pyridine-3-carboxylate (from Example 7 Step 1, 200 mg, 0.40 mmol) in DMF (30 mL) was added 1-methyl-4-(methyl-d3)-5-(tributylstannyl)-1H-1,2,3-triazole (378 mg, 0.97 mmol), tetrakis(triphenylphosphine)palladium (148 mg, 0.13 mmol), CuI (40 mg, 0.21 mmol) and TEA (415 mg, 3.77 mmol) under $N_2$. The mixture was vacuumed, backfilled with $N_2$ and this process was repeated three times. The resulting mixture was stirred at 85° C. for 3 hr and then cooled to room temperature. The reaction mixture was poured into water and extracted with EtOAc (100 mL). The organic phase was washed with brine, dried over anhydrous sodium sulfate, and concentrated. The residue was purified by silica gel chromatography using 0-5% MeOH in DCM to afford (S)-methyl 4-((3-fluoropyridin-2-yl)(tetrahydro-2H-pyran-4-yl)methyl)-1-methyl-6-(1-methyl-4-(methyl-d3)-1H-1,2,3-triazol-5-yl)-1,4-dihydropyrazolo[3',4':4,5]pyrrolo[3,2-b]pyridine-3-carboxylate (132 mg, 0.25 mmol, 63% yield), LC-MS $[M+H]^+$=522.

Step 2: (S)-2-(4-((3-Fluoropyridin-2-yl)(tetrahydro-2H-pyran-4-yl)methyl)-1-methyl-6-(1-methyl-4-(methyl-d3)-1H-1,2,3-triazol-5-yl)-1,4-dihydropyrazolo[3',4':4,5]pyrrolo[3,2-b]pyridin-3-yl)propan-2-ol Following the procedure analogous to that described in Step 3 for the synthesis of Example 3, (S)-methyl 4-((3-fluoropyridin-2-yl)(tetrahydro-2H-pyran-4-yl)methyl)-1-methyl-6-(1-methyl-4-(methyl-d3)-1H-1,2,3-triazol-5-yl)-1,4-dihydropyrazolo[3',4':4,5]pyrrolo[3,2-b]pyridine-3-carboxylate (132 mg, 0.25 mmol) was converted to (S)-2-(4-((3-Fluoropyridin-2-yl)(tetrahydro-2H-pyran-4-yl)methyl)-1-methyl-6-(1-methyl-4-(methyl-d3)-1H-1,2,3-triazol-5-yl)-1,4-dihydropyrazolo[3',4':4,5]pyrrolo[3,2-b]pyridin-3-yl)propan-2-ol (Compound 23, 51 mg, 0.098 mmol, 39% yield), LC-MS $[M+H]^+$=522.

$^1$H NMR (400 MHz, DMSO-$d_6$) δ 8.51 (t, J=5.5 Hz, 1H), 8.41 (d, J=1.4 Hz, 1H), 8.29 (d, J=1.2 Hz, 1H), 7.72 (t, J=9.2 Hz, 1H), 7.47 (dt, J=8.4, 4.3 Hz, 1H), 7.01 (d, J=10.8 Hz, 1H), 5.70 (s, 1H), 4.14 (s, 3H), 3.96 (s, 3H), 3.80 (d, J=9.4 Hz, 1H), 3.67 (d, J=8.7 Hz, 1H), 3.24 (dd, J=27.1, 11.1 Hz, 2H), 3.12 (t, J=11.5 Hz, 1H), 1.73 (s, 3H), 1.62 (dd, J=12.5, 3.9 Hz, 1H), 1.56 (s, 3H), 1.43 (m, 2H), 0.55 (d, J=12.4 Hz, 1H).

Example 24

2-(6-(1,4-Dimethyl-1H-1,2,3-triazol-5-yl)-4-((3-fluoropyridin-4-yl)(tetrahydro-2H-pyran-4-yl)methyl)-1-methyl-1,4-dihydropyrazolo[3',4':4,5]pyrrolo[3,2-b]pyridin-3-yl)propan-2-ol ("Compound 24")

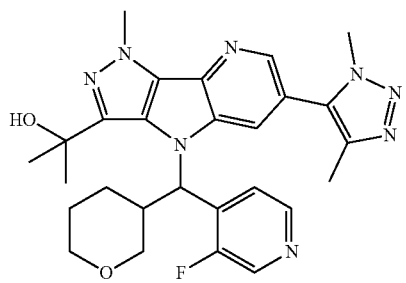 [SMILES: Cc1nnn(C)c1-c1cnc2c3c(c(C(C)(C)O)nn3C)n(C(c3ccncc3F)C3CCCOC3)c2c1]

Step 1: Methyl 6-bromo-4-((3-fluoropyridin-4-yl)(tetrahydro-2H-pyran-4-yl)methyl)-1-methyl-1,4-dihydropyrazolo[3',4':4,5]pyrrolo[3,2-b]pyridine-3-carboxylate Following the procedure analogous to that described in Step 1 for the synthesis of Example 3, methyl 6-bromo-1-methyl-1,4-dihydropyrazolo[3',4':4,5]pyrrolo[3,2-b]pyridine-3-carboxylate (from Example 1 Step 2, 202 mg, 0.65 mmol) and (3-fluoropyridin-4-yl)(tetrahydro-2H-pyran-4-yl)methanol (Intermediate 14, 184 mg, 0.87 mmol) were converted to methyl 6-bromo-4-((3-fluoropyridin-4-yl)(tetrahydro-2H-pyran-4-yl)methyl)-1-methyl-1,4-dihydropyrazolo[3',4':4,5]pyrrolo[3,2-b]pyridine-3-carboxylate (259 mg, 0.52 mmol, 80% yield), LC-MS $[M+H]^+$=502.

Step 2: Methyl 6-(1,4-dimethyl-1H-1,2,3-triazol-5-yl)-4-((3-fluoropyridin-4-yl)(tetrahydro-2H-pyran-4-yl)methyl)-1-methyl-1,4-dihydropyrazolo[3',4':4,5]pyrrolo[3,2-b]pyridine-3-carboxylate Following the procedure analogous to that described in Step 2 for the synthesis of Example 3, methyl 6-bromo-4-((3-fluoropyridin-4-yl)(tetrahydro-2H-pyran-4-yl)methyl)-1-methyl-1,4-dihydro pyrazolo[3',4':4,5]pyrrolo[3,2-b]pyridine-3-carboxylate (259 mg, 0.52 mmol) in DMF (30 mL) and 1,4-dimethyl-5-(tributylstannyl)-1H-1,2,3-triazole (383 mg, 0.98 mmol) were converted to methyl 6-(1,4-dimethyl-1H-1,2,3-triazol-5-yl)-4-((3-fluoropyridin-4-yl)(tetrahydro-2H-pyran-4-yl)methyl)-1-methyl-1,4-dihydropyrazolo[3',4':4,5]pyrrolo[3,2-b]pyridine-3-carboxylate (178 mg, 0.34 mmol, 65% yield), LC-MS $[M+H]^+$=519.

Step 3: 2-(6-(1,4-Dimethyl-1H-1,2,3-triazol-5-yl)-4-((3-fluoropyridin-4-yl)(tetrahydro-2H-pyran-4-yl)methyl)-1-methyl-1,4-dihydropyrazolo[3',4':4,5]pyrrolo[3,2-b]pyridin-3-yl)propan-2-ol Following the procedure analogous to that described in Step 3 for the synthesis of Example 3, methyl 6-(1,4- dimethyl-1H-1,2,3-triazol-5-yl)-4-((3-fluoropyridin-4-yl)(tetrahydro-2H-pyran-4-yl) methyl)-1-methyl-1,4-dihydropyrazolo[3',4':4,5]pyrrolo[3,2-b]pyridine-3-carboxylate (178 mg, 0.34 mmol) was converted to 2-(6-(1,4-Dimethyl-1H-1,2,3-triazol-5-yl)-4-((3-fluoropyridin-4-yl)(tetrahydro-2H-pyran-4-yl)methyl)-1-methyl-1,4-dihydropyrazolo[3',4':4,5]pyrrolo[3,2-b]pyridin-3-yl)propan-2-ol (Compound 24, 63 mg, 0.13 mmol, 38% yield), LC-MS [M+H]$^+$=519.

$^1$H NMR (400 MHz, DMSO-d$_6$) δ 8.48 (d, J=4.7 Hz, 2H), 8.41 (d, J=1.4 Hz, 1H), 8.02 (t, J=5.8 Hz, 1H), 7.92 (s, 1H), 6.89 (d, J=11.1 Hz, 1H), 5.77 (s, 1H), 4.15 (s, 3H), 3.86 (s, 3H), 3.74 (d, J=8.5 Hz, 1H), 3.41 (t, J=11.1 Hz, 1H), 3.22 (m, 2H), 2.16 (s, 3H), 1.70 (s, 3H), 1.66 (d, J=13.6 Hz, 2H), 1.58 (s, 3H), 1.46 (dd, J=20.5, 8.9 Hz, 2H), 0.75 (d, J=12.8 Hz, 1H).

Example 25

2-(6-(1,4-dimethyl-1H-1,2,3-triazol-5-yl)-4-((4-methoxypyridin-3-yl)(tetrahydro-2H-pyran-4-yl) methyl)-1-methyl-1,4-dihydropyrazolo[3',4':4,5] pyrrolo[3,2-b]pyridin-3-yl)propan-2-ol ("Compound 25")

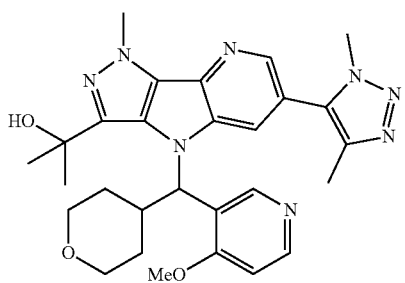 [SMILES: COc1ccncc1C(C1CCOCC1)n1c2cc(-c3c(C)nnn3C)cnc2c2c1c(C(C)(C)O)nn2C]

Step 1: Methyl 6-bromo-4-((4-methoxypyridin-3-yl)(tetrahydro-2H-pyran-4-yl)methyl)-1-methyl-1,4-dihydropyrazolo[3',4':4,5]pyrrolo[3,2-b]pyridine-3-carboxylate To a solution of methyl 6-bromo-1-methyl-1,4-dihydropyrazolo[3',4':4,5]pyrrolo[3,2-b]pyridine-3-carboxylate (from Example 1 Step 2, 142 mg, 0.46 mmol), (4-methoxypyridin-3-yl)(tetrahydro-2H-pyran-4-yl)methanol (Intermediate 16, 135 mg, 0.60 mmol) and triphenylphosphane (284 mg, 1.08 mmol) in dry THF (30 mL) was added diisopropyl azodicarboxylate (243 mg, 1.20 mmol) at r.t. under N$_2$.

The resulting solution was refluxed for 2 hr under N$_2$. After cooling to r.t., the reaction mixture was poured into EtOAc (50 mL) and washed with brine, dried over anhydrous sodium sulfate, and concentrated under reduced pressure. The residue was purified by silica gel chromatography using 30-50% EtOAc in hexane to afford methyl 6-bromo-4-((4-methoxypyridin-3-yl)(tetrahydro-2H-pyran-4-yl)methyl)-1-methyl-1,4-dihydropyrazolo[3',4':4,5]pyrrolo[3,2-b]pyridine-3-carboxylate (200 mg, 0.39 mmol, 85% yield), LC-MS [M+H]$^+$=514.

Step 2: Methyl 6-(1,4-dimethyl-1H-1,2,3-triazol-5-yl)-4-((4-methoxypyridin-3-yl)(tetrahydro-2H-pyran-4-yl)methyl)-1-methyl-1,4-dihydropyrazolo [3',4':4,5]pyrrolo[3,2-b]pyridine-3-carboxylate Following the procedure analogous to that described in Step 2 for the synthesis of Example 3, methyl 6-bromo-4-((4-methoxypyridin-3-yl)(tetrahydro-2H-pyran-4-yl) methyl)-1-methyl-1,4-dihydro pyrazolo[3',4':4,5]pyrrolo[3,2-b]pyridine-3-carboxylate (169 mg, 0.33 mmol) and 1,4-dimethyl-5-(tributylstannyl)-1H-1,2,3-triazole (318 mg, 0.82 mmol) were converted to methyl 6-(1,4-dimethyl-1H-1,2,3-triazol-5-yl)-4-((4-methoxypyridin-3-yl)(tetrahydro-2H-pyran-4-yl)methyl)-1-methyl-1,4-dihydropyrazolo[3',4':4,5]pyrrolo[3,2-b]pyridine-3-carboxylate (109 mg, 0.21 mmol, 64% yield), LC-MS [M+H]$^+$=531.

Step 3: 2-(6-(1,4-Dimethyl-1H-1,2,3-triazol-5-yl)-4-((4-methoxypyridin-3-yl)(tetrahydro-2H-pyran-4-yl) methyl)-1-methyl-1,4-dihydropyrazolo[3',4':4,5] pyrrolo[3,2-b]pyridin-3-yl)propan-2-ol Following the procedure analogous to that described in Step 3 for the synthesis of Example 3, methyl 6-(1,4-dimethyl-1H-1,2,3-triazol-5-yl)-4-((4-methoxypyridin-3-yl)(tetrahydro-2H-pyran-4-yl) methyl)-1-methyl-1,4-dihydropyrazolo[3',4':4,5]pyrrolo[3,2-b]pyridine-3-carboxylate (109 mg, 0.21 mmol) was converted to 2-(6-(1,4-dimethyl-1H-1,2,3-triazol-5-yl)-4-((4-methoxypyridin-3-yl) (tetrahydro-2H-pyran-4-yl)methyl)-1-methyl-1,4-dihydropyrazolo[3',4':4,5]pyrrolo[3,2-b]pyridin-3-yl)propan-2-ol (Compound 25, 9 mg, 0.017 mmol, 8% yield), LC-MS [M+H]$^+$=531.

$^1$H NMR (400 MHz, DMSO-d$_6$) δ 8.98 (s, 1H), 8.36 (m, 2H), 7.85 (s, 1H), 6.96 (d, J=5.5 Hz, 1H), 6.66 (d, J=10.9 Hz, 1H), 5.58 (s, 1H), 4.14 (s, 3H), 3.84 (s, 1H), 3.79 (s, 3H), 3.72 (d, J=9.8 Hz, 1H), 3.56 (s, 3H), 3.43 (t, J=11.4 Hz, 1H), 3.17 (t, J=11.6 Hz, 1H), 2.13 (s, 3H), 1.72 (s, 2H), 1.66 (s, 3H), 1.44 (dd, J=27.0, 8.9 Hz, 2H), 0.63 (d, J=12.3 Hz, 1H).

Example 26

2-(6-(1,4-Dimethyl-1H-1,2,3-triazol-5-yl)-4-((3-methoxypyridin-2-yl)(tetrahydro-2H-pyran-4-yl) methyl)-1-methyl-1,4-dihydropyrazolo[3',4':4,5] pyrrolo[3,2-b]pyridin-3-yl)propan-2-ol ("Compound 26")

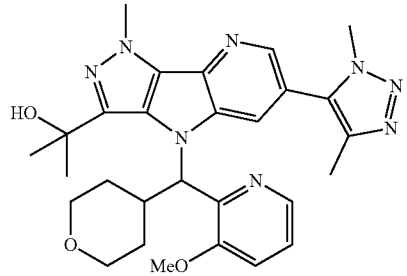 [SMILES: COc1cccnc1C(C1CCOCC1)n1c2cc(-c3c(C)nnn3C)cnc2c2c1c(C(C)(C)O)nn2C]

Step 1: Methyl 6-bromo-4-((3-methoxypyridin-2-yl)(tetrahydro-2H-pyran-4-yl)methyl)-1-methyl-1,4-dihydropyrazolo[3',4':4,5]pyrrolo[3,2-b]pyridine-3-carboxylate To a solution of methyl 6-bromo-1-methyl-1,4-dihydropyrazolo[3',4':4,5]pyrrolo[3,2-b]pyridine-3-carboxylate (from Example 1 Step 2, 290 mg, 0.94 mmol), (3-methoxypyridin-2-yl)(tetrahydro-2H-pyran-4-yl)methanol (Intermediate 17, 320 mg, 1.44 mmol) and triphenylphosphane (504 mg, 1.92 mmol) in dry THF (20 mL) was added DIAD (417 mg, 2.06 mmol) at 25° C. under N$_2$. After addition, the reaction was heated to 40° C. for 2 h. The reaction was then cooled slowly to room temperature and the reaction mixture was poured into water, and extracted with EtOAc (100 mL). The organic phase was washed with brine, dried over anhydrous sodium sulfate, and concentrated under reduced pressure. The residue was purified by C-18 chromatography using 60-70% Acetonitrile in water to afford methyl 6-bromo-4-((3-methoxypyridin-2-yl)(tetrahydro-2H-pyran-4-yl)methyl)-1-methyl-1,4-dihydropyrazolo[3',4':4,5]pyrrolo[3,2-b]pyridine-3-carboxylate (400 mg, 0.78 mmol, 83% yield), LC-MS [M+H]$^+$=515.

Step 2: Methyl 6-(1,4-dimethyl-1H-1,2,3-triazol-5-yl)-4-((3-methoxypyridin-2-yl) (tetrahydro-2H-pyran-4-yl)methyl)-1-methyl-1,4-dihydropyrazolo[3',4':4,5]pyrrolo[3,2-b]pyridine-3-carboxylate Following the procedure analogous to that described in Step 2 for the synthesis of Example 3, methyl 6-bromo-4-((3-methoxypyridin-2-yl)(tetrahydro-2H-pyran-4-yl)methyl)-1-methyl-1,4-dihydropyrazolo[3',4':4,5]pyrrolo[3,2-b]pyridine-3-carboxylate (125 mg, 0.24 mmol) and 1-methyl-4-(methyl)-5-(tributylstannyl)-1H-1,2,3-triazole (197 mg, 0.51 mmol) were converted to methyl 6-(1,4-dimethyl-1H-1,2,3-triazol-5-yl)-4-((3-methoxypyridin-2-yl) (tetrahydro-2H-pyran-4-yl)methyl)-1-methyl-1,4-dihydropyrazolo[3',4':4,5]pyrrolo[3,2-b]pyridine-3-carboxylate (120 mg, 93% yield), LC-MS [M+H]$^+$=531.

Step 3: 2-(6-(1,4-Dimethyl-1H-1,2,3-triazol-5-yl)-4-((3-methoxypyridin-2-yl)(tetrahydro-2H-pyran-4-yl)methyl)-1-methyl-1,4-dihydropyrazolo[3',4':4,5]pyrrolo[3,2-b]pyridin-3-yl)propan-2-ol Following the procedure analogous to that described in Step 3 for the synthesis of Example 3, methyl 6-(1,4-dimethyl-1H-1,2,3-triazol-5-yl)-4-((3-methoxypyridin-2-yl) (tetrahydro-2H-pyran-4-yl)methyl)-1-methyl-1,4-dihydropyrazolo[3',4':4,5]pyrrolo[3,2-b]pyridine-3-carboxylate (120 mg, 0.23 mmol) was converted to 2-(6-(1,4-Dimethyl-1H-1,2,3-triazol-5-yl)-4-((3-methoxypyridin-2-yl) (tetrahydro-2H-pyran-4-yl)methyl)-1-methyl-1,4-dihydropyrazolo[3',4':4,5]pyrrolo[3,2-b]pyridin-3-yl)propan-2-ol (Compound 26, 56 mg, 47% yield), LC-MS [M+H]$^+$=531.

$^1$H NMR (400 MHz, DMSO-d$_6$) δ 8.35 (d, J=1.4 Hz, 1H), 8.25 (d, J=3.9 Hz, 1H), 8.14 (d, J=1.3 Hz, 1H), 7.43 (d, J=8.0 Hz, 1H), 7.35 (dd, J=8.3, 4.6 Hz, 1H), 6.86 (d, J=10.7 Hz, 1H), 5.49 (s, 1H), 4.14 (s, 3H), 3.91 (s, 3H), 3.77 (d, J=10.7 Hz, 1H), 3.66 (s, 3H), 3.65 (s, 3H), 3.25 (dd, J=10.8, 3.3 Hz, 1H), 3.09 (t, J=11.4 Hz, 1H), 2.18 (s, 3H), 1.83-1.76 (m, 1H), 1.75 (s, 3H), 1.65 (s, 3H), 1.49-1.39 (m, 1H), 1.24 (s, 1H), 0.85 (t, J=6.8 Hz, 1H), 0.41 (d, J=12.3 Hz, 1H).

Example 27

2-(6-(1,4-Dimethyl-1H-1,2,3-triazol-5-yl)-4-(1-(4-fluoro-2,6-dimethylphenyl)ethyl)-1-methyl-1,4-dihydropyrazolo[3',4':4,5]pyrrolo[3,2-b]pyridin-3-yl) propan-2-ol ("Compound 27")

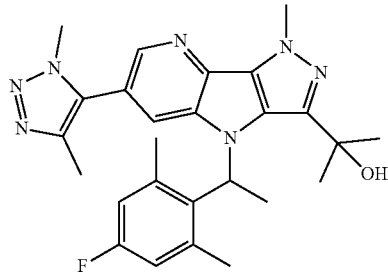 [SMILES: Cc1cc(F)cc(C)c1C(C)n1c2cc(-c3c(C)nnn3C)cnc2c2c1c(C(C)(C)O)nn2C]

Step 1: Methyl 6-bromo-4-(1-(4-fluoro-2,6-dimethylphenyl)ethyl)-1-methyl-1,4-dihydro pyrazolo[3',4':4,5]pyrrolo[3,2-b]pyridine-3-carboxylate Following the procedure analogous to that described in Step 1 for the synthesis of Example 26, methyl 6-bromo-1-methyl-1,4-dihydropyrazolo[3',4':4,5]pyrrolo[3,2-b]pyridine-3-carboxylate (from Example 1 Step 2, 200 mg, 0.65 mmol) and 1-(4-fluoro-2,6-dimethylphenyl)ethan-1-ol (Intermediate 15, 170 mg, 1.02 mmol) were converted to methyl 6-bromo-4-(1-(4-fluoro-2,6-dimethylphenyl)ethyl)-1-methyl-1,4-dihydropyrazolo[3',4':4,5]pyrrolo[3,2-b]pyridine-3-carboxylate (288 mg, 0.62 mmol, 96% yield), LC-MS[M+H]$^+$=460.

Step 2: Methyl 6-(1,4-dimethyl-1H-1,2,3-triazol-5-yl)-4-(1-(4-fluoro-2,6-dimethylphenyl)ethyl)-1-methyl-1,4-dihydropyrazolo[3',4':4,5]pyrrolo[3,2-b] pyridine-3-carboxylate Following the procedure analogous to that described in Step 2 for the synthesis of Example 3, methyl 6-bromo-4-(1-(4-fluoro-2,6-dimethylphenyl)ethyl)-1-methyl-1,4-dihydropyrazolo[3',4':4,5]pyrrolo[3,2-b]pyridine-3-carboxylate (288 mg, 0.62 mmol) in DMF (10 mL) and 1-methyl-4-(methyl)-5-(tributylstannyl)-1H-1,2,3-triazole (509 mg, 1.32 mmol) were converted to methyl 6-(1,4-dimethyl-1H-1,2,3-triazol-5-yl)-4-(1-(4-fluoro-2,6-dimethylphenyl) ethyl)-1-methyl-1,4-dihydropyrazolo[3',4':4,5]pyrrolo[3,2-b]pyridine-3-carboxylate (100 mg, 34% yield), LC-MS [M+H]$^+$=476.

Step 3: 2-(6-(1,4-Dimethyl-1H-1,2,3-triazol-5-yl)-4-(1-(4-fluoro-2,6-dimethylphenyl)ethyl)-1-methyl-1, 4-dihydropyrazolo[3',4':4,5]pyrrolo[3,2-b]pyridin-3-yl)propan-2-ol Following the procedure analogous to that described in Step 3 for the synthesis of Example 3, methyl 6-(1,4-dimethyl-1H-1,2,3-triazol-5-yl)-4-(1-(4-fluoro-2,6-dimethylphenyl)ethyl)-1-methyl-1,4-dihydropyrazolo[3',4':4,5] pyrrolo[3,2-b]pyridine-3-carboxylate (100 mg, 0.21 mmol) was converted to 2-(6-(1,4-dimethyl-1H-1,2,3-triazol-5-yl)-4-(1-(4-fluoro-2,6-dimethylphenyl)ethyl)-1-methyl-1,4-dihydropyrazolo[3',4':4,5]pyrrolo[3,2-b]pyridin-3-yl)propan-2-ol (Compound 27, 27 mg, 27% yield), LC-MS [M+H]⁺=476.

¹HNMR (400 MHz, DMSO-d₆) δ 8.40 (s, 1H), 7.48 (s, 1H), 6.88 (s, 2H), 6.84 (s, 1H), 5.61 (s, 1H), 4.18 (s, 3H), 3.87 (s, 3H), 3.33-3.28 (s, 6H), 2.11 (s, 3H), 2.03 (d, J=6.5 Hz, 3H), 1.64 (s, 3H), 1.31 (s, 3H).

Example 28

(S)—N-(6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-yl)methanesulfonamide ("Compound 28")

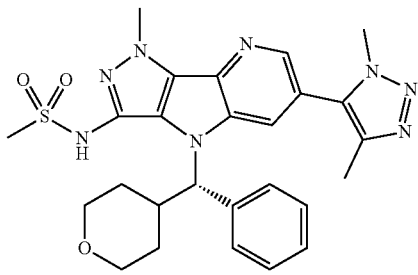 [SMILES: Cc1nnn(C)c1-c1cnc2c3c(c(NS(C)(=O)=O)nn3C)n([C@H](c3ccccc3)C3CCOCC3)c2c1]

Step 1: (S)-6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-amine To a solution of ammonia (25%, 6 mL) in DMSO (3 mL) were added (S)-3-bromo-6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridine (from Example 6 Step 5, 201 mg, 0.39 mmol), CuI (43 mg, 0.23 mmol) L-proline (35 mg, 0.30 mmol) and Cs₂CO₃ (593 mg, 1.82 mmol). The mixture was stirred 110° C. for 3 days. The mixture was poured into water (50 mL) and extracted with EtOAc (150 mL). The collected organic layer was washed with brine (50 mL), dried by Na₂SO₄, and concentrated on a rotary vacuum evaporator. The residue was purified by column chromatography on silica gel with DCM/MeOH (0%-5%) to afford (S)-6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-amine (70 mg, 39% yield). LC-MS [M+H]⁺=457.

Step 2: (S)—N-(6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-yl)methanesulfonamide To a solution of (S)-6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-amine (20 mg, 0.044 mmol) and DMAP (4 mg, 0.033 mmol) in Pyridine (1 mL) was added a solution of MsCl (17 mg, 0.15 mmol) in DCM (1 mL), The mixture was stirred at ambient temperature for 16 h. The mixture was poured into water (20 mL) and extracted with EtOAc (3×20 mL). The combined organic layers were dried over Na₂SO₄ and concentrated under vacuum. The residue was purified by Prep-HPLC to afford the expected (S)—N-(6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-yl)methanesulfonamide (Compound 28, 2 mg, 8% yield), LC-MS [M+H]⁺=535.

¹HNMR (400 MHz, CDCl₃) δ 8.34 (s, 1H), 7.59 (s, 1H), 7.53-7.48 (m, J=6.9 Hz, 2H), 7.33-7.29 (m, 3H), 6.38 (s, 1H), 5.49 (d, J=10.4, 1H), 4.31 (s, 3H), 4.02-3.89 (m, J=9.8 Hz, 2H), 3.88 (s, 3H), 2.55-2.44 (m, J=11.3 Hz, 2H), 3.33 (s, 3H), 3.15-3.09 (m, J=8.6 Hz, 1H), 2.31 (s, 3H), 1.81-1.78 (m, J=7.9 Hz, 1H), 1.57-1.50 (m, 1H), 1.39-1.25 (m, 2H).

Example 29

(S)—N-(6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-yl)acetamide ("Compound 29")

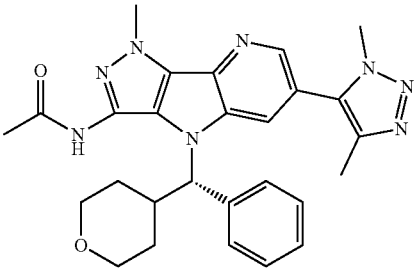 [SMILES: CC(=O)Nc1nn(C)c2c3ncc(-c4c(C)nnn4C)cc3n([C@H](c3ccccc3)C3CCOCC3)c12]

To a solution of (S)-6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-amine (from Example 28 Step 1, 21 mg, 0.046 mmol) and DMAP (4 mg, 0.033 mmol) in Pyridine (1 mL) was added a solution of acetic anhydride (15 mg, 0.15 mmol) in DCM (1 mL), The mixture was stirred at ambient temperature for 16 h.

The mixture was poured into water (20 mL) and extracted with EtOAc (60 mL). The combined organic layer was dried over Na₂SO₄, and concentrated under vacuum. The residue was added to methanol (2 mL) and K₂CO₃ (97 mg) and stirred at ambient temperature for 16 h. The mixture was added to EtOAc (20 mL) and filtered. The filtrate was concentrated under vacuum and the residue was purified by Prep-HPLC to afford (S)—N-(6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-yl)acetamide (Compound 29, 7 mg, 30% yield), LC-MS [M+H]⁺=499.

Example 30

(R)-2-(6-(1,4-dimethyl-1H-1,2,3-triazol-5-yl)-4-((3-fluoropyridin-2-yl)(tetrahydro-2H-pyran-4-yl)methyl)-1-methyl-1,4-dihydropyrazolo[3',4':4,5]pyrrolo[3,2-b]pyridin-3-yl)propan-2-ol ("Compound 30")

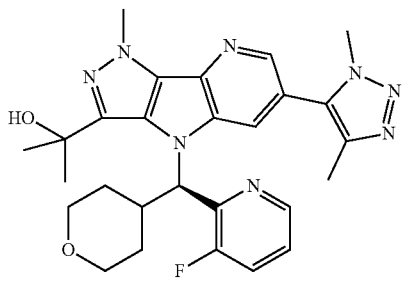 [SMILES: Cc1nnn(C)c1-c1cnc2c3c(c(C(C)(C)O)nn3C)n([C@@H](c3ncccc3F)C3CCOCC3)c2c1]

Step 1: (R)-Methyl 6-bromo-4-((3-fluoropyridin-2-yl)(tetrahydro-2H-pyran-4-yl)methyl)-1-methyl-1,4-dihydropyrazolo[3',4':4,5]pyrrolo[3,2-b]pyridine-3-carboxylate To a solution of methyl 6-bromo-1-methyl-1,4-dihydropyrazolo[3',4':4,5]pyrrolo[3,2-b]pyridine-3-carboxylate (from Example 1 step 2, 212 mg, 0.69 mmol), (S)-(3-fluoropyridin-2-yl)(tetrahydro-2H-pyran-4-yl)methanol (Enantiomer b1 from Example 2, 176 mg, 0.83 mmol) and triphenylphosphane (381 mg, 1.45 mmol) in dry THF (20 mL) was added diisopropyl azodicarboxylate (297 mg, 1.47 mmol) at r.t. under $N_2$. The resulting solution was refluxed for 2 hr under $N_2$. After cooling to r.t., the reaction mixture was extracted with EtOAc (30 mL). The resulting organic layer was washed with brine, dried over anhydrous sodium sulfate, and concentrated under reduced pressure. The residue was purified by silica gel chromatography using 30-50% EtOAc in hexane to afford (R)-methyl 6-bromo-4-((3-fluoropyridin-2-yl) (tetrahydro-2H-pyran-4-yl)methyl)-1-methyl-1,4-dihydropyrazolo[3',4':4,5]pyrrolo[3,2-b]pyridine-3-carboxylate (287 mg, 0.57 mmol, 83%), LC-MS [M+H]$^+$=502.

Step 2: (R)-Methyl 6-(1,4-dimethyl-1H-1,2,3-triazol-5-yl)-4-((3-fluoropyridin-2-yl)(tetrahydro-2H-pyran-4-yl)methyl)-1-methyl-1,4-dihydropyrazolo[3',4':4,5]pyrrolo[3,2-b]pyridine-3-carboxylate To a solution of (R)-methyl 6-bromo-4-((3-fluoropyridin-2-yl)(tetrahydro-2H-pyran-4-yl)methyl)-1-methyl-1,4-dihydropyrazolo[3',4':4,5]pyrrolo[3,2-b]pyridine-3-carboxylate (271 mg, 0.54 mmol) in DMF (20 mL) was added 1,4-dimethyl-5-(tributylstannyl)-1H-1,2,3-triazole (417 mg, 1.08 mmol), tetrakis(triphenylphosphine)palladium (103 mg, 0.092 mmol), CuI (40 mg, 0.21 mmol) and TEA (0.56 g, 5.12 mmol) under $N_2$. The mixture was vacuumed, backfilled with $N_2$ and this process was repeated three times. The resulting mixture was stirred at 85° C. for 3 h and then cooled to room temperature. The reaction mixture was poured into water and extracted with EtOAc (30 mL). The organic phase was washed with brine, dried over anhydrous sodium sulfate, and concentrated. The residue was purified by silica gel chromatography using 0-5% MeOH in DCM to afford (R)-methyl 6-(1,4-dimethyl-1H-1,2,3-triazol-5-yl)-4-((3-fluoropyridin-2-yl)(tetrahydro-2H-pyran-4-yl)methyl)-1-methyl-1,4-dihydropyrazolo[3',4':4,5]pyrrolo[3,2-b]pyridine-3-carboxylate (126 mg, 0.24 mmol, 45% yield), LC-MS [M+H]$^+$=519.

Step 3: (R)-2-(6-(1,4-dimethyl-1H-1,2,3-triazol-5-yl)-4-((3-fluoropyridin-2-yl)(tetrahydro-2H-pyran-4-yl)methyl)-1-methyl-1,4-dihydropyrazolo[3',4':4,5]pyrrolo[3,2-b]pyridin-3-yl)propan-2-ol Following the procedure analogous to that described for the synthesis of 2-(6-(3,5-dimethylisoxazol-4-yl)-4-((3-fluoropyridin-2-yl)(tetrahydro-2H-pyran-4-yl)methyl)-1-methyl-1,4-dihydropyrazolo[3',4':4,5]pyrrolo[3,2-b]pyridin-3-yl)propan-2-ol, (R)-methyl 6-(1,4-dimethyl-1H-1,2,3-triazol-5-yl)-4-((3-fluoropyridin-2-yl)(tetrahydro-2H-pyran-4-yl)methyl)-1-methyl-1,4-dihydropyrazolo[3',4':4,5]pyrrolo[3,2-b]pyridine-3-carboxylate (118 mg, 0.23 mmol) was converted to (R)-2-(6-(1,4-dimethyl-1H-1,2,3-triazol-5-yl)-4-((3-fluoropyridin-2-yl)(tetrahydro-2H-pyran-4-yl)methyl)-1-methyl-1,4-dihydropyrazolo[3,2-b]pyridin-3-yl)propan-2-ol (Compound 30.37 mg, 0.071 mmol, 31% yield), LC-MS[M+H]$^+$=519.

$^1$H NMR (400 MHz, DMSO-d$_6$) δ 8.56-8.48 (m, 1H), 8.42 (d, J=1.8 Hz, 1H), 8.29 (d, J=1.8 Hz, 1H), 7.73 (dd, J=10.0, 8.4, 1.2 Hz, 1H), 7.47 (dt, J=8.5, 4.3 Hz, 1H), 7.02 (d, J=10.9 Hz, 1H), 5.71 (s, 1H), 4.15 (s, 3H), 3.97 (s, 3H), 3.80 (d, J=9.0 Hz, 1H), 3.68 (dd, J=11.4, 2.8 Hz, 1H), 3.28 (dd, J=11.4, 2.4 Hz, 1H), 3.21 (d, J=11.2 Hz, 1H), 3.13 (t, J=11.1 Hz, 1H), 2.24 (s, 3H), 1.74 (s, 3H), 1.69-1.60 (m, 1H), 1.57 (s, 3H), 1.48 (d, J=12.9 Hz, 1H), 1.44-1.35 (m, 1H), 0.55 (d, J=12.1 Hz, 1H).

Example 31

(R)-2-(6-(3,5-dimethylisoxazol-4-yl)-4-((3-fluoropyridin-2-yl)(tetrahydro-2H-pyran-4-yl)methyl)-1-methyl-1,4-dihydropyrazolo[3',4':4,5]pyrrolo[3,2-b]pyridin-3-yl)propan-2-ol ("Compound 31")

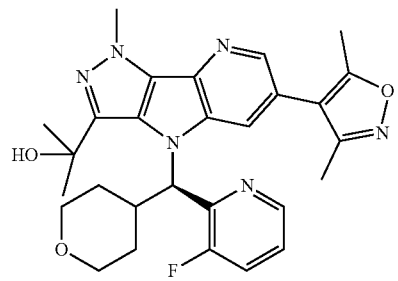 [SMILES: Cc1noc(C)c1-c1cnc2c3c(c(C(C)(C)O)nn3C)n([C@@H](c3ncccc3F)C3CCOCC3)c2c1]

Step 1: (R)-Methyl 6-bromo-4-((3-fluoropyridin-2-yl)(tetrahydro-2H-pyran-4-yl)methyl)-1-methyl-1,4-dihydropyrazolo[3',4':4,5]pyrrolo[3,2-b]pyridine-3-carboxylate Following the same procedure as depicted in the step 2 of Example 2, methyl 6-bromo-1-methyl-1,4-dihydropyrazolo[3',4':4,5]pyrrolo[3,2-b]pyridine-3-carboxylate (obtained from Example 1, step 2, 195 mg, 0.627 mmol) and (S)-(3-fluoropyridin-2-yl)(tetrahydro-2H-pyran-4-yl) methanol (Enantiomer b1 from Example 2, 180 mg, 0.856 mmol) were converted to (R)-methyl 6-bromo-4-((3-fluoropyridin-2-yl)(tetrahydro-2H-pyran-4-yl)methyl)-1-methyl-1,4-dihydropyrazolo[3',4':4,5]pyrrolo[3,2-b]pyridine-3-carboxylate (298 mg, 95% yield), LC-MS [M+H]$^+$=502.

Step 2: (R)-Methyl 6-(3,5-dimethylisoxazol-4-yl)-4-((3-fluoropyridin-2-yl)(tetrahydro-2H-pyran-4-yl)methyl)-1-methyl-1,4-dihydropyrazolo[3',4':4,5]pyrrolo[3,2-b]pyridine-3-carboxylate Following the same procedure as depicted in the step 3 of Example 2, (R)-methyl 6-bromo-4-((3-fluoropyridin-2-yl)(tetrahydro-2H-pyran-4-yl)methyl)-1-methyl-1,4-dihydropyrazolo[3',4':4,5]pyrrolo[3,2-b]pyridine-3-carboxylate (298 mg, 0.59 mmol) and 3,5-dimethyl-4-(4,4,5,5-tetramethyl-1,3,2-dioxaborolan-2-yl)isoxazole (198 mg, 0.890 mmol) were converted to (R)-methyl 6-(3,5-dimethyl isoxazol-4-yl)-4-((3-fluoropyridin-2-yl)(tetrahydro-2H-pyran-4-yl)methyl)-1-methyl-1,4-dihydropyrazolo[3',4':4,5]pyrrolo[3,2-b]pyridine-3-carboxylate (206 mg, 67% yield), LC-MS [M+H]$^+$=519.

Step 3: (R)-2-(6-(3,5-dimethylisoxazol-4-yl)-4-((3-fluoropyridin-2-yl)(tetrahydro-2H-pyran-4-yl)methyl)-1-methyl-1,4-dihydropyrazolo[3',4':4,5]pyrrolo[3,2-b]pyridin-3-yl)propan-2-ol Following the same procedure as depicted in the step 4 of Example 2, (R)-methyl 6-(3,5-dimethylisoxazol-4-yl)-4-((3-fluoropyridin-2-yl)(tetrahydro-2H-pyran-4-yl)methyl)-1-methyl-1,4-dihydropyrazolo [3',4':4,5]pyrrolo[3,2-b]pyridine-3-carboxylate (206 mg, 0.397 mmoL) was converted to (R)-2-(6-(3,5-dimethylisoxazol-4-yl)-4-((3-fluoropyridin-2-yl)(tetrahydro-2H-pyran-4-yl)methyl)-1-methyl-1,4-dihydropyrazolo[3',4':4,5]pyrrolo[3,2-b]pyridin-3-yl)propan-2-ol (Compound 31, 85 mg, 41% yield), LC-MS [M+H]$^+$=519. $^1$H NMR (400 MHz, DMSO-d$_6$) δ 8.54 (d, J=4.6 Hz, 1H), 8.32 (d, J=1.6 Hz, 1H), 8.10 (d, J=1.5 Hz, 1H), 7.72 (t, J=8.9 Hz, 1H), 7.47 (dt, J=8.5, 4.3 Hz, 1H), 6.98 (d, J=10.7 Hz, 1H), 5.67 (s, 1H), 4.13 (s, 3H), 3.80 (d, J=9.1 Hz, 1H), 3.68 (d, J=8.9 Hz, 1H), 3.30-3.17 (m, 2H), 3.11 (t, J=11.4 Hz, 1H), 2.41 (s, 3H), 2.23 (s, 3H), 1.73 (s, 3H), 1.69-1.60 (m, 1H), 1.57 (s, 3H), 1.51 (d, J=11.9 Hz, 1H), 1.40 (dd, J=19.9, 11.5 Hz, 1H), 0.51 (d, J=12.9 Hz, 1H).

Example 32

6-(1,4-dimethyl-1H-1,2,3-triazol-5-yl)-1-methyl-3-((4-methylpiperazin-1-yl)methyl)-4-(phenyl(tetrahydro-2H-pyran-4-yl)methyl)-1,4-dihydropyrazolo[3',4':4,5]pyrrolo[3,2-b]pyridine ("Compound 32")

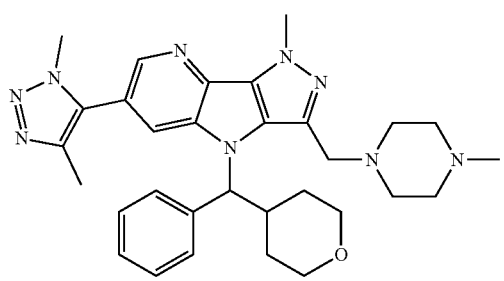 [SMILES: Cc1nnn(C)c1-c1cnc2c3c(c(CN4CCN(C)CC4)nn3C)n(C(c3ccccc3)C3CCOCC3)c2c1]

Step 1: methyl 6-bromo-1-methyl-4-(phenyl(tetrahydro-2H-pyran-4-yl)methyl)-1,4-dihydro pyrazolo[3',4':4,5]pyrrolo[3,2-b]pyridine-3-carboxylate To a solution of methyl 6-bromo-1-methyl-1,4-dihydropyrazolo[3',4':4,5]pyrrolo[3,2-b]pyridine-3-carboxylate (from Example 1 step 2, 1.00 g, 3.23 mmol), phenyl(tetrahydro-2H-pyran-4-yl)methanol (933 mg, 4.85 mmol) and Triphenyl phosphine (1.29 g, 6.82 mmol) in dry THF (60 mL) was added DIAD (600 mg, 2.97 mmol) at r.t. under N$_2$. The reaction system was stirred for 3 hours. The reaction mixture was poured into water and extracted with EtOAc (400 mL). The organic phase was washed with brine, dried over anhydrous sodium sulfate, and concentrated under reduced pressure. The residue was purified by silica gel chromatography using 5-30% EtOAc in hexane to afford of methyl 6-bromo-1-methyl-4-(phenyl(tetrahydro-2H-pyran-4-yl)methyl)-1,4-dihydropyrazolo[3',4':4,5]pyrrolo[3,2-b]pyridine-3-carboxylate (1.31 g, 83.28% yield), LC-MS [M+H]$^+$=483, 485.

Step 2: (6-bromo-1-methyl-4-(phenyl(tetrahydro-2H-pyran-4-yl)methyl)-1,4-dihydropyrazolo[3',4':4,5]pyrrolo[3,2-b]pyridin-3-yl)methanol To a solution of EtOH (20 mL) with Methyl 6-bromo-1-methyl-4-(phenyl(tetrahydro-2H-pyran-4-yl) methyl)-1,4-dihydropyrazolo[3',4':4,5]pyrrolo[3,2-b]pyridine-3-carboxylate (1.30 g, 2.69 mmol) was added NaBH$_4$ (540 mg, 14.27 mmol) and CaCl$_2$ (374 mg, 3.36 mmol) at room temperature. The reaction system was stirred for 3 hours. The reaction mixture was poured into water and extracted with EtOAc (200 mL). The organic phase was washed with brine, dried over anhydrous sodium sulfate, and concentrated under reduced pressure to afford of (6-bromo-1-methyl-4-(phenyl(tetrahydro-2H-pyran-4-yl)methyl)-1,4-dihydropyrazolo[3',4':4,5]pyrrolo[3,2-b]pyridin-3-yl)methanol (1.05 g, 86.24% yield), LC-MS [M+H]$^+$=455, 457.

Step 3: 6-bromo-3-(bromomethyl)-1-methyl-4-(phenyl(tetrahydro-2H-pyran-4-yl)methyl)-1,4-dihydropyrazolo[3',4':4,5]pyrrolo[3,2-b]pyridine To a solution of (6-bromo-1-methyl-4-(phenyl(tetrahydro-2H-pyran-4-yl)methyl)-1,4-dihydro pyrazolo[3',4':4,5]pyrrolo[3,2-b]pyridin-3-yl)methanol (1.05 g, 2.32 mmol) in dry DCM (40 mL) was added phosphorus tribromide (600 mg, 2.97 mmol) at room temperature. The reaction system was stirred for 1 hours. The reaction mixture was poured into NaHCO$_3$(aq) and extracted with DCM (400 mL). The resulting organic phase was washed with brine, dried over anhydrous sodium sulfate, and concentrated under reduced pressure to afford of 6-bromo-3-(bromomethyl)-1-methyl-4-(phenyl(tetrahydro-2H-pyran-4-yl)methyl)-1,4-dihydropyrazolo[3',4':4,5]pyrrolo[3,2-b]pyridine (1.12 g, 93.0% yield), LC-MS [M+H]$^+$=517, 519.

Step 4: 6-bromo-1-methyl-3-((4-methylpiperazin-1-yl)methyl)-4-(phenyl(tetrahydro-2H-pyran-4-yl)methyl)-1,4-dihydropyrazolo[3',4':4,5]pyrrolo[3,2-b]pyridine 6-bromo-3-(bromomethyl)-1-methyl-4-(phenyl(tetrahydro-2H-pyran-4-yl)methyl)-1,4-dihydropyrazolo[3',4':4,5]pyrrolo[3,2-b]pyridine (160 mg, 0.31 mmol), N-methyl piperazine (141 mg, 1.41 mmol) and K$_2$CO$_3$ (140 mg, 1.01 mmol) were mixtured in DMF (10 mL) at room temperature.

The reaction system was stirred for 2 hours. The reaction system was filtered and the organic phase was concentration under reduced pressure. The residue was purified by silica gel chromatography using 2-10% MeOH in DCM to afford of 6-bromo-1-methyl-3-((4-methylpiperazin-1-yl)methyl)-4-(phenyl(tetrahydro-2H-pyran-4-yl) methyl)-1,4-dihydropyrazolo[3',4':4,5]pyrrolo[3,2-b]pyridine (160 mg, 96.0% yield), LC-MS [M+H]⁺=538, 540.

Step 5:6-(1,4-dimethyl-1H-1,2,3-triazol-5-yl)-1-methyl-3-((4-methylpiperazin-1-yl)methyl)-4-(phenyl(tetrahydro-2H-pyran-4-yl)methyl)-1,4-dihydropyrazolo[3',4':4,5]pyrrolo[3,2-b]pyridine To a solution of 6-bromo-1-methyl-3-((4-methylpiperazin-1-yl)methyl)-4-(phenyl(tetrahydro-2H-pyran-4-yl) methyl)-1,4-dihydropyrazolo[3',4':4,5]pyrrolo[3,2-b]pyridine (160 mg, 0.30 mmol) in DMF (10 mL) was added 1,4-dimethyl-5-(tributylstannyl)-1H-1,2,3-triazole (290 mg, 0.75 mmol), CuI (40 mg, 0.21 mmol), Pd(PPh₃)₄ (30 mg, 0.026 mmol) and TEA (120 mg, 1.09 mmol) under N₂. The mixture was purged with N₂ for 2 min, and stirred at 110° C. for 16 hr. The reaction mixture was cooled to r.t, poured into water and extracted with EtOAc (100 mL). After separation, the organic layer was washed with brine, dried over anhydrous sodium sulfate, and concentrated. The residue was purified by silica gel chromatography using 10-60% EtOAc in hexane to afford of 6-(1,4-dimethyl-1H-1,2,3-triazol-5-yl)-1-methyl-3-((4-methylpiperazin-1-yl)methyl)-4-(phenyl (tetrahydro-2H-pyran-4-yl)methyl)-1,4-dihydropyrazolo[3',4':4,5]pyrrolo[3,2-b]pyridine (Compound 32, 20 mg), LC-MS [M+H]⁺=554.

Example 33

6-(1,4-dimethyl-1H-1,2,3-triazol-5-yl)-1-methyl-3-((methylsulfonyl)methyl)-4-(phenyl(tetrahydro-2H-pyran-4-yl)methyl)-1,4-dihydropyrazolo[3',4':4,5]pyrrolo[3,2-b]pyridine ("Compound 33")

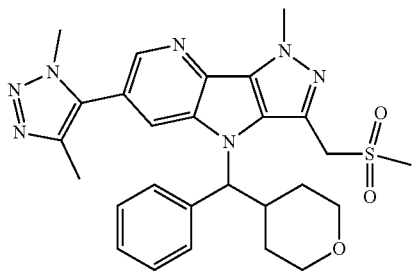 [SMILES: Cc1nnn(C)c1-c1cnc2c3c(c(CS(C)(=O)=O)nn3C)n(C(c3ccccc3)C3CCOCC3)c2c1]

Step 1:6-bromo-1-methyl-3-((methylsulfonyl)methyl)-4-(phenyl(tetrahydro-2H-pyran-4-yl)methyl)-1,4-dihydropyrazolo[3',4':4,5]pyrrolo[3,2-b]pyridine 6-bromo-3-(bromomethyl)-1-methyl-4-(phenyl(tetrahydro-2H-pyran-4-yl)methyl)-1,4-dihydropyrazolo[3',4':4,5]pyrrolo[3,2-b]pyridine (from Example 32 step 3, 300 mg, 0.58 mmol) and Sodium methanesulphinate (100 mg, 0.98 mmol) were stirred in DMF (10 mL) solution at 60° C. The mixture was stirred for 2 hours. The mixture was cooled to r.t. poured into water and extracted with EtOAc (100 mL).

After separation, the organic layer was washed with brine, dried over anhydrous sodium sulfate, and concentrated. The residue was purified by silica gel chromatography using 2-5% MeOH in DCM to afford of 6-bromo-1-methyl-3-((methylsulfonyl)methyl)-4-(phenyl(tetrahydro-2H-pyran-4-yl)methyl)-1,4-dihydropyrazolo[3',4':4,5]pyrrolo[3,2-b]pyridine (90 mg, 29.30% yield), LC-MS[M+H]⁺=517, 519.

Step 2:6-(1,4-dimethyl-1H-1,2,3-triazol-5-yl)-1-methyl-3-((methylsulfonyl)methyl)-4-(phenyl(tetrahydro-2H-pyran-4-yl)methyl)-1,4-dihydropyrazolo[3',4':4,5]pyrrolo[3,2-b]pyridine To a solution of 6-bromo-1-methyl-3-((methylsulfonyl)methyl)-4-(phenyl(tetrahydro-2H-pyran-4-yl) methyl)-1,4-dihydropyrazolo[3',4':4,5]pyrrolo[3,2-b]pyridine (90 mg, 0.17 mmol) in Dioxane (6 mL) was added 1,4-dimethyl-5-(tributylstannyl)-1H-1,2,3-triazole (190 mg, 0.49 mmol), PdCl₂(PPh₃)₂ (20 mg, 0.028 mmol) and DIEA (100 mg, 0.77 mmol) under N₂. The mixture was purged with N₂ for 2 min, stirred at 110° C. for 20 hr. The reaction mixture was cooled to r.t, poured into water and extracted with EtOAc (100 mL). After separation, the organic layer was washed with brine, dried over anhydrous sodium sulfate, and concentrated. The residue was purified by silica gel chromatography using 20-60% EtOAc in hexane to afford of 6-(1,4-dimethyl-1H-1,2,3-triazol-5-yl)-1-methyl-3-((methylsulfonyl)methyl)-4-(phenyl (tetrahydro-2H-pyran-4-yl)methyl)-1,4-dihydropyrazolo[3',4':4,5]pyrrolo[3,2-b]pyridine (Compound 33, 45 mg, 49.57% yield), LC-MS [M+H]1=534.

¹H NMR (400 MHz, DMSO-d₆) δ 8.44 (d, J=1.2 Hz, 1H), 8.18 (s, 1H), 7.63 (d, J=7.4 Hz, 2H), 7.32 (t, J=7.4 Hz, 2H), 7.26 (t, J=7.2 Hz, 1H), 5.48 (d, J=10.9 Hz, 1H), 4.85 (dd, J=31.6, 14.2 Hz, 2H), 4.23 (s, 3H), 3.92 (s, 3H), 3.85 (d, J=9.1 Hz, 1H), 3.73 (d, J=8.5 Hz, 1H), 3.43 (t, J=11.0 Hz, 1H), 3.26 (d, J=11.6 Hz, 2H), 3.17 (s, 3H), 2.24 (d, J=12.7 Hz, 3H), 1.64 (d, J=12.1 Hz, 1H), 1.59-1.45 (m, 2H), 1.00 (d, J=12.2 Hz, 1H).

Example 34

4-((6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-yl)methyl)morpholine ("Compound 34")

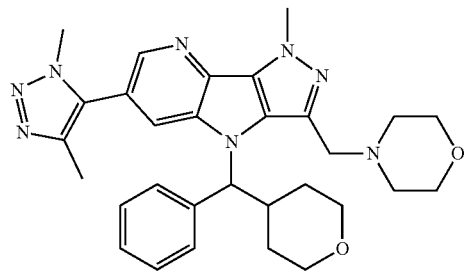 [SMILES: Cc1nnn(C)c1-c1cnc2c3c(c(CN4CCOCC4)nn3C)n(C(c3ccccc3)C3CCOCC3)c2c1]

Step 1:4-((6-bromo-1-methyl-4-(phenyl(tetrahydro-2H-pyran-4-yl)methyl)-1,4-dihydropyrazolo[3',4':4,5]pyrrolo[3,2-b]pyridin-3-yl)methyl)morpholine 6-bromo-3-(bromomethyl)-1-methyl-4-(phenyl(tetrahydro-2H-pyran-4-yl)methyl)-1,4-dihydropyrazolo[3',4':4, 5]pyrrolo[3,2-b]pyridine (from Example 32 step 3, 300 mg, 0.59 mmol), morpholine (100 mg, 1.15 mmol) and K$_2$CO$_3$ (300 mg, 2.17 mmol) were mixed in DMF (10 mL) at room temperature. The reaction system was stirred for 2 hours. The reaction system is filtered and decompressed for concentration. The residue was purified by silica gel chromatography using 2-10% MeOH in DCM to afford of 4-((6-bromo-1-methyl-4-(phenyl(tetrahydro-2H-pyran-4-yl)methyl)-1,4-dihydropyrazolo[3',4':4,5]pyrrolo[3,2-b]pyridin-3-yl)methyl)morpholine (120 mg, 39.00% yield), LC-MS [M+H]$^+$=524, 526.

Step 2:4-((6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-yl)methyl)morpholine To a solution of 4-((6-bromo-1-methyl-4-(phenyl(tetrahydro-2H-pyran-4-yl)methyl)-1,4-dihydropyrazolo[3',4':4,5]pyrrolo[3,2-b]pyridin-3-yl)methyl)morpholine (120 mg, 0.23 mmol) in Dioxane (6 mL) was added 1,4-dimethyl-5-(tributylstannyl)-1H-1,2,3-triazole (185 mg, 0.48 mmol), PdCl$_2$(PPh$_3$)$_2$ (30 mg, 0.043 mmol) and DIEA (100 mg, 0.77 mmol) under N$_2$. The mixture was purged with N$_2$ for 2 min, stirred at 110° C. for 20 hr. The reaction mixture was cooled to r.t., poured into water and extracted with EtOAc (100 mL). After separation, the organic layer was washed with brine, dried over anhydrous sodium sulfate and concentrated. The residue was purified by silica gel chromatography using 20-60% EtOAc in hexane to afford of 4-((6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-yl)methyl)morpholine (Compound 34, 84 mg, 67.50% yield), LC-MS [M+H]$^+$=541.

$^1$H NMR (400 MHz, DMSO-d$_6$) δ 8.39 (d, J=1.5 Hz, 1H), 8.19 (s, 1H), 7.70 (d, J=7.4 Hz, 2H), 7.32 (t, J=7.4 Hz, 2H), 7.24 (t, J=7.3 Hz, 1H), 5.68 (d, J=11.3 Hz, 1H), 4.15 (s, 3H), 3.92 (s, 3H), 3.90 (s, 1H), 3.86 (d, J=3.9 Hz, 1H), 3.82 (d, J=7.6 Hz, 1H), 3.79 (s, 1H), 3.71 (d, J=13.2 Hz, 1H), 3.64 (s, 4H), 3.47-3.33 (m, 4H), 2.22 (s, 3H), 1.63 (d, J=12.3 Hz, 1H), 1.51 (d, J=11.8 Hz, 1H), 1.42-1.33 (m, 1H), 1.14 (d, J=13.5 Hz, 1H).

Example 35

N-(6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-yl)-N-(methylsulfonyl)acetamide ("Compound 35")

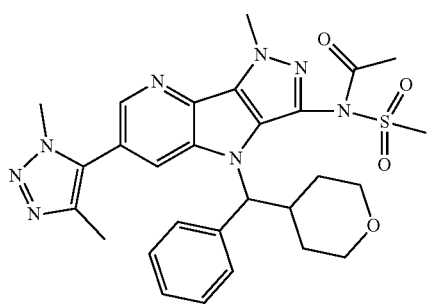 [SMILES: CC(=O)N(c1nn(C)c2c3ncc(-c4c(C)nnn4C)cc3n(C(c3ccccc3)C3CCOCC3)c12)S(C)(=O)=O]

Step 1: N-(6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-yl)-N-(methylsulfonyl)acetamide When the compound N-(6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-yl)methanesulfonamide (from Example 28 step 2), was purified by Prep-HPLC, also afford 3 mg of N-(6-(1,4-dimethyl-1H-1,2,3-triazol-5-yl)-1-methyl-4-(phenyl(tetrahydro-2H-pyran-4-yl)methyl)-1,4-dihydropyrazolo[3',4':4,5]pyrrolo[3,2-b]pyridin-3-yl)-N-(methylsulfonyl)acetamide (Compound 35, 12% yield), LC-MS [M+H]$^+$=577.

$^1$HNMR (400 MHz, CDCl$_3$) δ8.44 (s, 1H), 7.53 (s, 1H), 7.53-7.47 (m, J=6.8 Hz, 2H), 7.33-7.28 (m, 3H), 5.47 (d, J=10.4 Hz, 1H), 4.30 (s, 3H), 4.02-3.89 (m, J=9.4 Hz, 2H), 3.87 (s, 3H), 2.55-2.44 (m, J=11.0 Hz, 2H), 3.33 (s, 3H), 3.15-3.09 (m, J=10.3 Hz, 1H), 2.43 (s, 3H), 2.16 (s, 3H), 1.83-1.79 (m, J=7.1 Hz, 1H), 1.55-1.50 (m, 1H), 1.35-1.22 (m, 2H).

Pharmacological Testing

1. BRD4(BD1) Binding Assays

The BRD4(BD1) biochemical binding assay was performed by Sundia MediTech Co. Ltd. in 384-well white plate (OptiPlate-384, PerkinElmer) using HTRF technology.

Briefly, 20 nL of compounds were transferred to the 384-well plate by Echo® 550 liquid handler (Labcyte, USA), then 5 μL of BRD4(BD1) (Reaction Biology Company, RD-11-157) solution or the assay buffer was added to each well. After incubating at RT for 15 min, 5 μL of the biotinylated H4 derived acetylated peptide (synthesized by GL Biochem (Shanghai) Ltd) and 10 μL of the detection solution (Cisbio Assay) were added to each well. After incubating for 1 h at RT, the HTRF signal was measure at 615 nm and 665 nm using the EnVision Multilabel Plate Reader (PerkinElmer, USA). Results were analyzed with a two-wavelength signal ratio: intensity (665 nm)/intensity (615 nm). The inhibition percentage in the presence of the compound was calculated according to the equation, Percent inhibition=(Max−Signal)/(Max−Min)*100%. Fit the data in GraphPad Prism V5.0 software (San Diego, Calif.) to obtain IC$_{50}$ values with nonlinear regression analysis using equation, Y=Bottom+(Top−Bottom)/(1+10^((Log IC$_{50}$−X)×HillSlope), where Y stands for inhibition percentage and X stands for compound concentration.

Results:

The results of BRD4(BD1) binding assay are in the following Table 3.

TABLE 3

| The results of BRD4(BD1) binding assay | | | |
|---|---|---|---|
| Compound | BRD4(BD1) IC$_{50}$/nM | Compound | BRD4(BDl) IC$_{50}$/nM |
| Compound 1 | 0.48 | Compound 16 | 0.3 |
| Compound 2 | 0.35 | Compound 17 | 0.55 |
| Compound 3 | 0.66 | Compound 18 | 1.1 |
| Compound 4 | 0.57 | Compound 19 | 0.79 |
| Compound 5 | 0.59 | Compound 23 | 0.54 |
| Compound 6 | 0.49 | Compound 24 | 0.88 |
| Compound 7 | 0.97 | Compound 26 | 0.68 |
| Compound 8 | 12.0 | Compound 27 | 17 |
| Compound 9 | 0.99 | Compound 29 | 1.9 |
| Compound 10 | 2.2 | Compound 30 | 3.0 |

TABLE 3-continued

The results of BRD4(BD1) binding assay

| Compound | BRD4(BD1) IC$_{50}$/nM | Compound | BRD4(BD1) IC$_{50}$/nM |
|---|---|---|---|
| Compound 11 | 1.3 | Compound 31 | 4.6 |
| Compound 12 | 1.6 | Compound 33 | 4.67 |
| Compound 13 | 0.4 | Compound 34 | 0.34 |
| Compound 15 | 0.61 | | |

Table 3 shows that the compound of the present invention has a very strong affinity with BRD4 (BD1).

2. Cell Proliferation Assay

MTS Assay Protocol:

MV-4-11 cell proliferation analysis was conducted by the MIS (3-(4,5-dimethylthiazol-2-yl)-5-(3-carboxymethoxyphenyl)-2-(4-sulfophenyl)-2H-tetrazolium, inner salt) assay. Briefly, MV-4-11 cells will be cultured in IMDM (Iscove's Modified Dubecco's Medium) medium supplemented with 10% (v/v) FBS (fetal bovine serum), under the temperature of 37° C., 500 $CO_2$ and 95% humidity. The cells will be harvested respectively during the logarithmic growth period and counted with hemocytometer. The cell viability is over 9000 by trypan blue exclusion. Adjust MV-4-11 cells concentrations to $1.2 \times 10^5$ cells/mL with complete medium. Add 100 μL cell suspensions to 96-well plates (triplicates for each cell concentration), the final cell densities are $1.2 \times 10^4$ cells/well. The next day, dissolve the test compound with DMSO as stock solution. Dispense 5 μL of the stock solution in 1 mL culture media and add 25 μL drug media into 96-well plates. After serially diluting with culture media, the final concentration of the compound will be 0, 0.03, 0.1, 0.3, 1, 3, 10, 30, 100 nM. The plates will be cultured for 3 days, then measured by means of MTS assay. Add PMS (phenazinium methosulfate) solution to MITS solution (1:20) immediately before addition to the culture plate containing cells. Pipet 20 μL of the combined MTS/PMS Solution into each well of the 96 well assay plate containing 100 μL of cells in culture medium. Incubate the plate for 1-4 hours at 37° C. in a humidified, 5% $CO_2$ atmosphere. Record the absorbance at 490 nm using a microplate spectrophotometer (Envision®, PeikinElmer). Fit the data using GraphPad 5.0 and obtain IC$_{50}$ values.

Results:

The results of the cellular proliferation activity are in the following Table 4:

TABLE 4

The results of the cellular proliferation activity

| Compounds | MV-4-11 IC$_{50}$/nM | Compounds | MV-4-11 IC$_{50}$/nM |
|---|---|---|---|
| Compound 1 | 0.89 | Compound 15 | 25.12 |
| Compound 2 | 0.72 | Compound 16 | 3.60 |
| Compound 3 | 6.06 | Compound 17 | 12.69 |
| Compound 4 | 3.13 | Compound 18 | 3.93 |
| Compound 5 | 1.24 | Compound 19 | 7.17 |
| Compound 6 | 1.10 | Compound 21 | 0.77 |
| Compound 7 | 0.70 | Compound 23 | 0.83 |
| Compound 7-2 | 1.11 | Compound 24 | 5.00 |
| Compound 8 | 31.59 | Compound 25 | 8.25 |
| Compound 9 | 5.01 | Compound 26 | 0.91 |
| Compound 10 | 33.99 | Compound 28 | 10.48 |
| Compound 11 | 7.66 | Compound 29 | 24.68 |
| Compound 12 | 10.50 | Compound 34 | 2.16 |
| Compound 13 | 1.15 | Compound 35 | 15.49 |

Table 4 shows that the compound of the present invention has an excellent inhibitory effect on leukemia cell MV-4-11.

Furthermore, the compound of the present invention has a very excellent inhibitory effect on various cancer cells such as lung cancer cells, other leukemia cancer cells, myeloma cancer cells, esophageal cancer cells, and ovarian cancer cells, wherein the lung cancer cells include but are not limited to NCI-H526 lung cancer cells, NCI-H146 lung cancer cells, NCI-H820 lung cancer cells, DMS53 lung cancer cells, NCI-H446 lung cancer cells and the like; the leukemia cancer cells include but are not limited to NB4 leukemia cancer cells, JJN-3 leukemia cancer cells, Kasumi-1 leukemia cancer cells, OCI-AML3 leukemia cancer cells, THP-1 leukemia cancer cells and the like; the myeloma cancer cells include but are not limited to NCI-H929 myeloma cancer cells, KMS-11 myeloma cancer cells and the like; the esophageal cancer cells include but are not limited to COLO-680N esophageal cancer cells, KYSE-150 esophageal cancer cells, KYSE-270 esophageal cancer cells, KYSE-410 esophageal cancer cells, KYSE-70 esophageal cancer cells, OE19 esophageal cancer cells, T.Tn esophageal cancer cells, TE-1 esophageal cancer cells and the like; the ovarian cancer cells include but are not limited to RMG-I ovarian cancer cells, OVCAR-4 ovarian cancer cells and the like.

What is claimed is:

1. A compound, a pharmaceutically acceptable salt thereof or stereoisomer thereof, the compound is (S)-2-(6-(1,4-dimethyl-1H-1,2,3-triazol-5-yl)-4-((3-fluoropyridin-2-yl)(tetrahydro-2H-pyran-4-yl)methyl)-1-methyl-1,4-dihydropyrazolo[3',4T:4,5]pyrrolo[3,2-b]pyridin-3-yl)propan-2-ol.

2. A pharmaceutical composition comprising the compound, the pharmaceutically acceptable salt thereof or stereoisomer thereof according to claim 1, and at least one pharmaceutically acceptable excipient.

3. A method of treating a patient with a leukemia, said method comprising administering to the patient a therapeutically effective amount of the compound, the pharmaceutically acceptable salt thereof or stereoisomer thereof according to claim 1.

4. The method according to claim 3, wherein the patient has a blood tumor from the leukemia.

5. The method according to claim 3, wherein the leukemia is selected from acute myeloid leukemia (AML) and acute lymphocytic leukemia (ALL).

6. A method of treating a patient with a leukemia, said method comprising administering to the patient a therapeutically effective amount of at least one pharmaceutical composition according to claim 2.

7. The method according to claim 6, wherein the patient has a blood tumor from the leukemia.

8. The method according to claim 6, wherein the leukemia is selected from acute myeloid leukemia (AML) and acute lymphocytic leukemia (ALL).

* * * * *

UNITED STATES PATENT AND TRADEMARK OFFICE
CERTIFICATE OF CORRECTION

PATENT NO. : 11,466,005 B2
APPLICATION NO. : 17/561381
DATED : October 11, 2022
INVENTOR(S) : Fang et al.

Page 1 of 1

It is certified that error appears in the above-identified patent and that said Letters Patent is hereby corrected as shown below:

In the Claims

In Claim 1, at Column 144, at Line 39, delete "3',4T" and insert --3',4'-- therefor.

Signed and Sealed this
Third Day of October, 2023

Katherine Kelly Vidal
*Director of the United States Patent and Trademark Office*